US010626388B2

(12) United States Patent
Rasmussen et al.

(10) Patent No.: US 10,626,388 B2
(45) Date of Patent: *Apr. 21, 2020

(54) SUBTILASE VARIANTS AND POLYNUCLEOTIDES ENCODING SAME

(71) Applicant: NOVOZYMES A/S, Bagsvaerd (DK)

(72) Inventors: Frank Winther Rasmussen, Bagsvaerd (DK); Peter Kamp Hansen, Bagsvaerd (DK); Lars Lehman Hylling Christensen, Bagsvaerd (DK)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/323,882

(22) PCT Filed: Jul. 6, 2015

(86) PCT No.: PCT/EP2015/065376
§ 371 (c)(1),
(2) Date: Jan. 4, 2017

(87) PCT Pub. No.: WO2016/001450
PCT Pub. Date: Jan. 7, 2016

(65) Prior Publication Data
US 2017/0145400 A1 May 25, 2017

(30) Foreign Application Priority Data
Jul. 4, 2014 (DK) .................. 2014 00368

(51) Int. Cl.
*C12N 9/52* (2006.01)
*C12N 9/54* (2006.01)
*C11D 3/386* (2006.01)

(52) U.S. Cl.
CPC ............... *C12N 9/54* (2013.01); *C11D 3/386* (2013.01); *C12N 9/52* (2013.01); *C12Y 304/21062* (2013.01)

(58) Field of Classification Search
CPC ....................................................... C12N 9/52
USPC ....................................................... 435/212
See application file for complete search history.

(56) References Cited

U.S. PATENT DOCUMENTS

| | | |
|---|---|---|
| 5,185,258 A | 2/1993 | Caldwell |
| 5,858,757 A | 1/1999 | Van der Osten |
| 6,555,355 B1 | 4/2003 | Hansen |
| 6,831,053 B1 | 12/2004 | Ghosh et al. |
| 6,838,269 B1 | 1/2005 | Estell |
| 2009/0060933 A1 | 3/2009 | Estell |
| 2010/0192985 A1 | 8/2010 | Aehle |
| 2012/0252106 A1* | 10/2012 | Knotzel .................. C11D 3/386 435/264 |
| 2013/0260438 A1 | 10/2013 | Alekseyev |

FOREIGN PATENT DOCUMENTS

| | | |
|---|---|---|
| EP | 1612271 A2 | 1/2006 |
| WO | 88/08033 A1 | 10/1988 |
| WO | 91/00345 A1 | 1/1991 |
| WO | 95/10591 A1 | 4/1995 |
| WO | 95/10615 A1 | 4/1995 |
| WO | 98/020116 A1 | 5/1998 |
| WO | 99/020726 A1 | 4/1999 |
| WO | 2004/041979 A2 | 5/2004 |
| WO | 2007/006305 A1 | 1/2007 |
| WO | 2009/149200 A2 | 12/2009 |
| WO | 2010/056671 A1 | 5/2010 |
| WO | 2010/123754 A1 | 10/2010 |
| WO | 2011/130222 A2 | 10/2011 |
| WO | 2012/151534 A1 | 11/2012 |

OTHER PUBLICATIONS von der Osten et al Protein engineering of subtilisins to improve stability in detergent formulations. Journal of Biotechnology, 28 (1993) p. 55-68.*
Anonymous, 2016, Needle program.
Brown et al, 2012—Uniport Access No. J2GC38.
Brown et al, 2012—Uniport Access No. J3AWX1.
Bryan, 2000, Biochim Biophys Acta 1543 (2), 203-222.
Copeland et al, 2008—Uniport Access No. B2A7KO.
Dodson et al, 2008—Uniport Access No. B4ALD7.
Graycar et al, 1999, JMB, 292, 97-109.
Kudo et al, 2014—Uniport Access No. W7ZAM3.
Lai et al, 2012—Uniport Access No. K2N665.
Massilamany et al, 2014—Uniport Access No. U5LIK6.
Mulder et al, 1999, JMB, 292, 111-123.
Osten et al, 1993, J Biotech 28 (1), 55-68.
Pantoliano et al, 1989, Biochem 28, 7205-7213.
Timmery et al, 2013—Uniport Access No. R8XNW4.
Watanabe et al, 2013—Uniport Access No. L8AIU5.
Youssef et al, 2011—Uniport Access No. E7QYV0.
Wong et al, 1990, J Am Chem Soc, 112 (3), 945-953.
Zwick et al, 2009—Uniport Access No. C2ZHC0.
EP 1 403 282—EBI Access No. CQ793824—Patent Proteins (2004).
U.S. Pat. No. 7,303,907—EBI Access No. ABY09838—USPTO Proteins (2007).
WO 2006-122655 A1—EBI Access No. CS463976—Patent Proteins (2007).
WO 2009-131740 A2—EBI Access No. HC069929—Patent Proteins (2009).

* cited by examiner

*Primary Examiner* — Sheridan Swope
(74) *Attorney, Agent, or Firm* — David Fazzolare

(57) ABSTRACT

The present invention relates to novel subtilase variants exhibiting increased stability and preferably on par or improved wash performance. The variants of the invention are suitable for use in e.g. cleaning or detergent compositions, such as laundry detergent compositions and dish wash compositions, including automatic dish wash compositions. The present invention also relates to isolated DNA sequences encoding the variants, expression vectors, host cells, and methods for producing and using the variants of the invention.

13 Claims, No Drawings
Specification includes a Sequence Listing.

SEQUENCE LISTING

<160> NUMBER OF SEQ ID NOS: 4

<210> SEQ ID NO 1
<211> LENGTH: 269
<212> TYPE: PRT
<213> ORGANISM: Bacillus lentus

<400> SEQUENCE: 1

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

<210> SEQ ID NO 2

```
<211> LENGTH: 275
<212> TYPE: PRT
<213> ORGANISM: Bacillus amyloliquefaciens

<400> SEQUENCE: 2

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275

<210> SEQ ID NO 3
<211> LENGTH: 269
<212> TYPE: PRT
<213> ORGANISM: Bacillus lentus

<400> SEQUENCE: 3

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60
```

```
His Val Ala Gly Thr Ile Ala Ala Leu Asp Asn Ser Ile Gly Val Leu
 65                  70                  75                  80

Gly Val Ala Pro Ser Ala Glu Leu Tyr Ala Val Lys Val Leu Gly Ala
                 85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
            130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
            210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 4
<211> LENGTH: 275
<212> TYPE: PRT
<213> ORGANISM: Bacillus amyloliquefaciens

<400> SEQUENCE: 4

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
                20                  25                  30

Ser Gly Ile Asp Ser Ser His Pro Asp Leu Lys Val Ala Gly Gly Ala
            35                  40                  45

Ser Met Val Pro Ser Glu Thr Asn Pro Phe Gln Asp Asn Asn Ser His
        50                  55                  60

Gly Thr His Val Ala Gly Thr Val Ala Ala Leu Asp Asn Ser Ile Gly
 65                 70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
        130                 135                 140

Ser Gly Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
```

```
                    165             170             175
Val Gly Ala Val Asp Ser Ser Asn Gln Arg Ala Ser Phe Ser Ser Val
            180             185             190

Gly Pro Glu Leu Asp Val Met Ala Pro Gly Val Ser Ile Gln Ser Thr
        195             200             205

Leu Pro Gly Asn Lys Tyr Gly Ala Tyr Asn Gly Thr Ser Met Ala Ser
        210             215             220

Pro His Val Ala Gly Ala Ala Ala Leu Ile Leu Ser Lys His Pro Asn
225             230             235             240

Trp Thr Asn Thr Gln Val Arg Ser Ser Leu Glu Asn Thr Thr Thr Lys
            245             250             255

Leu Gly Asp Ser Phe Tyr Tyr Gly Lys Gly Leu Ile Asn Val Gln Ala
            260             265             270

Ala Ala Gln
    275
```

SUBTILASE VARIANTS AND POLYNUCLEOTIDES ENCODING SAME

CROSS-REFERENCE TO RELATED APPLICATIONS

This application is a 35 U.S.C. 371 national application of PCT/EP2015/065376 filed Jul. 6, 2015, which claims priority or the benefit under 35 U.S.C. 119 of Danish provisional application no. PA 2014 00368 filed Jul. 4, 2014, the contents of which are fully incorporated herein by reference.

BACKGROUND OF THE INVENTION

Field of the Invention

The present invention relates to novel subtilase variants exhibiting increased stability and preferably on par or improved wash performance. The variants of the invention are suitable for use in e.g. cleaning or detergent compositions, such as laundry detergent compositions and dish wash compositions, including automatic dish wash compositions. The present invention also relates to isolated DNA sequences encoding the variants, expression vectors, host cells, and methods for producing and using the variants of the invention.

Description of the Related Art

In the detergent industry, enzymes have for many decades been implemented in washing formulations. Enzymes used in such formulations comprise proteases, lipases, amylases, cellulases, mannosidases as well as other enzymes or mixtures thereof. Commercially the most important enzymes are proteases.

An increasing number of commercially used proteases are protein engineered variants of naturally occurring wild type proteases Everlase®, Relase®, Ovozyme®, Polarzyme®, Liquanase®, Liquanase Ultra® and Kannase® (Novozymes a/s), Purafast®, Purafect OXP®, FN3®, FN4® and Excellase® (Genencor International, Inc.). Further, a number of variants are described in the art, such as in WO2004/041979 (Novozymes NS) which describes subtilase variants exhibiting alterations relative to the parent subtilase in e.g. wash performance, thermal stability, storage stability or catalytic activity. The variants are suitable for use in e.g. cleaning or detergent compositions.

A number of useful subtilase variants have been described many of which have provided improved activity, stability, and solubility in different detergents. For example, WO95/10591 (Procter and Gamble Co.) describes cleaning compositions comprising variants comprising a substitution in position 76, in combination with a modification in one or more additional positions. WO88/08033 (Amgen Inc.) describes subtilisin analogues where amino acids in the calcium binding site, including position 76, are replaced by a negatively charged amino acid such as Asp or Glu.

However, various factors make further improvement of the proteases advantageous. The washing conditions such as temperature and pH changes over time and many stains are still difficult to completely remove under conventional washing conditions. Further, in wash conditions can result in inactivation of the enzymes (due to e.g. pH, temperature or chelation instability) resulting in loss of wash performance during the wash cycle. Thus despite the intensive research in protease development there remains a need for new and improved proteases that have improved stability, in particular improved in storage stability, and preferably similar or improved wash performance compared to the parent subtilase.

SUMMARY OF THE INVENTION

The present invention relates to subtilase variants having protease activity, comprising the substitution N76D and one or more substitutions selected from the group consisting of Q2R, W6I, I8{C,H}, S9{C,D,E,Q}, N18S, N43{A,C,L,R,W}, S49T, G53{A,L}, G61D, I72{A,V}, S78{D,N}, V104{F,P,T,Y}, A114V, G115{T,W}, H120{I,T,V}, P129D, V147W, V149{C,N,Q}, A158E, G160{D,P}, S161{C,Y,E}, I162L, S163{A, D}, Q182{C,E}, N184D, N185{C,E}, S188{C, D,E}, Q191N, A194{D,E}, N204{D,V}, V205{I,L}Q206{C,E,I,K,T,V,W,L,} Y209{L,W}, S212{A,D,G,N}, S216{,I,T,V}, L217{C,M}, N218T, M222{C,N,R}, P225{A,S}, T255{C,E,Q}, S256{A,C,D,V, Y}, S259D, T260{A,E,P}, N261{D,C,E,L,M,R,V,W,Y,F} and L262{Y, C,E,Q}, wherein each position corresponds to the position of the polypeptide of SEQ ID NO: 2.

Another aspect of the invention relates to subtilase variants having protease activity, comprising the substitution N76D and two or more substitutions selected from the group consisting of: of Q2R, W6I, I8{C,H}, S9{C,D,E,Q}, N18S, N43{A,C,L,R,W}, S49T, G53{A,L}, G61D, I72{A,V}, D78{D,N}, V104{F,P,T,Y}, A114V, G115{T,W}, H120{I,T,V}, P129D, V147W, V149{C,N,Q}, A158E, G160{D,P}, S161{C,Y,E}, I162L, S163{A, D}, Q182{C,E}, N184D, N185{C,E}, S188{C, D,E}, Q191N, A194{D,E}, N204{D,V}, V205{I,L}Q206{C,E,I,K,T,V,W,L}, Y209{L,W}, S212{A,D,G,N}, S216{I,T,V}, L217{C,M}, N218T, M222{C,N,R}, P225{A,S}, T255{C,E,Q}, S256{A,C,D,V,Y}, S259D, T260{A,E,P}, N261{D,C,E,L,M,R,V,W,Y,F} and L262{Y,C,E,Q}, wherein each position corresponds to the position of the polypeptide of SEQ ID NO: 2.

The present invention also relates to said subtilase variants having improved stability, in particular improved storage stability, and preferably on par or improved wash performance compared to the parent or compared to a reference protease. The present invention further relates to polynucleotides encoding the subtilase variants; compositions, preferably detergent compositions, comprising a subtilase variant; use of the compositions in a cleaning process and methods for obtaining a subtilase variant and for removing a stain from a surface.

Definitions

The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

The term "detergent component" is defined herein to mean the types of chemicals which can be used in detergent compositions. Examples of detergent components are surfactants, hydrotropes, builders, co-builders, chelators or chelating agents, bleaching system or bleach components, polymers, fabric hueing agents, fabric conditioners, foam boosters, suds suppressors, dispersants, dye transfer inhibitors, fluorescent whitening agents, perfume, optical brighteners, bactericides, fungicides, soil suspending agents, soil release polymers, anti-redeposition agents, enzyme inhibitors or stabilizers, enzyme activators, antioxidants, and solubilizers. The detergent composition may comprise of one or more of any type of detergent component.

The term "detergent composition" includes, unless otherwise indicated, all forms of detergent compositions such as gel, granulate, liquid, paste, powder, spray or tablet compositions including heavy-duty liquids (HDL), fine-fabric liquid detergents, liquid and/or solid laundry detergents and fine fabric detergents; hard surface cleaning formulations for e.g. glass, wood, ceramic and metal counter tops and windows; carpet cleaners; oven cleaners; fabric fresheners; fabric softeners; textile and laundry pre-spotters, as well as dish wash detergents such as hand dishwashing agents, light duty dishwashing agents, machine dishwashing agents; all-purpose or heavy-duty washing agents, liquid, gel or paste-form all-purpose washing agents, liquid cleaning and disinfecting agents, including antibacterial hand-wash types, cleaning bars, mouthwashes, denture cleaners, car or carpet shampoos, bathroom cleaners; hair shampoos and hair-rinses; shower gels, foam baths; metal cleaners; as well as cleaning auxiliaries such as bleach additives and "stain-stick" or pre-treat types.

In addition to containing a subtilase variant of the invention, the detergent formulation may contain one or more additional enzymes (such as proteases, amylases, lipases, cutinases, cellulases, endoglucanases, xyloglucanases, pectinases, pectin lyases, xanthanases, peroxidases, haloperoxygenases, catalases and mannanases, or any mixture thereof), and/or components such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

The term "dish wash" refers to all forms of washing dishes, e.g. by hand or automatic dish wash. Washing dishes includes, but is not limited to, the cleaning of all forms of crockery such as plates, cups, glasses, bowls, all forms of cutlery such as spoons, knives, forks and serving utensils as well as ceramics, plastics such as melamine, metals, china, glass and acrylics.

The term "dish washing composition" refers to all forms of compositions for cleaning hard surfaces. The present invention is not restricted to any particular type of dish wash composition or any particular detergent.

The term "expression" includes any step involved in the production of a variant including, but not limited to, transcription, post-transcriptional modification, translation, post-translational modification, and secretion.

The term "expression vector" means a linear or circular DNA molecule that comprises a polynucleotide encoding a variant and is operably linked to control sequences that provide for its expression.

The term "hard surface cleaning" is defined herein as cleaning of hard surfaces wherein hard surfaces may include floors, tables, walls, roofs etc. as well as surfaces of hard objects such as cars (car wash) and dishes (dish wash). Dish washing includes but are not limited to cleaning of plates, cups, glasses, bowls, and cutlery such as spoons, knives, forks, serving utensils, ceramics, plastics such as melamine, metals, china, glass and acrylics.

The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

The term "improved property" means a characteristic associated with a subtilase variant that is improved compared to the parent subtilase or compared to the polypeptide of SEQ ID NO: 2, or compared to a subtilase having the identical amino acid sequence of said variant but excluding the alterations in said variant. Such improved properties include, but are not limited to, wash performance, protease activity, thermal activity profile, thermostability, pH activity profile, pH stability, substrate/cofactor specificity, improved surface properties, substrate specificity, product specificity, increased stability, improved stability under storage conditions, and chemical stability.

The term "stability" includes storage stability and stability during use, e.g. during a wash process and reflects the stability of the subtilase variant according to the invention as a function of time e.g. how much activity is retained when the subtilase variant is kept in solution in particular in a detergent solution. The stability is influenced by many factors e.g. pH, temperature, detergent composition e.g. amount of builder, surfactants etc. The stability of the subtilase variant may be measured using the assay described in example 3. The term "improved stability" or "increased stability" is defined herein as a variant subtilase displaying an increased stability in solutions, relative to the stability of the parent subtilase, relative to a subtilase having the identical amino acid sequence of said variant but excluding the substitutions in said variant or relative to SEQ ID NO: 1. The terms "improved stability" and "increased stability" includes "improved chemical stability", "detergent stability" or "improved detergent stability.

The term "improved chemical stability" is defined herein as a variant subtilase displaying retention of enzymatic activity after a period of incubation in the presence of a chemical or chemicals, either naturally occurring or synthetic, which reduces the enzymatic activity of the parent enzyme. Improved chemical stability may also result in variants being more able to catalyze a reaction in the presence of such chemicals. In a particular aspect of the invention the improved chemical stability is an improved stability in a detergent, in particular in a liquid detergent. The term "detergent stability" or "improved detergent stability is in particular an improved stability of the protease activity when a subtilase variant of the present invention is mixed into a liquid detergent formulation, especially into a liquid detergent formulation according to table 1 and then stored at temperatures between 15 and 50° C., e.g. 20° C., 30° C. or 40° C.

The term "improved thermal activity" means a variant displaying an altered temperature-dependent activity profile at a specific temperature relative to the temperature-dependent activity profile of the parent, relative to a subtilase having the identical amino acid sequence of said variant but excluding the substitutions in said variant or relative to a protease with SEQ ID NO: 1. The thermal activity value provides a measure of the variant's efficiency in enhancing catalysis of a hydrolysis reaction over a range of temperatures. A more thermo active variant will lead to an increase in enhancing the rate of hydrolysis of a substrate by an enzyme composition thereby decreasing the time required and/or decreasing the enzyme concentration required for activity. Alternatively, a variant with a reduced thermal activity will enhance an enzymatic reaction at a temperature lower than the temperature optimum of the parent defined by the temperature-dependent activity profile of the parent.

The term "improved wash performance" is defined herein as a subtilase variant according to the invention displaying an improved wash performance relative to the wash performance of the parent protease, relative to a polypeptide with SEQ ID NO: 1 or relative to a subtilase having the identical amino acid sequence of said variant but excluding the substitutions in said variant e.g. by increased stain removal. The term "wash performance" includes wash performance in laundry but also e.g. in dish wash. The wash performance may be quantified as described under the definition of "wash performance" herein.

The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

The term "laundering" relates to both household laundering and industrial laundering and means the process of treating textiles and/or fabrics with a solution containing a detergent composition of the present invention. The laundering process can for example be carried out using e.g. a household or an industrial washing machine or can be carried out by hand.

The term "mature polypeptide" means a polypeptide in its final form following translation and any post-translational modifications, such as N-terminal processing, C-terminal truncation, glycosylation, phosphorylation, autocatalytic activation etc. the mature polypeptide is amino acids 1 to 269 of SEQ ID NO: 1 and 1 to 275 of SEQ ID NO 2. It is known in the art that a host cell may produce a mixture of two or more different mature polypeptides (i.e., with a different C-terminal and/or N-terminal amino acid) expressed by the same polynucleotide.

The term "mature polypeptide coding sequence" means a polynucleotide that encodes a mature polypeptide having protease activity.

The term "mutant" means a polynucleotide encoding a variant.

The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

The term "operably linked" means a configuration in which a control sequence is placed at an appropriate position relative to the coding sequence of a polynucleotide such that the control sequence directs expression of the coding sequence.

The term "parent" means a protease to which an alteration is made to produce the enzyme variants of the present invention. Thus the parent is a protease having the identical amino acid sequence of said variant but not having the alterations at one or more e.g. two or more of said specified positions. It will be understood that in the present context the expression "having identical amino acid sequence" relates to 100% sequence identity. The parent may be a naturally occurring (wild-type) polypeptide or a variant thereof. In a particular embodiment the parent is a protease with at least 60% identity, such as at least 65%, at least 70%, at least 75%, at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% identity to a polypeptide with SEQ ID NO: 1 or SEQ ID NO: 2.

The term "protease" is defined herein as an enzyme that hydrolyses peptide bonds. It includes any enzyme belonging to the EC 3.4 enzyme group (including each of the thirteen subclasses thereof). The EC number refers to Enzyme Nomenclature 1992 from NC-IUBMB, Academic Press, San Diego, Calif., including supplements 1-5 published in Eur. J. Biochem. 1994, 223, 1-5; Eur. J. Biochem. 1995, 232, 1-6; Eur. J. Biochem. 1996, 237, 1-5; Eur. J. Biochem. 1997, 250, 1-6; and Eur. J. Biochem. 1999, 264, 610-650; respectively. The most widely used proteases in the detergent industry such as laundry and dish wash are the serine proteases or serine peptidases which is a subgroup of proteases characterised by having a serine in the active site, which forms a covalent adduct with the substrate. Further the subtilases (and the serine proteases) are characterised by having two active site amino acid residues apart from the serine, namely a histidine and an aspartic acid residue. Subtilase refer to a sub-group of serine protease according to Siezen et al., Protein Engng. 4 (1991) 719-737 and Siezen et al. *Protein Science* 6 (1997) 501-523. The subtilases may be divided into 6 sub-divisions, i.e. the Subtilisin family, the Thermitase family, the Proteinase K family, the Lantibiotic peptidase family, the Kexin family and the Pyrolysin family. The term "protease activity" means a proteolytic activity (EC 3.4). Proteases usably in detergents are mainly endopeptidases (EC 3.4.21). There are several protease activity types: The three main activity types are: trypsin-like where there is cleavage of amide substrates following Arg or Lys at P1, chymotrypsin-like where cleavage occurs following one of the hydrophobic amino acids at P1, and elastase-like with cleavage following an Ala at P1. For purposes of the present invention, protein activity, such as protease activity is determined according to the procedure described in the Examples section below. In one aspect, the subtilase variants of the present invention have at least 20%, e.g., at least 40%, at least 50%, at least 60%, at least 70%, at least 80%, at least 90%, at least 95%, or at least 100% of the enzyme activity of the mature polypeptide of the parent enzyme. In one particular aspect the subtilase variants of the present invention have at least 20%, e.g., at least 40%, at least 50%, at least 60%, at least 70%, at least 80%, at least 90%, at least 95%, or at least 100% of the enzyme activity of the polypeptide of SEQ ID NO: 1.

The term "protease activity" means a proteolytic activity (EC 3.4). Proteases of the invention are endopeptidases (EC 3.4.21). There are several protease activity types: The three main activity types are: trypsin-like where there is cleavage of amide substrates following Arg or Lys at P1, chymotrypsin-like where cleavage occurs following one of the hydrophobic amino acids at P1, and elastase-like with cleavage following an Ala at P1. For purposes of the present invention, protease activity is determined according to the procedure described in "Materials and Methods" below. The subtilase variants of the present invention preferably have at least 20%, e.g., at least 40%, at least 50%, at least 60%, at least 70%, at least 80%, at least 90%, at least 95%, and at least 100% of the protease activity of the polypeptide of SEQ ID NO: 1.

The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment–
Total Number of Gaps in Alignment).

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of
Alignment–Total Number of Gaps in Alignment).

The different stringency conditions are defined as follows.

The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 1×SSC, 0.2% SDS at 60° C.

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 1×SSC, 0.2% SDS at 65° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.5×SSC, 0.2% SDS at 65° C.

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.3×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.15×SSC, 0.2% SDS at 65° C.

The term "substantially pure variant" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the variant is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The variants of the present invention are preferably in a substantially pure form. This can be accomplished, for example, by preparing the variant by well-known recombinant methods or by classical purification methods.

The term "substantially pure polynucleotide" means a polynucleotide preparation free of other extraneous or unwanted nucleotides and in a form suitable for use within genetically engineered polypeptide production systems. Thus, a substantially pure polynucleotide contains at most 10%, at most 8%, at most 6%, at most 5%, at most 4%, at most 3%, at most 2%, at most 1%, and at most 0.5% by weight of other polynucleotide material with which it is natively or recombinantly associated. A substantially pure polynucleotide may, however, include naturally occurring 5'- and 3'-untranslated regions, such as promoters and terminators. It is preferred that the substantially pure polynucleotide is at least 90% pure, e.g., at least 92% pure, at least 94% pure, at least 95% pure, at least 96% pure, at least 97% pure, at least 98% pure, at least 99% pure, and at least 99.5% pure by weight. The polynucleotides of the present invention are preferably in a substantially pure form.

The term "textile" means any textile material including yarns, yarn intermediates, fibers, non-woven materials, natural materials, synthetic materials, as well as fabrics made of these materials such as garments, cloths and other articles). When the term fabric or garment is used it is intended to include the broader term textiles as well.

The term "variant" means a polypeptide having protease activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding one or more (e.g. several) amino acids, e.g. 1, 2, 3, 4 or 5 amino acids adjacent to and immediately following the amino acid occupying a position. The term subtilase variant means a variant of a subtilase parent i.e. a subtilase variant is a subtilase which comprises alterations i.e., a substitution, insertion, and/or deletion, at one or more (e.g., several) positions compared to the parent subtilase.

The term "wash performance" is used as an enzyme's ability to remove stains present on the object to be cleaned during e.g. wash, such as laundry or hard surface cleaning. The improvement in the wash performance may be quantified by calculating the so-called intensity value (Int) defined in AMSA assay, as described in Materials and Methods section.

The term "wild-type subtilase" means a protease expressed by a naturally occurring organism, such as a bacterium, archaea, yeast, fungus, plant or animal found in nature. An example of a wild-type subtilase is BPN' i.e. amino acid 1 to 275 of SEQ ID NO: 2.

Conventions for Designation of Variants

For purposes of the present invention, the polypeptide disclosed in SEQ ID NO: 2 (BPN') is used to determine the corresponding amino acid residue in another protease. The amino acid sequence of another protease is aligned with the mature polypeptide disclosed in SEQ ID NO: 2, and based on the alignment, the amino acid position number corresponding to any amino acid residue in the polypeptide disclosed in SEQ ID NO: 2 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another protease can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537:_39-64; Katoh and Toh, 2010, *Bioinformatics* 26:_1899-1900), and EMBOSS EMMA employing ClustalW (1.83 or later; Thompson et al., 1994, *Nucleic Acids Research* 22: 4673-4680), using their respective default parameters.

When the other enzyme has diverged from the mature polypeptide of SEQ ID NO: 2 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions. For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions. For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions: The insertion of an additional amino acid residue such as e.g. a lysine after G195 may be indicated by:

Gly195GlyLys or G195GK. Alternatively insertion of an additional amino acid residue such as lysine after G195 may be indicated by: *195aK. When more than one amino acid residue is inserted, such as e.g. a Lys and Ala after G195 this may be indicated as: Gly195GlyLysAla or G195GKA. In such cases, the inserted amino acid residue(s) may also be numbered by the addition of lower case letters to the position number of the amino acid residue preceding the inserted amino acid residue(s), in this example: *195aK*195bA. In the above example, the sequences 194 to 196 would thus be:

|  | 194 195 196 |
|---|---|
| Savinase | A - G - L |
|  | 194 195 195a 195b 196 |
| Variant | A - G - K - A - L |

In cases where a substitution and an insertion occur at the same position, this may be indicated as S99SD+S99A or in short S99AD. The same modification may also be indicated as S99A+*99aD.

In cases where an amino acid residue identical to the existing amino acid residue is inserted, it is clear that degeneracy in the nomenclature arises. If for example a glycine is inserted after the glycine in the above example this would be indicated by G195GG or *195GaG. The same actual change could just as well be indicated as A194AG or *194aG for the change from:

|  | 194 195 196 |
|---|---|
| Savinase | A - G - L |

To:

|  | 194 195 195a 196 |
|---|---|
| Variant | A - G - G - L |
|  | 194 194a 195 196 |

Such instances will be apparent to the skilled person and the indication G195GG and corresponding indications for this type of insertions are thus meant to comprise such equivalent degenerate indications.

Multiple alterations: Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively. Alternatively multiple alterations may be separated be space or a comma e.g. A170Y G195E or A170Y, G195E respectively.

Different alterations: Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants:

"Tyr167Gly+Arg170Gly", "Tyr167Gly+Arg170Ala", "Tyr167Ala+Arg170Gly", and "Tyr167Ala+Arg170Ala".

Alternatively different alterations or optional substitutions may be indicated in brackets e.g. Arg170[Tyr, Gly] or, Arg170 [Tyr, Gly] or in short R170 [Y,G] or R170 {Y, G}.

Numbering of Amino Acid Positions/Residues

If nothing else is mentioned the amino acid numbering used herein correspond to that of the subtilase BPN' (BASBPN) sequence SEQ ID NO: 2 (amino acids 1 to 275) or Siezen et al., Protein Eng. 4 (1991) 719-737.

Table 1 of WO 89/06279 shows the alignment of the mature polypeptide of the subtilase BPN' (BASBPN) sequence (sequence c in table 1) and the mature polypeptide of subtilisin 309 from B. Lentus, also known as Savinase®, (BLSAVI) (sequence a in table 1).

DETAILED DESCRIPTION OF THE INVENTION

The inventors have surprisingly found that subtilase variants comprising the substitution N76D and one or more further alterations have improved stability, such as improved storage stability compared to the parent subtilase.

Thus, a first aspect of the invention relates to subtilase variants having protease activity, wherein the subtilase comprises the substitution N76D and one or more substitutions selected from the group consisting of Q2R, W6I, I8{C,H}, S9{C,D,E,Q}, N18S, N43{A,C,L,R,W}, S49T, G53{A,L}, G61D, I72{A,V}, S78{D,N}, V104{F,P,T,Y}, A114V, G115{T,W}, H120{I,T,V}, P129D, V147W, V149{C,N,Q}, A158E, G160{D,P}, S161{C,Y,E}, I162L, S163{A, D}, Q182{C,E}, N184D, N185{C,E}, S188{C, D,E}, Q191N, A194{D,E}, N204{D,V}, V205{I,L}, Q206{C,E,I,K,T,V,W,L}, Y209{L,W}, S212{A,D,G,N}, S216{I,T,V}, L217{C,M}, N218T, M222{C,N,R}, P225{A,S}, T255{C,E,Q}, S256{A,C,D,V,Y}, S259D, T260{A,E,P}, N261{D,C,E,L,M,R,V,W,Y,F} and L262{Y,C,E,Q}, wherein each position corresponds to the position of the polypeptide of SEQ ID NO: 2.

Another aspect of the invention relates to subtilase variants having protease activity, comprising the substitution N76D and two or more substitutions selected from the group consisting of Q2R, W6I, I8{C,H}, S9{C,D,E,Q}, N18S, N43{A,C,L,R,W}, S49T, G53{A,L}, G61D, I72{A,V}, S78{D,N}, V104{F,P,T,Y}, A114V, G115{T,W}, H120{I,T,V}, P129D, V147W, V149{C,N,Q}, A158E, G160{D,P}, S161{C,Y,E}, I162L, S163{A, D}, Q182{C,E}, N184D, N185{C,E}, S188{C, D,E}, Q191N, A194{D,E}, N204{D,V}, V205{I,L}, Q206{C,E,I,K,T,V,W,L}, Y209{L,W}, S212{A,D,G,N}, S216{I,T,V}, L217{C,M}, N218T, M222{C,N,R}, P225{A,S}, T255{C,E,Q}, S256{A,C,D,V,Y}, S259D, T260{A,E,P}, N261{D,C,E,L,M,R,V,W,Y,F} and L262{Y,C,E,Q}, wherein each position corresponds to the position of the polypeptide of SEQ ID NO: 2.

A third aspect of the invention relates to a polypeptide with the amino acid sequence of SEQ ID NO: 3 which comprise one or more substitutions selected the group consisting of Q2R, W6I, I8{C,H}, S9{C,D,E,Q}, N18S, N43{A,C,L,R,W}, S49T, G53{A,L}, G61D, I72{A,V}, S78{D,N}, V104{F,P,T,Y}, A114V, G115{T,W}, H120{I,T,V}, P129D, V147W, V149{C,N,Q}, A158E, G160{D,P}, S161{C,Y,E}, I162L, S163{A, D}, Q182{C,E}, N184D, N185{C,E}, S188{C, D,E}, Q191N, A194{D,E}, N204{D,V}, V205{I,L}, Q206{C,E,I,K,T,V,W,L}, Y209{L,W}, S212{A,D,G,N}, S216{I,T,V}, L217{C,M}, N218T, M222{C,N,R}, P225{A,S}, T255{C,E,Q}, S256{A,C,D,V,Y}, S259D, T260{A,E,P}, N261{D,C,E,L,M,R,V,W,Y,F} and L262{Y,C,E,Q}, wherein each position corresponds to the position of the polypeptide of SEQ ID NO: 2 and wherein the polypeptide has at least 80% identity to SEQ ID NO: 1.

A fourth aspect of the invention relates to a polypeptide with the amino acid sequence of SEQ ID NO 4 which comprise one or more substitutions selected the group consisting of Q2R, Y6I, V8{C,H}, S9{C,D,E,Q}, K43{A,C,L,R,W}, S49T, S53{A,L}, N61D, V72A, S78{D,N}, Y104{F,P,T}, A114V, I115{T,W}, D120{I,T,V}, P129D, V147W, V149{C,N,Q}, T158E, G160{D,P}, S161{C,Y,E}, S162L, S163{A, D}, S182{C,E}, N184D, Q185{C,E}, S188{C, D,E}, S191N, P194{D,E}, S204{D,V}, I205L, Q206{C,E,I,K,T,V,W,L}, L209W, N212{A,D,G}, A216{I, T,V}, Y217{C,M}, N218T, M222{C,N,R}, P225{A,S}, T255{C,E,Q}, K256{A,C,D,V, Y}, S260{A,E,P}, F261{D, C,E,L,M,R,V,W,Y,F} and Y262{C,E,Q}, wherein each position corresponds to the position of the polypeptide of SEQ ID NO: 2 and wherein the polypeptide has at least 80% identity to SEQ ID NO: 2.

In one embodiment, the subtilase variant has improved stability, in particular improved storage stability, compared to the mature polypeptide of the parent subtilase, to the polypeptide of SEQ ID NO: 1 or relative to a subtilase having the identical amino acid sequence of said variant but excluding the alterations in said variant. In a preferred embodiment, the subtilase variant has improved stability, in particular improved storage stability, and on par or improved wash performance compared to the polypeptide of the parent subtilase, to the polypeptide of SEQ ID NO: 1 or relative to a subtilase having the identical amino acid sequence of said variant but excluding the alterations in said variant.

In a further embodiment, the subtilase variant comprises the substitution N76D. The parent subtilase may be any wild type subtilase. In one aspect, the parent subtilase is amino acids 1 to 269 of SEQ ID NO: 1. In another aspect the parent subtilase is amino acids 1 to 275 of SEQ ID NO: 2.

Thus in one embodiment, the invention relates to subtilase variants having protease activity, wherein said variant comprises the substitution N76D and one or more substitutions selected from the group consisting of Q2R, W6I, I8{C,H}, S9{C,D,E,Q}, N18S, N43{A,C,L,R,W}, S49T, G53{A,L}, G61D, I72{A,V}, S78{D,N}, V104{F,P,T,Y}, A114V, G115{T,W}, H120{I,T,V}, P129D, V147W, V149{C,N,Q}, A158E, G160{D,P}, S161{C,Y,E}, I162L, S163{A, D}, Q182{C,E}, N184D, N185{C,E}, S188{C, D,E}, Q191N, A194{D,E}, N204{D,V}, V205{I,L}, Q206{C,E,I,K,T,V, W,L}, Y209{L,W}, S212{A,D,G,N}, S216{I,T,V}, L217{C,M}, N218T, M222{C,N,R}, P225{A,S}, T255{C, E,Q}, S256{A,C,D,V, Y}, S259D, T260{A,E,P}, N261{D, C,E,L,M,R,V,W,Y,F} and L262{Y,C,E,Q}, wherein each position corresponds to the position of the polypeptide of SEQ ID NO: 2 and wherein subtilase variant is a) a polypeptide that has at least 60% but less than 100% sequence identity to the amino acid sequence of the parent subtilase;
b) a polypeptide that is encoded by a polynucleotide that hybridizes under low stringency conditions, medium stringency conditions, medium-high stringency conditions, high stringency conditions, or very high stringency conditions with:
  (i) the mature polypeptide coding sequence of the parent subtilase or
  (ii) the full-length complement of (i); or
c) a polypeptide that is encoded by a polynucleotide having at least 60% but less than 100% sequence identity to the mature polypeptide coding sequence of the parent subtilase.

In an embodiment, the subtilase variant has at least 65% but less than 100% sequence identity to the mature polypeptide of the parent subtilase. In an embodiment, the subtilase variant has at least 70% but less than 100% sequence identity to the mature polypeptide of the parent subtilase. In an embodiment, the subtilase variant has at least 75% but less than 100% sequence identity to the mature polypeptide of the parent subtilase. In an embodiment, the subtilase variant has at least 80% but less than 100% sequence identity to the mature polypeptide of the parent subtilase. In an embodiment, the subtilase variant has at least 85% but less than 100% sequence identity to the mature polypeptide of the parent subtilase. In an embodiment, the subtilase variant has at least 90% but less than 100% sequence identity to the mature polypeptide of the parent subtilase. In an embodiment, the subtilase variant has at least 93% but less than 100% sequence identity to the mature polypeptide of the parent subtilase. In an embodiment, the subtilase variant has at least 95% but less than 100% sequence identity to the mature polypeptide of the parent subtilase. In an embodiment, the subtilase variant has at least 96% but less than 100% sequence identity to the mature polypeptide of the parent subtilase. In an embodiment, the subtilase variant has at least 97% but less than 100% sequence identity to the mature polypeptide of the parent subtilase. In an embodiment, the subtilase variant has at least 98% but less than 100% sequence identity to the mature polypeptide of the parent subtilase.

In one aspect, the total number of alterations in the parent subtilase is between 3 and 30, preferably between 3 and 20, more preferably between 3 and 15, even more preferably between 3 and 10, most preferably between 3 and 8 alterations. In another aspect, total number of alterations in the parent subtilase is 3, 4, 5, 6, 7, 8, 9, 10, 11, 12, 13, 14, 15, 16, 17, 18, 19, 20, 21, 22, 23, 24, 25, 26, 27, 28, 29 or 30 alterations.

In one embodiment, the subtilase variant has improved stability, in particular improved storage stability, compared to the mature polypeptide of the parent subtilase. In a preferred embodiment, the subtilase variant has improved stability, in particular improved storage stability, and on par or improved wash performance compared to the mature polypeptide of the parent subtilase.

In one embodiment, the invention relates to subtilase variants having protease activity, wherein said variant comprises the substitution N76D and one or more substitutions selected from the group consisting of Q2R, W6I, I8{C,H}, S9{C,D,E,Q}, N18S, N43{A,C,L,R,W}, S49T, G53{A,L}, G61D, I72{A,V}, S78{D,N}, V104{F,P,T,Y}, A114V, G115{T,W}, H120{I,T,V}, P129D, V147W, V149{C,N,Q}, A158E, G160{D,P}, S161{C,Y,E}, I162L, S163{A, D}, Q182{C,E}, N184D, N185{C,E}, S188{C, D,E}, Q191N, A194{D,E}, N204{D,V}, V205{I,L}, Q206{C,E,I,K,T,V, W,L}, Y209{L,W}, S212{A,D,G,N}, S216{I,T,V}, L217{C,M}, N218T, M222{C,N,R}, P225{A,S}, T255{C, E,Q}, S256{A,C,D,V, Y}, S259D, T260{A,E,P}, N261{D, C,E,L,M,R,V,W,Y,F} and L262{Y,C,E,Q}, wherein each position corresponds to the position of the polypeptide of SEQ ID NO: 2, and wherein subtilase variant is a polypeptide that has at least 60% but less than 100% sequence identity to the amino acid sequence of SEQ ID NO: 1.

In an embodiment, the subtilase variant has at least 65% but less than 100% sequence identity to the polypeptide of SEQ ID NO: 1. In an embodiment, the subtilase variant has at least 70% but less than 100% sequence identity to the polypeptide of SEQ ID NO: 1. In an embodiment, the subtilase variant has at least 75% but less than 100% sequence identity to the polypeptide of SEQ ID NO: 1. In an embodiment, the subtilase variant has at least 80% but less than 100% sequence identity to the polypeptide of SEQ ID NO: 1. In an embodiment, the subtilase variant has at least 85% but less than 100% sequence identity to the polypeptide of SEQ ID NO: 1. In an embodiment, the subtilase variant has at least 90% but less than 100% sequence identity to the polypeptide of SEQ ID NO: 1. In an embodiment, the subtilase variant has at least 93% but less than 100% sequence identity to the polypeptide of SEQ ID NO: 1. In an embodiment, the subtilase variant has at least 95% but less than 100% sequence identity to the polypeptide of SEQ ID NO: 1. In an embodiment, the subtilase variant has at least 96% but less than 100% sequence identity to the polypeptide of SEQ ID NO: 1. In an embodiment, the subtilase variant has at least 97% but less than 100% sequence identity to the polypeptide of SEQ ID NO: 1. In an embodiment, the subtilase variant has at least 98% but less than 100% sequence identity to the polypeptide of SEQ ID NO: 1.

In one aspect, the total number of alterations in the polypeptide of SEQ ID NO: 1 is between 3 and 30, preferably between 3 and 20, more preferably between 3 and 15, even more preferably between 3 and 10, most preferably between 3 and 8 alterations. In another aspect, total number of alterations in the polypeptide of SEQ ID NO: 1 is 3, 4, 5, 6, 7, 8, 9, 10, 11, 12, 13, 14, 15, 16, 17, 18, 19, 20, 21, 22, 23, 24, 25, 26, 27, 28, 29 or 30 alterations.

In one embodiment, the invention relates to subtilase variants having protease activity, wherein said variant comprises the substitution N76D and one or more substitutions selected from the group consisting of Q2R, Y6I, V8{C,H}, S9{C,D,E,Q}, K43{A,C,L,R,W}, S49T, S53{A,L}, N61D, V72A, S78{D,N}, Y104{F,P,T}, A114V, I115{T,W}, D120{I,T,V}, P129D, V147W, V149{C,N,Q}, T158E, G160{D,P}, S161{C,Y,E}, S162L, S163{A, D}, S182{C,E}, N184D, Q185{C,E}, S188{C, D,E}, S191N, P194{D,E}, S204{D,V}, I205L, Q206{C,E,I,K,T,V,W,L}, L209W, N212{A,D,G}, A216{I,T,V}, Y217{C,M}, N218T, M222{C,N,R}, P225{A,S}, T255{C,E,Q}, K256{A,C,D,V,Y}, S260{A,E,P}, F261{D,C,E,L,M,R,V,W,Y,F} and Y262{C,E,Q}, wherein each position corresponds to the position of the polypeptide of SEQ ID NO: 2 and wherein subtilase variant is a polypeptide that has at least 60% but less than 100% sequence identity to the amino acid sequence of SEQ ID NO 2.

In an embodiment, the subtilase variant has at least 65% but less than 100% sequence identity to the polypeptide of SEQ ID NO: 2. In an embodiment, the subtilase variant has at least 70% but less than 100% sequence identity to the polypeptide of SEQ ID NO: 2. In an embodiment, the subtilase variant has at least 75% but less than 100% sequence identity to the polypeptide of SEQ ID NO: 2. In an embodiment, the subtilase variant has at least 80% but less than 100% sequence identity to the polypeptide of SEQ ID NO: 2. In an embodiment, the subtilase variant has at least 85% but less than 100% sequence identity to the polypeptide of SEQ ID NO: 2. In an embodiment, the subtilase variant has at least 90% but less than 100% sequence identity to the polypeptide of SEQ ID NO: 2. In an embodiment, the subtilase variant has at least 93% but less than 100% sequence identity to the polypeptide of SEQ ID NO: 2. In an embodiment, the subtilase variant has at least 95% but less than 100% sequence identity to the polypeptide of SEQ ID NO: 2. In an embodiment, the subtilase variant has at least 96% but less than 100% sequence identity to the polypeptide of SEQ ID NO: 2. In an embodiment, the subtilase variant has at least 97% but less than 100% sequence identity to the polypeptide of SEQ ID NO: 2. In an embodiment, the subtilase variant has at least 98% but less than 100% sequence identity to the polypeptide of SEQ ID NO: 2.

In one embodiment, the subtilase variant has improved stability, in particular improved storage stability, compared to the polypeptide of SEQ ID NO: 2. In a preferred embodiment, the subtilase variant has improved stability, in particular improved in wash stability, and/or on par or improved wash performance compared to the polypeptide of SEQ ID NO: 2.

In one embodiment, the subtilase variant has improved stability, in particular improved in wash stability, compared to the mature polypeptide of the parent subtilase. In a preferred embodiment, the subtilase variant has improved stability, in particular improved storage stability, and on par or improved wash performance compared to the mature polypeptide of the parent subtilase.

In a second embodiment, the invention relates to subtilase variants having protease activity, wherein said variant comprises the substitution N76D and one or more substitutions selected from the group consisting of Q2R, W6I, I8{C,H}, S9{C,D,E,Q}, N18S, N43{A,C,L,R,W}, S49T, G53{A,L}, G61D, I72{A,V}, S78{D,N}, V104{F,P,T,Y}, A114V, G115{T,W}, H120{I,T,V}, P129D, V147W, V149{C,N,Q}, A158E, G160{D,P}, S161{C,Y,E}, I162L, S163{A, D}, Q182{C,E}, N184D, N185{C,E}, S188{C,D,E}, Q191N, A194{D,E}, N204{D,V}, V205{I,L}, Q206{C,E,I,K,T,V,W,L}, Y209{L,W}, S212{A,D,G,N}, S216{I,T,V}, L217{C,M}, N218T, M222{C,N,R}, P225{A,S}, T255{C,E,Q}, S256{A,C,D,V,Y}, S259D, T260{A,E,P}, N261{D,C,E,L,M,R,V,W,Y,F} and L262{Y,C,E,Q}, wherein each position corresponds to the position of the polypeptide of SEQ ID NO: 2 and wherein subtilase variant is a polypeptide that has at least 60% but less than 100% sequence identity to the polypeptide of SEQ ID NO: 1.

Variants

In one aspect of the invention, the subtilase variant comprises or consists of one or more of the substitutions in table 1, wherein each position corresponds to the corresponding position of the polypeptide of SEQ ID NO: 2. In one embodiment, the subtilase variant has improved stability, in particular improved storage stability, compared to the polypeptide of SEQ ID NO: 1 or to the polypeptide of SEQ ID NO: 2. In a preferred embodiment, the subtilase variant has improved stability, in particular improved in storage stability, and on par or improved wash performance compared to the polypeptide of SEQ ID NO: 1 or to the polypeptide of SEQ ID NO: 2.

TABLE 1

| Subtilase Variants |
| --- |
| N76D + Q2R |
| N76D + W6I |
| N76D + I8C |
| N76D + I8H |
| N76D + S9C |
| N76D + S9D |
| N76D + S9E |
| N76D + S9Q |
| N76D + N18S |
| N76D + N43A |
| N76D + N43C |
| N76D + N43L |
| N76D + N43R |
| N76D + N43W |
| N76D + S49T |
| N76D + G53A |
| N76D + G53L |
| N76D + G61D |
| N76D + I72A |
| N76D + I72V |
| N76D + S78D |
| N76D + S78N |
| N76D + V104F |
| N76D + V104P |
| N76D + V104T |

TABLE 1-continued

Subtilase Variants

N76D + V104Y
N76D + A114V
N76D + G115T
N76D + G115W
N76D + H120I
N76D + H120T
N76D + H120V
N76D + P129D
N76D + V147W
N76D + V149C
N76D + V149N
N76D + V149Q
N76D + A158E
N76D + G160D
N76D + G160P
N76D + S161C
N76D + S161Y
N76D + S161E
N76D + I162L
N76D + S163A
N76D + S163D
N76D + Q182C
N76D + Q182E
N76D + N184D
N76D + N185C
N76D + N185E
N76D + S188C
N76D + S188D
N76D + S188E
N76D + Q191N
N76D + A194D
N76D + A194E
N76D + N204D
N76D + N204V
N76D + V205I
N76D + V205L
N76D + Q206C
N76D + Q206E
N76D + Q206I
N76D + Q206K
N76D + Q206T
N76D + Q206V
N76D + Q206W
N76D + Q206L
N76D + Y209L
N76D + Y209W
N76D + S212A
N76D + S212D
N76D + S212G
N76D + S212N
N76D + S216I
N76D + S216T
N76D + S216V
N76D + L217C
N76D + L217M
N76D + N218T
N76D + M222C
N76D + M222N
N76D + M222R
N76D + P225A
N76D + P225S
N76D + T255C
N76D + T255E
N76D + T255Q
N76D + S256A
N76D + S256C
N76D + S256D
N76D + S256V
N76D + S256Y
N76D + S259D
N76D + T260A
N76D + T260E
N76D + T260P
N76D + N261D
N76D + N261C
N76D + N261E
N76D + N261L
N76D + N261M

TABLE 1-continued

Subtilase Variants

N76D + N261R
N76D + N261V
N76D + N261W
N76D + N261Y
N76D + N261F
N76D + L262Y
N76D + L262C
N76D + L262E
N76D + L262Q

In one embodiment, the parent subtilase is the subtilase having the amino acid sequence of SEQ ID NO 1. Thus in one embodiment, the subtilase variant comprises or consists of the substitutions N76D+Q2R in the polypeptide of SEQ ID NO: 1, wherein each position corresponds to the corresponding position of the polypeptide of SEQ ID NO: 2.

In one embodiment, the subtilase variant comprises or consists of the substitutions N76D+W6I in the polypeptide of SEQ ID NO: 1, wherein each position corresponds to the corresponding position of the polypeptide of SEQ ID NO: 2.

In one embodiment, the subtilase variant comprises or consists of the substitutions N76D+I8C in the polypeptide of SEQ ID NO: 1, wherein each position corresponds to the corresponding position of the polypeptide of SEQ ID NO: 2.

In one embodiment, the subtilase variant comprises or consists of the substitutions N76D+I8H in the polypeptide of SEQ ID NO: 1, wherein each position corresponds to the corresponding position of the polypeptide of SEQ ID NO: 2.

In one embodiment, the subtilase variant comprises or consists of the substitutions N76D+S9C in the polypeptide of SEQ ID NO: 1, wherein each position corresponds to the corresponding position of the polypeptide of SEQ ID NO: 2.

In one embodiment, the subtilase variant comprises or consists of the substitutions N76D+S9D in the polypeptide of SEQ ID NO: 1, wherein each position corresponds to the corresponding position of the polypeptide of SEQ ID NO: 2.

In one embodiment, the subtilase variant comprises or consists of the substitutions N76D+S9E in the polypeptide of SEQ ID NO: 1, wherein each position corresponds to the corresponding position of the polypeptide of SEQ ID NO: 2.

In one embodiment, the subtilase variant comprises or consists of the substitutions N76D+S9Q in the polypeptide of SEQ ID NO: 1, wherein each position corresponds to the corresponding position of the polypeptide of SEQ ID NO: 2.

In one embodiment, the subtilase variant comprises or consists of the substitutions N76D+N18S in the polypeptide of SEQ ID NO: 1, wherein each position corresponds to the corresponding position of the polypeptide of SEQ ID NO: 2.

In one embodiment, the subtilase variant comprises or consists of the substitutions N76D+N43A in the polypeptide of SEQ ID NO: 1, wherein each position corresponds to the corresponding position of the polypeptide of SEQ ID NO: 2.

In one embodiment, the subtilase variant comprises or consists of the substitutions N76D+N43C in the polypeptide of SEQ ID NO: 1, wherein each position corresponds to the corresponding position of the polypeptide of SEQ ID NO: 2.

In one embodiment, the subtilase variant comprises or consists of the substitutions N76D+N43L in the polypeptide of SEQ ID NO: 1, wherein each position corresponds to the corresponding position of the polypeptide of SEQ ID NO: 2.

In one embodiment, the subtilase variant comprises or consists of the substitutions N76D+N43R in the polypeptide of SEQ ID NO: 1, wherein each position corresponds to the corresponding position of the polypeptide of SEQ ID NO: 2.

In one embodiment, the subtilase variant comprises or consists of the substitutions N76D+N43W in the polypeptide of SEQ ID NO: 1, wherein each position corresponds to the corresponding position of the polypeptide of SEQ ID NO: 2.

In one embodiment, the subtilase variant comprises or consists of the substitutions N76D+S49T in the polypeptide of SEQ ID NO: 1, wherein each position corresponds to the corresponding position of the polypeptide of SEQ ID NO: 2.

In one embodiment, the subtilase variant comprises or consists of the substitutions N76D+G53A in the polypeptide of SEQ ID NO: 1, wherein each position corresponds to the corresponding position of the polypeptide of SEQ ID NO: 2.

In one embodiment, the subtilase variant comprises or consists of the substitutions N76D+G53L in the polypeptide of SEQ ID NO: 1, wherein each position corresponds to the corresponding position of the polypeptide of SEQ ID NO: 2.

In one embodiment, the subtilase variant comprises or consists of the substitutions N76D+G6lD in the polypeptide of SEQ ID NO: 1, wherein each position corresponds to the corresponding position of the polypeptide of SEQ ID NO: 2.

In one embodiment, the subtilase variant comprises or consists of the substitutions N76D+I72A in the polypeptide of SEQ ID NO: 1, wherein each position corresponds to the corresponding position of the polypeptide of SEQ ID NO: 2.

In one embodiment, the subtilase variant comprises or consists of the substitutions N76D+I72V in the polypeptide of SEQ ID NO: 1, wherein each position corresponds to the corresponding position of the polypeptide of SEQ ID NO: 2.

In one embodiment, the subtilase variant comprises or consists of the substitutions N76D+S78D in the polypeptide of SEQ ID NO: 1, wherein each position corresponds to the corresponding position of the polypeptide of SEQ ID NO: 2.

In one embodiment, the subtilase variant comprises or consists of the substitutions N76D+S78N in the polypeptide of SEQ ID NO: 1, wherein each position corresponds to the corresponding position of the polypeptide of SEQ ID NO: 2.

In one embodiment, the subtilase variant comprises or consists of the substitutions N76D+V104F in the polypeptide of SEQ ID NO: 1, wherein each position corresponds to the corresponding position of the polypeptide of SEQ ID NO: 2.

In one embodiment, the subtilase variant comprises or consists of the substitutions N76D+V104P in the polypeptide of SEQ ID NO: 1, wherein each position corresponds to the corresponding position of the polypeptide of SEQ ID NO: 2.

In one embodiment, the subtilase variant comprises or consists of the substitutions N76D+V104T in the polypeptide of SEQ ID NO: 1, wherein each position corresponds to the corresponding position of the polypeptide of SEQ ID NO: 2.

In one embodiment, the subtilase variant comprises or consists of the substitutions N76D+V104Y in the polypeptide of SEQ ID NO: 1, wherein each position corresponds to the corresponding position of the polypeptide of SEQ ID NO: 2.

In one embodiment, the subtilase variant comprises or consists of the substitutions N76D+A114V in the polypeptide of SEQ ID NO: 1, wherein each position corresponds to the corresponding position of the polypeptide of SEQ ID NO: 2.

In one embodiment, the subtilase variant comprises or consists of the substitutions N76D+G115T in the polypeptide of SEQ ID NO: 1, wherein each position corresponds to the corresponding position of the polypeptide of SEQ ID NO: 2.

In one embodiment, the subtilase variant comprises or consists of the substitutions N76D+G115W in the polypeptide of SEQ ID NO: 1, wherein each position corresponds to the corresponding position of the polypeptide of SEQ ID NO: 2.

In one embodiment, the subtilase variant comprises or consists of the substitutions N76D+H120I in the polypeptide of SEQ ID NO: 1, wherein each position corresponds to the corresponding position of the polypeptide of SEQ ID NO: 2.

In one embodiment, the subtilase variant comprises or consists of the substitutions N76D+H120T in the polypeptide of SEQ ID NO: 1, wherein each position corresponds to the corresponding position of the polypeptide of SEQ ID NO: 2.

In one embodiment, the subtilase variant comprises or consists of the substitutions N76D+H120V in the polypeptide of SEQ ID NO: 1, wherein each position corresponds to the corresponding position of the polypeptide of SEQ ID NO: 2.

In one embodiment, the subtilase variant comprises or consists of the substitutions N76D+P129D in the polypeptide of SEQ ID NO: 1, wherein each position corresponds to the corresponding position of the polypeptide of SEQ ID NO: 2.

In one embodiment, the subtilase variant comprises or consists of the substitutions N76D+V147W in the polypeptide of SEQ ID NO: 1, wherein each position corresponds to the corresponding position of the polypeptide of SEQ ID NO: 2.

In one embodiment, the subtilase variant comprises or consists of the substitutions N76D+V149C in the polypeptide of SEQ ID NO: 1, wherein each position corresponds to the corresponding position of the polypeptide of SEQ ID NO: 2.

In one embodiment, the subtilase variant comprises or consists of the substitutions N76D+V149N in the polypeptide of SEQ ID NO: 1, wherein each position corresponds to the corresponding position of the polypeptide of SEQ ID NO: 2.

In one embodiment, the subtilase variant comprises or consists of the substitutions N76D+V149Q in the polypeptide of SEQ ID NO: 1, wherein each position corresponds to the corresponding position of the polypeptide of SEQ ID NO: 2.

In one embodiment, the subtilase variant comprises or consists of the substitutions N76D+A158E in the polypeptide of SEQ ID NO: 1, wherein each position corresponds to the corresponding position of the polypeptide of SEQ ID NO: 2.

In one embodiment, the subtilase variant comprises or consists of the substitutions N76D+G160D in the polypeptide of SEQ ID NO: 1, wherein each position corresponds to the corresponding position of the polypeptide of SEQ ID NO: 2.

In one embodiment, the subtilase variant comprises or consists of the substitutions N76D+G160P in the polypeptide of SEQ ID NO: 1, wherein each position corresponds to the corresponding position of the polypeptide of SEQ ID NO: 2.

In one embodiment, the subtilase variant comprises or consists of the substitutions N76D+S161C in the polypeptide of SEQ ID NO: 1, wherein each position corresponds to the corresponding position of the polypeptide of SEQ ID NO: 2.

In one embodiment, the subtilase variant comprises or consists of the substitutions N76D+S161Y in the polypeptide of SEQ ID NO: 1, wherein each position corresponds to the corresponding position of the polypeptide of SEQ ID NO: 2.

In one embodiment, the subtilase variant comprises or consists of the substitutions N76D+S161E in the polypeptide of SEQ ID NO: 1, wherein each position corresponds to the corresponding position of the polypeptide of SEQ ID NO: 2.

In one embodiment, the subtilase variant comprises or consists of the substitutions N76D+I162L in the polypeptide of SEQ ID NO: 1, wherein each position corresponds to the corresponding position of the polypeptide of SEQ ID NO: 2.

In one embodiment, the subtilase variant comprises or consists of the substitutions N76D+S163A in the polypeptide of SEQ ID NO: 1, wherein each position corresponds to the corresponding position of the polypeptide of SEQ ID NO: 2.

In one embodiment, the subtilase variant comprises or consists of the substitutions N76D+S163D in the polypeptide of SEQ ID NO: 1, wherein each position corresponds to the corresponding position of the polypeptide of SEQ ID NO: 2.

In one embodiment, the subtilase variant comprises or consists of the substitutions N76D+Q182C in the polypeptide of SEQ ID NO: 1, wherein each position corresponds to the corresponding position of the polypeptide of SEQ ID NO: 2.

In one embodiment, the subtilase variant comprises or consists of the substitutions N76D+Q182E in the polypeptide of SEQ ID NO: 1, wherein each position corresponds to the corresponding position of the polypeptide of SEQ ID NO: 2.

In one embodiment, the subtilase variant comprises or consists of the substitutions N76D+N184D in the polypeptide of SEQ ID NO: 1, wherein each position corresponds to the corresponding position of the polypeptide of SEQ ID NO: 2.

In one embodiment, the subtilase variant comprises or consists of the substitutions N76D+N185C in the polypeptide of SEQ ID NO: 1, wherein each position corresponds to the corresponding position of the polypeptide of SEQ ID NO: 2.

In one embodiment, the subtilase variant comprises or consists of the substitutions N76D+N185E in the polypeptide of SEQ ID NO: 1, wherein each position corresponds to the corresponding position of the polypeptide of SEQ ID NO: 2.

In one embodiment, the subtilase variant comprises or consists of the substitutions N76D+S188C in the polypeptide of SEQ ID NO: 1, wherein each position corresponds to the corresponding position of the polypeptide of SEQ ID NO: 2.

In one embodiment, the subtilase variant comprises or consists of the substitutions N76D+S188D in the polypeptide of SEQ ID NO: 1, wherein each position corresponds to the corresponding position of the polypeptide of SEQ ID NO: 2.

In one embodiment, the subtilase variant comprises or consists of the substitutions N76D+S188E in the polypeptide of SEQ ID NO: 1, wherein each position corresponds to the corresponding position of the polypeptide of SEQ ID NO: 2.

In one embodiment, the subtilase variant comprises or consists of the substitutions N76D+Q191N in the polypeptide of SEQ ID NO: 1, wherein each position corresponds to the corresponding position of the polypeptide of SEQ ID NO: 2.

In one embodiment, the subtilase variant comprises or consists of the substitutions N76D+A194D in the polypeptide of SEQ ID NO: 1, wherein each position corresponds to the corresponding position of the polypeptide of SEQ ID NO: 2.

In one embodiment, the subtilase variant comprises or consists of the substitutions N76D+A194E in the polypeptide of SEQ ID NO: 1, wherein each position corresponds to the corresponding position of the polypeptide of SEQ ID NO: 2.

In one embodiment, the subtilase variant comprises or consists of the substitutions N76D+N204D in the polypeptide of SEQ ID NO: 1, wherein each position corresponds to the corresponding position of the polypeptide of SEQ ID NO: 2.

In one embodiment, the subtilase variant comprises or consists of the substitutions N76D+N204V in the polypeptide of SEQ ID NO: 1, wherein each position corresponds to the corresponding position of the polypeptide of SEQ ID NO: 2.

In one embodiment, the subtilase variant comprises or consists of the substitutions N76D+V205I in the polypeptide of SEQ ID NO: 1, wherein each position corresponds to the corresponding position of the polypeptide of SEQ ID NO: 2.

In one embodiment, the subtilase variant comprises or consists of the substitutions N76D+V205L in the polypeptide of SEQ ID NO: 1, wherein each position corresponds to the corresponding position of the polypeptide of SEQ ID NO: 2.

In one embodiment, the subtilase variant comprises or consists of the substitutions N76D+Q206C in the polypeptide of SEQ ID NO: 1, wherein each position corresponds to the corresponding position of the polypeptide of SEQ ID NO: 2.

In one embodiment, the subtilase variant comprises or consists of the substitutions N76D+Q206E in the polypeptide of SEQ ID NO: 1, wherein each position corresponds to the corresponding position of the polypeptide of SEQ ID NO: 2.

In one embodiment, the subtilase variant comprises or consists of the substitutions N76D+Q206I in the polypeptide of SEQ ID NO: 1, wherein each position corresponds to the corresponding position of the polypeptide of SEQ ID NO: 2.

In one embodiment, the subtilase variant comprises or consists of the substitutions N76D+Q206K in the polypeptide of SEQ ID NO: 1, wherein each position corresponds to the corresponding position of the polypeptide of SEQ ID NO: 2.

In one embodiment, the subtilase variant comprises or consists of the substitutions N76D+Q206T in the polypeptide of SEQ ID NO: 1, wherein each position corresponds to the corresponding position of the polypeptide of SEQ ID NO: 2.

In one embodiment, the subtilase variant comprises or consists of the substitutions N76D+Q206V in the polypeptide of SEQ ID NO: 1, wherein each position corresponds to the corresponding position of the polypeptide of SEQ ID NO: 2.

In one embodiment, the subtilase variant comprises or consists of the substitutions N76D+Q206W in the polypeptide of SEQ ID NO: 1, wherein each position corresponds to the corresponding position of the polypeptide of SEQ ID NO: 2.

In one embodiment, the subtilase variant comprises or consists of the substitutions N76D+Q206L in the polypep- In one embodiment, the subtilase variant comprises or consists of the substitutions N76D+Y209L in the polypeptide of SEQ ID NO: 1, wherein each position corresponds to the corresponding position of the polypeptide of SEQ ID NO: 2.

In one embodiment, the subtilase variant comprises or consists of the substitutions N76D+Y209W in the polypeptide of SEQ ID NO: 1, wherein each position corresponds to the corresponding position of the polypeptide of SEQ ID NO: 2.

In one embodiment, the subtilase variant comprises or consists of the substitutions N76D+S212A in the polypeptide of SEQ ID NO: 1, wherein each position corresponds to the corresponding position of the polypeptide of SEQ ID NO: 2.

In one embodiment, the subtilase variant comprises or consists of the substitutions N76D+S212D in the polypeptide of SEQ ID NO: 1, wherein each position corresponds to the corresponding position of the polypeptide of SEQ ID NO: 2.

In one embodiment, the subtilase variant comprises or consists of the substitutions N76D+S212G in the polypeptide of SEQ ID NO: 1, wherein each position corresponds to the corresponding position of the polypeptide of SEQ ID NO: 2.

In one embodiment, the subtilase variant comprises or consists of the substitutions N76D+S212N in the polypeptide of SEQ ID NO: 1, wherein each position corresponds to the corresponding position of the polypeptide of SEQ ID NO: 2.

In one embodiment, the subtilase variant comprises or consists of the substitutions N76D+S216I in the polypeptide of SEQ ID NO: 1, wherein each position corresponds to the corresponding position of the polypeptide of SEQ ID NO: 2.

In one embodiment, the subtilase variant comprises or consists of the substitutions N76D+S216T in the polypeptide of SEQ ID NO: 1, wherein each position corresponds to the corresponding position of the polypeptide of SEQ ID NO: 2.

In one embodiment, the subtilase variant comprises or consists of the substitutions N76D+S216V in the polypeptide of SEQ ID NO: 1, wherein each position corresponds to the corresponding position of the polypeptide of SEQ ID NO: 2.

In one embodiment, the subtilase variant comprises or consists of the substitutions N76D+L217C in the polypeptide of SEQ ID NO: 1, wherein each position corresponds to the corresponding position of the polypeptide of SEQ ID NO: 2.

In one embodiment, the subtilase variant comprises or consists of the substitutions N76D+L217M in the polypeptide of SEQ ID NO: 1, wherein each position corresponds to the corresponding position of the polypeptide of SEQ ID NO: 2.

In one embodiment, the subtilase variant comprises or consists of the substitutions N76D+N218T in the polypeptide of SEQ ID NO: 1, wherein each position corresponds to the corresponding position of the polypeptide of SEQ ID NO: 2.

In one embodiment, the subtilase variant comprises or consists of the substitutions N76D+M222C in the polypeptide of SEQ ID NO: 1, wherein each position corresponds to the corresponding position of the polypeptide of SEQ ID NO: 2.

In one embodiment, the subtilase variant comprises or consists of the substitutions N76D+M222N in the polypeptide of SEQ ID NO: 1, wherein each position corresponds to the corresponding position of the polypeptide of SEQ ID NO: 2.

In one embodiment, the subtilase variant comprises or consists of the substitutions N76D+M222R in the polypeptide of SEQ ID NO: 1, wherein each position corresponds to the corresponding position of the polypeptide of SEQ ID NO: 2.

In one embodiment, the subtilase variant comprises or consists of the substitutions N76D+P225A in the polypeptide of SEQ ID NO: 1, wherein each position corresponds to the corresponding position of the polypeptide of SEQ ID NO: 2.

In one embodiment, the subtilase variant comprises or consists of the substitutions N76D+P225S in the polypeptide of SEQ ID NO: 1, wherein each position corresponds to the corresponding position of the polypeptide of SEQ ID NO: 2.

In one embodiment, the subtilase variant comprises or consists of the substitutions N76D+T255C in the polypeptide of SEQ ID NO: 1, wherein each position corresponds to the corresponding position of the polypeptide of SEQ ID NO: 2.

In one embodiment, the subtilase variant comprises or consists of the substitutions N76D+T255E in the polypeptide of SEQ ID NO: 1, wherein each position corresponds to the corresponding position of the polypeptide of SEQ ID NO: 2.

In one embodiment, the subtilase variant comprises or consists of the substitutions N76D+T255Q in the polypeptide of SEQ ID NO: 1, wherein each position corresponds to the corresponding position of the polypeptide of SEQ ID NO: 2.

In one embodiment, the subtilase variant comprises or consists of the substitutions N76D+S256A in the polypeptide of SEQ ID NO: 1, wherein each position corresponds to the corresponding position of the polypeptide of SEQ ID NO: 2.

In one embodiment, the subtilase variant comprises or consists of the substitutions N76D+S256C in the polypeptide of SEQ ID NO: 1, wherein each position corresponds to the corresponding position of the polypeptide of SEQ ID NO: 2.

In one embodiment, the subtilase variant comprises or consists of the substitutions N76D+S256D in the polypeptide of SEQ ID NO: 1, wherein each position corresponds to the corresponding position of the polypeptide of SEQ ID NO: 2.

In one embodiment, the subtilase variant comprises or consists of the substitutions N76D+S256V in the polypeptide of SEQ ID NO: 1, wherein each position corresponds to the corresponding position of the polypeptide of SEQ ID NO: 2.

In one embodiment, the subtilase variant comprises or consists of the substitutions N76D+S256Y in the polypeptide of SEQ ID NO: 1, wherein each position corresponds to the corresponding position of the polypeptide of SEQ ID NO: 2.

In one embodiment, the subtilase variant comprises or consists of the substitutions N76D+S259D in the polypeptide of SEQ ID NO: 1, wherein each position corresponds to the corresponding position of the polypeptide of SEQ ID NO: 2.

In one embodiment, the subtilase variant comprises or consists of the substitutions N76D+T260A in the polypeptide of SEQ ID NO: 1, wherein each position corresponds to the corresponding position of the polypeptide of SEQ ID NO: 2.

In one embodiment, the subtilase variant comprises or consists of the substitutions N76D+T260E in the polypeptide of SEQ ID NO: 1, wherein each position corresponds to the corresponding position of the polypeptide of SEQ ID NO: 2.

In one embodiment, the subtilase variant comprises or consists of the substitutions N76D+T260P in the polypeptide of SEQ ID NO: 1, wherein each position corresponds to the corresponding position of the polypeptide of SEQ ID NO: 2.

In one embodiment, the subtilase variant comprises or consists of the substitutions N76D+N261 D in the polypeptide of SEQ ID NO: 1, wherein each position corresponds to the corresponding position of the polypeptide of SEQ ID NO: 2.

In one embodiment, the subtilase variant comprises or consists of the substitutions N76D+N261C in the polypeptide of SEQ ID NO: 1, wherein each position corresponds to the corresponding position of the polypeptide of SEQ ID NO: 2.

In one embodiment, the subtilase variant comprises or consists of the substitutions N76D+N261E in the polypeptide of SEQ ID NO: 1, wherein each position corresponds to the corresponding position of the polypeptide of SEQ ID NO: 2.

In one embodiment, the subtilase variant comprises or consists of the substitutions N76D+N261L in the polypeptide of SEQ ID NO: 1, wherein each position corresponds to the corresponding position of the polypeptide of SEQ ID NO: 2.

In one embodiment, the subtilase variant comprises or consists of the substitutions N76D+N261M in the polypeptide of SEQ ID NO: 1, wherein each position corresponds to the corresponding position of the polypeptide of SEQ ID NO: 2.

In one embodiment, the subtilase variant comprises or consists of the substitutions N76D+N261R in the polypeptide of SEQ ID NO: 1, wherein each position corresponds to the corresponding position of the polypeptide of SEQ ID NO: 2.

In one embodiment, the subtilase variant comprises or consists of the substitutions N76D+N261V in the polypeptide of SEQ ID NO: 1, wherein each position corresponds to the corresponding position of the polypeptide of SEQ ID NO: 2.

In one embodiment, the subtilase variant comprises or consists of the substitutions N76D+N261W in the polypeptide of SEQ ID NO: 1, wherein each position corresponds to the corresponding position of the polypeptide of SEQ ID NO: 2.

In one embodiment, the subtilase variant comprises or consists of the substitutions N76D+N261Y in the polypeptide of SEQ ID NO: 1, wherein each position corresponds to the corresponding position of the polypeptide of SEQ ID NO: 2.

In one embodiment, the subtilase variant comprises or consists of the substitutions N76D+N261 F in the polypeptide of SEQ ID NO: 1, wherein each position corresponds to the corresponding position of the polypeptide of SEQ ID NO: 2.

In one embodiment, the subtilase variant comprises or consists of the substitutions N76D+L262Y in the polypeptide of SEQ ID NO: 1, wherein each position corresponds to the corresponding position of the polypeptide of SEQ ID NO: 2.

In one embodiment, the subtilase variant comprises or consists of the substitutions N76D+L262C in the polypeptide of SEQ ID NO: 1, wherein each position corresponds to the corresponding position of the polypeptide of SEQ ID NO: 2.

In one embodiment, the subtilase variant comprises or consists of the substitutions N76D+L262E in the polypeptide of SEQ ID NO: 1, wherein each position corresponds to the corresponding position of the polypeptide of SEQ ID NO: 2.

In one embodiment, the subtilase variant comprises or consists of the substitutions N76D+L262Q in the polypeptide of SEQ ID NO: 1, wherein each position corresponds to the corresponding position of the polypeptide of SEQ ID NO: 2.

In another preferred embodiment of the invention, the variant is a polypeptide having said substitutions according to the invention and having an amino acid sequence which is at least 60% identical to SEQ ID NO: 1. Thus in one embodiment, the subtilase variant comprises or consists of the substitutions N76D+W6I, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+I8C, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+I8H, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+S9C, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+S9D, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+S9E, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+S9Q, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+N18S, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+N43A, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+N43C, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+N43L, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+N43R, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+N43W, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+S49T, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+G53A, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+G53L, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+G61D, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+I72A, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+I72V, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+S78D, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+S78N, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+V104F, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+V104P, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+V104T, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+V104Y, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+A114V, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+G115T, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+G115W, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+H120I, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+H120T, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+H120V, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+P129D, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+V147W, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+V149C, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+V149N, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+V149Q, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+A158E, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+G160D, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+G160P, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+S161C, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+S161Y, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+S161E, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+I162L, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+S163A, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+S163D, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+Q182C, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+Q182E, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+N184D, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+N185C, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+N185E, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+S188C, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+S188D, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+S188E, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+Q191N, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+A194D, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+A194E, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+N204D, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+N204V, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+V205I, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+V205L, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+Q206C, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+Q206E, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+Q206I, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+Q206K, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+Q206T, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+Q206V, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+Q206W, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+Q206L, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+Y209L, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+Y209W, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+S212A, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+S212D, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+S212G, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+S212N, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+S216I, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+S216T, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+S216V, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+L217C, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+L217M, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+N218T, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+M222C, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+M222N, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+M222R, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+P225A, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+P225S, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+T255C, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+T255E, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+T255Q, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+S256A, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+S256C, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+S256D, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+S256V, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+S256Y, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+S259D, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+T260A, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+T260E, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+T260P, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+N261D, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+N261C, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+N261E, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+N261L, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+N261M, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+N261R, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+N261V, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+N261W, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+N261Y, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+N261F, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+L262Y, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+L262C, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+L262E, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the subtilase variant comprises or consists of the substitutions N76D+L262Q, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 1.

In one embodiment, the parent subtilase is the subtilase having the amino acid sequence of SEQ ID NO: 1. Thus in one embodiment, the subtilase variant comprises or consists of the substitutions N76D+Q2R in the polypeptide of SEQ ID NO: 1, wherein each position corresponds to the corresponding position of SEQ ID NO: 2.

In one embodiment, the subtilase variant comprises or consists of the substitutions N76D+Y6I in the polypeptide of SEQ ID NO: 1, wherein each position corresponds to the corresponding position of SEQ ID NO: 2.

In one embodiment, the subtilase variant comprises or consists of the substitutions N76D+V8C in the polypeptide of SEQ ID NO: 2, wherein each position corresponds to the corresponding position of SEQ ID NO: 2.

In one embodiment, the subtilase variant comprises or consists of the substitutions N76D+V8H in the polypeptide of SEQ ID NO: 2, wherein each position corresponds to the corresponding position of SEQ ID NO: 2.

In one embodiment, the subtilase variant comprises or consists of the substitutions N76D+S9C in the polypeptide of SEQ ID NO: 2, wherein each position corresponds to the corresponding position of SEQ ID NO: 2.

In one embodiment, the subtilase variant comprises or consists of the substitutions N76D+S9D in the polypeptide of SEQ ID NO: 2, wherein each position corresponds to the corresponding position of SEQ ID NO: 2.

In one embodiment, the subtilase variant comprises or consists of the substitutions N76D+S9E in the polypeptide of SEQ ID NO: 2, wherein each position corresponds to the corresponding position of SEQ ID NO: 2.

In one embodiment, the subtilase variant comprises or consists of the substitutions N76D+S9Q in the polypeptide of SEQ ID NO: 2, wherein each position corresponds to the corresponding position of SEQ ID NO: 2.

In one embodiment, the subtilase variant comprises or consists of the substitutions N76D+K43A in the polypeptide of SEQ ID NO: 2, wherein each position corresponds to the corresponding position of SEQ ID NO: 2.

In one embodiment, the subtilase variant comprises or consists of the substitutions N76D+K43C in the polypeptide of SEQ ID NO: 2, wherein each position corresponds to the corresponding position of SEQ ID NO: 2.

In one embodiment, the subtilase variant comprises or consists of the substitutions N76D+K43L in the polypeptide of SEQ ID NO: 2, wherein each position corresponds to the corresponding position of SEQ ID NO: 2.

In one embodiment, the subtilase variant comprises or consists of the substitutions N76D+K43R in the polypeptide of SEQ ID NO: 1, wherein each position corresponds to the corresponding position of SEQ ID NO: 2.

In one embodiment, the subtilase variant comprises or consists of the substitutions N76D+K43W in the polypeptide of SEQ ID NO: 1, wherein each position corresponds to the corresponding position of SEQ ID NO: 2.

In one embodiment, the subtilase variant comprises or consists of the substitutions N76D+S49T in the polypeptide of SEQ ID NO: 1, wherein each position corresponds to the corresponding position of SEQ ID NO: 2.

In one embodiment, the subtilase variant comprises or consists of the substitutions N76D+S53A in the polypeptide of SEQ ID NO: 1, wherein each position corresponds to the corresponding position of SEQ ID NO: 2.

In one embodiment, the subtilase variant comprises or consists of the substitutions N76D+S53L in the polypeptide of SEQ ID NO: 1, wherein each position corresponds to the corresponding position of SEQ ID NO: 2.

In one embodiment, the subtilase variant comprises or consists of the substitutions N76D+N61D in the polypeptide of SEQ ID NO: 1, wherein each position corresponds to the corresponding position of SEQ ID NO: 2.

In one embodiment, the subtilase variant comprises or consists of the substitutions N76D+V72A in the polypeptide of SEQ ID NO: 1, wherein each position corresponds to the corresponding position of SEQ ID NO: 2.

In one embodiment, the subtilase variant comprises or consists of the substitutions N76D+S78D in the polypeptide of SEQ ID NO: 1, wherein each position corresponds to the corresponding position of SEQ ID NO: 2.

In one embodiment, the subtilase variant comprises or consists of the substitutions N76D+S78N in the polypeptide of SEQ ID NO: 1, wherein each position corresponds to the corresponding position of SEQ ID NO: 2.

In one embodiment, the subtilase variant comprises or consists of the substitutions N76D+Y104F in the polypeptide of SEQ ID NO: 1, wherein each position corresponds to the corresponding position of SEQ ID NO: 2.

In one embodiment, the subtilase variant comprises or consists of the substitutions N76D+Y104P in the polypeptide of SEQ ID NO: 1, wherein each position corresponds to the corresponding position of SEQ ID NO: 2.

In one embodiment, the subtilase variant comprises or consists of the substitutions N76D+Y104T in the polypeptide of SEQ ID NO: 1, wherein each position corresponds to the corresponding position of SEQ ID NO: 2.

In one embodiment, the subtilase variant comprises or consists of the substitutions N76D+Y104Y in the polypep- In one embodiment, the subtilase variant comprises or consists of the substitutions N76D+Y114V in the polypeptide of SEQ ID NO: 1, wherein each position corresponds to the corresponding position of SEQ ID NO: 2.

In one embodiment, the subtilase variant comprises or consists of the substitutions N76D+I115T in the polypeptide of SEQ ID NO: 1, wherein each position corresponds to the corresponding position of SEQ ID NO: 2.

In one embodiment, the subtilase variant comprises or consists of the substitutions N76D+I115W in the polypeptide of SEQ ID NO: 1, wherein each position corresponds to the corresponding position of SEQ ID NO: 2.

In one embodiment, the subtilase variant comprises or consists of the substitutions N76D+D201I in the polypeptide of SEQ ID NO: 1, wherein each position corresponds to the corresponding position of SEQ ID NO: 2.

In one embodiment, the subtilase variant comprises or consists of the substitutions N76D+D120T in the polypeptide of SEQ ID NO: 1, wherein each position corresponds to the corresponding position of SEQ ID NO: 2.

In one embodiment, the subtilase variant comprises or consists of the substitutions N76D+D120V in the polypeptide of SEQ ID NO: 1, wherein each position corresponds to the corresponding position of SEQ ID NO: 2.

In one embodiment, the subtilase variant comprises or consists of the substitutions N76D+P129D in the polypeptide of SEQ ID NO: 1, wherein each position corresponds to the corresponding position of SEQ ID NO: 2.

In one embodiment, the subtilase variant comprises or consists of the substitutions N76D+V147W in the polypeptide of SEQ ID NO: 1, wherein each position corresponds to the corresponding position of SEQ ID NO: 2.

In one embodiment, the subtilase variant comprises or consists of the substitutions N76D+V149C in the polypeptide of SEQ ID NO: 1, wherein each position corresponds to the corresponding position of SEQ ID NO: 2.

In one embodiment, the subtilase variant comprises or consists of the substitutions N76D+V149N in the polypeptide of SEQ ID NO: 1, wherein each position corresponds to the corresponding position of SEQ ID NO: 2.

In one embodiment, the subtilase variant comprises or consists of the substitutions N76D+V149Q in the polypeptide of SEQ ID NO: 1, wherein each position corresponds to the corresponding position of SEQ ID NO: 2.

In one embodiment, the subtilase variant comprises or consists of the substitutions N76D+T158E in the polypeptide of SEQ ID NO: 1, wherein each position corresponds to the corresponding position of SEQ ID NO: 2.

In one embodiment, the subtilase variant comprises or consists of the substitutions N76D+G160D in the polypeptide of SEQ ID NO: 1, wherein each position corresponds to the corresponding position of SEQ ID NO: 2.

In one embodiment, the subtilase variant comprises or consists of the substitutions N76D+G160P in the polypeptide of SEQ ID NO: 1, wherein each position corresponds to the corresponding position of SEQ ID NO: 2.

In one embodiment, the subtilase variant comprises or consists of the substitutions N76D+S161C in the polypeptide of SEQ ID NO: 1, wherein each position corresponds to the corresponding position of SEQ ID NO: 2.

In one embodiment, the subtilase variant comprises or consists of the substitutions N76D+S161Y in the polypeptide of SEQ ID NO: 1, wherein each position corresponds to the corresponding position of SEQ ID NO: 2.

In one embodiment, the subtilase variant comprises or consists of the substitutions N76D+S161E in the polypeptide of SEQ ID NO: 1, wherein each position corresponds to the corresponding position of SEQ ID NO: 2.

In one embodiment, the subtilase variant comprises or consists of the substitutions N76D+S162L in the polypeptide of SEQ ID NO: 1, wherein each position corresponds to the corresponding position of SEQ ID NO: 2.

In one embodiment, the subtilase variant comprises or consists of the substitutions N76D+S163A in the polypeptide of SEQ ID NO: 1, wherein each position corresponds to the corresponding position of SEQ ID NO: 2.

In one embodiment, the subtilase variant comprises or consists of the substitutions N76D+S163D in the polypeptide of SEQ ID NO: 1, wherein each position corresponds to the corresponding position of SEQ ID NO: 2.

In one embodiment, the subtilase variant comprises or consists of the substitutions N76D+S182C in the polypeptide of SEQ ID NO: 1, wherein each position corresponds to the corresponding position of SEQ ID NO: 2.

In one embodiment, the subtilase variant comprises or consists of the substitutions N76D+S182E in the polypeptide of SEQ ID NO: 1, wherein each position corresponds to the corresponding position of SEQ ID NO: 2.

In one embodiment, the subtilase variant comprises or consists of the substitutions N76D+N184D in the polypeptide of SEQ ID NO: 1, wherein each position corresponds to the corresponding position of SEQ ID NO: 2.

In one embodiment, the subtilase variant comprises or consists of the substitutions N76D+Q185C in the polypeptide of SEQ ID NO: 1, wherein each position corresponds to the corresponding position of SEQ ID NO: 2.

In one embodiment, the subtilase variant comprises or consists of the substitutions N76D+Q185E in the polypeptide of SEQ ID NO: 1, wherein each position corresponds to the corresponding position of SEQ ID NO: 2.

In one embodiment, the subtilase variant comprises or consists of the substitutions N76D+S188O in the polypeptide of SEQ ID NO: 1, wherein each position corresponds to the corresponding position of SEQ ID NO: 2.

In one embodiment, the subtilase variant comprises or consists of the substitutions N76D+S188D in the polypeptide of SEQ ID NO: 1, wherein each position corresponds to the corresponding position of SEQ ID NO: 2.

In one embodiment, the subtilase variant comprises or consists of the substitutions N76D+S188E in the polypeptide of SEQ ID NO: 1, wherein each position corresponds to the corresponding position of SEQ ID NO: 2.

In one embodiment, the subtilase variant comprises or consists of the substitutions N76D+S191N in the polypeptide of SEQ ID NO: 1, wherein each position corresponds to the corresponding position of SEQ ID NO: 2.

In one embodiment, the subtilase variant comprises or consists of the substitutions N76D+P194D in the polypeptide of SEQ ID NO: 1, wherein each position corresponds to the corresponding position of SEQ ID NO: 2.

In one embodiment, the subtilase variant comprises or consists of the substitutions N76D+P194E in the polypeptide of SEQ ID NO: 1, wherein each position corresponds to the corresponding position of SEQ ID NO: 2.

In one embodiment, the subtilase variant comprises or consists of the substitutions N76D+S204D in the polypeptide of SEQ ID NO: 1, wherein each position corresponds to the corresponding position of SEQ ID NO: 2.

In one embodiment, the subtilase variant comprises or consists of the substitutions N76D+S204V in the polypep- In one embodiment, the subtilase variant comprises or consists of the substitutions N76D+I205L in the polypeptide of SEQ ID NO: 1, wherein each position corresponds to the corresponding position of SEQ ID NO: 2.

In one embodiment, the subtilase variant comprises or consists of the substitutions N76D+Q206C in the polypeptide of SEQ ID NO: 1, wherein each position corresponds to the corresponding position of SEQ ID NO: 2.

In one embodiment, the subtilase variant comprises or consists of the substitutions N76D+Q206E in the polypeptide of SEQ ID NO: 1, wherein each position corresponds to the corresponding position of SEQ ID NO: 2.

In one embodiment, the subtilase variant comprises or consists of the substitutions N76D+Q206I in the polypeptide of SEQ ID NO: 1, wherein each position corresponds to the corresponding position of SEQ ID NO: 2.

In one embodiment, the subtilase variant comprises or consists of the substitutions N76D+Q206K in the polypeptide of SEQ ID NO: 1, wherein each position corresponds to the corresponding position of SEQ ID NO: 2.

In one embodiment, the subtilase variant comprises or consists of the substitutions N76D+Q206T in the polypeptide of SEQ ID NO: 1, wherein each position corresponds to the corresponding position of SEQ ID NO: 2.

In one embodiment, the subtilase variant comprises or consists of the substitutions N76D+Q206V in the polypeptide of SEQ ID NO: 1, wherein each position corresponds to the corresponding position of SEQ ID NO: 2.

In one embodiment, the subtilase variant comprises or consists of the substitutions N76D+Q206W in the polypeptide of SEQ ID NO: 1, wherein each position corresponds to the corresponding position of SEQ ID NO: 2.

In one embodiment, the subtilase variant comprises or consists of the substitutions N76D+Q206L in the polypeptide of SEQ ID NO: 1, wherein each position corresponds to the corresponding position of SEQ ID NO: 2.

In one embodiment, the subtilase variant comprises or consists of the substitutions N76D+L209W in the polypeptide of SEQ ID NO: 1, wherein each position corresponds to the corresponding position of SEQ ID NO: 2.

In one embodiment, the subtilase variant comprises or consists of the substitutions N76D+N212A in the polypeptide of SEQ ID NO: 1, wherein each position corresponds to the corresponding position of SEQ ID NO: 2.

In one embodiment, the subtilase variant comprises or consists of the substitutions N76D+N212D in the polypeptide of SEQ ID NO: 1, wherein each position corresponds to the corresponding position of SEQ ID NO: 2.

In one embodiment, the subtilase variant comprises or consists of the substitutions N76D+N212G in the polypeptide of SEQ ID NO: 1, wherein each position corresponds to the corresponding position of SEQ ID NO: 2.

In one embodiment, the subtilase variant comprises or consists of the substitutions N76D+A216I in the polypeptide of SEQ ID NO: 1, wherein each position corresponds to the corresponding position of SEQ ID NO: 2.

In one embodiment, the subtilase variant comprises or consists of the substitutions N76D+A216T in the polypeptide of SEQ ID NO: 1, wherein each position corresponds to the corresponding position of SEQ ID NO: 2.

In one embodiment, the subtilase variant comprises or consists of the substitutions N76D+A216V in the polypeptide of SEQ ID NO: 1, wherein each position corresponds to the corresponding position of SEQ ID NO: 2.

In one embodiment, the subtilase variant comprises or consists of the substitutions N76D+Y217C in the polypeptide of SEQ ID NO: 1, wherein each position corresponds to the corresponding position of SEQ ID NO: 2.

In one embodiment, the subtilase variant comprises or consists of the substitutions N76D+Y217M in the polypeptide of SEQ ID NO: 1, wherein each position corresponds to the corresponding position of SEQ ID NO: 2.

In one embodiment, the subtilase variant comprises or consists of the substitutions N76D+N218T in the polypeptide of SEQ ID NO: 1, wherein each position corresponds to the corresponding position of SEQ ID NO: 2.

In one embodiment, the subtilase variant comprises or consists of the substitutions N76D+M222C in the polypeptide of SEQ ID NO: 1, wherein each position corresponds to the corresponding position of SEQ ID NO: 2.

In one embodiment, the subtilase variant comprises or consists of the substitutions N76D+M222N in the polypeptide of SEQ ID NO: 1, wherein each position corresponds to the corresponding position of SEQ ID NO: 2.

In one embodiment, the subtilase variant comprises or consists of the substitutions N76D+M222R in the polypeptide of SEQ ID NO: 1, wherein each position corresponds to the corresponding position of SEQ ID NO: 2.

In one embodiment, the subtilase variant comprises or consists of the substitutions N76D+P225A in the polypeptide of SEQ ID NO: 1, wherein each position corresponds to the corresponding position of SEQ ID NO: 2.

In one embodiment, the subtilase variant comprises or consists of the substitutions N76D+P225S in the polypeptide of SEQ ID NO: 1, wherein each position corresponds to the corresponding position of SEQ ID NO: 2.

In one embodiment, the subtilase variant comprises or consists of the substitutions N76D+T255C in the polypeptide of SEQ ID NO: 1, wherein each position corresponds to the corresponding position of SEQ ID NO: 2.

In one embodiment, the subtilase variant comprises or consists of the substitutions N76D+T255E in the polypeptide of SEQ ID NO: 1, wherein each position corresponds to the corresponding position of SEQ ID NO: 2.

In one embodiment, the subtilase variant comprises or consists of the substitutions N76D+T255Q in the polypeptide of SEQ ID NO: 1, wherein each position corresponds to the corresponding position of SEQ ID NO: 2.

In one embodiment, the subtilase variant comprises or consists of the substitutions N76D+K256A in the polypeptide of SEQ ID NO: 1, wherein each position corresponds to the corresponding position of SEQ ID NO: 2.

In one embodiment, the subtilase variant comprises or consists of the substitutions N76D+K256C in the polypeptide of SEQ ID NO: 1, wherein each position corresponds to the corresponding position of SEQ ID NO: 2.

In one embodiment, the subtilase variant comprises or consists of the substitutions N76D+K256D in the polypeptide of SEQ ID NO: 1, wherein each position corresponds to the corresponding position of SEQ ID NO: 2.

In one embodiment, the subtilase variant comprises or consists of the substitutions N76D+K256V in the polypeptide of SEQ ID NO: 1, wherein each position corresponds to the corresponding position of SEQ ID NO: 2.

In one embodiment, the subtilase variant comprises or consists of the substitutions N76D+K256Y in the polypeptide of SEQ ID NO: 1, wherein each position corresponds to the corresponding position of SEQ ID NO: 2.

In one embodiment, the subtilase variant comprises or consists of the substitutions N76D+S260A in the polypeptide of SEQ ID NO: 1, wherein each position corresponds to the corresponding position of SEQ ID NO: 2.

In one embodiment, the subtilase variant comprises or consists of the substitutions N76D+S260E in the polypeptide of SEQ ID NO: 1, wherein each position corresponds to the corresponding position of SEQ ID NO: 2.

In one embodiment, the subtilase variant comprises or consists of the substitutions N76D+S260P in the polypeptide of SEQ ID NO: 1, wherein each position corresponds to the corresponding position of SEQ ID NO: 2.

In one embodiment, the subtilase variant comprises or consists of the substitutions N76D+F261 D in the polypeptide of SEQ ID NO: 1, wherein each position corresponds to the corresponding position of SEQ ID NO: 2.

In one embodiment, the subtilase variant comprises or consists of the substitutions N76D+F261C in the polypeptide of SEQ ID NO: 1, wherein each position corresponds to the corresponding position of SEQ ID NO: 2.

In one embodiment, the subtilase variant comprises or consists of the substitutions N76D+F261E in the polypeptide of SEQ ID NO: 1, wherein each position corresponds to the corresponding position of SEQ ID NO: 2.

In one embodiment, the subtilase variant comprises or consists of the substitutions N76D+F261L in the polypeptide of SEQ ID NO: 1, wherein each position corresponds to the corresponding position of SEQ ID NO: 2.

In one embodiment, the subtilase variant comprises or consists of the substitutions N76D+F261M in the polypeptide of SEQ ID NO: 1, wherein each position corresponds to the corresponding position of SEQ ID NO: 2.

In one embodiment, the subtilase variant comprises or consists of the substitutions N76D+F261R in the polypeptide of SEQ ID NO: 1, wherein each position corresponds to the corresponding position of SEQ ID NO: 2.

In one embodiment, the subtilase variant comprises or consists of the substitutions N76D+F261V in the polypeptide of SEQ ID NO: 1, wherein each position corresponds to the corresponding position of SEQ ID NO: 2.

In one embodiment, the subtilase variant comprises or consists of the substitutions N76D+F261W in the polypeptide of SEQ ID NO: 1, wherein each position corresponds to the corresponding position of SEQ ID NO: 2.

In one embodiment, the subtilase variant comprises or consists of the substitutions N76D+F261Y in the polypeptide of SEQ ID NO: 1, wherein each position corresponds to the corresponding position of SEQ ID NO: 2.

In one embodiment, the subtilase variant comprises or consists of the substitutions N76D+Y262C in the polypeptide of SEQ ID NO: 1, wherein each position corresponds to the corresponding position of SEQ ID NO: 2.

In one embodiment, the subtilase variant comprises or consists of the substitutions N76D+Y262E in the polypeptide of SEQ ID NO: 1, wherein each position corresponds to the corresponding position of SEQ ID NO: 2.

In one embodiment, the subtilase variant comprises or consists of the substitutions N76D+Y262Q in the polypeptide of SEQ ID NO: 1, wherein each position corresponds to the corresponding position of SEQ ID NO: 2.

In another preferred embodiment of the invention the variant is a polypeptide having said substitutions according to the invention and having an amino acid sequence which is at least 60% identical to SEQ ID NO: 2. Thus in one embodiment, the subtilase variant comprises or consists of the substitutions N76D+Q2R, wherein each position corresponds to the corresponding position of SEQ ID NO: 2 and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+Y6I, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+V8C, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+V8H, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+S9C, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+S9D, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+S9E, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+S9Q, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+K43A, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+K43C, wherein each position corresponds to the corresponding position of SEQ ID NO: 2, and wherein the said subtilase variant is a polypeptide having at least 60%, such as at least 70%, such In one embodiment, the subtilase variant comprises or consists of the substitutions N76D+K43L, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+K43R, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+K43W, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+S49T, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+S53A, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+S53L, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+N61D, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+V72A, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+S78D, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+S78N, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+Y104F, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+Y104P, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+Y104T, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+Y104Y, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+Y114V, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+I115T, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+I115W, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+D120I, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+D120T, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+D120V, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+P129D, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+V147W, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+V149C, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+V149N, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+V149Q, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+T158E, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+G160D, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+G160P, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+S161C, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+S161Y, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+S161E, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+S162L, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+S163A, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+S163D, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+S182C, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+S182E, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+N184D, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+Q185C, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+Q185E, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+S188C, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+S188D, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+S188E, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+S191N, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+P194D, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+P194E, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+S204D, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+S204V, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+I205L, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+Q206C, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+Q206E, wherein each position corresponds to the corresponding position of SEQ ID NO: 2, and wherein the said subtilase variant is a polypeptide having at least 60%, such as at least 70%, such as as at least 80%, such as at least 90%, such as at least 95% sequence identity to the amino acid sequence with SEQ ID NO: 2.

In one embodiment, the subtilase variant comprises or consists of the substitutions N76D+Q206I, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+Q206K, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+Q206T, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+Q206V, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+Q206W, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2

In one embodiment, the subtilase variant comprises or consists of the substitutions N76D+Q206L, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+L209W, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+N212A, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+N212D, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+N212G, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+A216I, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+A216T, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+A216V, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2

In one embodiment, the subtilase variant comprises or consists of the substitutions N76D+Y217C, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+Y217M, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+N218T, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+M222C, wherein each position corresponds to the corresponding position of SEQ In one embodiment, the subtilase variant comprises or consists of the substitutions N76D+M222N, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+M222R, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+P225A, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+P225S, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+T255C, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+T255E, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+T255Q, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+K256A, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+K256C, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+K256D, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+K256V, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+K256Y, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+S260A, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+S260E, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+S260P, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+F261 D, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+F261C, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+F261E, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+F261 L, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+F261M, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+F261R, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+F261V, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+F261W, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+F261Y, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+Y262C, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+Y262E, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one embodiment, the subtilase variant comprises or consists of the substitutions N76D+Y262Q, wherein each position corresponds to the corresponding position of SEQ ID NO: 2, and wherein the said subtilase variant is a polypeptide having at least 60%, such as at least 70%, such as at least 80%, such as at least 90%, such as at least 95% sequence identity to the amino acid sequence with SEQ ID NO: 2.

In one preferred aspect of the invention, the subtilase variants of the invention comprises or consists of a substitution at a position corresponding to position 206 of the polypeptide of SEQ ID NO: 2. In another preferred aspect, the amino acid at a position corresponding to position 206 of the polypeptide of SEQ ID NO: 2 is substituted with C,E,I,K,T,V,L or W preferably with C or W. In another aspect, the variant comprises or consists of the substitution Q206L, Q206W or Q206C in the polypeptide of SEQ ID NO: 3 (BPN' numbering).

In one preferred aspect of the invention, the subtilase variants of the invention comprises or consists of a substitution at a position corresponding to position 262 of the polypeptide of SEQ ID NO: 2. In another preferred aspect, the amino acid at a position corresponding to position 262 of the polypeptide of SEQ ID NO: 2 is substituted with Y, C, E or Q preferably with E or C. In another aspect, the variant comprises or consists of the substitution L262E or L262C in the polypeptide of SEQ ID NO: 3 (BPN' numbering).

In one preferred aspect of the invention, the subtilase variants of the invention comprises or consists of a substitution at a position corresponding to position 225 of the polypeptide of SEQ ID NO: 2. In another preferred aspect, the amino acid at a position corresponding to position 225 of the polypeptide of SEQ ID NO: 2 is substituted with A or S preferably with A. In another aspect, the variant comprises or consists of the substitution P225A in the polypeptide of SEQ ID NO: 3 (BPN' numbering).

In one preferred aspect of the invention, the subtilase variants of the invention comprises or consists of a substitution at a position corresponding to position 9 of the polypeptide of SEQ ID NO: 2. In another preferred aspect, the amino acid at a position corresponding to position 9 of the polypeptide of SEQ ID NO: 2 is substituted with C, D, E or Q preferably with E. In another aspect, the variant comprises or consists of the substitution S9E in the polypeptide of SEQ ID NO: 3 (BPN' numbering).

In one preferred aspect of the invention, the subtilase variants of the invention comprises or consists of a substitution at a position corresponding to position 209 of the polypeptide of SEQ ID NO: 2. In another preferred aspect, the amino acid at a position corresponding to position 209 of the polypeptide of SEQ ID NO: 2 is substituted with L or W preferably with W. In another aspect, the variant comprises or consists of the substitution Y209W in the polypeptide of SEQ ID NO: 3 (BPN' numbering).

In one preferred aspect of the invention, the subtilase variants of the invention comprises or consists of a substitution at a position corresponding to position 261 of the polypeptide of SEQ ID NO: 2. In another preferred aspect, the amino acid at a position corresponding to position 261 of the polypeptide of SEQ ID NO: 2 is substituted with D, C, E, L, M, R, V, W, Y or F preferably with W. In another aspect, the variant comprises or consists of the substitution N261W in the polypeptide of SEQ ID NO: 3 (BPN' numbering).

In one preferred aspect of the invention, the subtilase variants of the invention comprises or consists of a substitution at a position corresponding to position 206 of the polypeptide of SEQ ID NO: 2. In another preferred aspect, the amino acid at a position corresponding to position 206 of the polypeptide of SEQ ID NO: 2 is substituted with C,E,I,K,T,V,L or W preferably with C or W. In another aspect, the variant comprises or consists of the substitution Q206L, Q206W or Q206C in the polypeptide of SEQ ID NO: 4 (BPN' numbering).

In one preferred aspect of the invention, the subtilase variants of the invention comprises or consists of a substitution at a position corresponding to position 262 of the polypeptide of SEQ ID NO: 2. In another preferred aspect, the amino acid at a position corresponding to position 262 of the polypeptide of SEQ ID NO: 2 is substituted with C, E or Q preferably with E or C. In another aspect, the variant comprises or consists of the substitution Y262E or Y262C in the polypeptide of SEQ ID NO: 4 (BPN' numbering).

In one preferred aspect of the invention, the subtilase variants of the invention comprises or consists of a substitution at a position corresponding to position 225 of the polypeptide of SEQ ID NO: 2. In another preferred aspect, the amino acid at a position corresponding to position 225 of the polypeptide of SEQ ID NO: 2 is substituted with A or S preferably with A. In another aspect, the variant comprises or consists of the substitution P225A in the polypeptide of SEQ ID NO: 4 (BPN' numbering).

In one preferred aspect of the invention, the subtilase variants of the invention comprises or consists of a substitution at a position corresponding to position 9 of the polypeptide of SEQ ID NO: 2. In another preferred aspect, the amino acid at a position corresponding to position 9 of the polypeptide of SEQ ID NO: 2 is substituted with C, D, E or Q preferably with E. In another aspect, the variant comprises or consists of the substitution S9E in the polypeptide of SEQ ID NO: 4 (BPN' numbering).

In one preferred aspect of the invention, the subtilase variants of the invention comprises or consists of a substitution at a position corresponding to position 209 of the polypeptide of SEQ ID NO: 2. In another preferred aspect, the amino acid at a position corresponding to position 209 of the polypeptide of SEQ ID NO: 2 is substituted with W. In another aspect, the variant comprises or consists of the substitution L209W in the polypeptide of SEQ ID NO: 4 (BPN' numbering).

In one preferred aspect of the invention, the subtilase variants of the invention comprises or consists of a substitution at a position corresponding to position 261 of the polypeptide of SEQ ID NO: 2. In another preferred aspect, the amino acid at a position corresponding to position 261 of the polypeptide of SEQ ID NO: 2 is substituted with D, C, E, L, M, R, V, W or Y preferably with W. In another aspect, the variant comprises or consists of the substitution F261W in the polypeptide of SEQ ID NO: 4 (BPN' numbering)

The inventors have shown that each of the mutations selected from the list consisting of Q2R, W6I, I8{C,H}, S9{C,D,E,Q}, N18S, N43{A,C,L,R,W}, S49T, G53{A,L}, G61D, I72{A,V}, S78{D,N}, V104{F,P,T,Y}, A114V, G115{T,W}, H120{I,T,V}, P129D, V147W, V149{C,N,Q}, A158E, G160{D,P}, S161{C,Y,E}, I162L, S163{A, D}, Q182{C,E}, N184D, N185{C,E}, S188{C, D,E}, Q191N, A194{D,E}, N204{D,V}, V205{I,L}, Q206{C,E,I,K,T,V,W,L}, Y209{L,W}, S212{A,D,G,N}, S216{I,T,V}, L217{C,M}, N218T, M222{C,N,R}, P225{A,S}, T255{C,E,Q}, S256{A,C,D,V,Y}, S259D, T260{A,E,P}, N261{D,C,E,L,M,R,V,W,Y,F} and L262{Y,C,E,Q} provides a stabilizing effect on said subtilase. This stabilizing effect is increased when more stabilizing mutations are added.

Thus, another aspect of the invention relates to subtilase variants having protease activity, wherein said variant comprises the substitution N76D and two of the alterations selected from the list consisting Q2R, W6I, I8{C,H}, S9{C,D,E,Q}, N18S, N43{A,C,L,R,W}, S49T, G53{A,L}, G61D, I72{A,V}, S78{D,N}, V104{F,P,T,Y}, A114V, G115{T,W}, H120{I,T,V}, P129D, V147W, V149{C,N,Q}, A158E, G160{D,P}, S161{C,Y,E}, I162L, S163{A, D}, Q182{C, E}, N184D, N185{C,E}, S188{C, D,E}, Q191N, A194{D, E}, N204{D,V}, V205{I,L}, Q206{C,E,I,K,T,V,W,L}, Y209{L,W}, S212{A,D,G,N}, S216{I,T,V}, L217{C,M}, N218T, M222{C,N,R}, P225{A,S}, T255{C,E,Q}, S256{A,C,D,V,Y}, S259D, T260{A,E,P}, N261{D,C,E,L, M,R,V,W,Y,F} and L262{Y,C,E,Q} wherein each position corresponds to the corresponding position of the polypeptide of SEQ ID NO: 2. In one embodiment, the subtilase variant has improved stability, in particular improved storage stability, compared to the polypeptide of SEQ ID NO: 1 or to the polypeptide of SEQ ID NO: 2. In a preferred embodiment, the subtilase variant has improved stability, in particular improved in storage stability, and on par or improved wash performance compared to the polypeptide of SEQ ID NO: 1 or to the polypeptide of SEQ ID NO: 2.

TABLE 2

Subtilase Variants

| | | | |
|---|---|---|---|
| Q2R + W6I + N76D | Q2R + I8C + N76D | Q2R + I8H + N76D | Q2R + S9C + N76D |
| Q2R + S9D + N76D | Q2R + S9E + N76D | Q2R + S9Q + N76D | Q2R + S9R + N76D |
| Q2R + N18S + N76D | Q2R + N43A + N76D | Q2R + N43C + N76D | Q2R + N43L + N76D |
| Q2R + N43R + N76D | Q2R + N43W + N76D | Q2R + S49T + N76D | Q2R + G53A + N76D |
| Q2R + G53L + N76D | Q2R + G61D + N76D | Q2R + I72A + N76D | Q2R + I72V + N76D |
| Q2R + S78D + N76D | Q2R + S78N + N76D | Q2R + V104F + N76D | Q2R + V104P + N76D |
| Q2R + V104T + N76D | Q2R + V104Y + N76D | Q2R + A114V + N76D | Q2R + G115T + N76D |
| Q2R + G115W + N76D | Q2R + H120I + N76D | Q2R + H120T + N76D | Q2R + H120V + N76D |
| Q2R + P129D + N76D | Q2R + P131* + N76D | Q2R + V147W + N76D | Q2R + V149C + N76D |
| Q2R + V149N + N76D | Q2R + V149Q + N76D | Q2R + A158E + N76D | Q2R + G160D + N76D |
| Q2R + G160P + N76D | Q2R + S161C + N76D | Q2R + S161Y + N76D | Q2R + S161E + N76D |
| Q2R + I162L + N76D | Q2R + S163A + N76D | Q2R + S163D + N76D | Q2R + Q182C + N76D |
| Q2R + Q182E + N76D | Q2R + N184D + N76D | Q2R + N185C + N76D | Q2R + N185E + N76D |

TABLE 2-continued

Subtilase Variants

| | | | |
|---|---|---|---|
| Q2R + S188C + N76D | Q2R + S188D + N76D | Q2R + S188E + N76D | Q2R + Q191N + N76D |
| Q2R + A194E + N76D | Q2R + A194P + N76D | Q2R + A194E + N76D | Q2R + G195E + N76D |
| Q2R + N204D + N76D | Q2R + N204V + N76D | Q2R + V205I + N76D | Q2R + V205L + N76D |
| Q2R + Q206C + N76D | Q2R + Q206E + N76D | Q2R + Q206I + N76D | Q2R + Q206K + N76D |
| Q2R + Q206L + N76D | Q2R + Q206T + N76D | Q2R + Q206V + N76D | Q2R + Q206W + N76D |
| Q2R + Y209L + N76D | Q2R + Y209W + N76D | Q2R + S212A + N76D | Q2R + S212D + N76D |
| Q2R + S212G + N76D | Q2R + S212N + N76D | Q2R + S216I + N76D | Q2R + S216T + N76D |
| Q2R + S216V + N76D | Q2R + L217C + N76D | Q2R + L217M + N76D | Q2R + N218T + N76D |
| Q2R + S216V + N76D | Q2R + M222C + N76D | Q2R + M222N + N76D | Q2R + M222R + N76D |
| Q2R + Q206L + N76D | Q2R + P225A + N76D | Q2R + P225S + N76D | Q2R + T255C + N76D |
| Q2R + T255E + N76D | Q2R + T255Q + N76D | Q2R + S256A + N76D | Q2R + S256C + N76D |
| Q2R + S256D + N76D | Q2R + S256V + N76D | Q2R + S256Y + N76D | Q2R + S259D + N76D |
| Q2R + T260A + N76D | Q2R + T260E + N76D | Q2R + T260P + N76D | Q2R + N261D + N76D |
| Q2R + N261C + N76D | Q2R + N261E + N76D | Q2R + N261L + N76D | Q2R + N261M + N76D |
| Q2R + N261R + N76D | Q2R + N261V + N76D | Q2R + N261W + N76D | Q2R + N261Y + N76D |
| Q2R + N261F + N76D | Q2R + L262Y + N76D | Q2R + L262C + N76D | Q2R + L262E + N76D |
| Q2R + L262Q + N76D | W6I + I8C + N76D | W6I + I8H + N76D | W6I + S9C + N76D |
| W6I + S9D + N76D | W6I + S9E + N76D | W6I + S9Q + N76D | W6I + S9R + N76D |
| W6I + N18S + N76D | W6I + N43A + N76D | W6I + N43C + N76D | W6I + N43L + N76D |
| W6I + N43R + N76D | W6I + N43W + N76D | W6I + S49T + N76D | W6I + G53A + N76D |
| W6I + G53L + N76D | W6I + G61D + N76D | W6I + I72A + N76D | W6I + I72V + N76D |
| W6I + S78D + N76D | W6I + S78N + N76D | W6I + V104F + N76D | W6I + V104P + N76D |
| W6I + V104T + N76D | W6I + V104Y + N76D | W6I + A114V + N76D | W6I + G115T + N76D |
| W6I + G115W + N76D | W6I + H120I + N76D | W6I + H120T + N76D | W6I + H120V + N76D |
| W6I + P129D + N76D | W6I + P131* + N76D | W6I + V147W + N76D | W6I + V149C + N76D |
| W6I + V149N + N76D | W6I + V149Q + N76D | W6I + A158E + N76D | W6I + G160D + N76D |
| W6I + G160P + N76D | W6I + S161C + N76D | W6I + S161Y + N76D | W6I + S161E + N76D |
| W6I + I162L + N76D | W6I + S163A + N76D | W6I + S163D + N76D | W6I + Q182C + N76D |
| W6I + Q182E + N76D | W6I + N184D + N76D | W6I + N185C + N76D | W6I + N185E + N76D |
| W6I + S188C + N76D | W6I + S188D + N76D | W6I + S188E + N76D | W6I + Q191N + N76D |
| W6I + A194E + N76D | W6I + A194P + N76D | W6I + A194E + N76D | W6I + G195E + N76D |
| W6I + N204D + N76D | W6I + N204V + N76D | W6I + V205I + N76D | W6I + V205L + N76D |
| W6I + Q206C + N76D | W6I + Q206E + N76D | W6I + Q206I + N76D | W6I + Q206K + N76D |
| W6I + Q206L + N76D | W6I + Q206T + N76D | W6I + Q206V + N76D | W6I + Q206W + N76D |
| W6I + Y209L + N76D | W6I + Y209W + N76D | W6I + S212A + N76D | W6I + S212D + N76D |
| W6I + S212G + N76D | W6I + S212N + N76D | W6I + S216I + N76D | W6I + S216T + N76D |
| W6I + S216V + N76D | W6I + L217C + N76D | W6I + L217M + N76D | W6I + N218T + N76D |
| W6I + S216V + N76D | W6I + M222C + N76D | W6I + M222N + N76D | W6I + M222R + N76D |
| W6I + Q206L + N76D | W6I + P225A + N76D | W6I + P225S + N76D | W6I + T255C + N76D |
| W6I + T255E + N76D | W6I + T255Q + N76D | W6I + S256A + N76D | W6I + S256C + N76D |
| W6I + S256D + N76D | W6I + S256V + N76D | W6I + S256Y + N76D | W6I + S259D + N76D |
| W6I + T260A + N76D | W6I + T260E + N76D | W6I + T260P + N76D | W6I + N261D + N76D |
| W6I + N261C + N76D | W6I + N261E + N76D | W6I + N261L + N76D | W6I + N261M + N76D |
| W6I + N261R + N76D | W6I + N261V + N76D | W6I + N261W + N76D | W6I + N261Y + N76D |
| W6I + N261F + N76D | W6I + L262Y + N76D | W6I + L262C + N76D | W6I + L262E + N76D |
| W6I + L262Q + N76D | I8C + S9C + N76D | I8C + S9D + N76D | I8C + S9E + N76D |
| I8C + S9Q + N76D | I8C + S9R + N76D | I8C + N18S + N76D | I8C + N43A + N76D |
| I8C + N43C + N76D | I8C + N43L + N76D | I8C + N43R + N76D | I8C + N43W + N76D |
| I8C + S49T + N76D | I8C + G53A + N76D | I8C + G53L + N76D | I8C + G61D + N76D |
| I8C + I72A + N76D | I8C + I72V + N76D | I8C + S78D + N76D | I8C + S78N + N76D |
| I8C + V104F + N76D | I8C + V104P + N76D | I8C + V104T + N76D | I8C + V104Y + N76D |
| I8C + A114V + N76D | I8C + G115T + N76D | I8C + G115W + N76D | I8C + H120I + N76D |
| I8C + H120T + N76D | I8C + H120V + N76D | I8C + P129D + N76D | I8C + P131* + N76D |
| I8C + V147W + N76D | I8C + V149C + N76D | I8C + V149N + N76D | I8C + V149Q + N76D |
| I8C + A158E + N76D | I8C + G160D + N76D | I8C + G160P + N76D | I8C + S161C + N76D |
| I8C + S161Y + N76D | I8C + S161E + N76D | I8C + I162L + N76D | I8C + S163A + N76D |
| I8C + S163D + N76D | I8C + Q182C + N76D | I8C + Q182E + N76D | I8C + N184D + N76D |
| I8C + N185C + N76D | I8C + N185E + N76D | I8C + S188C + N76D | I8C + S188D + N76D |
| I8C + S188E + N76D | I8C + Q191N + N76D | I8C + A194D + N76D | I8C + A194E + N76D |
| I8C + A194P + N76D | I8C + G195E + N76D | I8C + N204D + N76D | I8C + N204V + N76D |
| I8C + V205I + N76D | I8C + V205L + N76D | I8C + Q206C + N76D | I8C + Q206E + N76D |
| I8C + Q206I + N76D | I8C + Q206K + N76D | I8C + Q206L + N76D | I8C + Q206T + N76D |
| I8C + Q206V + N76D | I8C + Q206W + N76D | I8C + Y209L + N76D | I8C + Y209W + N76D |
| I8C + S212A + N76D | I8C + S212D + N76D | I8C + S212G + N76D | I8C + S212N + N76D |
| I8C + S216I + N76D | I8C + S216T + N76D | I8C + S216V + N76D | I8C + L217C + N76D |
| I8C + L217M + N76D | I8C + N218T + N76D | I8C + S216V + N76D | I8C + M222C + N76D |
| I8C + M222N + N76D | I8C + M222R + N76D | I8C + Q206L + N76D | I8C + P225A + N76D |
| I8C + P225S + N76D | I8C + T255C + N76D | I8C + T255E + N76D | I8C + T255Q + N76D |
| I8C + S256A + N76D | I8C + S256C + N76D | I8C + S256D + N76D | I8C + S256V + N76D |
| I8C + S256Y + N76D | I8C + S259D + N76D | I8C + T260A + N76D | I8C + T260E + N76D |
| I8C + T260P + N76D | I8C + N261D + N76D | I8C + N261C + N76D | I8C + N261E + N76D |
| I8C + N261L + N76D | I8C + N261M + N76D | I8C + N261R + N76D | I8C + N261V + N76D |
| I8C + N261W + N76D | I8C + N261Y + N76D | I8C + N261F + N76D | I8C + L262Y + N76D |
| I8C + L262C + N76D | I8C + L262E + N76D | I8C + L262Q + N76D | I8H + S9C + N76D |
| I8H + S9D + N76D | I8H + S9E + N76D | I8H + S9Q + N76D | I8H + S9R + N76D |
| I8H + N18S + N76D | I8H + N43A + N76D | I8H + N43C + N76D | I8H + N43L + N76D |
| I8H + N43R + N76D | I8H + N43W + N76D | I8H + S49T + N76D | I8H + G53A + N76D |
| I8H + G53L + N76D | I8H + G61D + N76D | I8H + I72A + N76D | I8H + I72V + N76D |

TABLE 2-continued

| Subtilase Variants | | | |
|---|---|---|---|
| I8H + S78D + N76D | I8H + S78N + N76D | I8H + V104F + N76D | I8H + V104P + N76D |
| I8H + V104T + N76D | I8H + V104Y + N76D | I8H + A114V + N76D | I8H + G115T + N76D |
| I8H + G115W + N76D | I8H + H120I + N76D | I8H + H120T + N76D | I8H + H120V + N76D |
| I8H + P129D + N76D | I8H + P131* + N76D | I8H + V147W + N76D | I8H + V149C + N76D |
| I8H + V149N + N76D | I8H + V149Q + N76D | I8H + A158E + N76D | I8H + G160D + N76D |
| I8H + G160P + N76D | I8H + S161C + N76D | I8H + S161Y + N76D | I8H + S161E + N76D |
| I8H + I162L + N76D | I8H + S163A + N76D | I8H + S163D + N76D | I8H + Q182C + N76D |
| I8H + Q182E + N76D | I8H + N184D + N76D | I8H + N185C + N76D | I8H + N185E + N76D |
| I8H + S188C + N76D | I8H + S188D + N76D | I8H + S188E + N76D | I8H + Q191N + N76D |
| I8H + A194P + N76D | I8H + A194E + N76D | I8H + A194P + N76D | I8H + G195E + N76D |
| I8H + N204D + N76D | I8H + N204V + N76D | I8H + V205I + N76D | I8H + V205L + N76D |
| I8H + Q206C + N76D | I8H + Q206E + N76D | I8H + Q206I + N76D | I8H + Q206K + N76D |
| I8H + Q206L + N76D | I8H + Q206T + N76D | I8H + Q206V + N76D | I8H + Q206W + N76D |
| I8H + Y209L + N76D | I8H + Y209W + N76D | I8H + S212A + N76D | I8H + S212D + N76D |
| I8H + S212G + N76D | I8H + S212N + N76D | I8H + S216I + N76D | I8H + S216T + N76D |
| I8H + S216V + N76D | I8H + L217C + N76D | I8H + L217M + N76D | I8H + N218T + N76D |
| I8H + S216V + N76D | I8H + M222C + N76D | I8H + M222N + N76D | I8H + M222R + N76D |
| I8H + Q206L + N76D | I8H + P225A + N76D | I8H + P225S + N76D | I8H + T255C + N76D |
| I8H + T255E + N76D | I8H + T255Q + N76D | I8H + S256A + N76D | I8H + S256C + N76D |
| I8H + S256D + N76D | I8H + S256V + N76D | I8H + S256Y + N76D | I8H + S259D + N76D |
| I8H + T260A + N76D | I8H + T260E + N76D | I8H + T260P + N76D | I8H + N261D + N76D |
| I8H + N261C + N76D | I8H + N261E + N76D | I8H + N261L + N76D | I8H + N261M + N76D |
| I8H + N261R + N76D | I8H + N261V + N76D | I8H + N261W + N76D | I8H + N261Y + N76D |
| I8H + N261F + N76D | I8H + L262Y + N76D | I8H + L262C + N76D | I8H + L262E + N76D |
| I8H + L262Q + N76D | S9C + N18S + N76D | S9C + N43A + N76D | S9C + N43C + N76D |
| S9C + N43L + N76D | S9C + N43R + N76D | S9C + N43W + N76D | S9C + S49T + N76D |
| S9C + G53A + N76D | S9C + G53L + N76D | S9C + G61D + N76D | S9C + I72A + N76D |
| S9C + I72V + N76D | S9C + S78D + N76D | S9C + S78N + N76D | S9C + V104F + N76D |
| S9C + V104P + N76D | S9C + V104T + N76D | S9C + V104Y + N76D | S9C + A114V + N76D |
| S9C + G115T + N76D | S9C + G115W + N76D | S9C + H120I + N76D | S9C + H120T + N76D |
| S9C + H120V + N76D | S9C + P129D + N76D | S9C + P131* + N76D | S9C + V147W + N76D |
| S9C + V149C + N76D | S9C + V149N + N76D | S9C + V149Q + N76D | S9C + A158E + N76D |
| S9C + G160D + N76D | S9C + G160P + N76D | S9C + S161C + N76D | S9C + S161Y + N76D |
| S9C + S161E + N76D | S9C + I162L + N76D | S9C + S163A + N76D | S9C + S163D + N76D |
| S9C + Q182C + N76D | S9C + Q182E + N76D | S9C + N184D + N76D | S9C + N185C + N76D |
| S9C + N185E + N76D | S9C + S188C + N76D | S9C + S188D + N76D | S9C + S188E + N76D |
| S9C + Q191N + N76D | S9C + A194D + N76D | S9C + A194E + N76D | S9C + A194P + N76D |
| S9C + G195E + N76D | S9C + N204D + N76D | S9C + N204V + N76D | S9C + V205I + N76D |
| S9C + V205L + N76D | S9C + Q206C + N76D | S9C + Q206E + N76D | S9C + Q206I + N76D |
| S9C + Q206K + N76D | S9C + Q206L + N76D | S9C + Q206T + N76D | S9C + Q206V + N76D |
| S9C + Q206W + N76D | S9C + Y209L + N76D | S9C + Y209W + N76D | S9C + S212A + N76D |
| S9C + S212D + N76D | S9C + S212G + N76D | S9C + S212N + N76D | S9C + S216I + N76D |
| S9C + S216T + N76D | S9C + S216V + N76D | S9C + L217C + N76D | S9C + L217M + N76D |
| S9C + N218T + N76D | S9C + S216V + N76D | S9C + M222C + N76D | S9C + M222N + N76D |
| S9C + M222R + N76D | S9C + Q206L + N76D | S9C + P225A + N76D | S9C + P225S + N76D |
| S9C + T255C + N76D | S9C + T255E + N76D | S9C + T255Q + N76D | S9C + S256A + N76D |
| S9C + S256C + N76D | S9C + S256D + N76D | S9C + S256V + N76D | S9C + S256Y + N76D |
| S9C + S259D + N76D | S9C + T260A + N76D | S9C + T260E + N76D | S9C + T260P + N76D |
| S9C + N261D + N76D | S9C + N261C + N76D | S9C + N261E + N76D | S9C + N261L + N76D |
| S9C + N261M + N76D | S9C + N261R + N76D | S9C + N261V + N76D | S9C + N261W + N76D |
| S9C + N261Y + N76D | S9C + N261F + N76D | S9C + L262Y + N76D | S9C + L262C + N76D |
| S9C + L262E + N76D | S9C + L262Q + N76D | S9D + N18S + N76D | S9D + N43A + N76D |
| S9D + N43C + N76D | S9D + N43L + N76D | S9D + N43R + N76D | S9D + N43W + N76D |
| S9D + S49T + N76D | S9D + G53A + N76D | S9D + G53L + N76D | S9D + G61D + N76D |
| S9D + I72A + N76D | S9D + I72V + N76D | S9D + S78D + N76D | S9D + S78N + N76D |
| S9D + V104F + N76D | S9D + V104P + N76D | S9D + V104T + N76D | S9D + V104Y + N76D |
| S9D + A114V + N76D | S9D + G115T + N76D | S9D + G115W + N76D | S9D + H120I + N76D |
| S9D + H120T + N76D | S9D + H120V + N76D | S9D + P129D + N76D | S9D + P131* + N76D |
| S9D + V147W + N76D | S9D + V149C + N76D | S9D + V149N + N76D | S9D + V149Q + N76D |
| S9D + A158E + N76D | S9D + G160D + N76D | S9D + G160P + N76D | S9D + S161C + N76D |
| S9D + S161Y + N76D | S9D + S161E + N76D | S9D + I162L + N76D | S9D + S163A + N76D |
| S9D + S163D + N76D | S9D + Q182C + N76D | S9D + Q182E + N76D | S9D + N184D + N76D |
| S9D + N185C + N76D | S9D + N185E + N76D | S9D + S188C + N76D | S9D + S188D + N76D |
| S9D + S188E + N76D | S9D + Q191N + N76D | S9D + A194D + N76D | S9D + A194E + N76D |
| S9D + A194P + N76D | S9D + G195E + N76D | S9D + N204D + N76D | S9D + N204V + N76D |
| S9D + V205I + N76D | S9D + V205L + N76D | S9D + Q206C + N76D | S9D + Q206E + N76D |
| S9D + Q206I + N76D | S9D + Q206K + N76D | S9D + Q206L + N76D | S9D + Q206T + N76D |
| S9D + Q206V + N76D | S9D + Q206W + N76D | S9D + Y209L + N76D | S9D + Y209W + N76D |
| S9D + S212A + N76D | S9D + S212G + N76D | S9D + S212D + N76D | S9D + S212N + N76D |
| S9D + S216I + N76D | S9D + S216T + N76D | S9D + S216V + N76D | S9D + L217C + N76D |
| S9D + L217M + N76D | S9D + N218T + N76D | S9D + S216V + N76D | S9D + M222C + N76D |
| S9D + M222N + N76D | S9D + M222R + N76D | S9D + Q206L + N76D | S9D + P225A + N76D |
| S9D + P225S + N76D | S9D + T255E + N76D | S9D + T255Q + N76D | S9D + T255E + N76D |
| S9D + S256A + N76D | S9D + S256C + N76D | S9D + S256D + N76D | S9D + S256V + N76D |
| S9D + S256Y + N76D | S9D + S259D + N76D | S9D + T260A + N76D | S9D + T260E + N76D |
| S9D + T260P + N76D | S9D + N261D + N76D | S9D + N261C + N76D | S9D + N261E + N76D |
| S9D + N261L + N76D | S9D + N261M + N76D | S9D + N261R + N76D | S9D + N261V + N76D |
| S9D + N261W + N76D | S9D + N261Y + N76D | S9D + N261F + N76D | S9D + L262Y + N76D |

TABLE 2-continued

| Subtilase Variants | | | |
|---|---|---|---|
| S9D + L262C + N76D | S9D + L262E + N76D | S9D + L262Q + N76D | S9E + N18S + N76D |
| S9E + N43L + N76D | S9E + N43C + N76D | S9E + N43L + N76D | S9E + N43R + N76D |
| S9E + N43W + N76D | S9E + S49T + N76D | S9E + G53A + N76D | S9E + G53L + N76D |
| S9E + G61D + N76D | S9E + I72A + N76D | S9E + I72V + N76D | S9E + S78D + N76D |
| S9E + S78N + N76D | S9E + V104F + N76D | S9E + V104P + N76D | S9E + V104T + N76D |
| S9E + V104Y + N76D | S9E + A114V + N76D | S9E + G115T + N76D | S9E + G115W + N76D |
| S9E + H120I + N76D | S9E + H120T + N76D | S9E + H120V + N76D | S9E + P129D + N76D |
| S9E + P131* + N76D | S9E + V147W + N76D | S9E + V149C + N76D | S9E + V149N + N76D |
| S9E + V149Q + N76D | S9E + A158E + N76D | S9E + G160D + N76D | S9E + G160P + N76D |
| S9E + S161C + N76D | S9E + S161Y + N76D | S9E + S161E + N76D | S9E + I162L + N76D |
| S9E + S163A + N76D | S9E + S163D + N76D | S9E + Q182C + N76D | S9E + Q182E + N76D |
| S9E + N184D + N76D | S9E + N185C + N76D | S9E + N185E + N76D | S9E + S188C + N76D |
| S9E + S188D + N76D | S9E + S188E + N76D | S9E + Q191N + N76D | S9E + A194D + N76D |
| S9E + A194E + N76D | S9E + A194P + N76D | S9E + G195E + N76D | S9E + N204D + N76D |
| S9E + N204V + N76D | S9E + V205I + N76D | S9E + V205L + N76D | S9E + Q206C + N76D |
| S9E + Q206E + N76D | S9E + Q206I + N76D | S9E + Q206K + N76D | S9E + Q206L + N76D |
| S9E + Q206T + N76D | S9E + Q206V + N76D | S9E + Q206W + N76D | S9E + Y209L + N76D |
| S9E + Y209W + N76D | S9E + S212A + N76D | S9E + S212D + N76D | S9E + S212G + N76D |
| S9E + S212N + N76D | S9E + S216I + N76D | S9E + S216T + N76D | S9E + S216V + N76D |
| S9E + L217C + N76D | S9E + L217M + N76D | S9E + N218T + N76D | S9E + S216V + N76D |
| S9E + M222C + N76D | S9E + M222N + N76D | S9E + M222R + N76D | S9E + Q206L + N76D |
| S9E + P225A + N76D | S9E + P225S + N76D | S9E + T255C + N76D | S9E + T255E + N76D |
| S9E + T255Q + N76D | S9E + S256A + N76D | S9E + S256C + N76D | S9E + S256D + N76D |
| S9E + S256V + N76D | S9E + S256Y + N76D | S9E + S259D + N76D | S9E + T260A + N76D |
| S9E + T260E + N76D | S9E + T260P + N76D | S9E + N261D + N76D | S9E + N261C + N76D |
| S9E + N261E + N76D | S9E + N261L + N76D | S9E + N261M + N76D | S9E + N261R + N76D |
| S9E + N261V + N76D | S9E + N261W + N76D | S9E + N261Y + N76D | S9E + N261F + N76D |
| S9E + L262Y + N76D | S9E + L262C + N76D | S9E + L262E + N76D | S9E + L262Q + N76D |
| S9Q + N18S + N76D | S9Q + N43A + N76D | S9Q + N43C + N76D | S9Q + N43L + N76D |
| S9Q + N43R + N76D | S9Q + N43W + N76D | S9Q + S49T + N76D | S9Q + G53A + N76D |
| S9Q + G53L + N76D | S9Q + G61D + N76D | S9Q + I72A + N76D | S9Q + I72V + N76D |
| S9Q + S78D + N76D | S9Q + S78N + N76D | S9Q + V104F + N76D | S9Q + V104P + N76D |
| S9Q + V104T + N76D | S9Q + V104Y + N76D | S9Q + A114V + N76D | S9Q + G115T + N76D |
| S9Q + G115W + N76D | S9Q + H120I + N76D | S9Q + H120T + N76D | S9Q + H120V + N76D |
| S9Q + P129D + N76D | S9Q + P131* + N76D | S9Q + V147W + N76D | S9Q + V149C + N76D |
| S9Q + V149N + N76D | S9Q + V149Q + N76D | S9Q + A158E + N76D | S9Q + G160D + N76D |
| S9Q + G160P + N76D | S9Q + S161C + N76D | S9Q + S161Y + N76D | S9Q + S161E + N76D |
| S9Q + I162L + N76D | S9Q + S163A + N76D | S9Q + S163D + N76D | S9Q + Q182C + N76D |
| S9Q + Q182E + N76D | S9Q + N184D + N76D | S9Q + N185C + N76D | S9Q + N185E + N76D |
| S9Q + S188C + N76D | S9Q + S188D + N76D | S9Q + S188E + N76D | S9Q + Q191N + N76D |
| S9Q + A194D + N76D | S9Q + A194E + N76D | S9Q + A194P + N76D | S9Q + G195E + N76D |
| S9Q + N204D + N76D | S9Q + N204V + N76D | S9Q + V205I + N76D | S9Q + V205L + N76D |
| S9Q + Q206C + N76D | S9Q + Q206E + N76D | S9Q + Q206I + N76D | S9Q + Q206K + N76D |
| S9Q + Q206T + N76D | S9Q + Q206V + N76D | S9Q + Q206W + N76D | S9Q + S212D + N76D |
| S9Q + Y209L + N76D | S9Q + Y209W + N76D | S9Q + S212A + N76D | S9Q + S212D + N76D |
| S9Q + S212G + N76D | S9Q + S212N + N76D | S9Q + S216I + N76D | S9Q + S216T + N76D |
| S9Q + S216V + N76D | S9Q + L217C + N76D | S9Q + L217M + N76D | S9Q + N218T + N76D |
| S9Q + S216V + N76D | S9Q + M222C + N76D | S9Q + M222N + N76D | S9Q + M222R + N76D |
| S9Q + Q206L + N76D | S9Q + P225A + N76D | S9Q + P225S + N76D | S9Q + T255C + N76D |
| S9Q + T255E + N76D | S9Q + T255Q + N76D | S9Q + S256A + N76D | S9Q + S256C + N76D |
| S9Q + S256D + N76D | S9Q + S256V + N76D | S9Q + S256Y + N76D | S9Q + S259D + N76D |
| S9Q + T260A + N76D | S9Q + T260E + N76D | S9Q + T260P + N76D | S9Q + N261D + N76D |
| S9Q + N261C + N76D | S9Q + N261E + N76D | S9Q + N261L + N76D | S9Q + N261M + N76D |
| S9Q + N261R + N76D | S9Q + N261V + N76D | S9Q + N261W + N76D | S9Q + N261Y + N76D |
| S9Q + N261F + N76D | S9Q + L262Y + N76D | S9Q + L262C + N76D | S9Q + L262E + N76D |
| S9Q + L262Q + N76D | S9R + N18S + N76D | S9R + N43A + N76D | S9R + N43C + N76D |
| S9R + N43L + N76D | S9R + N43R + N76D | S9R + N43W + N76D | S9R + S49T + N76D |
| S9R + G53A + N76D | S9R + G53L + N76D | S9R + G61D + N76D | S9R + I72A + N76D |
| S9R + I72V + N76D | S9R + S78D + N76D | S9R + S78N + N76D | S9R + V104F + N76D |
| S9R + V104P + N76D | S9R + V104T + N76D | S9R + V104Y + N76D | S9R + A114V + N76D |
| S9R + G115T + N76D | S9R + G115W + N76D | S9R + H120I + N76D | S9R + H120T + N76D |
| S9R + H120V + N76D | S9R + P129D + N76D | S9R + P131* + N76D | S9R + V147W + N76D |
| S9R + V149C + N76D | S9R + V149N + N76D | S9R + V149Q + N76D | S9R + A158E + N76D |
| S9R + G160D + N76D | S9R + G160P + N76D | S9R + S161C + N76D | S9R + S161Y + N76D |
| S9R + S161E + N76D | S9R + I162L + N76D | S9R + S163A + N76D | S9R + S163D + N76D |
| S9R + Q182C + N76D | S9R + Q182E + N76D | S9R + N184D + N76D | S9R + N185C + N76D |
| S9R + N185E + N76D | S9R + S188C + N76D | S9R + S188D + N76D | S9R + S188E + N76D |
| S9R + Q191N + N76D | S9R + A194D + N76D | S9R + A194E + N76D | S9R + A194P + N76D |
| S9R + G195E + N76D | S9R + N204D + N76D | S9R + N204V + N76D | S9R + V205I + N76D |
| S9R + V205L + N76D | S9R + Q206C + N76D | S9R + Q206E + N76D | S9R + Q206I + N76D |
| S9R + Q206K + N76D | S9R + Q206L + N76D | S9R + Q206T + N76D | S9R + Q206V + N76D |
| S9R + Q206W + N76D | S9R + Y209L + N76D | S9R + Y209W + N76D | S9R + S212A + N76D |
| S9R + S212G + N76D | S9R + S212N + N76D | S9R + S212D + N76D | S9R + S216I + N76D |
| S9R + S216T + N76D | S9R + S216V + N76D | S9R + L217C + N76D | S9R + L217M + N76D |
| S9R + N218T + N76D | S9R + S216V + N76D | S9R + M222C + N76D | S9R + M222N + N76D |
| S9R + M222R + N76D | S9R + Q206L + N76D | S9R + P225A + N76D | S9R + P225S + N76D |
| S9R + T255C + N76D | S9R + T255E + N76D | S9R + T255Q + N76D | S9R + S256A + N76D |
| S9R + S256C + N76D | S9R + S256D + N76D | S9R + S256V + N76D | S9R + S256Y + N76D |

TABLE 2-continued

Subtilase Variants

| | | | |
|---|---|---|---|
| S9R + S259D + N76D | S9R + T260A + N76D | S9R + T260E + N76D | S9R + T260P + N76D |
| S9R + N261D + N76D | S9R + N261C + N76D | S9R + N261E + N76D | S9R + N261L + N76D |
| S9R + N261M + N76D | S9R + N261R + N76D | S9R + N261V + N76D | S9R + N261W + N76D |
| S9R + N261Y + N76D | S9R + N261F + N76D | S9R + L262Y + N76D | S9R + L262C + N76D |
| S9R + L262E + N76D | S9R + L262Q + N76D | N18S + N43A + N76D | N18S + N43C + N76D |
| N18S + N43L + N76D | N18S + N43R + N76D | N18S + N43W + N76D | N18S + S49T + N76D |
| N18S + G53A + N76D | N18S + G53L + N76D | N18S + G61D + N76D | N18S + I72A + N76D |
| N18S + I72V + N76D | N18S + S78D + N76D | N18S + S78N + N76D | N18S + V104F + N76D |
| N18S + V104P + N76D | N18S + V104T + N76D | N18S + V104Y + N76D | N18S + A114V + N76D |
| N18S + G115T + N76D | N18S + G115W + N76D | N18S + H120I + N76D | N18S + H120T + N76D |
| N18S + H120V + N76D | N18S + P129D + N76D | N18S + P131* + N76D | N18S + V147W + N76D |
| N18S + V149C + N76D | N18S + V149N + N76D | N18S + V149Q + N76D | N18S + A158E + N76D |
| N18S + G160D + N76D | N18S + G160P + N76D | N18S + S161C + N76D | N18S + S161Y + N76D |
| N18S + S161E + N76D | N18S + I162L + N76D | N18S + S163A + N76D | N18S + S163D + N76D |
| N18S + Q182C + N76D | N18S + Q182E + N76D | N18S + N184D + N76D | N18S + N185C + N76D |
| N18S + N185E + N76D | N18S + S188C + N76D | N18S + S188D + N76D | N18S + S188E + N76D |
| N18S + Q191N + N76D | N18S + A194D + N76D | N18S + A194E + N76D | N18S + A194P + N76D |
| N18S + G195E + N76D | N18S + N204D + N76D | N18S + N204V + N76D | N18S + V205I + N76D |
| N18S + V205L + N76D | N18S + Q206C + N76D | N18S + Q206I + N76D | N18S + Q206J + N76D |
| N18S + Q206K + N76D | N18S + Q206L + N76D | N18S + Q206T + N76D | N18S + Q206V + N76D |
| N18S + Q206W + N76D | N18S + Y209L + N76D | N18S + Y209W + N76D | N18S + S212A + N76D |
| N18S + S212D + N76D | N18S + S212G + N76D | N18S + S212N + N76D | N18S + S216I + N76D |
| N18S + S217T + N76D | N18S + S216V + N76D | N18S + S216T + N76D | N18S + L217M + N76D |
| N18S + N218T + N76D | N18S + S216V + N76D | N18S + M222C + N76D | N18S + M222N + N76D |
| N18S + M222R + N76D | N18S + Q206L + N76D | N18S + P225A + N76D | N18S + P225S + N76D |
| N18S + T255C + N76D | N18S + T255E + N76D | N18S + T255Q + N76D | N18S + S256A + N76D |
| N18S + S256C + N76D | N18S + S256D + N76D | N18S + S256V + N76D | N18S + S256Y + N76D |
| N18S + S259D + N76D | N18S + T260A + N76D | N18S + T260E + N76D | N18S + T260P + N76D |
| N18S + N261D + N76D | N18S + N261C + N76D | N18S + N261E + N76D | N18S + N261L + N76D |
| N18S + N261M + N76D | N18S + N261R + N76D | N18S + N261V + N76D | N18S + N261W + N76D |
| N18S + N261Y + N76D | N18S + N261F + N76D | N18S + L262Y + N76D | N18S + L262C + N76D |
| N18S + L262E + N76D | N18S + L262Q + N76D | N43A + S49T + N76D | N43A + G53A + N76D |
| N43A + G53L + N76D | N43A + G61D + N76D | N43A + I72A + N76D | N43A + I72V + N76D |
| N43A + S78D + N76D | N43A + S78N + N76D | N43A + V104F + N76D | N43A + V104P + N76D |
| N43A + V104T + N76D | N43A + V104Y + N76D | N43A + A114V + N76D | N43A + G115T + N76D |
| N43A + G115W + N76D | N43A + H120I + N76D | N43A + H120T + N76D | N43A + H120V + N76D |
| N43A + P129D + N76D | N43A + P131* + N76D | N43A + V147W + N76D | N43A + V149C + N76D |
| N43A + V149N + N76D | N43A + V149Q + N76D | N43A + A158E + N76D | N43A + G160D + N76D |
| N43A + G160P + N76D | N43A + S161C + N76D | N43A + S161Y + N76D | N43A + S161E + N76D |
| N43A + I162L + N76D | N43A + S163A + N76D | N43A + S163D + N76D | N43A + Q182C + N76D |
| N43A + Q182E + N76D | N43A + N184D + N76D | N43A + N185C + N76D | N43A + N185E + N76D |
| N43A + S188C + N76D | N43A + S188D + N76D | N43A + S188E + N76D | N43A + Q191N + N76D |
| N43A + A194D + N76D | N43A + A194E + N76D | N43A + A194P + N76D | N43A + G195E + N76D |
| N43A + N204D + N76D | N43A + N204V + N76D | N43A + V205I + N76D | N43A + V205L + N76D |
| N43A + Q206C + N76D | N43A + Q206E + N76D | N43A + Q206I + N76D | N43A + Q206K + N76D |
| N43A + Q206L + N76D | N43A + Q206T + N76D | N43A + Q206V + N76D | N43A + Q206W + N76D |
| N43A + Y209L + N76D | N43A + Y209W + N76D | N43A + S212A + N76D | N43A + S212D + N76D |
| N43A + S212G + N76D | N43A + S212N + N76D | N43A + S216I + N76D | N43A + S216T + N76D |
| N43A + S216V + N76D | N43A + L217C + N76D | N43A + L217M + N76D | N43A + N218T + N76D |
| N43A + S216V + N76D | N43A + M222C + N76D | N43A + M222N + N76D | N43A + M222R + N76D |
| N43A + Q206L + N76D | N43A + P225A + N76D | N43A + P225S + N76D | N43A + T255C + N76D |
| N43A + T255E + N76D | N43A + T255Q + N76D | N43A + S256A + N76D | N43A + S256C + N76D |
| N43A + S256D + N76D | N43A + S256V + N76D | N43A + S256Y + N76D | N43A + S259D + N76D |
| N43A + T260A + N76D | N43A + T260E + N76D | N43A + T260P + N76D | N43A + N261D + N76D |
| N43A + N261C + N76D | N43A + N261E + N76D | N43A + N261L + N76D | N43A + N261M + N76D |
| N43A + N261R + N76D | N43A + N261V + N76D | N43A + N261W + N76D | N43A + N261Y + N76D |
| N43A + N261F + N76D | N43A + L262Y + N76D | N43A + L262C + N76D | N43A + L262E + N76D |
| N43A + L262Q + N76D | N43C + S49T + N76D | N43C + G53A + N76D | N43C + G53L + N76D |
| N43C + G61D + N76D | N43C + I72A + N76D | N43C + I72V + N76D | N43C + S78D + N76D |
| N43C + S78N + N76D | N43C + V104P + N76D | N43C + V104F + N76D | N43C + V104T + N76D |
| N43C + V104Y + N76D | N43C + A114V + N76D | N43C + G115T + N76D | N43C + G115W + N76D |
| N43C + H120I + N76D | N43C + H120T + N76D | N43C + H120V + N76D | N43C + P129D + N76D |
| N43C + P131* + N76D | N43C + V147W + N76D | N43C + V149C + N76D | N43C + V149N + N76D |
| N43C + V149Q + N76D | N43C + A158E + N76D | N43C + G160D + N76D | N43C + G160P + N76D |
| N43C + S161E + N76D | N43C + S161C + N76D | N43C + S161Y + N76D | N43C + I162L + N76D |
| N43C + S163A + N76D | N43C + S163D + N76D | N43C + Q182C + N76D | N43C + Q182E + N76D |
| N43C + N184D + N76D | N43C + N185C + N76D | N43C + N185E + N76D | N43C + S188C + N76D |
| N43C + S188D + N76D | N43C + S188E + N76D | N43C + Q191N + N76D | N43C + A194D + N76D |
| N43C + A194E + N76D | N43C + A194P + N76D | N43C + G195E + N76D | N43C + N204D + N76D |
| N43C + N204V + N76D | N43C + V205I + N76D | N43C + V205L + N76D | N43C + Q206C + N76D |
| N43C + Q206E + N76D | N43C + Q206I + N76D | N43C + Q206K + N76D | N43C + Q206L + N76D |
| N43C + Q206T + N76D | N43C + Q206V + N76D | N43C + Q206W + N76D | N43C + Y209L + N76D |
| N43C + Y209W + N76D | N43C + S212A + N76D | N43C + S212G + N76D | N43C + S212D + N76D |
| N43C + S212N + N76D | N43C + S216I + N76D | N43C + S216T + N76D | N43C + S216V + N76D |
| N43C + L217C + N76D | N43C + L217M + N76D | N43C + N218T + N76D | N43C + S216V + N76D |
| N43C + M222C + N76D | N43C + M222N + N76D | N43C + M222R + N76D | N43C + Q206L + N76D |
| N43C + P225A + N76D | N43C + P225S + N76D | N43C + T255C + N76D | N43C + T255E + N76D |
| N43C + T255Q + N76D | N43C + S256A + N76D | N43C + S256C + N76D | N43C + S256D + N76D |

TABLE 2-continued

Subtilase Variants

| | | | |
|---|---|---|---|
| N43C + S256V + N76D | N43C + S256Y + N76D | N43C + S259D + N76D | N43C + T260A + N76D |
| N43C + T260E + N76D | N43C + T260P + N76D | N43C + N261D + N76D | N43C + N261C + N76D |
| N43C + N261E + N76D | N43C + N261L + N76D | N43C + N261M + N76D | N43C + N261R + N76D |
| N43C + N261V + N76D | N43C + N261W + N76D | N43C + N261Y + N76D | N43C + N261F + N76D |
| N43C + L262Y + N76D | N43C + L262C + N76D | N43C + L262E + N76D | N43C + L262Q + N76D |
| N43L + S49T + N76D | N43L + G53A + N76D | N43L + G53L + N76D | N43L + G61D + N76D |
| N43L + I72A + N76D | N43L + I72V + N76D | N43L + S78D + N76D | N43L + S78N + N76D |
| N43L + V104F + N76D | N43L + V104P + N76D | N43L + V104T + N76D | N43L + V104Y + N76D |
| N43L + A114V + N76D | N43L + G115T + N76D | N43L + G115W + N76D | N43L + H120I + N76D |
| N43L + H120T + N76D | N43L + H120V + N76D | N43L + P129D + N76D | N43L + P131* + N76D |
| N43L + V147W + N76D | N43L + V149C + N76D | N43L + V149N + N76D | N43L + V149Q + N76D |
| N43L + A158E + N76D | N43L + G160D + N76D | N43L + G160P + N76D | N43L + S161C + N76D |
| N43L + S161Y + N76D | N43L + S161E + N76D | N43L + I162L + N76D | N43L + S163A + N76D |
| N43L + S163D + N76D | N43L + Q182C + N76D | N43L + Q182E + N76D | N43L + N184D + N76D |
| N43L + N185C + N76D | N43L + N185E + N76D | N43L + S188C + N76D | N43L + S188D + N76D |
| N43L + S188E + N76D | N43L + Q191N + N76D | N43L + A194D + N76D | N43L + A194E + N76D |
| N43L + A194P + N76D | N43L + G195E + N76D | N43L + N204D + N76D | N43L + N204V + N76D |
| N43L + V205I + N76D | N43L + V205L + N76D | N43L + Q206C + N76D | N43L + Q206E + N76D |
| N43L + Q206I + N76D | N43L + Q206K + N76D | N43L + Q206L + N76D | N43L + Q206T + N76D |
| N43L + Q206V + N76D | N43L + Q206W + N76D | N43L + Y209L + N76D | N43L + Y209W + N76D |
| N43L + S212A + N76D | N43L + S212D + N76D | N43L + S212G + N76D | N43L + S212N + N76D |
| N43L + S216I + N76D | N43L + S216T + N76D | N43L + S216V + N76D | N43L + L217C + N76D |
| N43L + L217M + N76D | N43L + N218T + N76D | N43L + S216V + N76D | N43L + M222C + N76D |
| N43L + M222N + N76D | N43L + M222R + N76D | N43L + Q206L + N76D | N43L + P225A + N76D |
| N43L + P225S + N76D | N43L + T255C + N76D | N43L + T255E + N76D | N43L + T255Q + N76D |
| N43L + S256A + N76D | N43L + S256C + N76D | N43L + S256D + N76D | N43L + S256V + N76D |
| N43L + S256Y + N76D | N43L + S259D + N76D | N43L + T260A + N76D | N43L + T260E + N76D |
| N43L + T260P + N76D | N43L + N261D + N76D | N43L + N261C + N76D | N43L + N261E + N76D |
| N43L + N261L + N76D | N43L + N261M + N76D | N43L + N261R + N76D | N43L + N261V + N76D |
| N43L + N261W + N76D | N43L + N261Y + N76D | N43L + N261F + N76D | N43L + L262Y + N76D |
| N43L + L262C + N76D | N43L + L262E + N76D | N43L + L262Q + N76D | N43R + S49T + N76D |
| N43R + G53A + N76D | N43R + G53L + N76D | N43R + G61D + N76D | N43R + I72A + N76D |
| N43R + I72V + N76D | N43R + S78D + N76D | N43R + S78N + N76D | N43R + V104F + N76D |
| N43R + V104P + N76D | N43R + V104T + N76D | N43R + V104Y + N76D | N43R + A114V + N76D |
| N43R + G115T + N76D | N43R + G115W + N76D | N43R + H120I + N76D | N43R + H120T + N76D |
| N43R + H120V + N76D | N43R + P129D + N76D | N43R + P131* + N76D | N43R + V147W + N76D |
| N43R + V149C + N76D | N43R + V149N + N76D | N43R + V149Q + N76D | N43R + A158E + N76D |
| N43R + G160D + N76D | N43R + G160P + N76D | N43R + S161C + N76D | N43R + S161Y + N76D |
| N43R + S161E + N76D | N43R + I162L + N76D | N43R + S163A + N76D | N43R + S163D + N76D |
| N43R + Q182C + N76D | N43R + Q182E + N76D | N43R + N184D + N76D | N43R + N185C + N76D |
| N43R + N185E + N76D | N43R + S188C + N76D | N43R + S188D + N76D | N43R + S188E + N76D |
| N43R + Q191N + N76D | N43R + A194D + N76D | N43R + A194E + N76D | N43R + A194P + N76D |
| N43R + G195E + N76D | N43R + N204D + N76D | N43R + N204V + N76D | N43R + V205I + N76D |
| N43R + V205E + N76D | N43R + Q206C + N76D | N43R + Q206E + N76D | N43R + Q206I + N76D |
| N43R + Q206K + N76D | N43R + Q206L + N76D | N43R + Q206T + N76D | N43R + Q206V + N76D |
| N43R + Q206W + N76D | N43R + Y209L + N76D | N43R + Y209W + N76D | N43R + S212A + N76D |
| N43R + S212D + N76D | N43R + S212G + N76D | N43R + S212N + N76D | N43R + S216I + N76D |
| N43R + S216T + N76D | N43R + S216V + N76D | N43R + S216T + N76D | N43R + L217M + N76D |
| N43R + N218T + N76D | N43R + S216V + N76D | N43R + M222C + N76D | N43R + M222N + N76D |
| N43R + M222R + N76D | N43R + Q206L + N76D | N43R + P225A + N76D | N43R + P225S + N76D |
| N43R + T255C + N76D | N43R + T255E + N76D | N43R + T255Q + N76D | N43R + S256A + N76D |
| N43R + S256C + N76D | N43R + S256D + N76D | N43R + S256V + N76D | N43R + S256Y + N76D |
| N43R + S259D + N76D | N43R + T260A + N76D | N43R + T260E + N76D | N43R + T260P + N76D |
| N43R + N261D + N76D | N43R + N261C + N76D | N43R + N261E + N76D | N43R + N261L + N76D |
| N43R + N261M + N76D | N43R + N261R + N76D | N43R + N261V + N76D | N43R + N261W + N76D |
| N43R + N261Y + N76D | N43R + N261F + N76D | N43R + L262Y + N76D | N43R + L262C + N76D |
| N43R + L262E + N76D | N43R + L262Q + N76D | N43W + S49T + N76D | N43W + G53A + N76D |
| N43W + G53L + N76D | N43W + G61D + N76D | N43W + I72A + N76D | N43W + I72V + N76D |
| N43W + S78D + N76D | N43W + S78N + N76D | N43W + V104F + N76D | N43W + V104P + N76D |
| N43W + V104T + N76D | N43W + V104Y + N76D | N43W + A114V + N76D | N43W + G115T + N76D |
| N43W + G115W + N76D | N43W + H120I + N76D | N43W + H120T + N76D | N43W + H120V + N76D |
| N43W + P129D + N76D | N43W + P131* + N76D | N43W + V147W + N76D | N43W + V149C + N76D |
| N43W + V149N + N76D | N43W + V149Q + N76D | N43W + A158E + N76D | N43W + G160D + N76D |
| N43W + G160P + N76D | N43W + S161C + N76D | N43W + S161Y + N76D | N43W + S161E + N76D |
| N43W + I162L + N76D | N43W + S163A + N76D | N43W + S163D + N76D | N43W + Q182C + N76D |
| N43W + Q182E + N76D | N43W + N184D + N76D | N43W + N185C + N76D | N43W + N185E + N76D |
| N43W + S188C + N76D | N43W + S188D + N76D | N43W + S188E + N76D | N43W + Q191N + N76D |
| N43W + A194D + N76D | N43W + A194E + N76D | N43W + A194P + N76D | N43W + G195E + N76D |
| N43W + N204D + N76D | N43W + N204V + N76D | N43W + V205I + N76D | N43W + V205L + N76D |
| N43W + Q206C + N76D | N43W + Q206E + N76D | N43W + Q206I + N76D | N43W + Q206K + N76D |
| N43W + Q206L + N76D | N43W + Q206T + N76D | N43W + Q206V + N76D | N43W + Q206W + N76D |
| N43W + Y209L + N76D | N43W + Y209W + N76D | N43W + S212A + N76D | N43W + S212D + N76D |
| N43W + S212G + N76D | N43W + S212N + N76D | N43W + S216I + N76D | N43W + S216T + N76D |
| N43W + S216V + N76D | N43W + L217C + N76D | N43W + L217M + N76D | N43W + N218T + N76D |
| N43W + S216V + N76D | N43W + M222C + N76D | N43W + M222N + N76D | N43W + M222R + N76D |
| N43W + Q206L + N76D | N43W + P225A + N76D | N43W + P225S + N76D | N43W + T255C + N76D |
| N43W + T255E + N76D | N43W + T255Q + N76D | N43W + S256A + N76D | N43W + S256C + N76D |
| N43W + S256D + N76D | N43W + S256V + N76D | N43W + S256Y + N76D | N43W + S259D + N76D |

TABLE 2-continued

Subtilase Variants

| | | | |
|---|---|---|---|
| N43W + T260A + N76D | N43W + T260E + N76D | N43W + T260P + N76D | N43W + N261D + N76D |
| N43W + N261C + N76D | N43W + N261E + N76D | N43W + N261L + N76D | N43W + N261M + N76D |
| N43W + N261R + N76D | N43W + N261V + N76D | N43W + N261W + N76D | N43W + N261Y + N76D |
| N43W + N261F + N76D | N43W + L262Y + N76D | N43W + L262C + N76D | N43W + L262E + N76D |
| N43W + L262Q + N76D | S49T + G53A + N76D | S49T + G53L + N76D | S49T + G61D + N76D |
| S49T + I72A + N76D | S49T + I72V + N76D | S49T + S78D + N76D | S49T + S78N + N76D |
| S49T + V104F + N76D | S49T + V104P + N76D | S49T + V104T + N76D | S49T + V104Y + N76D |
| S49T + A114V + N76D | S49T + G115T + N76D | S49T + G115W + N76D | S49T + H120I + N76D |
| S49T + H120T + N76D | S49T + H120V + N76D | S49T + P129D + N76D | S49T + P131* + N76D |
| S49T + V147W + N76D | S49T + V149C + N76D | S49T + V149N + N76D | S49T + V149Q + N76D |
| S49T + A158E + N76D | S49T + G160D + N76D | S49T + G160P + N76D | S49T + S161C + N76D |
| S49T + S161Y + N76D | S49T + S161E + N76D | S49T + I162L + N76D | S49T + S163A + N76D |
| S49T + S163D + N76D | S49T + Q182C + N76D | S49T + Q182E + N76D | S49T + N184D + N76D |
| S49T + N185C + N76D | S49T + N185E + N76D | S49T + S188C + N76D | S49T + S188D + N76D |
| S49T + S188E + N76D | S49T + Q191N + N76D | S49T + A194D + N76D | S49T + A194E + N76D |
| S49T + A194P + N76D | S49T + G195E + N76D | S49T + N204D + N76D | S49T + N204V + N76D |
| S49T + V205I + N76D | S49T + V205L + N76D | S49T + Q206C + N76D | S49T + Q206E + N76D |
| S49T + Q206I + N76D | S49T + Q206K + N76D | S49T + Q206L + N76D | S49T + Q206T + N76D |
| S49T + Q206V + N76D | S49T + Q206W + N76D | S49T + Y209V + N76D | S49T + Y209W + N76D |
| S49T + S212A + N76D | S49T + S212D + N76D | S49T + S212G + N76D | S49T + S212N + N76D |
| S49T + S216I + N76D | S49T + S216T + N76D | S49T + S216V + N76D | S49T + L217C + N76D |
| S49T + L217M + N76D | S49T + N218T + N76D | S49T + S216V + N76D | S49T + M222C + N76D |
| S49T + M222N + N76D | S49T + M222R + N76D | S49T + Q206L + N76D | S49T + P225A + N76D |
| S49T + P225S + N76D | S49T + T255C + N76D | S49T + T255E + N76D | S49T + T255Q + N76D |
| S49T + S256A + N76D | S49T + S256C + N76D | S49T + S256D + N76D | S49T + S256V + N76D |
| S49T + S256Y + N76D | S49T + S259D + N76D | S49T + T260A + N76D | S49T + T260E + N76D |
| S49T + T260P + N76D | S49T + N261D + N76D | S49T + N261C + N76D | S49T + N261E + N76D |
| S49T + N261L + N76D | S49T + N261M + N76D | S49T + N261R + N76D | S49T + N261V + N76D |
| S49T + N261W + N76D | S49T + N261Y + N76D | S49T + N261F + N76D | S49T + L262Y + N76D |
| S49T + L262C + N76D | S49T + L262E + N76D | S49T + L262Q + N76D | G53A + G61D + N76D |
| G53A + I72A + N76D | G53A + I72V + N76D | G53A + S78D + N76D | G53A + S78N + N76D |
| G53A + V104F + N76D | G53A + V104P + N76D | G53A + V104T + N76D | G53A + V104Y + N76D |
| G53A + A114V + N76D | G53A + G115T + N76D | G53A + G115W + N76D | G53A + H120I + N76D |
| G53A + H120T + N76D | G53A + H120V + N76D | G53A + P129D + N76D | G53A + P131* + N76D |
| G53A + V147W + N76D | G53A + V149C + N76D | G53A + V149N + N76D | G53A + V149Q + N76D |
| G53A + A158E + N76D | G53A + G160D + N76D | G53A + G160P + N76D | G53A + S161C + N76D |
| G53A + S161Y + N76D | G53A + S161E + N76D | G53A + I162L + N76D | G53A + S163A + N76D |
| G53A + S163D + N76D | G53A + Q182C + N76D | G53A + Q182E + N76D | G53A + N184D + N76D |
| G53A + N185C + N76D | G53A + N185E + N76D | G53A + S188C + N76D | G53A + S188D + N76D |
| G53A + S188E + N76D | G53A + Q191N + N76D | G53A + A194D + N76D | G53A + A194E + N76D |
| G53A + A194P + N76D | G53A + G195E + N76D | G53A + N204D + N76D | G53A + N204V + N76D |
| G53A + V205I + N76D | G53A + V205L + N76D | G53A + Q206C + N76D | G53A + Q206E + N76D |
| G53A + Q206I + N76D | G53A + Q206K + N76D | G53A + Q206L + N76D | G53A + Q206T + N76D |
| G53A + Q206V + N76D | G53A + Q206W + N76D | G53A + Y209V + N76D | G53A + Y209W + N76D |
| G53A + S212A + N76D | G53A + S212D + N76D | G53A + S212G + N76D | G53A + S212N + N76D |
| G53A + S216I + N76D | G53A + S216T + N76D | G53A + S216V + N76D | G53A + L217C + N76D |
| G53A + L217M + N76D | G53A + N218T + N76D | G53A + S216V + N76D | G53A + M222C + N76D |
| G53A + M222N + N76D | G53A + M222R + N76D | G53A + Q206L + N76D | G53A + P225A + N76D |
| G53A + P225S + N76D | G53A + T255C + N76D | G53A + T255E + N76D | G53A + T255Q + N76D |
| G53A + S256A + N76D | G53A + S256C + N76D | G53A + S256D + N76D | G53A + S256V + N76D |
| G53A + S256Y + N76D | G53A + S259D + N76D | G53A + T260A + N76D | G53A + T260E + N76D |
| G53A + T260P + N76D | G53A + N261D + N76D | G53A + N261C + N76D | G53A + N261E + N76D |
| G53A + N261L + N76D | G53A + N261M + N76D | G53A + N261R + N76D | G53A + N261V + N76D |
| G53A + N261W + N76D | G53A + N261Y + N76D | G53A + N261F + N76D | G53A + L262Y + N76D |
| G53A + L262C + N76D | G53A + L262E + N76D | G53A + L262Q + N76D | G53L + G61D + N76D |
| G53L + I72A + N76D | G53L + I72V + N76D | G53L + S78D + N76D | G53L + S78N + N76D |
| G53L + V104F + N76D | G53L + V104P + N76D | G53L + V104T + N76D | G53L + V104Y + N76D |
| G53L + A114V + N76D | G53L + G115T + N76D | G53L + G115W + N76D | G53L + H120I + N76D |
| G53L + H120T + N76D | G53L + H120V + N76D | G53L + P129D + N76D | G53L + P131* + N76D |
| G53L + V147W + N76D | G53L + V149C + N76D | G53L + V149N + N76D | G53L + V149Q + N76D |
| G53L + A158E + N76D | G53L + G160D + N76D | G53L + G160P + N76D | G53L + S161C + N76D |
| G53L + S161Y + N76D | G53L + S161E + N76D | G53L + I162L + N76D | G53L + S163A + N76D |
| G53L + S163D + N76D | G53L + Q182C + N76D | G53L + Q182E + N76D | G53L + N184D + N76D |
| G53L + N185C + N76D | G53L + N185E + N76D | G53L + S188C + N76D | G53L + S188D + N76D |
| G53L + S188E + N76D | G53L + Q191N + N76D | G53L + A194D + N76D | G53L + A194E + N76D |
| G53L + A194P + N76D | G53L + G195E + N76D | G53L + N204D + N76D | G53L + N204V + N76D |
| G53L + V205I + N76D | G53L + V205L + N76D | G53L + Q206C + N76D | G53L + Q206E + N76D |
| G53L + Q206I + N76D | G53L + Q206K + N76D | G53L + Q206L + N76D | G53L + Q206T + N76D |
| G53L + Q206V + N76D | G53L + Q206W + N76D | G53L + Y209V + N76D | G53L + Y209W + N76D |
| G53L + S212A + N76D | G53L + S212D + N76D | G53L + S212G + N76D | G53L + S212N + N76D |
| G53L + S216I + N76D | G53L + S216T + N76D | G53L + S216V + N76D | G53L + L217C + N76D |
| G53L + L217M + N76D | G53L + N218T + N76D | G53L + S216V + N76D | G53L + M222C + N76D |
| G53L + M222N + N76D | G53L + M222R + N76D | G53L + Q206L + N76D | G53L + P225A + N76D |
| G53L + P225S + N76D | G53L + T255C + N76D | G53L + T255E + N76D | G53L + T255Q + N76D |
| G53L + S256A + N76D | G53L + S256C + N76D | G53L + S256D + N76D | G53L + S256V + N76D |
| G53L + S256Y + N76D | G53L + S259D + N76D | G53L + T260A + N76D | G53L + T260E + N76D |
| G53L + T260P + N76D | G53L + N261D + N76D | G53L + N261C + N76D | G53L + N261E + N76D |
| G53L + N261L + N76D | G53L + N261M + N76D | G53L + N261R + N76D | G53L + N261V + N76D |

TABLE 2-continued

Subtilase Variants

| | | | |
|---|---|---|---|
| G53L + N261W + N76D | G53L + N261Y + N76D | G53L + N261F + N76D | G53L + L262Y + N76D |
| G53L + L262C + N76D | G53L + L262E + N76D | G53L + L262Q + N76D | G61D + I72A + N76D |
| G61D + I72V + N76D | G61D + S78D + N76D | G61D + S78N + N76D | G61D + V104F + N76D |
| G61D + V104P + N76D | G61D + V104T + N76D | G61D + V104Y + N76D | G61D + A114V + N76D |
| G61D + G115T + N76D | G61D + G115W + N76D | G61D + H120I + N76D | G61D + H120T + N76D |
| G61D + H120V + N76D | G61D + P129D + N76D | G61D + P131* + N76D | G61D + V147W + N76D |
| G61D + V149C + N76D | G61D + V149N + N76D | G61D + V149Q + N76D | G61D + A158E + N76D |
| G61D + G160D + N76D | G61D + G160P + N76D | G61D + S161C + N76D | G61D + S161Y + N76D |
| G61D + S161E + N76D | G61D + I162L + N76D | G61D + S163A + N76D | G61D + S163D + N76D |
| G61D + Q182C + N76D | G61D + Q182E + N76D | G61D + N184D + N76D | G61D + N185C + N76D |
| G61D + N185E + N76D | G61D + S188C + N76D | G61D + S188D + N76D | G61D + S188E + N76D |
| G61D + Q191N + N76D | G61D + A194D + N76D | G61D + A194E + N76D | G61D + A194P + N76D |
| G61D + G195E + N76D | G61D + N204D + N76D | G61D + N204V + N76D | G61D + V205I + N76D |
| G61D + V205L + N76D | G61D + Q206C + N76D | G61D + Q206E + N76D | G61D + Q206I + N76D |
| G61D + Q206K + N76D | G61D + Q206L + N76D | G61D + Q206T + N76D | G61D + Q206V + N76D |
| G61D + Q206W + N76D | G61D + Y209L + N76D | G61D + Y209W + N76D | G61D + S212A + N76D |
| G61D + S212D + N76D | G61D + S212G + N76D | G61D + S212N + N76D | G61D + S216I + N76D |
| G61D + S216T + N76D | G61D + S216V + N76D | G61D + L217C + N76D | G61D + L217M + N76D |
| G61D + N218T + N76D | G61D + S216V + N76D | G61D + M222C + N76D | G61D + M222N + N76D |
| G61D + M222R + N76D | G61D + Q206L + N76D | G61D + P225A + N76D | G61D + P225S + N76D |
| G61D + T255C + N76D | G61D + T255E + N76D | G61D + T255Q + N76D | G61D + S256A + N76D |
| G61D + S256C + N76D | G61D + S256D + N76D | G61D + S256V + N76D | G61D + S256Y + N76D |
| G61D + S259D + N76D | G61D + T260A + N76D | G61D + T260E + N76D | G61D + T260P + N76D |
| G61D + N261D + N76D | G61D + N261C + N76D | G61D + N261E + N76D | G61D + N261L + N76D |
| G61D + N261M + N76D | G61D + N261R + N76D | G61D + N261V + N76D | G61D + N261W + N76D |
| G61D + N261Y + N76D | G61D + N261F + N76D | G61D + L262Y + N76D | G61D + L262C + N76D |
| G61D + L262E + N76D | G61D + L262Q + N76D | I72A + S78D + N76D | I72A + S78N + N76D |
| I72A + V104F + N76D | I72A + V104P + N76D | I72A + V104T + N76D | I72A + V104Y + N76D |
| I72A + A114V + N76D | I72A + G115T + N76D | I72A + G115W + N76D | I72A + H120I + N76D |
| I72A + H120T + N76D | I72A + H120V + N76D | I72A + P129D + N76D | I72A + P131* + N76D |
| I72A + V147W + N76D | I72A + V149N + N76D | I72A + V149Q + N76D | I72A + V149C + N76D |
| I72A + A158E + N76D | I72A + G160D + N76D | I72A + G160P + N76D | I72A + S161C + N76D |
| I72A + S161Y + N76D | I72A + S161E + N76D | I72A + I162L + N76D | I72A + S163A + N76D |
| I72A + S163D + N76D | I72A + Q182C + N76D | I72A + Q182E + N76D | I72A + N184D + N76D |
| I72A + N185C + N76D | I72A + N185E + N76D | I72A + S188C + N76D | I72A + S188D + N76D |
| I72A + S188E + N76D | I72A + Q191N + N76D | I72A + A194D + N76D | I72A + A194E + N76D |
| I72A + A194P + N76D | I72A + G195E + N76D | I72A + N204D + N76D | I72A + N204V + N76D |
| I72A + V205I + N76D | I72A + V205L + N76D | I72A + Q206C + N76D | I72A + Q206E + N76D |
| I72A + Q206I + N76D | I72A + Q206K + N76D | I72A + Q206L + N76D | I72A + Q206T + N76D |
| I72A + Q206V + N76D | I72A + Q206W + N76D | I72A + Y209L + N76D | I72A + Y209W + N76D |
| I72A + S212A + N76D | I72A + S212D + N76D | I72A + S212G + N76D | I72A + S212N + N76D |
| I72A + S216I + N76D | I72A + S216T + N76D | I72A + S216V + N76D | I72A + L217C + N76D |
| I72A + L217M + N76D | I72A + N218T + N76D | I72A + S216V + N76D | I72A + M222C + N76D |
| I72A + M222N + N76D | I72A + M222R + N76D | I72A + Q206L + N76D | I72A + P225A + N76D |
| I72A + P225S + N76D | I72A + T255C + N76D | I72A + T255E + N76D | I72A + T255Q + N76D |
| I72A + S256A + N76D | I72A + S256C + N76D | I72A + S256D + N76D | I72A + S256V + N76D |
| I72A + S256Y + N76D | I72A + S259D + N76D | I72A + T260A + N76D | I72A + T260E + N76D |
| I72A + T260P + N76D | I72A + N261D + N76D | I72A + N261C + N76D | I72A + N261E + N76D |
| I72A + N261L + N76D | I72A + N261M + N76D | I72A + N261R + N76D | I72A + N261V + N76D |
| I72A + N261W + N76D | I72A + N261Y + N76D | I72A + N261F + N76D | I72A + L262Y + N76D |
| I72A + L262C + N76D | I72A + L262E + N76D | I72A + L262Q + N76D | I72V + S78D + N76D |
| I72V + S78N + N76D | I72V + V104F + N76D | I72V + V104P + N76D | I72V + V104T + N76D |
| I72V + V104Y + N76D | I72V + A114V + N76D | I72V + G115T + N76D | I72V + G115W + N76D |
| I72V + H120I + N76D | I72V + H120T + N76D | I72V + H120V + N76D | I72V + P129D + N76D |
| I72V + P131* + N76D | I72V + V147W + N76D | I72V + V149C + N76D | I72V + V149N + N76D |
| I72V + V149Q + N76D | I72V + A158E + N76D | I72V + G160D + N76D | I72V + G160P + N76D |
| I72V + S161C + N76D | I72V + S161Y + N76D | I72V + S161E + N76D | I72V + I162L + N76D |
| I72V + S163A + N76D | I72V + S163D + N76D | I72V + Q182C + N76D | I72V + Q182E + N76D |
| I72V + N184D + N76D | I72V + N185C + N76D | I72V + N185E + N76D | I72V + S188C + N76D |
| I72V + S188D + N76D | I72V + S188E + N76D | I72V + Q191N + N76D | I72V + A194D + N76D |
| I72V + A194E + N76D | I72V + A194P + N76D | I72V + G195E + N76D | I72V + N204D + N76D |
| I72V + N204V + N76D | I72V + V205I + N76D | I72V + V205L + N76D | I72V + Q206C + N76D |
| I72V + Q206E + N76D | I72V + Q206I + N76D | I72V + Q206K + N76D | I72V + Q206L + N76D |
| I72V + Q206T + N76D | I72V + Q206V + N76D | I72V + Q206W + N76D | I72V + Y209L + N76D |
| I72V + Y209W + N76D | I72V + S212A + N76D | I72V + S212D + N76D | I72V + S212G + N76D |
| I72V + S212N + N76D | I72V + S216I + N76D | I72V + S216T + N76D | I72V + S216V + N76D |
| I72V + L217C + N76D | I72V + L217M + N76D | I72V + N218T + N76D | I72V + S216V + N76D |
| I72V + M222C + N76D | I72V + M222N + N76D | I72V + M222R + N76D | I72V + Q206L + N76D |
| I72V + P225A + N76D | I72V + P225S + N76D | I72V + T255C + N76D | I72V + T255E + N76D |
| I72V + T255Q + N76D | I72V + S256A + N76D | I72V + S256C + N76D | I72V + S256D + N76D |
| I72V + S256V + N76D | I72V + S256Y + N76D | I72V + S259D + N76D | I72V + T260A + N76D |
| I72V + T260E + N76D | I72V + T260P + N76D | I72V + N261D + N76D | I72V + N261C + N76D |
| I72V + N261E + N76D | I72V + N261L + N76D | I72V + N261M + N76D | I72V + N261R + N76D |
| I72V + N261V + N76D | I72V + N261W + N76D | I72V + N261Y + N76D | I72V + N261F + N76D |
| I72V + L262Y + N76D | I72V + L262C + N76D | I72V + L262E + N76D | I72V + L262Q + N76D |
| S78D + V104F + N76D | S78D + V104P + N76D | S78D + V104T + N76D | S78D + V104Y + N76D |
| S78D + A114V + N76D | S78D + G115T + N76D | S78D + G115W + N76D | S78D + H120I + N76D |
| S78D + H120T + N76D | S78D + H120V + N76D | S78D + P129D + N76D | S78D + P131* + N76D |

TABLE 2-continued

Subtilase Variants

| | | | |
|---|---|---|---|
| S78D + V147W + N76D | S78D + V149C + N76D | S78D + V149N + N76D | S78D + V149Q + N76D |
| S78D + A158E + N76D | S78D + G160P + N76D | S78D + G160P + N76D | S78D + S161C + N76D |
| S78D + S161Y + N76D | S78D + S161E + N76D | S78D + I162L + N76D | S78D + S163A + N76D |
| S78D + S163D + N76D | S78D + Q182C + N76D | S78D + Q182E + N76D | S78D + N184D + N76D |
| S78D + N185C + N76D | S78D + N185E + N76D | S78D + S188C + N76D | S78D + S188D + N76D |
| S78D + S188E + N76D | S78D + Q191N + N76D | S78D + A194D + N76D | S78D + A194E + N76D |
| S78D + A194P + N76D | S78D + G195E + N76D | S78D + N204D + N76D | S78D + N204V + N76D |
| S78D + V205I + N76D | S78D + V205L + N76D | S78D + Q206C + N76D | S78D + Q206E + N76D |
| S78D + Q206I + N76D | S78D + Q206K + N76D | S78D + Q206L + N76D | S78D + Q206T + N76D |
| S78D + Q209V + N76D | S78D + Q206W + N76D | S78D + Y209L + N76D | S78D + Y209W + N76D |
| S78D + S212A + N76D | S78D + S212D + N76D | S78D + S212G + N76D | S78D + S212N + N76D |
| S78D + S216I + N76D | S78D + S216T + N76D | S78D + S216V + N76D | S78D + L217C + N76D |
| S78D + L217M + N76D | S78D + N218T + N76D | S78D + S216V + N76D | S78D + M222C + N76D |
| S78D + M222N + N76D | S78D + M222R + N76D | S78D + Q206L + N76D | S78D + P225A + N76D |
| S78D + P225S + N76D | S78D + T255C + N76D | S78D + T255E + N76D | S78D + T255Q + N76D |
| S78D + S256A + N76D | S78D + S256C + N76D | S78D + S256D + N76D | S78D + S256V + N76D |
| S78D + S256Y + N76D | S78D + S259D + N76D | S78D + T260A + N76D | S78D + T260E + N76D |
| S78D + T260P + N76D | S78D + N261D + N76D | S78D + N261C + N76D | S78D + N261E + N76D |
| S78D + N261L + N76D | S78D + N261M + N76D | S78D + N261R + N76D | S78D + N261V + N76D |
| S78D + N261W + N76D | S78D + N261Y + N76D | S78D + N261F + N76D | S78D + L262Y + N76D |
| S78D + L262C + N76D | S78D + L262E + N76D | S78D + L262Q + N76D | S78N + V104F + N76D |
| S78N + V104P + N76D | S78N + V104T + N76D | S78N + V104Y + N76D | S78N + A114V + N76D |
| S78N + G115T + N76D | S78N + G115W + N76D | S78N + H120I + N76D | S78N + H120T + N76D |
| S78N + H120V + N76D | S78N + P129D + N76D | S78N + P131* + N76D | S78N + V147W + N76D |
| S78N + V149C + N76D | S78N + V149N + N76D | S78N + V149Q + N76D | S78N + A158E + N76D |
| S78N + G160D + N76D | S78N + G160P + N76D | S78N + S161C + N76D | S78N + S161Y + N76D |
| S78N + S161E + N76D | S78N + I162L + N76D | S78N + S163A + N76D | S78N + S163D + N76D |
| S78N + Q182C + N76D | S78N + Q182E + N76D | S78N + N184D + N76D | S78N + N185C + N76D |
| S78N + N185E + N76D | S78N + S188C + N76D | S78N + S188D + N76D | S78N + S188E + N76D |
| S78N + Q191N + N76D | S78N + A194D + N76D | S78N + A194E + N76D | S78N + A194P + N76D |
| S78N + G195E + N76D | S78N + N204D + N76D | S78N + N204V + N76D | S78N + V205I + N76D |
| S78N + V205L + N76D | S78N + Q206C + N76D | S78N + Q206E + N76D | S78N + Q206I + N76D |
| S78N + Q206K + N76D | S78N + Q206L + N76D | S78N + Q206T + N76D | S78N + Q206V + N76D |
| S78N + Q206W + N76D | S78N + Y209L + N76D | S78N + Y209W + N76D | S78N + S212A + N76D |
| S78N + S212D + N76D | S78N + S212G + N76D | S78N + S212N + N76D | S78N + S216I + N76D |
| S78N + S216T + N76D | S78N + S216V + N76D | S78N + L217C + N76D | S78N + L217M + N76D |
| S78N + N218T + N76D | S78N + S216V + N76D | S78N + M222C + N76D | S78N + M222N + N76D |
| S78N + M222R + N76D | S78N + Q206L + N76D | S78N + P225A + N76D | S78N + P225S + N76D |
| S78N + T255C + N76D | S78N + T255E + N76D | S78N + T255Q + N76D | S78N + S256A + N76D |
| S78N + S256C + N76D | S78N + S256D + N76D | S78N + S256V + N76D | S78N + S256Y + N76D |
| S78N + S259D + N76D | S78N + T260A + N76D | S78N + T260E + N76D | S78N + T260P + N76D |
| S78N + N261D + N76D | S78N + N261C + N76D | S78N + N261E + N76D | S78N + N261L + N76D |
| S78N + N261M + N76D | S78N + N261R + N76D | S78N + N261V + N76D | S78N + N261W + N76D |
| S78N + N261Y + N76D | S78N + N261F + N76D | S78N + L262Y + N76D | S78N + L262C + N76D |
| S78N + L262E + N76D | S78N + L262Q + N76D | V104F + A114V + N76D | V104F + G115T + N76D |
| V104F + G115W + N76D | V104F + H120I + N76D | V104F + H120T + N76D | V104F + H120V + N76D |
| V104F + P129D + N76D | V104F + P131* + N76D | V104F + V147W + N76D | V104F + V149C + N76D |
| V104F + V149N + N76D | V104F + V149Q + N76D | V104F + A158E + N76D | V104F + G160D + N76D |
| V104F + G160P + N76D | V104F + S161C + N76D | V104F + S161Y + N76D | V104F + S161E + N76D |
| V104F + I162L + N76D | V104F + S163A + N76D | V104F + S163D + N76D | V104F + Q182C + N76D |
| V104F + Q182E + N76D | V104F + N184D + N76D | V104F + N185C + N76D | V104F + N185E + N76D |
| V104F + S188C + N76D | V104F + S188D + N76D | V104F + Q191N + N76D | V104F + G195E + N76D |
| V104F + A194D + N76D | V104F + A194E + N76D | V104F + A194P + N76D | V104F + G195E + N76D |
| V104F + N204D + N76D | V104F + N204V + N76D | V104F + V205I + N76D | V104F + V205L + N76D |
| V104F + Q206C + N76D | V104F + Q206E + N76D | V104F + Q206I + N76D | V104F + Q206K + N76D |
| V104F + Q206L + N76D | V104F + Q206T + N76D | V104F + Q206V + N76D | V104F + Q206W + N76D |
| V104F + Y209L + N76D | V104F + Y209W + N76D | V104F + S212A + N76D | V104F + S212D + N76D |
| V104F + S212G + N76D | V104F + S212N + N76D | V104F + S216I + N76D | V104F + S216T + N76D |
| V104F + S216V + N76D | V104F + L217C + N76D | V104F + L217M + N76D | V104F + N218T + N76D |
| V104F + S216V + N76D | V104F + M222C + N76D | V104F + M222N + N76D | V104F + M222R + N76D |
| V104F + Q206L + N76D | V104F + P225A + N76D | V104F + P225S + N76D | V104F + T255C + N76D |
| V104F + T255E + N76D | V104F + T255Q + N76D | V104F + S256A + N76D | V104F + S256C + N76D |
| V104F + S256D + N76D | V104F + S256V + N76D | V104F + S256Y + N76D | V104F + S259D + N76D |
| V104F + T260A + N76D | V104F + T260E + N76D | V104F + T260P + N76D | V104F + N261D + N76D |
| V104F + N261C + N76D | V104F + N261E + N76D | V104F + N261L + N76D | V104F + N261M + N76D |
| V104F + N261R + N76D | V104F + N261V + N76D | V104F + N261W + N76D | V104F + N261Y + N76D |
| V104F + N261F + N76D | V104F + L262Y + N76D | V104F + L262C + N76D | V104F + L262E + N76D |
| V104F + L262Q + N76D | V104P + A114V + N76D | V104P + G115T + N76D | V104P + G115W + N76D |
| V104P + H120I + N76D | V104P + H120T + N76D | V104P + H120V + N76D | V104P + P129D + N76D |
| V104P + P131* + N76D | V104P + V147W + N76D | V104P + V149C + N76D | V104P + V149N + N76D |
| V104P + V149Q + N76D | V104P + A158E + N76D | V104P + G160D + N76D | V104P + G160P + N76D |
| V104P + S161C + N76D | V104P + S161Y + N76D | V104P + S161E + N76D | V104P + I162L + N76D |
| V104P + S163A + N76D | V104P + S163D + N76D | V104P + Q182C + N76D | V104P + Q182E + N76D |
| V104P + N184D + N76D | V104P + N185C + N76D | V104P + N185E + N76D | V104P + S188C + N76D |
| V104P + S188D + N76D | V104P + S188E + N76D | V104P + Q191N + N76D | V104P + A194D + N76D |
| V104P + A194E + N76D | V104P + A194P + N76D | V104P + G195E + N76D | V104P + N204D + N76D |
| V104P + N204V + N76D | V104P + V205I + N76D | V104P + V205L + N76D | V104P + Q206C + N76D |
| V104P + Q206E + N76D | V104P + Q206I + N76D | V104P + Q206K + N76D | V104P + Q206L + N76D |

TABLE 2-continued

Subtilase Variants

| | | | |
|---|---|---|---|
| V104P + Q206T + N76D | V104P + Q206V + N76D | V104P + Q206W + N76D | V104P + Y209L + N76D |
| V104P + Y209W + N76D | V104P + S212A + N76D | V104P + S212D + N76D | V104P + S212G + N76D |
| V104P + S212N + N76D | V104P + S216I + N76D | V104P + S216T + N76D | V104P + S216V + N76D |
| V104P + L217C + N76D | V104P + L217M + N76D | V104P + N218T + N76D | V104P + S216V + N76D |
| V104P + M222C + N76D | V104P + M222N + N76D | V104P + M222R + N76D | V104P + Q206L + N76D |
| V104P + P225A + N76D | V104P + P225S + N76D | V104P + T255C + N76D | V104P + T255E + N76D |
| V104P + T255Q + N76D | V104P + S256A + N76D | V104P + S256C + N76D | V104P + S256D + N76D |
| V104P + S256V + N76D | V104P + S256Y + N76D | V104P + S259D + N76D | V104P + T260A + N76D |
| V104P + T260E + N76D | V104P + T260P + N76D | V104P + N261D + N76D | V104P + N261C + N76D |
| V104P + N261E + N76D | V104P + N261L + N76D | V104P + N261M + N76D | V104P + N261R + N76D |
| V104P + N261V + N76D | V104P + N261W + N76D | V104P + N261Y + N76D | V104P + N261F + N76D |
| V104P + L262Y + N76D | V104P + L262C + N76D | V104P + L262E + N76D | V104P + L262Q + N76D |
| V104T + A114V + N76D | V104T + G115T + N76D | V104T + G115W + N76D | V104T + H120I + N76D |
| V104T + H120T + N76D | V104T + H120V + N76D | V104T + P129D + N76D | V104T + P131* + N76D |
| V104T + V147W + N76D | V104T + V149C + N76D | V104T + V149N + N76D | V104T + V149Q + N76D |
| V104T + A158E + N76D | V104T + G160D + N76D | V104T + G160P + N76D | V104T + S161C + N76D |
| V104T + S161Y + N76D | V104T + S161E + N76D | V104T + I162L + N76D | V104T + S163A + N76D |
| V104T + S163D + N76D | V104T + Q182C + N76D | V104T + Q182E + N76D | V104T + N184D + N76D |
| V104T + N185C + N76D | V104T + N185E + N76D | V104T + S188C + N76D | V104T + S188D + N76D |
| V104T + S188E + N76D | V104T + Q191N + N76D | V104T + A194D + N76D | V104T + A194E + N76D |
| V104T + A194P + N76D | V104T + G195E + N76D | V104T + N204D + N76D | V104T + N204V + N76D |
| V104T + V205I + N76D | V104T + V205L + N76D | V104T + Q206C + N76D | V104T + Q206E + N76D |
| V104T + Q206I + N76D | V104T + Q206L + N76D | V104T + Q206K + N76D | V104T + Q206T + N76D |
| V104T + Q206V + N76D | V104T + Q206W + N76D | V104T + Y209L + N76D | V104T + Y209W + N76D |
| V104T + S212A + N76D | V104T + S212D + N76D | V104T + S212G + N76D | V104T + S212N + N76D |
| V104T + S216I + N76D | V104T + S216T + N76D | V104T + S216V + N76D | V104T + L217C + N76D |
| V104T + L217M + N76D | V104T + N218T + N76D | V104T + S216V + N76D | V104T + M222C + N76D |
| V104T + M222N + N76D | V104T + M222R + N76D | V104T + Q206L + N76D | V104T + P225A + N76D |
| V104T + P225S + N76D | V104T + T255C + N76D | V104T + T255E + N76D | V104T + T255Q + N76D |
| V104T + S256A + N76D | V104T + S256C + N76D | V104T + S256D + N76D | V104T + S256V + N76D |
| V104T + S256Y + N76D | V104T + S259D + N76D | V104T + T260A + N76D | V104T + T260E + N76D |
| V104T + T260P + N76D | V104T + N261D + N76D | V104T + N261C + N76D | V104T + N261E + N76D |
| V104T + N261L + N76D | V104T + N261M + N76D | V104T + N261R + N76D | V104T + N261V + N76D |
| V104T + N261W + N76D | V104T + N261Y + N76D | V104T + N261F + N76D | V104T + L262Y + N76D |
| V104T + L262C + N76D | V104T + L262E + N76D | V104T + L262Q + N76D | V104Y + A114V + N76D |
| V104Y + G115T + N76D | V104Y + G115W + N76D | V104Y + H120I + N76D | V104Y + H120T + N76D |
| V104Y + H120V + N76D | V104Y + P129D + N76D | V104Y + P131* + N76D | V104Y + V147W + N76D |
| V104Y + V149C + N76D | V104Y + V149N + N76D | V104Y + V149Q + N76D | V104Y + A158E + N76D |
| V104Y + G160D + N76D | V104Y + G160P + N76D | V104Y + S161C + N76D | V104Y + S161Y + N76D |
| V104Y + S161E + N76D | V104Y + I162L + N76D | V104Y + S163A + N76D | V104Y + S163D + N76D |
| V104Y + Q182C + N76D | V104Y + Q182E + N76D | V104Y + N184D + N76D | V104Y + N185C + N76D |
| V104Y + N185E + N76D | V104Y + S188C + N76D | V104Y + S188D + N76D | V104Y + S188E + N76D |
| V104Y + Q191N + N76D | V104Y + A194D + N76D | V104Y + A194E + N76D | V104Y + A194P + N76D |
| V104Y + G195E + N76D | V104Y + N204D + N76D | V104Y + N204V + N76D | V104Y + V205I + N76D |
| V104Y + V205L + N76D | V104Y + Q206C + N76D | V104Y + Q206E + N76D | V104Y + Q206I + N76D |
| V104Y + Q206K + N76D | V104Y + Q206L + N76D | V104Y + Q206T + N76D | V104Y + Q206V + N76D |
| V104Y + Q206W + N76D | V104Y + Y209L + N76D | V104Y + Y209W + N76D | V104Y + S212A + N76D |
| V104Y + S212D + N76D | V104Y + S212G + N76D | V104Y + S212N + N76D | V104Y + S216I + N76D |
| V104Y + S216T + N76D | V104Y + S216V + N76D | V104Y + L217C + N76D | V104Y + L217M + N76D |
| V104Y + N218T + N76D | V104Y + S216V + N76D | V104Y + M222C + N76D | V104Y + M222N + N76D |
| V104Y + M222R + N76D | V104Y + Q206L + N76D | V104Y + P225A + N76D | V104Y + P225S + N76D |
| V104Y + T255C + N76D | V104Y + T255E + N76D | V104Y + T255Q + N76D | V104Y + S256A + N76D |
| V104Y + S256C + N76D | V104Y + S256D + N76D | V104Y + S256V + N76D | V104Y + S256Y + N76D |
| V104Y + S259D + N76D | V104Y + T260A + N76D | V104Y + T260E + N76D | V104Y + T260P + N76D |
| V104Y + N261D + N76D | V104Y + N261C + N76D | V104Y + N261E + N76D | V104Y + N261L + N76D |
| V104Y + N261M + N76D | V104Y + N261R + N76D | V104Y + N261V + N76D | V104Y + N261W + N76D |
| V104Y + N261Y + N76D | V104Y + N261F + N76D | V104Y + L262Y + N76D | V104Y + L262C + N76D |
| V104Y + L262E + N76D | V104Y + L262Q + N76D | A114V + G115T + N76D | A114V + G115W + N76D |
| A114V + H120I + N76D | A114V + H120T + N76D | A114V + H120V + N76D | A114V + P129D + N76D |
| A114V + P131* + N76D | A114V + V147W + N76D | A114V + V149C + N76D | A114V + V149N + N76D |
| A114V + V149Q + N76D | A114V + A158E + N76D | A114V + G160D + N76D | A114V + G160P + N76D |
| A114V + S161C + N76D | A114V + S161Y + N76D | A114V + S161E + N76D | A114V + I162L + N76D |
| A114V + S163A + N76D | A114V + S163D + N76D | A114V + Q182C + N76D | A114V + Q182E + N76D |
| A114V + N184D + N76D | A114V + N185C + N76D | A114V + N185E + N76D | A114V + S188C + N76D |
| A114V + S188D + N76D | A114V + S188E + N76D | A114V + Q191N + N76D | A114V + A194D + N76D |
| A114V + A194E + N76D | A114V + A194P + N76D | A114V + G195E + N76D | A114V + N204D + N76D |
| A114V + N204V + N76D | A114V + V205I + N76D | A114V + V205L + N76D | A114V + Q206C + N76D |
| A114V + Q206E + N76D | A114V + Q206I + N76D | A114V + Q206K + N76D | A114V + Q206L + N76D |
| A114V + Q206T + N76D | A114V + Q206V + N76D | A114V + Q206W + N76D | A114V + Y209L + N76D |
| A114V + Y209W + N76D | A114V + S212A + N76D | A114V + S212D + N76D | A114V + S212G + N76D |
| A114V + S212N + N76D | A114V + S216I + N76D | A114V + S216T + N76D | A114V + S216V + N76D |
| A114V + L217C + N76D | A114V + L217M + N76D | A114V + N218T + N76D | A114V + S216V + N76D |
| A114V + M222C + N76D | A114V + M222N + N76D | A114V + M222R + N76D | A114V + Q206L + N76D |
| A114V + P225A + N76D | A114V + P225S + N76D | A114V + T255C + N76D | A114V + T255E + N76D |
| A114V + T255Q + N76D | A114V + S256A + N76D | A114V + S256C + N76D | A114V + S256D + N76D |
| A114V + S256V + N76D | A114V + S256Y + N76D | A114V + S259D + N76D | A114V + T260A + N76D |
| A114V + T260E + N76D | A114V + T260P + N76D | A114V + N261D + N76D | A114V + N261C + N76D |
| A114V + N261E + N76D | A114V + N261L + N76D | A114V + N261M + N76D | A114V + N261R + N76D |

TABLE 2-continued

Subtilase Variants

| | | | |
|---|---|---|---|
| A114V + N261V + N76D | A114V + N261W + N76D | A114V + N261Y + N76D | A114V + N261F + N76D |
| A114V + L262Y + N76D | A114V + L262C + N76D | A114V + L262E + N76D | A114V + L262Q + N76D |
| G115T + H120I + N76D | G115T + H120T + N76D | G115T + H120V + N76D | G115T + P129D + N76D |
| G115T + P131* + N76D | G115T + V147W + N76D | G115T + V149C + N76D | G115T + V149N + N76D |
| G115T + V149Q + N76D | G115T + A158E + N76D | G115T + G160D + N76D | G115T + G160P + N76D |
| G115T + S161C + N76D | G115T + S161Y + N76D | G115T + S161E + N76D | G115T + I162L + N76D |
| G115T + S163A + N76D | G115T + S163D + N76D | G115T + Q182C + N76D | G115T + Q182E + N76D |
| G115T + N184D + N76D | G115T + N185C + N76D | G115T + N185E + N76D | G115T + S188C + N76D |
| G115T + S188D + N76D | G115T + S188E + N76D | G115T + Q191N + N76D | G115T + A194D + N76D |
| G115T + A194E + N76D | G115T + A194P + N76D | G115T + G195E + N76D | G115T + N204D + N76D |
| G115T + N204V + N76D | G115T + V205I + N76D | G115T + V205L + N76D | G115T + Q206C + N76D |
| G115T + Q206E + N76D | G115T + Q206I + N76D | G115T + Q206K + N76D | G115T + Q206L + N76D |
| G115T + Q206T + N76D | G115T + Q206V + N76D | G115T + Q206W + N76D | G115T + Y209L + N76D |
| G115T + Y209W + N76D | G115T + S212A + N76D | G115T + S212D + N76D | G115T + S212G + N76D |
| G115T + S212N + N76D | G115T + S216I + N76D | G115T + S216T + N76D | G115T + S216V + N76D |
| G115T + L217C + N76D | G115T + L217M + N76D | G115T + N218T + N76D | G115T + S216V + N76D |
| G115T + M222C + N76D | G115T + M222N + N76D | G115T + M222R + N76D | G115T + Q206L + N76D |
| G115T + P225A + N76D | G115T + P225S + N76D | G115T + T255C + N76D | G115T + T255E + N76D |
| G115T + T255Q + N76D | G115T + S256A + N76D | G115T + S256C + N76D | G115T + S256D + N76D |
| G115T + S256V + N76D | G115T + S256Y + N76D | G115T + S259D + N76D | G115T + T260A + N76D |
| G115T + T260E + N76D | G115T + T260P + N76D | G115T + N261D + N76D | G115T + N261C + N76D |
| G115T + N261E + N76D | G115T + N261L + N76D | G115T + N261M + N76D | G115T + N261R + N76D |
| G115T + N261V + N76D | G115T + N261W + N76D | G115T + N261Y + N76D | G115T + N261F + N76D |
| G115T + L262Y + N76D | G115T + L262C + N76D | G115T + L262E + N76D | G115T + L262Q + N76D |
| G115W + H120I + N76D | G115W + H120T + N76D | G115W + H120V + N76D | G115W + P129D + N76D |
| G115W + P131* + N76D | G115W + V147W + N76D | G115W + V149C + N76D | G115W + V149N + N76D |
| G115W + V149Q + N76D | G115W + A158E + N76D | G115W + G160D + N76D | G115W + G160P + N76D |
| G115W + S161C + N76D | G115W + S161Y + N76D | G115W + S161E + N76D | G115W + I162L + N76D |
| G115W + S163A + N76D | G115W + S163D + N76D | G115W + Q182C + N76D | G115W + Q182E + N76D |
| G115W + N184D + N76D | G115W + N185C + N76D | G115W + N185E + N76D | G115W + S188C + N76D |
| G115W + S188D + N76D | G115W + S188E + N76D | G115W + Q191N + N76D | G115W + A194D + N76D |
| G115W + A194E + N76D | G115W + A194P + N76D | G115W + G195E + N76D | G115W + N204D + N76D |
| G115W + N204V + N76D | G115W + V205I + N76D | G115W + V205L + N76D | G115W + Q206C + N76D |
| G115W + Q206E + N76D | G115W + Q206I + N76D | G115W + Q206K + N76D | G115W + Q206L + N76D |
| G115W + Q206T + N76D | G115W + Q206V + N76D | G115W + Q206W + N76D | G115W + Y209L + N76D |
| G115W + Y209W + N76D | G115W + S212A + N76D | G115W + S212D + N76D | G115W + S212G + N76D |
| G115W + S212N + N76D | G115W + S216I + N76D | G115W + S216T + N76D | G115W + S216V + N76D |
| G115W + L217C + N76D | G115W + L217M + N76D | G115W + N218T + N76D | G115W + S216V + N76D |
| G115W + M222C + N76D | G115W + M222N + N76D | G115W + M222R + N76D | G115W + Q206L + N76D |
| G115W + P225A + N76D | G115W + P225S + N76D | G115W + T255C + N76D | G115W + T255E + N76D |
| G115W + T255Q + N76D | G115W + S256A + N76D | G115W + S256C + N76D | G115W + S256D + N76D |
| G115W + S256V + N76D | G115W + S256Y + N76D | G115W + S259D + N76D | G115W + T260A + N76D |
| G115W + T260E + N76D | G115W + T260P + N76D | G115W + N261D + N76D | G115W + N261C + N76D |
| G115W + N261E + N76D | G115W + N261L + N76D | G115W + N261M + N76D | G115W + N261R + N76D |
| G115W + N261V + N76D | G115W + N261W + N76D | G115W + N261Y + N76D | G115W + N261F + N76D |
| G115W + L262Y + N76D | G115W + L262C + N76D | G115W + L262E + N76D | G115W + L262Q + N76D |
| H120I + P129D + N76D | H120I + P131* + N76D | H120I + V147W + N76D | H120I + V149C + N76D |
| H120I + V149N + N76D | H120I + V149Q + N76D | H120I + A158E + N76D | H120I + G160D + N76D |
| H120I + G160P + N76D | H120I + S161C + N76D | H120I + S161Y + N76D | H120I + S161E + N76D |
| H120I + I162L + N76D | H120I + S163A + N76D | H120I + S163D + N76D | H120I + Q182C + N76D |
| H120I + Q182E + N76D | H120I + N184D + N76D | H120I + N185C + N76D | H120I + N185E + N76D |
| H120I + S188C + N76D | H120I + S188D + N76D | H120I + S188E + N76D | H120I + Q191N + N76D |
| H120I + A194D + N76D | H120I + A194E + N76D | H120I + A194P + N76D | H120I + G195E + N76D |
| H120I + N204D + N76D | H120I + N204V + N76D | H120I + V205I + N76D | H120I + V205L + N76D |
| H120I + Q206C + N76D | H120I + Q206E + N76D | H120I + Q206I + N76D | H120I + Q206K + N76D |
| H120I + Q206L + N76D | H120I + Q206T + N76D | H120I + Q206V + N76D | H120I + Q206W + N76D |
| H120I + Y209L + N76D | H120I + Y209W + N76D | H120I + S212A + N76D | H120I + S212D + N76D |
| H120I + S212G + N76D | H120I + S212N + N76D | H120I + S216I + N76D | H120I + S216T + N76D |
| H120I + S216V + N76D | H120I + L217C + N76D | H120I + L217M + N76D | H120I + N218T + N76D |
| H120I + S216V + N76D | H120I + M222C + N76D | H120I + M222N + N76D | H120I + M222R + N76D |
| H120I + Q206L + N76D | H120I + P225A + N76D | H120I + P225S + N76D | H120I + T255C + N76D |
| H120I + T255E + N76D | H120I + T255Q + N76D | H120I + S256A + N76D | H120I + S256C + N76D |
| H120I + S256D + N76D | H120I + S256V + N76D | H120I + S256Y + N76D | H120I + S259D + N76D |
| H120I + T260A + N76D | H120I + T260E + N76D | H120I + T260P + N76D | H120I + N261D + N76D |
| H120I + N261C + N76D | H120I + N261L + N76D | H120I + N261E + N76D | H120I + N261M + N76D |
| H120I + N261R + N76D | H120I + N261V + N76D | H120I + N261W + N76D | H120I + N261Y + N76D |
| H120I + N261F + N76D | H120I + L262Y + N76D | H120I + L262C + N76D | H120I + L262E + N76D |
| H120I + L262Q + N76D | H120T + P129D + N76D | H120T + P131* + N76D | H120T + V147W + N76D |
| H120T + V149C + N76D | H120T + V149N + N76D | H120T + V149Q + N76D | H120T + A158E + N76D |
| H120T + G160D + N76D | H120T + G160P + N76D | H120T + S161C + N76D | H120T + S161Y + N76D |
| H120T + S161E + N76D | H120T + I162L + N76D | H120T + S163A + N76D | H120T + S163D + N76D |
| H120T + Q182C + N76D | H120T + Q182E + N76D | H120T + N184D + N76D | H120T + N185C + N76D |
| H120T + N185E + N76D | H120T + S188C + N76D | H120T + S188D + N76D | H120T + S188E + N76D |
| H120T + Q191N + N76D | H120T + A194D + N76D | H120T + A194E + N76D | H120T + A194P + N76D |
| H120T + G195E + N76D | H120T + N204D + N76D | H120T + N204V + N76D | H120T + V205I + N76D |
| H120T + V205L + N76D | H120T + Q206C + N76D | H120T + Q206E + N76D | H120T + Q206I + N76D |
| H120T + Q206K + N76D | H120T + Q206L + N76D | H120T + Q206T + N76D | H120T + Q206V + N76D |
| H120T + Q206W + N76D | H120T + Y209L + N76D | H120T + Y209W + N76D | H120T + S212A + N76D |

TABLE 2-continued

Subtilase Variants

| | | | |
|---|---|---|---|
| H120T + S212D + N76D | H120T + S212G + N76D | H120T + S212N + N76D | H120T + S216I + N76D |
| H120T + L217C + N76D | H120T + S216V + N76D | H120T + L217M + N76D | H120T + L217W + N76D |
| H120T + N218T + N76D | H120T + S216V + N76D | H120T + M222C + N76D | H120T + M222N + N76D |
| H120T + M222R + N76D | H120T + Q206L + N76D | H120T + P225A + N76D | H120T + P225S + N76D |
| H120T + T255C + N76D | H120T + T255E + N76D | H120T + T255Q + N76D | H120T + S256A + N76D |
| H120T + S256C + N76D | H120T + S256D + N76D | H120T + S256V + N76D | H120T + S256Y + N76D |
| H120T + S259D + N76D | H120T + T260A + N76D | H120T + T260E + N76D | H120T + T260P + N76D |
| H120T + N261D + N76D | H120T + N261C + N76D | H120T + N261E + N76D | H120T + N261L + N76D |
| H120T + N261M + N76D | H120T + N261R + N76D | H120T + N261V + N76D | H120T + N261W + N76D |
| H120T + N261Y + N76D | H120T + N261F + N76D | H120T + L262Y + N76D | H120T + L262C + N76D |
| H120T + L262E + N76D | H120T + L262Q + N76D | H120V + P129D + N76D | H120V + P131* + N76D |
| H120V + V147W + N76D | H120V + V149C + N76D | H120V + V149N + N76D | H120V + V149Q + N76D |
| H120V + A158E + N76D | H120V + G160D + N76D | H120V + G160P + N76D | H120V + S161C + N76D |
| H120V + S161Y + N76D | H120V + S161E + N76D | H120V + I162L + N76D | H120V + S163A + N76D |
| H120V + S163D + N76D | H120V + Q182C + N76D | H120V + Q182E + N76D | H120V + N184D + N76D |
| H120V + N185C + N76D | H120V + N185E + N76D | H120V + S188C + N76D | H120V + S188D + N76D |
| H120V + S188E + N76D | H120V + Q191N + N76D | H120V + A194D + N76D | H120V + A194E + N76D |
| H120V + A194P + N76D | H120V + G195E + N76D | H120V + N204D + N76D | H120V + N204V + N76D |
| H120V + V205I + N76D | H120V + V205L + N76D | H120V + Q206C + N76D | H120V + Q206E + N76D |
| H120V + Q206I + N76D | H120V + Q206K + N76D | H120V + Q206L + N76D | H120V + Q206T + N76D |
| H120V + Q206V + N76D | H120V + Q206W + N76D | H120V + Y209L + N76D | H120V + Y209W + N76D |
| H120V + S212A + N76D | H120V + S212D + N76D | H120V + S212G + N76D | H120V + S212N + N76D |
| H120V + S216I + N76D | H120V + S216T + N76D | H120V + S216V + N76D | H120V + L217C + N76D |
| H120V + L217M + N76D | H120V + N218T + N76D | H120V + S216V + N76D | H120V + M222C + N76D |
| H120V + M222N + N76D | H120V + M222R + N76D | H120V + Q206L + N76D | H120V + P225A + N76D |
| H120V + P225S + N76D | H120V + T255C + N76D | H120V + T255E + N76D | H120V + T255Q + N76D |
| H120V + S256A + N76D | H120V + S256C + N76D | H120V + S256D + N76D | H120V + S256V + N76D |
| H120V + S256Y + N76D | H120V + S259D + N76D | H120V + T260A + N76D | H120V + T260E + N76D |
| H120V + T260P + N76D | H120V + N261D + N76D | H120V + N261C + N76D | H120V + N261E + N76D |
| H120V + N261L + N76D | H120V + N261M + N76D | H120V + N261R + N76D | H120V + N261V + N76D |
| H120V + N261W + N76D | H120V + N261Y + N76D | H120V + N261F + N76D | H120V + L262Y + N76D |
| H120V + L262C + N76D | H120V + L262E + N76D | H120V + L262Q + N76D | P129D + P131* + N76D |
| P129D + V147W + N76D | P129D + V149C + N76D | P129D + V149N + N76D | P129D + V149Q + N76D |
| P129D + A158E + N76D | P129D + G160D + N76D | P129D + G160P + N76D | P129D + S161C + N76D |
| P129D + S161Y + N76D | P129D + S161E + N76D | P129D + I162L + N76D | P129D + S163A + N76D |
| P129D + S163D + N76D | P129D + Q182C + N76D | P129D + Q182E + N76D | P129D + N184D + N76D |
| P129D + N185C + N76D | P129D + N185E + N76D | P129D + S188C + N76D | P129D + S188D + N76D |
| P129D + S188E + N76D | P129D + Q191N + N76D | P129D + A194D + N76D | P129D + A194E + N76D |
| P129D + A194P + N76D | P129D + G195E + N76D | P129D + N204D + N76D | P129D + N204V + N76D |
| P129D + V205I + N76D | P129D + V205L + N76D | P129D + Q206C + N76D | P129D + Q206E + N76D |
| P129D + Q206I + N76D | P129D + Q206K + N76D | P129D + Q206L + N76D | P129D + Q206T + N76D |
| P129D + Q206V + N76D | P129D + Q206W + N76D | P129D + Y209L + N76D | P129D + Y209W + N76D |
| P129D + S212A + N76D | P129D + S212D + N76D | P129D + S212G + N76D | P129D + S212N + N76D |
| P129D + S216I + N76D | P129D + S216T + N76D | P129D + S216V + N76D | P129D + L217C + N76D |
| P129D + L217M + N76D | P129D + N218T + N76D | P129D + S216V + N76D | P129D + M222C + N76D |
| P129D + M222N + N76D | P129D + M222R + N76D | P129D + Q206L + N76D | P129D + P225A + N76D |
| P129D + P225S + N76D | P129D + T255C + N76D | P129D + T255E + N76D | P129D + T255Q + N76D |
| P129D + S256A + N76D | P129D + S256C + N76D | P129D + S256D + N76D | P129D + S256V + N76D |
| P129D + S256Y + N76D | P129D + S259D + N76D | P129D + T260A + N76D | P129D + T260E + N76D |
| P129D + T260P + N76D | P129D + N261D + N76D | P129D + N261C + N76D | P129D + N261E + N76D |
| P129D + N261L + N76D | P129D + N261M + N76D | P129D + N261R + N76D | P129D + N261V + N76D |
| P129D + N261W + N76D | P129D + N261Y + N76D | P129D + N261F + N76D | P129D + L262Y + N76D |
| P129D + L262C + N76D | P129D + L262E + N76D | P129D + L262Q + N76D | P131* + V147W + N76D |
| P131* + V149C + N76D | P131* + V149N + N76D | P131* + V149Q + N76D | P131* + A158E + N76D |
| P131* + G160D + N76D | P131* + G160P + N76D | P131* + S161C + N76D | P131* + S161Y + N76D |
| P131* + S161E + N76D | P131* + I162L + N76D | P131* + S163A + N76D | P131* + S163D + N76D |
| P131* + Q182C + N76D | P131* + Q182E + N76D | P131* + N184D + N76D | P131* + N185C + N76D |
| P131* + N185E + N76D | P131* + S188C + N76D | P131* + S188D + N76D | P131* + S188E + N76D |
| P131* + Q191N + N76D | P131* + A194D + N76D | P131* + A194E + N76D | P131* + A194P + N76D |
| P131* + G195E + N76D | P131* + N204D + N76D | P131* + N204V + N76D | P131* + V205I + N76D |
| P131* + V205L + N76D | P131* + Q206C + N76D | P131* + Q206E + N76D | P131* + Q206I + N76D |
| P131* + Q206K + N76D | P131* + Q206L + N76D | P131* + Q206T + N76D | P131* + Q206V + N76D |
| P131* + Q206W + N76D | P131* + Y209L + N76D | P131* + Y209W + N76D | P131* + S212A + N76D |
| P131* + S212D + N76D | P131* + S212G + N76D | P131* + S212N + N76D | P131* + S216I + N76D |
| P131* + S216T + N76D | P131* + S216V + N76D | P131* + L217C + N76D | P131* + L217M + N76D |
| P131* + N218T + N76D | P131* + S216V + N76D | P131* + M222C + N76D | P131* + M222N + N76D |
| P131* + M222R + N76D | P131* + Q206L + N76D | P131* + P225A + N76D | P131* + P225S + N76D |
| P131* + T255C + N76D | P131* + T255E + N76D | P131* + T255Q + N76D | P131* + S256A + N76D |
| P131* + S256C + N76D | P131* + S256D + N76D | P131* + S256V + N76D | P131* + S256Y + N76D |
| P131* + S259D + N76D | P131* + T260A + N76D | P131* + T260E + N76D | P131* + T260P + N76D |
| P131* + N261D + N76D | P131* + N261C + N76D | P131* + N261E + N76D | P131* + N261L + N76D |
| P131* + N261M + N76D | P131* + N261R + N76D | P131* + N261V + N76D | P131* + N261W + N76D |
| P131* + N261Y + N76D | P131* + N261F + N76D | P131* + L262Y + N76D | P131* + L262C + N76D |
| P131* + L262E + N76D | P131* + L262Q + N76D | V147W + V149C + N76D | V147W + V149N + N76D |
| V147W + V149Q + N76D | V147W + A158E + N76D | V147W + G160D + N76D | V147W + G160P + N76D |
| V147W + S161C + N76D | V147W + S161Y + N76D | V147W + S161E + N76D | V147W + I162L + N76D |
| V147W + S163A + N76D | V147W + S163D + N76D | V147W + Q182C + N76D | V147W + Q182E + N76D |
| V147W + N184D + N76D | V147W + N185C + N76D | V147W + N185E + N76D | V147W + S188C + N76D |

TABLE 2-continued

Subtilase Variants

| | | | |
|---|---|---|---|
| V147W + S188D + N76D | V147W + S188E + N76D | V147W + Q191N + N76D | V147W + A194D + N76D |
| V147W + A194P + N76D | V147W + G195E + N76D | V147W + N204D + N76D | V147W + N204V + N76D |
| V147W + N204V + N76D | V147W + V205I + N76D | V147W + V205L + N76D | V147W + Q206C + N76D |
| V147W + Q206E + N76D | V147W + Q206I + N76D | V147W + Q206K + N76D | V147W + Q206L + N76D |
| V147W + Q206T + N76D | V147W + Q206V + N76D | V147W + Q206W + N76D | V147W + Y209L + N76D |
| V147W + Y209W + N76D | V147W + S212A + N76D | V147W + S212D + N76D | V147W + S212G + N76D |
| V147W + S212N + N76D | V147W + S216I + N76D | V147W + S216T + N76D | V147W + S216V + N76D |
| V147W + L217C + N76D | V147W + L217M + N76D | V147W + N218T + N76D | V147W + S216V + N76D |
| V147W + M222C + N76D | V147W + M222N + N76D | V147W + M222R + N76D | V147W + Q206L + N76D |
| V147W + P225A + N76D | V147W + P225S + N76D | V147W + T255C + N76D | V147W + T255E + N76D |
| V147W + T255Q + N76D | V147W + S256A + N76D | V147W + S256C + N76D | V147W + S256D + N76D |
| V147W + S256V + N76D | V147W + S256Y + N76D | V147W + S259D + N76D | V147W + T260A + N76D |
| V147W + T260E + N76D | V147W + T260P + N76D | V147W + N261D + N76D | V147W + N261C + N76D |
| V147W + N261E + N76D | V147W + N261L + N76D | V147W + N261M + N76D | V147W + N261R + N76D |
| V147W + N261Y + N76D | V147W + N261W + N76D | V147W + N261V + N76D | V147W + N261F + N76D |
| V147W + L262Y + N76D | V147W + L262C + N76D | V147W + L262E + N76D | V147W + L262Q + N76D |
| V149C + A158E + N76D | V149C + G160D + N76D | V149C + G160P + N76D | V149C + S161C + N76D |
| V149C + S161Y + N76D | V149C + S161E + N76D | V149C + I162L + N76D | V149C + S163A + N76D |
| V149C + S163D + N76D | V149C + Q182C + N76D | V149C + Q182E + N76D | V149C + N184D + N76D |
| V149C + N185C + N76D | V149C + N185E + N76D | V149C + S188C + N76D | V149C + S188D + N76D |
| V149C + S188E + N76D | V149C + Q191N + N76D | V149C + A194D + N76D | V149C + A194E + N76D |
| V149C + A194P + N76D | V149C + G195E + N76D | V149C + N204D + N76D | V149C + N204V + N76D |
| V149C + V205I + N76D | V149C + V205L + N76D | V149C + Q206C + N76D | V149C + Q206E + N76D |
| V149C + Q206I + N76D | V149C + Q206K + N76D | V149C + Q206L + N76D | V149C + Q206T + N76D |
| V149C + Q206V + N76D | V149C + Q206W + N76D | V149C + Y209L + N76D | V149C + Y209W + N76D |
| V149C + S212A + N76D | V149C + S212D + N76D | V149C + S212G + N76D | V149C + S212N + N76D |
| V149C + S216I + N76D | V149C + S216T + N76D | V149C + S216V + N76D | V149C + L217C + N76D |
| V149C + L217M + N76D | V149C + N218T + N76D | V149C + S216V + N76D | V149C + M222C + N76D |
| V149C + M222N + N76D | V149C + M222R + N76D | V149C + Q206L + N76D | V149C + P225A + N76D |
| V149C + P225S + N76D | V149C + T255C + N76D | V149C + T255E + N76D | V149C + T255Q + N76D |
| V149C + S256A + N76D | V149C + S256C + N76D | V149C + S256V + N76D | V149C + S256D + N76D |
| V149C + S256Y + N76D | V149C + S259D + N76D | V149C + T260A + N76D | V149C + T260E + N76D |
| V149C + T260P + N76D | V149C + N261D + N76D | V149C + N261C + N76D | V149C + N261E + N76D |
| V149C + N261L + N76D | V149C + N261M + N76D | V149C + N261R + N76D | V149C + N261V + N76D |
| V149C + N261W + N76D | V149C + N261Y + N76D | V149C + N261F + N76D | V149C + L262Y + N76D |
| V149C + L262C + N76D | V149C + L262E + N76D | V149C + L262Q + N76D | V149N + A158E + N76D |
| V149N + G160D + N76D | V149N + G160P + N76D | V149N + S161C + N76D | V149N + S161Y + N76D |
| V149N + S161E + N76D | V149N + I162L + N76D | V149N + S163A + N76D | V149N + S163D + N76D |
| V149N + Q182C + N76D | V149N + Q182E + N76D | V149N + N184D + N76D | V149N + N185C + N76D |
| V149N + N185E + N76D | V149N + S188C + N76D | V149N + S188D + N76D | V149N + S188E + N76D |
| V149N + Q191N + N76D | V149N + A194D + N76D | V149N + A194E + N76D | V149N + A194P + N76D |
| V149N + G195E + N76D | V149N + N204D + N76D | V149N + N204V + N76D | V149N + V205I + N76D |
| V149N + V205L + N76D | V149N + Q206C + N76D | V149N + Q206E + N76D | V149N + Q206I + N76D |
| V149N + Q206K + N76D | V149N + Q206L + N76D | V149N + Q206T + N76D | V149N + Q206V + N76D |
| V149N + Q206W + N76D | V149N + Y209L + N76D | V149N + Y209W + N76D | V149N + S212A + N76D |
| V149N + S212D + N76D | V149N + S212G + N76D | V149N + S212N + N76D | V149N + S216I + N76D |
| V149N + S216T + N76D | V149N + S216V + N76D | V149N + L217C + N76D | V149N + L217M + N76D |
| V149N + N218T + N76D | V149N + S216V + N76D | V149N + M222C + N76D | V149N + M222N + N76D |
| V149N + M222R + N76D | V149N + Q206L + N76D | V149N + P225A + N76D | V149N + P225S + N76D |
| V149N + T255C + N76D | V149N + T255E + N76D | V149N + T255Q + N76D | V149N + S256A + N76D |
| V149N + S256C + N76D | V149N + S256D + N76D | V149N + S256V + N76D | V149N + S256Y + N76D |
| V149N + S259D + N76D | V149N + T260A + N76D | V149N + T260E + N76D | V149N + T260P + N76D |
| V149N + N261D + N76D | V149N + N261C + N76D | V149N + N261E + N76D | V149N + N261L + N76D |
| V149N + N261M + N76D | V149N + N261R + N76D | V149N + N261V + N76D | V149N + N261W + N76D |
| V149N + N261Y + N76D | V149N + N261F + N76D | V149N + L262Y + N76D | V149N + L262C + N76D |
| V149N + L262E + N76D | V149N + L262Q + N76D | V149Q + A158E + N76D | V149Q + G160D + N76D |
| V149Q + G160P + N76D | V149Q + S161C + N76D | V149Q + S161Y + N76D | V149Q + S161E + N76D |
| V149Q + I162L + N76D | V149Q + S163A + N76D | V149Q + S163D + N76D | V149Q + Q182C + N76D |
| V149Q + Q182E + N76D | V149Q + N184D + N76D | V149Q + N185C + N76D | V149Q + N185E + N76D |
| V149Q + S188C + N76D | V149Q + S188D + N76D | V149Q + S188E + N76D | V149Q + Q191N + N76D |
| V149Q + A194D + N76D | V149Q + A194E + N76D | V149Q + A194P + N76D | V149Q + G195E + N76D |
| V149Q + N204D + N76D | V149Q + N204V + N76D | V149Q + V205I + N76D | V149Q + V205L + N76D |
| V149Q + Q206C + N76D | V149Q + Q206E + N76D | V149Q + Q206I + N76D | V149Q + Q206K + N76D |
| V149Q + Q206L + N76D | V149Q + Q206T + N76D | V149Q + Q206V + N76D | V149Q + Q206W + N76D |
| V149Q + Y209L + N76D | V149Q + Y209W + N76D | V149Q + S212A + N76D | V149Q + S212D + N76D |
| V149Q + S212G + N76D | V149Q + S212N + N76D | V149Q + S216I + N76D | V149Q + S216T + N76D |
| V149Q + S216V + N76D | V149Q + L217C + N76D | V149Q + L217M + N76D | V149Q + N218T + N76D |
| V149Q + S216V + N76D | V149Q + M222C + N76D | V149Q + M222N + N76D | V149Q + M222R + N76D |
| V149Q + P225A + N76D | V149Q + P225S + N76D | V149Q + T255C + N76D | V149Q + T255E + N76D |
| V149Q + T255Q + N76D | V149Q + S256A + N76D | V149Q + S256C + N76D | V149Q + S256D + N76D |
| V149Q + S256V + N76D | V149Q + S256Y + N76D | V149Q + S259D + N76D | V149Q + T260A + N76D |
| V149Q + T260E + N76D | V149Q + T260P + N76D | V149Q + N261D + N76D | V149Q + N261C + N76D |
| V149Q + N261E + N76D | V149Q + N261L + N76D | V149Q + N261M + N76D | V149Q + N261R + N76D |
| V149Q + N261V + N76D | V149Q + N261W + N76D | V149Q + N261Y + N76D | V149Q + N261F + N76D |
| V149Q + L262Y + N76D | V149Q + L262C + N76D | V149Q + L262E + N76D | V149Q + L262Q + N76D |
| A158E + G160D + N76D | A158E + G160P + N76D | A158E + S161C + N76D | A158E + S161Y + N76D |
| A158E + S161E + N76D | A158E + I162L + N76D | A158E + S163A + N76D | A158E + S163D + N76D |
| A158E + Q182C + N76D | A158E + Q182E + N76D | A158E + N184D + N76D |

TABLE 2-continued

Subtilase Variants

| | | | |
|---|---|---|---|
| A158E + N185C + N76D | A158E + N185E + N76D | A158E + S188C + N76D | A158E + S188D + N76D |
| A158E + S188E + N76D | A158E + Q191N + N76D | A158E + A194D + N76D | A158E + A194E + N76D |
| A158E + A194P + N76D | A158E + G195E + N76D | A158E + N204D + N76D | A158E + N204V + N76D |
| A158E + V205I + N76D | A158E + V205L + N76D | A158E + Q206C + N76D | A158E + Q206E + N76D |
| A158E + Q206I + N76D | A158E + Q206K + N76D | A158E + Q206L + N76D | A158E + Q206T + N76D |
| A158E + Q206V + N76D | A158E + Q206W + N76D | A158E + Y209L + N76D | A158E + Y209W + N76D |
| A158E + S212A + N76D | A158E + S212D + N76D | A158E + S212G + N76D | A158E + S212N + N76D |
| A158E + S216I + N76D | A158E + S216T + N76D | A158E + S216V + N76D | A158E + L217C + N76D |
| A158E + L217M + N76D | A158E + N218T + N76D | A158E + S216V + N76D | A158E + M222C + N76D |
| A158E + M222N + N76D | A158E + M222R + N76D | A158E + Q206L + N76D | A158E + P225A + N76D |
| A158E + P225S + N76D | A158E + T255C + N76D | A158E + T255E + N76D | A158E + T255Q + N76D |
| A158E + S256A + N76D | A158E + S256C + N76D | A158E + S256D + N76D | A158E + S256V + N76D |
| A158E + S256Y + N76D | A158E + S259D + N76D | A158E + T260A + N76D | A158E + T260E + N76D |
| A158E + T260P + N76D | A158E + N261D + N76D | A158E + N261C + N76D | A158E + N261E + N76D |
| A158E + N261L + N76D | A158E + N261M + N76D | A158E + N261R + N76D | A158E + N261V + N76D |
| A158E + N261W + N76D | A158E + N261Y + N76D | A158E + N261F + N76D | A158E + L262Y + N76D |
| A158E + L262C + N76D | A158E + L262E + N76D | A158E + L262Q + N76D | G160D + S161C + N76D |
| G160D + S161Y + N76D | G160D + S161E + N76D | G160D + I162L + N76D | G160D + S163A + N76D |
| G160D + S163D + N76D | G160D + Q182C + N76D | G160D + Q182E + N76D | G160D + N184D + N76D |
| G160D + N185C + N76D | G160D + N185E + N76D | G160D + S188C + N76D | G160D + S188D + N76D |
| G160D + S188E + N76D | G160D + Q191N + N76D | G160D + A194D + N76D | G160D + A194E + N76D |
| G160D + A194P + N76D | G160D + G195E + N76D | G160D + N204D + N76D | G160D + N204V + N76D |
| G160D + V205I + N76D | G160D + V205L + N76D | G160D + Q206C + N76D | G160D + Q206E + N76D |
| G160D + Q206I + N76D | G160D + Q206K + N76D | G160D + Q206L + N76D | G160D + Q206T + N76D |
| G160D + Q206V + N76D | G160D + Q206W + N76D | G160D + Y209L + N76D | G160D + Y209W + N76D |
| G160D + S212A + N76D | G160D + S212D + N76D | G160D + S212G + N76D | G160D + S212N + N76D |
| G160D + S216I + N76D | G160D + S216T + N76D | G160D + S216V + N76D | G160D + L217C + N76D |
| G160D + L217M + N76D | G160D + N218T + N76D | G160D + S216V + N76D | G160D + M222C + N76D |
| G160D + M222N + N76D | G160D + M222R + N76D | G160D + Q206L + N76D | G160D + P225A + N76D |
| G160D + P225S + N76D | G160D + T255C + N76D | G160D + T255E + N76D | G160D + T255Q + N76D |
| G160D + S256A + N76D | G160D + S256C + N76D | G160D + S256D + N76D | G160D + S256V + N76D |
| G160D + S256Y + N76D | G160D + S259D + N76D | G160D + T260A + N76D | G160D + T260E + N76D |
| G160D + T260P + N76D | G160D + N261D + N76D | G160D + N261C + N76D | G160D + N261E + N76D |
| G160D + N261L + N76D | G160D + N261M + N76D | G160D + N261R + N76D | G160D + N261V + N76D |
| G160D + N261W + N76D | G160D + N261Y + N76D | G160D + N261F + N76D | G160D + L262Y + N76D |
| G160D + L262C + N76D | G160D + L262E + N76D | G160D + L262Q + N76D | G160P + S161C + N76D |
| G160P + S161Y + N76D | G160P + S161E + N76D | G160P + I162L + N76D | G160P + S163A + N76D |
| G160P + S163D + N76D | G160P + Q182C + N76D | G160P + Q182E + N76D | G160P + N184D + N76D |
| G160P + N185C + N76D | G160P + N185E + N76D | G160P + S188C + N76D | G160P + S188D + N76D |
| G160P + S188E + N76D | G160P + Q191N + N76D | G160P + A194D + N76D | G160P + A194E + N76D |
| G160P + A194P + N76D | G160P + G195E + N76D | G160P + N204D + N76D | G160P + N204V + N76D |
| G160P + V205I + N76D | G160P + V205L + N76D | G160P + Q206C + N76D | G160P + Q206E + N76D |
| G160P + Q206I + N76D | G160P + Q206K + N76D | G160P + Q206L + N76D | G160P + Q206T + N76D |
| G160P + Q206V + N76D | G160P + Q206W + N76D | G160P + Y209L + N76D | G160P + Y209W + N76D |
| G160P + S212A + N76D | G160P + S212D + N76D | G160P + S212G + N76D | G160P + S212N + N76D |
| G160P + S216I + N76D | G160P + S216T + N76D | G160P + S216V + N76D | G160P + L217C + N76D |
| G160P + L217M + N76D | G160P + N218T + N76D | G160P + S216V + N76D | G160P + M222C + N76D |
| G160P + M222N + N76D | G160P + M222R + N76D | G160P + Q206L + N76D | G160P + P225A + N76D |
| G160P + P225S + N76D | G160P + T255C + N76D | G160P + T255E + N76D | G160P + T255Q + N76D |
| G160P + S256A + N76D | G160P + S256C + N76D | G160P + S256D + N76D | G160P + S256V + N76D |
| G160P + S256Y + N76D | G160P + S259D + N76D | G160P + T260A + N76D | G160P + T260E + N76D |
| G160P + T260P + N76D | G160P + N261D + N76D | G160P + N261C + N76D | G160P + N261E + N76D |
| G160P + N261L + N76D | G160P + N261M + N76D | G160P + N261R + N76D | G160P + N261V + N76D |
| G160P + N261W + N76D | G160P + N261Y + N76D | G160P + N261F + N76D | G160P + L262Y + N76D |
| G160P + L262C + N76D | G160P + L262E + N76D | G160P + L262Q + N76D | S161C + I162L + N76D |
| S161C + S163A + N76D | S161C + S163D + N76D | S161C + Q182C + N76D | S161C + Q182E + N76D |
| S161C + N184D + N76D | S161C + N185C + N76D | S161C + N185E + N76D | S161C + S188C + N76D |
| S161C + S188D + N76D | S161C + S188E + N76D | S161C + Q191N + N76D | S161C + A194D + N76D |
| S161C + A194E + N76D | S161C + A194P + N76D | S161C + G195E + N76D | S161C + N204D + N76D |
| S161C + N204V + N76D | S161C + V205I + N76D | S161C + V205L + N76D | S161C + Q206C + N76D |
| S161C + Q206E + N76D | S161C + Q206I + N76D | S161C + Q206K + N76D | S161C + Q206L + N76D |
| S161C + Q206T + N76D | S161C + Q206V + N76D | S161C + Q206W + N76D | S161C + Y209L + N76D |
| S161C + Y209W + N76D | S161C + S212A + N76D | S161C + S212D + N76D | S161C + S212G + N76D |
| S161C + S212N + N76D | S161C + S216I + N76D | S161C + S216T + N76D | S161C + S216V + N76D |
| S161C + L217C + N76D | S161C + L217M + N76D | S161C + N218T + N76D | S161C + S216V + N76D |
| S161C + M222C + N76D | S161C + M222N + N76D | S161C + M222R + N76D | S161C + Q206L + N76D |
| S161C + P225A + N76D | S161C + P225S + N76D | S161C + T255C + N76D | S161C + T255E + N76D |
| S161C + T255Q + N76D | S161C + S256A + N76D | S161C + S256C + N76D | S161C + S256D + N76D |
| S161C + S256V + N76D | S161C + S256Y + N76D | S161C + S259D + N76D | S161C + T260A + N76D |
| S161C + T260E + N76D | S161C + T260P + N76D | S161C + N261D + N76D | S161C + N261C + N76D |
| S161C + N261E + N76D | S161C + N261L + N76D | S161C + N261M + N76D | S161C + N261R + N76D |
| S161C + N261V + N76D | S161C + N261W + N76D | S161C + N261Y + N76D | S161C + N261F + N76D |
| S161C + L262Y + N76D | S161C + L262C + N76D | S161C + L262E + N76D | S161C + L262Q + N76D |
| S161Y + I162L + N76D | S161Y + S163A + N76D | S161Y + S163D + N76D | S161Y + Q182C + N76D |
| S161Y + Q182E + N76D | S161Y + N184D + N76D | S161Y + N185C + N76D | S161Y + N185E + N76D |
| S161Y + S188C + N76D | S161Y + S188D + N76D | S161Y + S188E + N76D | S161Y + Q191N + N76D |
| S161Y + A194D + N76D | S161Y + A194E + N76D | S161Y + A194P + N76D | S161Y + G195E + N76D |
| S161Y + N204D + N76D | S161Y + N204V + N76D | S161Y + V205I + N76D | S161Y + V205L + N76D |

TABLE 2-continued

Subtilase Variants

| | | | |
|---|---|---|---|
| S161Y + Q206C + N76D | S161Y + Q206E + N76D | S161Y + Q206I + N76D | S161Y + Q206K + N76D |
| S161Y + Q206L + N76D | S161Y + Q206T + N76D | S161Y + Q206V + N76D | S161Y + Q206W + N76D |
| S161Y + Y209L + N76D | S161Y + Y209W + N76D | S161Y + S212A + N76D | S161Y + S212D + N76D |
| S161Y + S212G + N76D | S161Y + S212N + N76D | S161Y + S216I + N76D | S161Y + S216T + N76D |
| S161Y + S216V + N76D | S161Y + L217C + N76D | S161Y + L217M + N76D | S161Y + N218T + N76D |
| S161Y + S216V + N76D | S161Y + M222C + N76D | S161Y + M222N + N76D | S161Y + M222R + N76D |
| S161Y + Q206L + N76D | S161Y + P225A + N76D | S161Y + P225S + N76D | S161Y + T255C + N76D |
| S161Y + T255E + N76D | S161Y + T255Q + N76D | S161Y + S256A + N76D | S161Y + S256C + N76D |
| S161Y + S256D + N76D | S161Y + S256V + N76D | S161Y + S256Y + N76D | S161Y + S259D + N76D |
| S161Y + T260A + N76D | S161Y + T260E + N76D | S161Y + T260P + N76D | S161Y + N261D + N76D |
| S161Y + N261C + N76D | S161Y + N261E + N76D | S161Y + N261L + N76D | S161Y + N261M + N76D |
| S161Y + N261R + N76D | S161Y + N261V + N76D | S161Y + N261W + N76D | S161Y + N261Y + N76D |
| S161Y + N261F + N76D | S161Y + L262Y + N76D | S161Y + L262C + N76D | S161Y + L262E + N76D |
| S161Y + L262Q + N76D | S161E + I162L + N76D | S161E + S163A + N76D | S161E + S163D + N76D |
| S161E + Q182C + N76D | S161E + Q182E + N76D | S161E + N184D + N76D | S161E + N185C + N76D |
| S161E + N185E + N76D | S161E + S188C + N76D | S161E + S188D + N76D | S161E + S188E + N76D |
| S161E + Q191N + N76D | S161E + A194D + N76D | S161E + A194E + N76D | S161E + A194P + N76D |
| S161E + G195E + N76D | S161E + N204D + N76D | S161E + N204V + N76D | S161E + V205I + N76D |
| S161E + V205L + N76D | S161E + Q206C + N76D | S161E + Q206E + N76D | S161E + Q206I + N76D |
| S161E + Q206K + N76D | S161E + Q206L + N76D | S161E + Q206T + N76D | S161E + Q206V + N76D |
| S161E + Q206W + N76D | S161E + Y209L + N76D | S161E + Y209W + N76D | S161E + S212A + N76D |
| S161E + S212D + N76D | S161E + S212G + N76D | S161E + S212N + N76D | S161E + S216I + N76D |
| S161E + S216T + N76D | S161E + S216V + N76D | S161E + L217C + N76D | S161E + L217M + N76D |
| S161E + N218T + N76D | S161E + S216V + N76D | S161E + M222C + N76D | S161E + M222N + N76D |
| S161E + M222R + N76D | S161E + Q206L + N76D | S161E + P225A + N76D | S161E + P225S + N76D |
| S161E + T255C + N76D | S161E + T255E + N76D | S161E + T255Q + N76D | S161E + S256A + N76D |
| S161E + S256C + N76D | S161E + S256D + N76D | S161E + S256V + N76D | S161E + S256Y + N76D |
| S161E + S259D + N76D | S161E + T260A + N76D | S161E + T260E + N76D | S161E + T260P + N76D |
| S161E + N261D + N76D | S161E + N261C + N76D | S161E + N261E + N76D | S161E + N261L + N76D |
| S161E + N261M + N76D | S161E + N261R + N76D | S161E + N261V + N76D | S161E + N261W + N76D |
| S161E + N261Y + N76D | S161E + N261F + N76D | S161E + L262Y + N76D | S161E + L262C + N76D |
| S161E + L262E + N76D | S161E + L262Q + N76D | I162L + S163A + N76D | I162L + S163D + N76D |
| I162L + Q182C + N76D | I162L + Q182E + N76D | I162L + N184D + N76D | I162L + N185C + N76D |
| I162L + N185E + N76D | I162L + S188C + N76D | I162L + S188D + N76D | I162L + S188E + N76D |
| I162L + Q191N + N76D | I162L + A194D + N76D | I162L + A194E + N76D | I162L + A194P + N76D |
| I162L + G195E + N76D | I162L + N204D + N76D | I162L + N204V + N76D | I162L + V205I + N76D |
| I162L + V205L + N76D | I162L + Q206C + N76D | I162L + Q206E + N76D | I162L + Q206I + N76D |
| I162L + Q206K + N76D | I162L + Q206L + N76D | I162L + Q206T + N76D | I162L + Q206V + N76D |
| I162L + Q206W + N76D | I162L + Y209L + N76D | I162L + Y209W + N76D | I162L + S212A + N76D |
| I162L + S212D + N76D | I162L + S212G + N76D | I162L + S212N + N76D | I162L + S216I + N76D |
| I162L + S216T + N76D | I162L + S216V + N76D | I162L + L217C + N76D | I162L + L217M + N76D |
| I162L + N218T + N76D | I162L + S216V + N76D | I162L + M222C + N76D | I162L + M222N + N76D |
| I162L + M222R + N76D | I162L + Q206L + N76D | I162L + P225A + N76D | I162L + P225S + N76D |
| I162L + T255C + N76D | I162L + T255E + N76D | I162L + T255Q + N76D | I162L + S256A + N76D |
| I162L + S256C + N76D | I162L + S256D + N76D | I162L + S256V + N76D | I162L + S256Y + N76D |
| I162L + S259D + N76D | I162L + T260A + N76D | I162L + T260E + N76D | I162L + T260P + N76D |
| I162L + N261D + N76D | I162L + N261C + N76D | I162L + N261E + N76D | I162L + N261L + N76D |
| I162L + N261M + N76D | I162L + N261R + N76D | I162L + N261V + N76D | I162L + N261W + N76D |
| I162L + N261Y + N76D | I162L + N261F + N76D | I162L + L262Y + N76D | I162L + L262C + N76D |
| I162L + L262E + N76D | I162L + L262Q + N76D | S163A + Q182C + N76D | S163A + Q182E + N76D |
| S163A + N184D + N76D | S163A + N185C + N76D | S163A + N185E + N76D | S163A + S188C + N76D |
| S163A + S188D + N76D | S163A + S188E + N76D | S163A + Q191N + N76D | S163A + A194D + N76D |
| S163A + A194E + N76D | S163A + A194P + N76D | S163A + G195E + N76D | S163A + N204D + N76D |
| S163A + N204V + N76D | S163A + V205I + N76D | S163A + V205L + N76D | S163A + Q206C + N76D |
| S163A + Q206E + N76D | S163A + Q206I + N76D | S163A + Q206K + N76D | S163A + Q206L + N76D |
| S163A + Q206T + N76D | S163A + Q206V + N76D | S163A + Q206W + N76D | S163A + Y209L + N76D |
| S163A + Y209W + N76D | S163A + S212A + N76D | S163A + S212D + N76D | S163A + S212G + N76D |
| S163A + S212N + N76D | S163A + S216I + N76D | S163A + S216T + N76D | S163A + S216V + N76D |
| S163A + L217C + N76D | S163A + L217M + N76D | S163A + N218T + N76D | S163A + S216V + N76D |
| S163A + M222C + N76D | S163A + M222N + N76D | S163A + M222R + N76D | S163A + Q206L + N76D |
| S163A + P225A + N76D | S163A + P225S + N76D | S163A + T255C + N76D | S163A + T255E + N76D |
| S163A + T255Q + N76D | S163A + S256A + N76D | S163A + S256C + N76D | S163A + S256D + N76D |
| S163A + S256V + N76D | S163A + S256Y + N76D | S163A + S259D + N76D | S163A + T260A + N76D |
| S163A + T260E + N76D | S163A + T260P + N76D | S163A + N261D + N76D | S163A + N261C + N76D |
| S163A + N261E + N76D | S163A + N261L + N76D | S163A + N261M + N76D | S163A + N261R + N76D |
| S163A + N261V + N76D | S163A + N261W + N76D | S163A + N261Y + N76D | S163A + N261F + N76D |
| S163A + L262Y + N76D | S163A + L262C + N76D | S163A + L262E + N76D | S163A + L262Q + N76D |
| S163D + Q182C + N76D | S163D + Q182E + N76D | S163D + N184D + N76D | S163D + N185C + N76D |
| S163D + N185E + N76D | S163D + S188D + N76D | S163D + S188E + N76D | S163D + S188C + N76D |
| S163D + Q191N + N76D | S163D + A194D + N76D | S163D + A194E + N76D | S163D + A194P + N76D |
| S163D + G195E + N76D | S163D + N204D + N76D | S163D + N204V + N76D | S163D + V205I + N76D |
| S163D + V205L + N76D | S163D + Q206C + N76D | S163D + Q206E + N76D | S163D + Q206I + N76D |
| S163D + Q206K + N76D | S163D + Q206L + N76D | S163D + Q206T + N76D | S163D + Q206V + N76D |
| S163D + Q206W + N76D | S163D + Y209L + N76D | S163D + Y209W + N76D | S163D + S212A + N76D |
| S163D + S212D + N76D | S163D + S212G + N76D | S163D + S212N + N76D | S163D + S216I + N76D |
| S163D + S216T + N76D | S163D + S216V + N76D | S163D + L217C + N76D | S163D + L217M + N76D |
| S163D + N218T + N76D | S163D + S216V + N76D | S163D + M222C + N76D | S163D + M222N + N76D |
| S163D + M222R + N76D | S163D + Q206L + N76D | S163D + P225A + N76D | S163D + P225S + N76D |

TABLE 2-continued

Subtilase Variants

| | | | |
|---|---|---|---|
| S163D + T255C + N76D | S163D + T255E + N76D | S163D + T255Q + N76D | S163D + S256A + N76D |
| S163D + S256C + N76D | S163D + S256V + N76D | S163D + S256D + N76D | S163D + S256Y + N76D |
| S163D + S259D + N76D | S163D + T260A + N76D | S163D + T260E + N76D | S163D + T260P + N76D |
| S163D + N261D + N76D | S163D + N261C + N76D | S163D + N261E + N76D | S163D + N261L + N76D |
| S163D + N261M + N76D | S163D + N261R + N76D | S163D + N261V + N76D | S163D + N261W + N76D |
| S163D + N261Y + N76D | S163D + N261F + N76D | S163D + L262Y + N76D | S163D + L262C + N76D |
| S163D + L262E + N76D | S163D + L262Q + N76D | Q182C + N184D + N76D | Q182C + N185C + N76D |
| Q182C + N185E + N76D | Q182C + S188C + N76D | Q182C + S188D + N76D | Q182C + S188E + N76D |
| Q182C + Q191N + N76D | Q182C + A194D + N76D | Q182C + A194E + N76D | Q182C + A194P + N76D |
| Q182C + G195E + N76D | Q182C + N204D + N76D | Q182C + N204V + N76D | Q182C + V205I + N76D |
| Q182C + V205L + N76D | Q182C + Q206C + N76D | Q182C + Q206E + N76D | Q182C + Q206I + N76D |
| Q182C + Q206K + N76D | Q182C + Q206L + N76D | Q182C + Q206T + N76D | Q182C + Q206V + N76D |
| Q182C + Q206W + N76D | Q182C + Y209L + N76D | Q182C + Y209W + N76D | Q182C + S212A + N76D |
| Q182C + S212D + N76D | Q182C + S212G + N76D | Q182C + S212N + N76D | Q182C + S216I + N76D |
| Q182C + S216T + N76D | Q182C + S216V + N76D | Q182C + L217C + N76D | Q182C + L217M + N76D |
| Q182C + N218T + N76D | Q182C + S216V + N76D | Q182C + M222C + N76D | Q182C + M222N + N76D |
| Q182C + M222R + N76D | Q182C + Q206L + N76D | Q182C + P225A + N76D | Q182C + P225S + N76D |
| Q182C + T255C + N76D | Q182C + T255E + N76D | Q182C + T255Q + N76D | Q182C + S256A + N76D |
| Q182C + S256C + N76D | Q182C + S256D + N76D | Q182C + S256V + N76D | Q182C + S256Y + N76D |
| Q182C + S259D + N76D | Q182C + T260A + N76D | Q182C + T260E + N76D | Q182C + T260P + N76D |
| Q182C + N261D + N76D | Q182C + N261C + N76D | Q182C + N261E + N76D | Q182C + N261L + N76D |
| Q182C + N261M + N76D | Q182C + N261R + N76D | Q182C + N261V + N76D | Q182C + N261W + N76D |
| Q182C + N261Y + N76D | Q182C + N261F + N76D | Q182C + L262Y + N76D | Q182C + L262C + N76D |
| Q182C + L262E + N76D | Q182C + L262Q + N76D | Q182E + N184D + N76D | Q182E + N185C + N76D |
| Q182E + N185E + N76D | Q182E + S188C + N76D | Q182E + S188D + N76D | Q182E + S188E + N76D |
| Q182E + Q191N + N76D | Q182E + A194D + N76D | Q182E + A194E + N76D | Q182E + A194P + N76D |
| Q182E + G195E + N76D | Q182E + N204D + N76D | Q182E + N204V + N76D | Q182E + V205I + N76D |
| Q182E + V205L + N76D | Q182E + Q206C + N76D | Q182E + Q206E + N76D | Q182E + Q206I + N76D |
| Q182E + Q206K + N76D | Q182E + Q206L + N76D | Q182E + Q206T + N76D | Q182E + Q206V + N76D |
| Q182E + Q206W + N76D | Q182E + Y209L + N76D | Q182E + Y209W + N76D | Q182E + S212A + N76D |
| Q182E + S212D + N76D | Q182E + S212G + N76D | Q182E + S212N + N76D | Q182E + S216I + N76D |
| Q182E + S216T + N76D | Q182E + S216V + N76D | Q182E + L217C + N76D | Q182E + L217M + N76D |
| Q182E + N218T + N76D | Q182E + S216V + N76D | Q182E + M222C + N76D | Q182E + M222N + N76D |
| Q182E + M222R + N76D | Q182E + Q206L + N76D | Q182E + P225A + N76D | Q182E + P225S + N76D |
| Q182E + T255C + N76D | Q182E + T255E + N76D | Q182E + T255Q + N76D | Q182E + S256A + N76D |
| Q182E + S256C + N76D | Q182E + S256D + N76D | Q182E + S256V + N76D | Q182E + S256Y + N76D |
| Q182E + S259D + N76D | Q182E + T260A + N76D | Q182E + T260E + N76D | Q182E + T260P + N76D |
| Q182E + N261D + N76D | Q182E + N261C + N76D | Q182E + N261E + N76D | Q182E + N261L + N76D |
| Q182E + N261M + N76D | Q182E + N261R + N76D | Q182E + N261V + N76D | Q182E + N261W + N76D |
| Q182E + N261Y + N76D | Q182E + N261F + N76D | Q182E + L262Y + N76D | Q182E + L262C + N76D |
| Q182E + L262E + N76D | Q182E + L262Q + N76D | N184D + N185C + N76D | N184D + N185E + N76D |
| N184D + S188C + N76D | N184D + S188D + N76D | N184D + S188E + N76D | N184D + Q191N + N76D |
| N184D + A194D + N76D | N184D + A194E + N76D | N184D + A194P + N76D | N184D + G195E + N76D |
| N184D + N204D + N76D | N184D + N204V + N76D | N184D + V205I + N76D | N184D + V205L + N76D |
| N184D + Q206C + N76D | N184D + Q206E + N76D | N184D + Q206I + N76D | N184D + Q206K + N76D |
| N184D + Q206L + N76D | N184D + Q206T + N76D | N184D + Q206V + N76D | N184D + Q206W + N76D |
| N184D + Y209L + N76D | N184D + Y209W + N76D | N184D + S212A + N76D | N184D + S212D + N76D |
| N184D + S212G + N76D | N184D + S212N + N76D | N184D + S212I + N76D | N184D + S216T + N76D |
| N184D + S216V + N76D | N184D + L217C + N76D | N184D + L217M + N76D | N184D + N218T + N76D |
| N184D + S216V + N76D | N184D + M222C + N76D | N184D + M222N + N76D | N184D + M222R + N76D |
| N184D + Q206L + N76D | N184D + P225A + N76D | N184D + P225S + N76D | N184D + T255C + N76D |
| N184D + T255E + N76D | N184D + T255Q + N76D | N184D + T255D + N76D | N184D + S256C + N76D |
| N184D + S256D + N76D | N184D + S256V + N76D | N184D + S256Y + N76D | N184D + S259D + N76D |
| N184D + T260A + N76D | N184D + T260E + N76D | N184D + T260P + N76D | N184D + N261D + N76D |
| N184D + N261C + N76D | N184D + N261E + N76D | N184D + N261L + N76D | N184D + N261M + N76D |
| N184D + N261R + N76D | N184D + N261V + N76D | N184D + N261W + N76D | N184D + N261Y + N76D |
| N184D + N261F + N76D | N184D + L262Y + N76D | N184D + L262C + N76D | N184D + L262E + N76D |
| N184D + L262Q + N76D | N185C + S188C + N76D | N185C + S188D + N76D | N185C + S188E + N76D |
| N185C + Q191N + N76D | N185C + A194D + N76D | N185C + A194E + N76D | N185C + A194P + N76D |
| N185C + G195E + N76D | N185C + N204D + N76D | N185C + N204V + N76D | N185C + V205I + N76D |
| N185C + V205L + N76D | N185C + Q206C + N76D | N185C + Q206E + N76D | N185C + Q206I + N76D |
| N185C + Q206K + N76D | N185C + Q206L + N76D | N185C + Q206T + N76D | N185C + Q206V + N76D |
| N185C + Q206W + N76D | N185C + Y209L + N76D | N185C + Y209W + N76D | N185C + S212A + N76D |
| N185C + S212D + N76D | N185C + S212G + N76D | N185C + S212N + N76D | N185C + S216I + N76D |
| N185C + S216T + N76D | N185C + S216V + N76D | N185C + S216V + N76D | N185C + L217M + N76D |
| N185C + N218T + N76D | N185C + S216V + N76D | N185C + M222C + N76D | N185C + M222N + N76D |
| N185C + M222R + N76D | N185C + Q206L + N76D | N185C + P225A + N76D | N185C + P225S + N76D |
| N185C + T255C + N76D | N185C + T255E + N76D | N185C + T255Q + N76D | N185C + S256A + N76D |
| N185C + S256C + N76D | N185C + S256D + N76D | N185C + S256V + N76D | N185C + S256Y + N76D |
| N185C + S259D + N76D | N185C + T260A + N76D | N185C + T260E + N76D | N185C + T260P + N76D |
| N185C + N261D + N76D | N185C + N261C + N76D | N185C + N261E + N76D | N185C + N261L + N76D |
| N185C + N261M + N76D | N185C + N261R + N76D | N185C + N261V + N76D | N185C + N261W + N76D |
| N185C + N261Y + N76D | N185C + N261F + N76D | N185C + L262Y + N76D | N185C + L262C + N76D |
| N185C + L262E + N76D | N185C + L262Q + N76D | N185E + S188C + N76D | N185E + S188D + N76D |
| N185E + S188E + N76D | N185E + Q191N + N76D | N185E + A194D + N76D | N185E + A194E + N76D |
| N185E + A194P + N76D | N185E + G195E + N76D | N185E + N204D + N76D | N185E + N204V + N76D |
| N185E + V205I + N76D | N185E + V205L + N76D | N185E + Q206C + N76D | N185E + Q206E + N76D |
| N185E + Q206I + N76D | N185E + Q206K + N76D | N185E + Q206L + N76D | N185E + Q206T + N76D |

TABLE 2-continued

Subtilase Variants

| | | | |
|---|---|---|---|
| N185E + Q206V + N76D | N185E + Q206W + N76D | N185E + Y209L + N76D | N185E + Y209W + N76D |
| N185E + S212A + N76D | N185E + S212D + N76D | N185E + S212G + N76D | N185E + S212N + N76D |
| N185E + S216I + N76D | N185E + S216T + N76D | N185E + S216V + N76D | N185E + L217C + N76D |
| N185E + L217M + N76D | N185E + N218T + N76D | N185E + S216V + N76D | N185E + M222C + N76D |
| N185E + M222N + N76D | N185E + M222R + N76D | N185E + Q206L + N76D | N185E + P225A + N76D |
| N185E + P225S + N76D | N185E + T255C + N76D | N185E + T255E + N76D | N185E + T255Q + N76D |
| N185E + S256A + N76D | N185E + S256C + N76D | N185E + S256D + N76D | N185E + S256V + N76D |
| N185E + S256Y + N76D | N185E + S259D + N76D | N185E + T260A + N76D | N185E + T260E + N76D |
| N185E + T260P + N76D | N185E + N261D + N76D | N185E + N261C + N76D | N185E + N261E + N76D |
| N185E + N261L + N76D | N185E + N261M + N76D | N185E + N261R + N76D | N185E + N261V + N76D |
| N185E + N261W + N76D | N185E + N261Y + N76D | N185E + N261F + N76D | N185E + L262Y + N76D |
| N185E + L262C + N76D | N185E + L262E + N76D | N185E + L262Q + N76D | S188C + Q191N + N76D |
| S188C + A194D + N76D | S188C + A194E + N76D | S188C + A194P + N76D | S188C + G195E + N76D |
| S188C + N204D + N76D | S188C + N204V + N76D | S188C + V205I + N76D | S188C + V205L + N76D |
| S188C + Q206C + N76D | S188C + Q206E + N76D | S188C + Q206I + N76D | S188C + Q206K + N76D |
| S188C + Q206L + N76D | S188C + Q206T + N76D | S188C + Q206V + N76D | S188C + Q206W + N76D |
| S188C + Y209L + N76D | S188C + Y209W + N76D | S188C + S212A + N76D | S188C + S212D + N76D |
| S188C + S212G + N76D | S188C + S212N + N76D | S188C + S216I + N76D | S188C + S216T + N76D |
| S188C + S216V + N76D | S188C + L217C + N76D | S188C + L217M + N76D | S188C + N218T + N76D |
| S188C + S216V + N76D | S188C + M222C + N76D | S188C + M222N + N76D | S188C + M222R + N76D |
| S188C + Q206L + N76D | S188C + P225A + N76D | S188C + P225S + N76D | S188C + T255C + N76D |
| S188C + T255E + N76D | S188C + T255Q + N76D | S188C + S256A + N76D | S188C + S256C + N76D |
| S188C + S256D + N76D | S188C + S256V + N76D | S188C + S256Y + N76D | S188C + S259D + N76D |
| S188C + T260A + N76D | S188C + T260E + N76D | S188C + T260P + N76D | S188C + N261D + N76D |
| S188C + N261C + N76D | S188C + N261E + N76D | S188C + N261L + N76D | S188C + N261M + N76D |
| S188C + N261R + N76D | S188C + N261V + N76D | S188C + N261W + N76D | S188C + N261Y + N76D |
| S188C + N261F + N76D | S188C + L262Y + N76D | S188C + L262C + N76D | S188C + L262E + N76D |
| S188C + L262Q + N76D | S188D + Q191N + N76D | S188D + A194D + N76D | S188D + A194E + N76D |
| S188D + A194P + N76D | S188D + G195E + N76D | S188D + N204D + N76D | S188D + N204V + N76D |
| S188D + V205I + N76D | S188D + V205L + N76D | S188D + Q206C + N76D | S188D + Q206E + N76D |
| S188D + Q206I + N76D | S188D + Q206K + N76D | S188D + Q206L + N76D | S188D + Q206T + N76D |
| S188D + Q206V + N76D | S188D + Q206W + N76D | S188D + Y209L + N76D | S188D + Y209W + N76D |
| S188D + S212A + N76D | S188D + S212D + N76D | S188D + S212G + N76D | S188D + S212N + N76D |
| S188D + S216I + N76D | S188D + S216T + N76D | S188D + S216V + N76D | S188D + L217C + N76D |
| S188D + L217M + N76D | S188D + N218T + N76D | S188D + S216V + N76D | S188D + M222C + N76D |
| S188D + M222N + N76D | S188D + M222R + N76D | S188D + Q206L + N76D | S188D + P225A + N76D |
| S188D + P225S + N76D | S188D + T255C + N76D | S188D + T255E + N76D | S188D + T255Q + N76D |
| S188D + S256A + N76D | S188D + S256C + N76D | S188D + S256D + N76D | S188D + S256V + N76D |
| S188D + S256Y + N76D | S188D + S259D + N76D | S188D + T260A + N76D | S188D + T260E + N76D |
| S188D + T260P + N76D | S188D + N261D + N76D | S188D + N261C + N76D | S188D + N261E + N76D |
| S188D + N261L + N76D | S188D + N261M + N76D | S188D + N261R + N76D | S188D + N261V + N76D |
| S188D + N261W + N76D | S188D + N261Y + N76D | S188D + N261F + N76D | S188D + L262Y + N76D |
| S188D + L262C + N76D | S188D + L262E + N76D | S188D + L262Q + N76D | S188E + Q191N + N76D |
| S188E + A194D + N76D | S188E + A194E + N76D | S188E + A194P + N76D | S188E + G195E + N76D |
| S188E + N204D + N76D | S188E + N204V + N76D | S188E + V205I + N76D | S188E + V205L + N76D |
| S188E + Q206C + N76D | S188E + Q206E + N76D | S188E + Q206I + N76D | S188E + Q206K + N76D |
| S188E + Q206L + N76D | S188E + Q206T + N76D | S188E + Q206V + N76D | S188E + Q206W + N76D |
| S188E + Y209L + N76D | S188E + Y209W + N76D | S188E + S212A + N76D | S188E + S212D + N76D |
| S188E + S212G + N76D | S188E + S212N + N76D | S188E + S216I + N76D | S188E + S216T + N76D |
| S188E + S216V + N76D | S188E + L217C + N76D | S188E + L217M + N76D | S188E + N218T + N76D |
| S188E + S216V + N76D | S188E + M222C + N76D | S188E + M222N + N76D | S188E + M222R + N76D |
| S188E + Q206L + N76D | S188E + P225A + N76D | S188E + P225S + N76D | S188E + T255C + N76D |
| S188E + T255E + N76D | S188E + T255Q + N76D | S188E + S256A + N76D | S188E + S256C + N76D |
| S188E + S256D + N76D | S188E + S256V + N76D | S188E + S256Y + N76D | S188E + S259D + N76D |
| S188E + T260A + N76D | S188E + T260E + N76D | S188E + T260P + N76D | S188E + N261D + N76D |
| S188E + N261C + N76D | S188E + N261E + N76D | S188E + N261L + N76D | S188E + N261M + N76D |
| S188E + N261R + N76D | S188E + N261V + N76D | S188E + N261W + N76D | S188E + N261Y + N76D |
| S188E + N261F + N76D | S188E + L262Y + N76D | S188E + L262C + N76D | S188E + L262E + N76D |
| S188E + L262Q + N76D | Q191N + A194D + N76D | Q191N + A194E + N76D | Q191N + A194P + N76D |
| Q191N + G195E + N76D | Q191N + N204D + N76D | Q191N + N204V + N76D | Q191N + V205I + N76D |
| Q191N + V205L + N76D | Q191N + Q206C + N76D | Q191N + Q206E + N76D | Q191N + Q206I + N76D |
| Q191N + Q206K + N76D | Q191N + Q206L + N76D | Q191N + Q206T + N76D | Q191N + Q206V + N76D |
| Q191N + Q206W + N76D | Q191N + Y209L + N76D | Q191N + Y209W + N76D | Q191N + S212A + N76D |
| Q191N + S212D + N76D | Q191N + S212G + N76D | Q191N + S212N + N76D | Q191N + S216I + N76D |
| Q191N + S216T + N76D | Q191N + S216V + N76D | Q191N + L217C + N76D | Q191N + L217M + N76D |
| Q191N + N218T + N76D | Q191N + S216V + N76D | Q191N + M222C + N76D | Q191N + M222N + N76D |
| Q191N + M222R + N76D | Q191N + Q206L + N76D | Q191N + P225A + N76D | Q191N + P225S + N76D |
| Q191N + T255C + N76D | Q191N + T255E + N76D | Q191N + T255Q + N76D | Q191N + S256A + N76D |
| Q191N + S256C + N76D | Q191N + S256D + N76D | Q191N + S256V + N76D | Q191N + S256Y + N76D |
| Q191N + S259D + N76D | Q191N + T260A + N76D | Q191N + T260E + N76D | Q191N + T260P + N76D |
| Q191N + N261D + N76D | Q191N + N261C + N76D | Q191N + N261E + N76D | Q191N + N261L + N76D |
| Q191N + N261M + N76D | Q191N + N261R + N76D | Q191N + N261V + N76D | Q191N + N261W + N76D |
| Q191N + N261Y + N76D | Q191N + N261F + N76D | Q191N + L262Y + N76D | Q191N + L262C + N76D |
| Q191N + L262E + N76D | Q191N + L262Q + N76D | A194D + G195E + N76D | A194D + N204D + N76D |
| A194D + N204V + N76D | A194D + V205I + N76D | A194D + V205L + N76D | A194D + Q206C + N76D |
| A194D + Q206E + N76D | A194D + Q206I + N76D | A194D + Q206K + N76D | A194D + Q206L + N76D |
| A194D + Q206T + N76D | A194D + Q206V + N76D | A194D + Q206W + N76D | A194D + Y209L + N76D |
| A194D + Y209W + N76D | A194D + S212A + N76D | A194D + S212D + N76D | A194D + S212G + N76D |

TABLE 2-continued

Subtilase Variants

| | | | |
|---|---|---|---|
| A194D + S212N + N76D | A194D + S216I + N76D | A194D + S216T + N76D | A194D + S216V + N76D |
| A194D + L217C + N76D | A194D + L217M + N76D | A194D + N218T + N76D | A194D + S216V + N76D |
| A194D + M222C + N76D | A194D + M222N + N76D | A194D + M222R + N76D | A194D + Q206L + N76D |
| A194D + P225A + N76D | A194D + P225S + N76D | A194D + T255C + N76D | A194D + T255E + N76D |
| A194D + T255Q + N76D | A194D + S256A + N76D | A194D + S256C + N76D | A194D + S256D + N76D |
| A194D + S256V + N76D | A194D + S256Y + N76D | A194D + S259D + N76D | A194D + T260A + N76D |
| A194D + T260E + N76D | A194D + T260P + N76D | A194D + N261D + N76D | A194D + N261C + N76D |
| A194D + N261E + N76D | A194D + N261L + N76D | A194D + N261M + N76D | A194D + N261R + N76D |
| A194D + N261V + N76D | A194D + N261W + N76D | A194D + N261Y + N76D | A194D + N261F + N76D |
| A194D + L262Y + N76D | A194D + L262C + N76D | A194D + L262E + N76D | A194D + L262Q + N76D |
| A194E + G195E + N76D | A194E + N204D + N76D | A194E + N204V + N76D | A194E + V205I + N76D |
| A194E + V205L + N76D | A194E + Q206C + N76D | A194E + Q206E + N76D | A194E + Q206I + N76D |
| A194E + Q206K + N76D | A194E + Q206L + N76D | A194E + Q206T + N76D | A194E + Q206V + N76D |
| A194E + Q206W + N76D | A194E + Y209L + N76D | A194E + Y209W + N76D | A194E + S212A + N76D |
| A194E + S212D + N76D | A194E + S212G + N76D | A194E + S212N + N76D | A194E + S216I + N76D |
| A194E + S216T + N76D | A194E + S216V + N76D | A194E + L217C + N76D | A194E + L217M + N76D |
| A194E + N218T + N76D | A194E + S216V + N76D | A194E + M222C + N76D | A194E + M222N + N76D |
| A194E + M222R + N76D | A194E + Q206L + N76D | A194E + P225A + N76D | A194E + P225S + N76D |
| A194E + T255Q + N76D | A194E + T255E + N76D | A194E + T255Q + N76D | A194E + S256A + N76D |
| A194E + S256C + N76D | A194E + S256D + N76D | A194E + S256V + N76D | A194E + S256Y + N76D |
| A194E + S259D + N76D | A194E + T260A + N76D | A194E + T260E + N76D | A194E + T260P + N76D |
| A194E + N261D + N76D | A194E + N261C + N76D | A194E + N261E + N76D | A194E + N261L + N76D |
| A194E + N261M + N76D | A194E + N261R + N76D | A194E + N261W + N76D | A194E + N261Y + N76D |
| A194E + N261Y + N76D | A194E + N261F + N76D | A194E + L262Y + N76D | A194E + L262C + N76D |
| A194E + L262E + N76D | A194E + L262Q + N76D | A194P + G195E + N76D | A194P + N204D + N76D |
| A194P + N204V + N76D | A194P + V205I + N76D | A194P + V205L + N76D | A194P + Q206C + N76D |
| A194P + Q206E + N76D | A194P + Q206I + N76D | A194P + Q206K + N76D | A194P + Q206L + N76D |
| A194P + Q206T + N76D | A194P + Q206V + N76D | A194P + Q206W + N76D | A194P + Y209L + N76D |
| A194P + Y209W + N76D | A194P + S212A + N76D | A194P + S212D + N76D | A194P + S212G + N76D |
| A194P + S212N + N76D | A194P + S216I + N76D | A194P + S216T + N76D | A194P + S216V + N76D |
| A194P + L217C + N76D | A194P + L217M + N76D | A194P + N218T + N76D | A194P + S216V + N76D |
| A194P + M222C + N76D | A194P + M222N + N76D | A194P + M222R + N76D | A194P + Q206L + N76D |
| A194P + P225A + N76D | A194P + P225S + N76D | A194P + T255C + N76D | A194P + T255E + N76D |
| A194P + T255Q + N76D | A194P + S256A + N76D | A194P + S256C + N76D | A194P + S256D + N76D |
| A194P + S256V + N76D | A194P + S256Y + N76D | A194P + S259D + N76D | A194P + T260A + N76D |
| A194P + T260E + N76D | A194P + T260P + N76D | A194P + N261D + N76D | A194P + N261C + N76D |
| A194P + N261E + N76D | A194P + N261L + N76D | A194P + N261M + N76D | A194P + N261R + N76D |
| A194P + N261V + N76D | A194P + N261W + N76D | A194P + N261Y + N76D | A194P + N261F + N76D |
| A194P + L262Y + N76D | A194P + L262C + N76D | A194P + L262E + N76D | A194P + L262Q + N76D |
| G195E + N204D + N76D | G195E + N204V + N76D | G195E + V205I + N76D | G195E + V205L + N76D |
| G195E + Q206C + N76D | G195E + Q206E + N76D | G195E + Q206I + N76D | G195E + Q206K + N76D |
| G195E + Q206L + N76D | G195E + Q206T + N76D | G195E + Q206V + N76D | G195E + Q206W + N76D |
| G195E + Y209L + N76D | G195E + Y209W + N76D | G195E + S212A + N76D | G195E + S212D + N76D |
| G195E + S212G + N76D | G195E + S212N + N76D | G195E + S216I + N76D | G195E + S216T + N76D |
| G195E + S216V + N76D | G195E + L217C + N76D | G195E + L217M + N76D | G195E + N218T + N76D |
| G195E + S216V + N76D | G195E + M222C + N76D | G195E + M222N + N76D | G195E + M222R + N76D |
| G195E + Q206L + N76D | G195E + P225A + N76D | G195E + P225S + N76D | G195E + T255C + N76D |
| G195E + T255E + N76D | G195E + T255Q + N76D | G195E + S256A + N76D | G195E + S256C + N76D |
| G195E + S256D + N76D | G195E + S256V + N76D | G195E + S256Y + N76D | G195E + S259D + N76D |
| G195E + T260A + N76D | G195E + T260E + N76D | G195E + T260P + N76D | G195E + N261D + N76D |
| G195E + N261C + N76D | G195E + N261E + N76D | G195E + N261L + N76D | G195E + N261M + N76D |
| G195E + N261R + N76D | G195E + N261V + N76D | G195E + N261W + N76D | G195E + N261Y + N76D |
| G195E + N261F + N76D | G195E + L262Y + N76D | G195E + L262C + N76D | G195E + L262E + N76D |
| G195E + L262Q + N76D | N204D + V205I + N76D | N204D + V205L + N76D | N204D + Q206C + N76D |
| N204D + Q206E + N76D | N204D + Q206I + N76D | N204D + Q206K + N76D | N204D + Q206L + N76D |
| N204D + Q206T + N76D | N204D + Q206V + N76D | N204D + Q206W + N76D | N204D + Y209L + N76D |
| N204D + Y209W + N76D | N204D + S212A + N76D | N204D + S212D + N76D | N204D + S212G + N76D |
| N204D + S212N + N76D | N204D + S216I + N76D | N204D + S216T + N76D | N204D + S216V + N76D |
| N204D + L217C + N76D | N204D + L217M + N76D | N204D + N218T + N76D | N204D + S216V + N76D |
| N204D + M222C + N76D | N204D + M222N + N76D | N204D + M222R + N76D | N204D + Q206L + N76D |
| N204D + P225A + N76D | N204D + P225S + N76D | N204D + T255C + N76D | N204D + T255E + N76D |
| N204D + T255Q + N76D | N204D + S256A + N76D | N204D + S256C + N76D | N204D + S256D + N76D |
| N204D + S256V + N76D | N204D + S256Y + N76D | N204D + S259D + N76D | N204D + T260A + N76D |
| N204D + T260E + N76D | N204D + T260P + N76D | N204D + N261D + N76D | N204D + N261C + N76D |
| N204D + N261M + N76D | N204D + N261L + N76D | N204D + N261R + N76D | N204D + N261W + N76D |
| N204D + N261V + N76D | N204D + N261W + N76D | N204D + N261Y + N76D | N204D + N261F + N76D |
| N204D + L262Y + N76D | N204D + L262C + N76D | N204D + L262E + N76D | N204D + L262Q + N76D |
| N204V + V205I + N76D | N204V + V205L + N76D | N204V + Q206C + N76D | N204V + Q206E + N76D |
| N204V + Q206I + N76D | N204V + Q206K + N76D | N204V + Q206L + N76D | N204V + Q206T + N76D |
| N204V + Q206V + N76D | N204V + Q206W + N76D | N204V + Y209L + N76D | N204V + Y209W + N76D |
| N204V + S212A + N76D | N204V + S212D + N76D | N204V + S212G + N76D | N204V + S212N + N76D |
| N204V + S216I + N76D | N204V + S216T + N76D | N204V + S216V + N76D | N204V + L217C + N76D |
| N204V + L217M + N76D | N204V + N218T + N76D | N204V + M222C + N76D | N204V + M222N + N76D |
| N204V + M222R + N76D | N204V + Q206L + N76D | N204V + P225A + N76D | N204V + P225S + N76D |
| N204V + T255C + N76D | N204V + T255E + N76D | N204V + T255Q + N76D | N204V + S256A + N76D |
| N204V + S256C + N76D | N204V + S256D + N76D | N204V + S256V + N76D | N204V + S256Y + N76D |
| N204V + S259D + N76D | N204V + T260A + N76D | N204V + T260E + N76D | N204V + T260P + N76D |
| N204V + N261D + N76D | N204V + N261C + N76D | N204V + N261E + N76D | |

TABLE 2-continued

| Subtilase Variants | | | |
|---|---|---|---|
| N204V + N261L + N76D | N204V + N261M + N76D | N204V + N261R + N76D | N204V + N261V + N76D |
| N204V + N261W + N76D | N204V + N261Y + N76D | N204V + N261F + N76D | N204V + L262Y + N76D |
| N204V + L262C + N76D | N204V + L262E + N76D | N204V + L262Q + N76D | V205I + Q206C + N76D |
| V205I + Q206E + N76D | V205I + Q206I + N76D | V205I + Q206K + N76D | V205I + Q206L + N76D |
| V205I + Q206T + N76D | V205I + Q206V + N76D | V205I + Q206W + N76D | V205I + Y209L + N76D |
| V205I + Y209W + N76D | V205I + S212A + N76D | V205I + S212D + N76D | V205I + S212G + N76D |
| V205I + S212N + N76D | V205I + S216I + N76D | V205I + S216T + N76D | V205I + S216V + N76D |
| V205I + L217C + N76D | V205I + L217M + N76D | V205I + N218T + N76D | V205I + S216V + N76D |
| V205I + M222C + N76D | V205I + M222N + N76D | V205I + M222R + N76D | V205I + Q206L + N76D |
| V205I + P225A + N76D | V205I + P225S + N76D | V205I + T255C + N76D | V205I + T255E + N76D |
| V205I + T255Q + N76D | V205I + S256A + N76D | V205I + S256C + N76D | V205I + S256D + N76D |
| V205I + S256V + N76D | V205I + S256Y + N76D | V205I + S259D + N76D | V205I + T260A + N76D |
| V205I + T260E + N76D | V205I + T260P + N76D | V205I + N261D + N76D | V205I + N261C + N76D |
| V205I + N261E + N76D | V205I + N261L + N76D | V205I + N261M + N76D | V205I + N261R + N76D |
| V205I + N261V + N76D | V205I + N261W + N76D | V205I + N261Y + N76D | V205I + N261F + N76D |
| V205I + L262Y + N76D | V205I + L262C + N76D | V205I + L262E + N76D | V205I + L262Q + N76D |
| V205L + Q206C + N76D | V205L + Q206E + N76D | V205L + Q206I + N76D | V205L + Q206K + N76D |
| V205L + Q206L + N76D | V205L + Q206T + N76D | V205L + Q206V + N76D | V205L + Q206W + N76D |
| V205L + Y209L + N76D | V205L + Y209W + N76D | V205L + S212A + N76D | V205L + S212D + N76D |
| V205L + S212G + N76D | V205L + S212N + N76D | V205L + S216I + N76D | V205L + S216T + N76D |
| V205L + S216V + N76D | V205L + L217C + N76D | V205L + L217M + N76D | V205L + N218T + N76D |
| V205L + S216V + N76D | V205L + M222C + N76D | V205L + M222N + N76D | V205L + M222R + N76D |
| V205L + Q206L + N76D | V205L + P225A + N76D | V205L + P225S + N76D | V205L + T255C + N76D |
| V205L + T255E + N76D | V205L + T255Q + N76D | V205L + S256A + N76D | V205L + S256C + N76D |
| V205L + S256D + N76D | V205L + S256V + N76D | V205L + S256Y + N76D | V205L + S259D + N76D |
| V205L + T260A + N76D | V205L + T260E + N76D | V205L + T260P + N76D | V205L + N261D + N76D |
| V205L + N261C + N76D | V205L + N261E + N76D | V205L + N261L + N76D | V205L + N261M + N76D |
| V205L + N261R + N76D | V205L + N261V + N76D | V205L + N261W + N76D | V205L + N261Y + N76D |
| V205L + N261F + N76D | V205L + L262Y + N76D | V205L + L262C + N76D | V205L + L262E + N76D |
| V205L + L262Q + N76D | Q206C + Y209L + N76D | Q206C + Y209W + N76D | Q206C + S212A + N76D |
| Q206C + S212D + N76D | Q206C + S212G + N76D | Q206C + S212N + N76D | Q206C + S216I + N76D |
| Q206C + S216T + N76D | Q206C + S216V + N76D | Q206C + L217C + N76D | Q206C + L217M + N76D |
| Q206C + N218T + N76D | Q206C + S216V + N76D | Q206C + M222C + N76D | Q206C + M222N + N76D |
| Q206C + M222R + N76D | Q206C + Q206L + N76D | Q206C + P225A + N76D | Q206C + P225S + N76D |
| Q206C + T255C + N76D | Q206C + T255E + N76D | Q206C + T255Q + N76D | Q206C + S256A + N76D |
| Q206C + S256C + N76D | Q206C + S256D + N76D | Q206C + S256V + N76D | Q206C + S256Y + N76D |
| Q206C + S259D + N76D | Q206C + T260A + N76D | Q206C + T260E + N76D | Q206C + T260P + N76D |
| Q206C + N261D + N76D | Q206C + N261C + N76D | Q206C + N261E + N76D | Q206C + N261L + N76D |
| Q206C + N261M + N76D | Q206C + N261R + N76D | Q206C + N261V + N76D | Q206C + N261W + N76D |
| Q206C + N261Y + N76D | Q206C + N261F + N76D | Q206C + L262C + N76D | Q206C + L262E + N76D |
| Q206C + L262Q + N76D | Q206E + Y209L + N76D | Q206E + Y209W + N76D | |
| Q206E + S212A + N76D | Q206E + S212D + N76D | Q206E + S212G + N76D | Q206E + S212N + N76D |
| Q206E + S216I + N76D | Q206E + S216T + N76D | Q206E + S216V + N76D | Q206E + L217C + N76D |
| Q206E + L217M + N76D | Q206E + N218T + N76D | Q206E + M222C + N76D | Q206E + M222N + N76D |
| Q206E + M222R + N76D | Q206E + Q206L + N76D | Q206E + P225A + N76D | |
| Q206E + P225S + N76D | Q206E + T255C + N76D | Q206E + T255E + N76D | Q206E + T255Q + N76D |
| Q206E + S256A + N76D | Q206E + S256C + N76D | Q206E + S256D + N76D | Q206E + S256V + N76D |
| Q206E + S256Y + N76D | Q206E + S259D + N76D | Q206E + T260A + N76D | Q206E + T260E + N76D |
| Q206E + T260P + N76D | Q206E + N261D + N76D | Q206E + N261C + N76D | Q206E + N261E + N76D |
| Q206E + N261L + N76D | Q206E + N261M + N76D | Q206E + N261R + N76D | Q206E + N261V + N76D |
| Q206E + N261W + N76D | Q206E + N261Y + N76D | Q206E + N261F + N76D | Q206E + L262Y + N76D |
| Q206E + L262C + N76D | Q206E + L262E + N76D | Q206E + L262Q + N76D | Q206I + Y209L + N76D |
| Q206I + Y209W + N76D | Q206I + S212A + N76D | Q206I + S212D + N76D | Q206I + S212G + N76D |
| Q206I + S212N + N76D | Q206I + S216I + N76D | Q206I + S216T + N76D | Q206I + S216V + N76D |
| Q206I + L217C + N76D | Q206I + L217M + N76D | Q206I + N218T + N76D | Q206I + S216V + N76D |
| Q206I + M222C + N76D | Q206I + M222N + N76D | Q206I + M222R + N76D | Q206I + Q206L + N76D |
| Q206I + P225A + N76D | Q206I + P225S + N76D | Q206I + T255C + N76D | Q206I + T255E + N76D |
| Q206I + T255Q + N76D | Q206I + S256A + N76D | Q206I + S256C + N76D | Q206I + S256D + N76D |
| Q206I + S256V + N76D | Q206I + S256Y + N76D | Q206I + S259D + N76D | Q206I + T260A + N76D |
| Q206I + T260E + N76D | Q206I + T260P + N76D | Q206I + N261D + N76D | Q206I + N261C + N76D |
| Q206I + N261E + N76D | Q206I + N261L + N76D | Q206I + N261M + N76D | Q206I + N261R + N76D |
| Q206I + N261V + N76D | Q206I + N261W + N76D | Q206I + N261Y + N76D | Q206I + N261F + N76D |
| Q206I + L262Y + N76D | Q206I + L262C + N76D | Q206I + L262E + N76D | Q206I + L262Q + N76D |
| Q206K + Y209L + N76D | Q206K + Y209W + N76D | Q206K + S212A + N76D | Q206K + S212D + N76D |
| Q206K + S212G + N76D | Q206K + S212N + N76D | Q206K + S216I + N76D | Q206K + S216T + N76D |
| Q206K + S216V + N76D | Q206K + L217C + N76D | Q206K + L217M + N76D | Q206K + N218T + N76D |
| Q206K + S216V + N76D | Q206K + M222C + N76D | Q206K + M222N + N76D | Q206K + M222R + N76D |
| Q206K + Q206L + N76D | Q206K + P225A + N76D | Q206K + P225S + N76D | Q206K + T255C + N76D |
| Q206K + T255E + N76D | Q206K + T255Q + N76D | Q206K + S256A + N76D | Q206K + S256C + N76D |
| Q206K + S256D + N76D | Q206K + S256V + N76D | Q206K + S256Y + N76D | Q206K + S259D + N76D |
| Q206K + T260A + N76D | Q206K + T260E + N76D | Q206K + T260P + N76D | Q206K + N261D + N76D |
| Q206K + N261C + N76D | Q206K + N261E + N76D | Q206K + N261L + N76D | Q206K + N261M + N76D |
| Q206K + N261R + N76D | Q206K + N261V + N76D | Q206K + N261W + N76D | Q206K + N261Y + N76D |
| Q206K + N261F + N76D | Q206K + L262Y + N76D | Q206K + L262C + N76D | Q206K + L262E + N76D |
| Q206K + L262Q + N76D | Q206L + Y209L + N76D | Q206L + Y209W + N76D | Q206L + S212A + N76D |
| Q206L + S212D + N76D | Q206L + S212G + N76D | Q206L + S212N + N76D | Q206L + S216I + N76D |
| Q206L + S216T + N76D | Q206L + S216V + N76D | Q206L + L217C + N76D | Q206L + L217M + N76D |
| Q206L + N218T + N76D | Q206L + S216V + N76D | Q206L + M222C + N76D | Q206L + M222N + N76D |

TABLE 2-continued

Subtilase Variants

| | | | |
|---|---|---|---|
| Q206L + M222R + N76D | Q206L + Q206L + N76D | Q206L + P225A + N76D | Q206L + P225S + N76D |
| Q206L + T255C + N76D | Q206L + T255E + N76D | Q206L + T255Q + N76D | Q206L + S256A + N76D |
| Q206L + S256C + N76D | Q206L + S256D + N76D | Q206L + S256V + N76D | Q206L + S256Y + N76D |
| Q206L + S259D + N76D | Q206L + T260A + N76D | Q206L + T260E + N76D | Q206L + T260P + N76D |
| Q206L + N261D + N76D | Q206L + N261C + N76D | Q206L + N261E + N76D | Q206L + N261L + N76D |
| Q206L + N261M + N76D | Q206L + N261R + N76D | Q206L + N261V + N76D | Q206L + N261W + N76D |
| Q206L + N261Y + N76D | Q206L + N261F + N76D | Q206L + L262Y + N76D | Q206L + L262C + N76D |
| Q206L + L262E + N76D | Q206L + L262Q + N76D | Q206T + Y209L + N76D | Q206T + Y209W + N76D |
| Q206T + S212A + N76D | Q206T + S212D + N76D | Q206T + S212G + N76D | Q206T + S212N + N76D |
| Q206T + S216I + N76D | Q206T + S216T + N76D | Q206T + S216V + N76D | Q206T + L217C + N76D |
| Q206T + L217M + N76D | Q206T + N218T + N76D | Q206T + S216V + N76D | Q206T + M222C + N76D |
| Q206T + M222N + N76D | Q206T + M222R + N76D | Q206T + Q206L + N76D | Q206T + P225A + N76D |
| Q206T + P225S + N76D | Q206T + T255C + N76D | Q206T + T255E + N76D | Q206T + T255Q + N76D |
| Q206T + S256A + N76D | Q206T + S256C + N76D | Q206T + S256D + N76D | Q206T + S256V + N76D |
| Q206T + S256Y + N76D | Q206T + S259D + N76D | Q206T + T260A + N76D | Q206T + T260E + N76D |
| Q206T + T260P + N76D | Q206T + N261D + N76D | Q206T + N261C + N76D | Q206T + N261E + N76D |
| Q206T + N261L + N76D | Q206T + N261M + N76D | Q206T + N261R + N76D | Q206T + N261V + N76D |
| Q206T + N261W + N76D | Q206T + N261Y + N76D | Q206T + N261F + N76D | Q206T + L262Y + N76D |
| Q206T + L262C + N76D | Q206T + L262E + N76D | Q206T + L262Q + N76D | Q206V + Y209L + N76D |
| Q206V + Y209W + N76D | Q206V + S212A + N76D | Q206V + S212D + N76D | Q206V + S212G + N76D |
| Q206V + S212N + N76D | Q206V + S216I + N76D | Q206V + S216T + N76D | Q206V + S216V + N76D |
| Q206V + L217C + N76D | Q206V + L217M + N76D | Q206V + N218T + N76D | Q206V + S216V + N76D |
| Q206V + M222C + N76D | Q206V + M222N + N76D | Q206V + M222R + N76D | Q206V + Q206L + N76D |
| Q206V + P225A + N76D | Q206V + P225S + N76D | Q206V + T255C + N76D | Q206V + T255E + N76D |
| Q206V + T255Q + N76D | Q206V + S256A + N76D | Q206V + S256C + N76D | Q206V + S256D + N76D |
| Q206V + S256V + N76D | Q206V + S256Y + N76D | Q206V + S259D + N76D | Q206V + T260A + N76D |
| Q206V + T260E + N76D | Q206V + T260P + N76D | Q206V + N261D + N76D | Q206V + N261C + N76D |
| Q206V + N261E + N76D | Q206V + N261L + N76D | Q206V + N261M + N76D | Q206V + N261R + N76D |
| Q206V + N261V + N76D | Q206V + N261W + N76D | Q206V + N261Y + N76D | Q206V + N261F + N76D |
| Q206V + L262Y + N76D | Q206V + L262C + N76D | Q206V + L262E + N76D | Q206V + L262Q + N76D |
| Q206W + Y209L + N76D | Q206W + Y209W + N76D | Q206W + S212A + N76D | Q206W + S212D + N76D |
| Q206W + S212G + N76D | Q206W + S212N + N76D | Q206W + S216I + N76D | Q206W + S216T + N76D |
| Q206W + S216V + N76D | Q206W + L217C + N76D | Q206W + L217M + N76D | Q206W + N218T + N76D |
| Q206W + S216V + N76D | Q206W + M222C + N76D | Q206W + M222N + N76D | Q206W + M222R + N76D |
| Q206W + Q206L + N76D | Q206W + P225A + N76D | Q206W + P225S + N76D | Q206W + T255C + N76D |
| Q206W + T255E + N76D | Q206W + T255Q + N76D | Q206W + S256A + N76D | Q206W + S256C + N76D |
| Q206W + S256D + N76D | Q206W + S256V + N76D | Q206W + S256Y + N76D | Q206W + S259D + N76D |
| Q206W + T260A + N76D | Q206W + T260E + N76D | Q206W + T260P + N76D | Q206W + N261D + N76D |
| Q206W + N261C + N76D | Q206W + N261E + N76D | Q206W + N261L + N76D | Q206W + N261M + N76D |
| Q206W + N261R + N76D | Q206W + N261W + N76D | Q206W + N261V + N76D | Q206W + N261Y + N76D |
| Q206W + N261F + N76D | Q206W + L262Y + N76D | Q206W + L262C + N76D | Q206W + L262E + N76D |
| Q206W + L262Q + N76D | Y209L + S212A + N76D | Y209L + S212D + N76D | Y209L + S212G + N76D |
| Y209L + S212N + N76D | Y209L + S216I + N76D | Y209L + S216T + N76D | Y209L + S216V + N76D |
| Y209L + L217C + N76D | Y209L + L217M + N76D | Y209L + N218T + N76D | Y209L + S216V + N76D |
| Y209L + M222C + N76D | Y209L + M222N + N76D | Y209L + M222R + N76D | Y209L + Q206L + N76D |
| Y209L + P225A + N76D | Y209L + P225S + N76D | Y209L + T255C + N76D | Y209L + T255E + N76D |
| Y209L + T255Q + N76D | Y209L + S256A + N76D | Y209L + S256C + N76D | Y209L + S256D + N76D |
| Y209L + S256V + N76D | Y209L + S256Y + N76D | Y209L + S259D + N76D | Y209L + T260A + N76D |
| Y209L + T260E + N76D | Y209L + T260P + N76D | Y209L + N261D + N76D | Y209L + N261C + N76D |
| Y209L + N261E + N76D | Y209L + N261L + N76D | Y209L + N261M + N76D | Y209L + N261R + N76D |
| Y209L + N261V + N76D | Y209L + N261W + N76D | Y209L + N261Y + N76D | Y209L + N261F + N76D |
| Y209L + L262Y + N76D | Y209L + L262C + N76D | Y209L + L262E + N76D | Y209L + L262Q + N76D |
| Y209W + S212A + N76D | Y209W + S212D + N76D | Y209W + S212G + N76D | Y209W + S212N + N76D |
| Y209W + S216I + N76D | Y209W + S216T + N76D | Y209W + S216V + N76D | Y209W + L217C + N76D |
| Y209W + L217M + N76D | Y209W + N218T + N76D | Y209W + S216V + N76D | Y209W + M222C + N76D |
| Y209W + M222N + N76D | Y209W + M222R + N76D | Y209W + Q206L + N76D | Y209W + P225A + N76D |
| Y209W + P225S + N76D | Y209W + T255C + N76D | Y209W + T255E + N76D | Y209W + T255Q + N76D |
| Y209W + S256A + N76D | Y209W + S256C + N76D | Y209W + S256D + N76D | Y209W + S256V + N76D |
| Y209W + S256Y + N76D | Y209W + S259D + N76D | Y209W + T260A + N76D | Y209W + T260E + N76D |
| Y209W + T260P + N76D | Y209W + N261D + N76D | Y209W + N261C + N76D | Y209W + N261E + N76D |
| Y209W + N261L + N76D | Y209W + N261M + N76D | Y209W + N261R + N76D | Y209W + N261V + N76D |
| Y209W + N261W + N76D | Y209W + N261Y + N76D | Y209W + N261F + N76D | Y209W + L262Y + N76D |
| Y209W + L262C + N76D | Y209W + L262E + N76D | Y209W + L262Q + N76D | S212A + S216I + N76D |
| S212A + S216T + N76D | S212A + S216V + N76D | S212A + L217C + N76D | S212A + L217M + N76D |
| S212A + N218T + N76D | S212A + S216V + N76D | S212A + M222C + N76D | S212A + M222N + N76D |
| S212A + M222R + N76D | S212A + Q206L + N76D | S212A + P225A + N76D | S212A + P225S + N76D |
| S212A + T255C + N76D | S212A + T255E + N76D | S212A + T255Q + N76D | S212A + S256A + N76D |
| S212A + S256C + N76D | S212A + S256D + N76D | S212A + S256V + N76D | S212A + S256Y + N76D |
| S212A + S259D + N76D | S212A + T260A + N76D | S212A + T260E + N76D | S212A + T260P + N76D |
| S212A + N261D + N76D | S212A + N261C + N76D | S212A + N261E + N76D | S212A + N261L + N76D |
| S212A + N261M + N76D | S212A + N261R + N76D | S212A + N261V + N76D | S212A + N261W + N76D |
| S212A + N261Y + N76D | S212A + N261F + N76D | S212A + L262Y + N76D | S212A + L262C + N76D |
| S212A + L262E + N76D | S212A + L262Q + N76D | S212D + S216I + N76D | S212D + S216T + N76D |
| S212D + S216V + N76D | S212D + L217C + N76D | S212D + L217M + N76D | S212D + N218T + N76D |
| S212D + S216V + N76D | S212D + M222C + N76D | S212D + M222N + N76D | S212D + M222R + N76D |
| S212D + Q206L + N76D | S212D + P225A + N76D | S212D + P225S + N76D | S212D + T255C + N76D |
| S212D + T255E + N76D | S212D + T255Q + N76D | S212D + S256A + N76D | S212D + S256C + N76D |
| S212D + S256D + N76D | S212D + S256V + N76D | S212D + S256Y + N76D | S212D + S259D + N76D |

TABLE 2-continued

Subtilase Variants

| | | | |
|---|---|---|---|
| S212D + T260A + N76D | S212D + T260E + N76D | S212D + T260P + N76D | S212D + N261D + N76D |
| S212D + N261C + N76D | S212D + N261E + N76D | S212D + N261L + N76D | S212D + N261M + N76D |
| S212D + N261R + N76D | S212D + N261V + N76D | S212D + N261W + N76D | S212D + N261Y + N76D |
| S212D + N261F + N76D | S212D + L262Y + N76D | S212D + L262C + N76D | S212D + L262E + N76D |
| S212D + L262Q + N76D | S212G + S216I + N76D | S212G + S216T + N76D | S212G + S216V + N76D |
| S212G + L217C + N76D | S212G + L217M + N76D | S212G + S216V + N76D | S212G + S216V + N76D |
| S212G + M222C + N76D | S212G + M222N + N76D | S212G + M222R + N76D | S212G + Q206L + N76D |
| S212G + P225A + N76D | S212G + P225S + N76D | S212G + T255C + N76D | S212G + T255E + N76D |
| S212G + T255Q + N76D | S212G + S256A + N76D | S212G + S256C + N76D | S212G + S256D + N76D |
| S212G + S256V + N76D | S212G + S256Y + N76D | S212G + S259D + N76D | S212G + T260A + N76D |
| S212G + T260E + N76D | S212G + T260P + N76D | S212G + N261D + N76D | S212G + N261C + N76D |
| S212G + N261E + N76D | S212G + N261L + N76D | S212G + N261M + N76D | S212G + N261R + N76D |
| S212G + N261V + N76D | S212G + N261W + N76D | S212G + N261Y + N76D | S212G + N261F + N76D |
| S212G + L262Y + N76D | S212G + L262C + N76D | S212G + L262E + N76D | S212G + L262Q + N76D |
| S212N + S216I + N76D | S212N + S216T + N76D | S212N + S216V + N76D | S212N + L217C + N76D |
| S212N + L217M + N76D | S212N + N218T + N76D | S212N + S216V + N76D | S212N + M222C + N76D |
| S212N + M222N + N76D | S212N + M222R + N76D | S212N + Q206L + N76D | S212N + P225A + N76D |
| S212N + P225S + N76D | S212N + T255C + N76D | S212N + T255E + N76D | S212N + T255Q + N76D |
| S212N + S256A + N76D | S212N + S256C + N76D | S212N + S256D + N76D | S212N + S256V + N76D |
| S212N + S256Y + N76D | S212N + S259D + N76D | S212N + T260A + N76D | S212N + T260E + N76D |
| S212N + T260P + N76D | S212N + N261D + N76D | S212N + N261C + N76D | S212N + N261E + N76D |
| S212N + N261L + N76D | S212N + N261M + N76D | S212N + N261R + N76D | S212N + N261V + N76D |
| S212N + N261W + N76D | S212N + N261Y + N76D | S212N + N261F + N76D | S212N + L262Y + N76D |
| S212N + L262C + N76D | S212N + L262E + N76D | S212N + L262Q + N76D | S216I + L217C + N76D |
| S216I + L217M + N76D | S216I + N218T + N76D | S216I + S216V + N76D | S216I + M222C + N76D |
| S216I + M222N + N76D | S216I + M222R + N76D | S216I + Q206L + N76D | S216I + P225A + N76D |
| S216I + P225S + N76D | S216I + T255C + N76D | S216I + T255E + N76D | S216I + T255Q + N76D |
| S216I + S256A + N76D | S216I + S256C + N76D | S216I + S256D + N76D | S216I + S256V + N76D |
| S216I + S256Y + N76D | S216I + S259D + N76D | S216I + T260A + N76D | S216I + T260E + N76D |
| S216I + T260P + N76D | S216I + N261D + N76D | S216I + N261C + N76D | S216I + N261E + N76D |
| S216I + N261L + N76D | S216I + N261M + N76D | S216I + N261R + N76D | S216I + N261V + N76D |
| S216I + N261W + N76D | S216I + N261Y + N76D | S216I + N261F + N76D | S216I + L262Y + N76D |
| S216I + L262C + N76D | S216I + L262E + N76D | S216I + L262Q + N76D | S216T + L217C + N76D |
| S216T + L217M + N76D | S216T + N218T + N76D | S216T + S216V + N76D | S216T + M222C + N76D |
| S216T + M222N + N76D | S216T + M222R + N76D | S216T + Q206L + N76D | S216T + P225A + N76D |
| S216T + P225S + N76D | S216T + T255C + N76D | S216T + T255E + N76D | S216T + T255Q + N76D |
| S216T + S256A + N76D | S216T + S256C + N76D | S216T + S256D + N76D | S216T + S256V + N76D |
| S216T + S256Y + N76D | S216T + S259D + N76D | S216T + T260A + N76D | S216T + T260E + N76D |
| S216T + T260P + N76D | S216T + N261D + N76D | S216T + N261C + N76D | S216T + N261E + N76D |
| S216T + N261L + N76D | S216T + N261M + N76D | S216T + N261R + N76D | S216T + N261V + N76D |
| S216T + N261W + N76D | S216T + N261Y + N76D | S216T + N261F + N76D | S216T + L262Y + N76D |
| S216T + L262C + N76D | S216T + L262E + N76D | S216T + L262Q + N76D | S216V + L217C + N76D |
| S216V + L217M + N76D | S216V + N218T + N76D | S216V + S216V + N76D | S216V + M222C + N76D |
| S216V + M222N + N76D | S216V + M222R + N76D | S216V + Q206L + N76D | S216V + P225A + N76D |
| S216V + P225S + N76D | S216V + T255C + N76D | S216V + T255E + N76D | S216V + T255Q + N76D |
| S216V + S256A + N76D | S216V + S256C + N76D | S216V + S256D + N76D | S216V + S256V + N76D |
| S216V + S256Y + N76D | S216V + S259D + N76D | S216V + T260A + N76D | S216V + T260E + N76D |
| S216V + T260P + N76D | S216V + N261D + N76D | S216V + N261C + N76D | S216V + N261E + N76D |
| S216V + N261L + N76D | S216V + N261M + N76D | S216V + N261R + N76D | S216V + N261V + N76D |
| S216V + N261W + N76D | S216V + N261Y + N76D | S216V + N261F + N76D | S216V + L262Y + N76D |
| S216V + L262C + N76D | S216V + L262E + N76D | S216V + L262Q + N76D | L217C + N218T + N76D |
| L217C + S216V + N76D | L217C + M222N + N76D | L217C + M222N + N76D | L217C + M222R + N76D |
| L217C + Q206L + N76D | L217C + P225A + N76D | L217C + P225S + N76D | L217C + T255C + N76D |
| L217C + T255E + N76D | L217C + T255Q + N76D | L217C + S256A + N76D | L217C + S256C + N76D |
| L217C + S256D + N76D | L217C + S256V + N76D | L217C + S256Y + N76D | L217C + S259D + N76D |
| L217C + T260A + N76D | L217C + T260E + N76D | L217C + T260P + N76D | L217C + N261D + N76D |
| L217C + N261C + N76D | L217C + N261E + N76D | L217C + N261L + N76D | L217C + N261M + N76D |
| L217C + N261R + N76D | L217C + N261V + N76D | L217C + N261W + N76D | L217C + N261Y + N76D |
| L217C + N261F + N76D | L217C + L262Y + N76D | L217C + L262C + N76D | L217C + L262E + N76D |
| L217C + L262Q + N76D | L217M + N218T + N76D | L217M + S216V + N76D | L217M + M222C + N76D |
| L217M + M222N + N76D | L217M + M222R + N76D | L217M + Q206L + N76D | L217M + P225A + N76D |
| L217M + P225S + N76D | L217M + T255C + N76D | L217M + T255E + N76D | L217M + T255Q + N76D |
| L217M + S256A + N76D | L217M + S256C + N76D | L217M + S256D + N76D | L217M + S256V + N76D |
| L217M + S256Y + N76D | L217M + S259D + N76D | L217M + T260A + N76D | L217M + T260E + N76D |
| L217M + T260P + N76D | L217M + N261D + N76D | L217M + N261C + N76D | L217M + N261E + N76D |
| L217M + N261L + N76D | L217M + N261M + N76D | L217M + N261R + N76D | L217M + N261V + N76D |
| L217M + N261W + N76D | L217M + N261Y + N76D | L217M + N261F + N76D | L217M + L262Y + N76D |
| L217M + L262C + N76D | L217M + L262E + N76D | L217M + L262Q + N76D | N218T + S216V + N76D |
| N218T + M222C + N76D | N218T + M222N + N76D | N218T + M222R + N76D | N218T + Q206L + N76D |
| N218T + P225A + N76D | N218T + P225S + N76D | N218T + T255C + N76D | N218T + T255E + N76D |
| N218T + T255Q + N76D | N218T + S256A + N76D | N218T + S256C + N76D | N218T + S256D + N76D |
| N218T + S256V + N76D | N218T + S256Y + N76D | N218T + S259D + N76D | N218T + T260A + N76D |
| N218T + T260E + N76D | N218T + T260P + N76D | N218T + N261D + N76D | N218T + N261C + N76D |
| N218T + N261E + N76D | N218T + N261L + N76D | N218T + N261M + N76D | N218T + N261R + N76D |
| N218T + N261V + N76D | N218T + N261W + N76D | N218T + N261Y + N76D | N218T + N261F + N76D |
| N218T + L262Y + N76D | N218T + L262C + N76D | N218T + L262E + N76D | N218T + L262Q + N76D |
| S216V + P225A + N76D | S216V + P225S + N76D | S216V + T255C + N76D | S216V + T255E + N76D |
| S216V + T255Q + N76D | S216V + S256A + N76D | S216V + S256C + N76D | S216V + S256D + N76D |

TABLE 2-continued

Subtilase Variants

| | | | |
|---|---|---|---|
| S216V + S256V + N76D | S216V + S256Y + N76D | S216V + S259D + N76D | S216V + T260A + N76D |
| S216V + T260E + N76D | S216V + T260P + N76D | S216V + N261D + N76D | S216V + N261C + N76D |
| S216V + N261E + N76D | S216V + N261L + N76D | S216V + N261M + N76D | S216V + N261R + N76D |
| S216V + N261V + N76D | S216V + N261W + N76D | S216V + N261Y + N76D | S216V + N261F + N76D |
| S216V + L262Y + N76D | S216V + L262C + N76D | S216V + L262E + N76D | S216V + L262Q + N76D |
| M222C + P225A + N76D | M222C + P225S + N76D | M222C + T255C + N76D | M222C + T255E + N76D |
| M222C + T255Q + N76D | M222C + S256A + N76D | M222C + S256C + N76D | M222C + S256D + N76D |
| M222C + S256V + N76D | M222C + S256Y + N76D | M222C + S259D + N76D | M222C + T260A + N76D |
| M222C + T260E + N76D | M222C + T260P + N76D | M222C + N261D + N76D | M222C + N261C + N76D |
| M222C + N261E + N76D | M222C + N261L + N76D | M222C + N261M + N76D | M222C + N261R + N76D |
| M222C + N261V + N76D | M222C + N261W + N76D | M222C + N261Y + N76D | M222C + N261F + N76D |
| M222C + L262Y + N76D | M222C + L262C + N76D | M222C + L262E + N76D | M222C + L262Q + N76D |
| M222N + P225A + N76D | M222N + P225S + N76D | M222N + T255C + N76D | M222N + T255E + N76D |
| M222N + T255Q + N76D | M222N + S256A + N76D | M222N + S256C + N76D | M222N + S256D + N76D |
| M222N + S256V + N76D | M222N + S256Y + N76D | M222N + S259D + N76D | M222N + T260A + N76D |
| M222N + T260E + N76D | M222N + T260P + N76D | M222N + N261D + N76D | M222N + N261C + N76D |
| M222N + N261E + N76D | M222N + N261L + N76D | M222N + N261M + N76D | M222N + N261R + N76D |
| M222N + N261V + N76D | M222N + N261W + N76D | M222N + N261Y + N76D | M222N + N261F + N76D |
| M222N + L262Y + N76D | M222N + L262C + N76D | M222N + L262E + N76D | M222N + L262Q + N76D |
| M222R + P225A + N76D | M222R + P225S + N76D | M222R + T255C + N76D | M222R + T255E + N76D |
| M222R + T255Q + N76D | M222R + S256A + N76D | M222R + S256C + N76D | M222R + S256D + N76D |
| M222R + S256V + N76D | M222R + S256Y + N76D | M222R + S259D + N76D | M222R + T260A + N76D |
| M222R + T260E + N76D | M222R + T260P + N76D | M222R + N261D + N76D | M222R + N261C + N76D |
| M222R + N261E + N76D | M222R + N261L + N76D | M222R + N261M + N76D | M222R + N261R + N76D |
| M222R + N261V + N76D | M222R + N261W + N76D | M222R + N261Y + N76D | M222R + N261F + N76D |
| M222R + L262Y + N76D | M222R + L262C + N76D | M222R + L262E + N76D | M222R + L262Q + N76D |
| Q206L + P225A + N76D | Q206L + P225S + N76D | Q206L + T255C + N76D | Q206L + T255E + N76D |
| Q206L + T255Q + N76D | Q206L + S256A + N76D | Q206L + S256C + N76D | Q206L + S256D + N76D |
| Q206L + S256V + N76D | Q206L + S256Y + N76D | Q206L + S259D + N76D | Q206L + T260A + N76D |
| Q206L + T260E + N76D | Q206L + T260P + N76D | Q206L + N261D + N76D | Q206L + N261C + N76D |
| Q206L + N261E + N76D | Q206L + N261L + N76D | Q206L + N261M + N76D | Q206L + N261R + N76D |
| Q206L + N261V + N76D | Q206L + N261W + N76D | Q206L + N261Y + N76D | Q206L + N261F + N76D |
| Q206L + L262Y + N76D | Q206L + L262C + N76D | Q206L + L262E + N76D | Q206L + L262Q + N76D |
| P225A + T255C + N76D | P225A + T255E + N76D | P225A + T255Q + N76D | P225A + S256A + N76D |
| P225A + S256C + N76D | P225A + S256D + N76D | P225A + S256V + N76D | P225A + S256Y + N76D |
| P225A + S259D + N76D | P225A + T260A + N76D | P225A + T260E + N76D | P225A + T260P + N76D |
| P225A + N261D + N76D | P225A + N261C + N76D | P225A + N261E + N76D | P225A + N261L + N76D |
| P225A + N261M + N76D | P225A + N261R + N76D | P225A + N261V + N76D | P225A + N261W + N76D |
| P225A + N261Y + N76D | P225A + N261F + N76D | P225A + L262Y + N76D | P225A + L262C + N76D |
| P225A + L262E + N76D | P225A + L262Q + N76D | P225S + T255C + N76D | P225S + T255E + N76D |
| P225S + T255Q + N76D | P225S + S256A + N76D | P225S + S256C + N76D | P225S + S256D + N76D |
| P225S + S256V + N76D | P225S + S256Y + N76D | P225S + S259D + N76D | P225S + T260A + N76D |
| P225S + T260E + N76D | P225S + T260P + N76D | P225S + N261D + N76D | P225S + N261C + N76D |
| P225S + N261E + N76D | P225S + N261L + N76D | P225S + N261M + N76D | P225S + N261R + N76D |
| P225S + N261V + N76D | P225S + N261W + N76D | P225S + N261Y + N76D | P225S + N261F + N76D |
| P225S + L262Y + N76D | P225S + L262C + N76D | P225S + L262E + N76D | P225S + L262Q + N76D |
| T255C + S256A + N76D | T255C + S256C + N76D | T255C + S256D + N76D | T255C + S256V + N76D |
| T255C + S256Y + N76D | T255C + S259D + N76D | T255C + T260A + N76D | T255C + T260E + N76D |
| T255C + T260P + N76D | T255C + N261D + N76D | T255C + N261C + N76D | T255C + N261E + N76D |
| T255C + N261L + N76D | T255C + N261M + N76D | T255C + N261R + N76D | T255C + N261V + N76D |
| T255C + N261W + N76D | T255C + N261Y + N76D | T255C + N261F + N76D | T255C + L262Y + N76D |
| T255C + L262C + N76D | T255C + L262Q + N76D | T255C + L262E + N76D | T255E + S256A + N76D |
| T255E + S256C + N76D | T255E + S256D + N76D | T255E + S256V + N76D | T255E + S256Y + N76D |
| T255E + S259D + N76D | T255E + T260A + N76D | T255E + T260E + N76D | T255E + T260P + N76D |
| T255E + N261D + N76D | T255E + N261C + N76D | T255E + N261E + N76D | T255E + N261L + N76D |
| T255E + N261M + N76D | T255E + N261R + N76D | T255E + N261V + N76D | T255E + N261W + N76D |
| T255E + N261Y + N76D | T255E + N261F + N76D | T255E + L262Y + N76D | T255E + L262C + N76D |
| T255E + L262E + N76D | T255E + L262Q + N76D | T255Q + S256A + N76D | T255Q + S256C + N76D |
| T255Q + S256D + N76D | T255Q + S256V + N76D | T255Q + S256Y + N76D | T255Q + S259D + N76D |
| T255Q + T260A + N76D | T255Q + T260E + N76D | T255Q + T260P + N76D | T255Q + N261D + N76D |
| T255Q + N261C + N76D | T255Q + N261E + N76D | T255Q + N261L + N76D | T255Q + N261M + N76D |
| T255Q + N261R + N76D | T255Q + N261V + N76D | T255Q + N261W + N76D | T255Q + N261Y + N76D |
| T255Q + N261F + N76D | T255Q + L262Y + N76D | T255Q + L262C + N76D | T255Q + L262E + N76D |
| T255Q + L262Q + N76D | S256A + S259D + N76D | S256A + T260A + N76D | S256A + T260E + N76D |
| S256A + T260P + N76D | S256A + N261D + N76D | S256A + N261C + N76D | S256A + N261E + N76D |
| S256A + N261L + N76D | S256A + N261M + N76D | S256A + N261R + N76D | S256A + N261V + N76D |
| S256A + N261W + N76D | S256A + N261Y + N76D | S256A + N261F + N76D | S256A + L262Y + N76D |
| S256A + L262C + N76D | S256A + L262E + N76D | S256A + L262Q + N76D | S256C + S259D + N76D |
| S256C + T260A + N76D | S256C + T260E + N76D | S256C + T260P + N76D | S256C + N261D + N76D |
| S256C + N261C + N76D | S256C + N261E + N76D | S256C + N261L + N76D | S256C + N261M + N76D |
| S256C + N261R + N76D | S256C + N261V + N76D | S256C + N261W + N76D | S256C + N261Y + N76D |
| S256C + N261F + N76D | S256C + L262Y + N76D | S256C + L262C + N76D | S256C + L262E + N76D |
| S256C + L262Q + N76D | S256D + S259D + N76D | S256D + T260A + N76D | S256D + T260E + N76D |
| S256D + T260P + N76D | S256D + N261D + N76D | S256D + N261C + N76D | S256D + N261E + N76D |
| S256D + N261L + N76D | S256D + N261M + N76D | S256D + N261R + N76D | S256D + N261V + N76D |
| S256D + N261W + N76D | S256D + N261Y + N76D | S256D + N261F + N76D | S256D + L262Y + N76D |
| S256D + L262C + N76D | S256D + L262E + N76D | S256D + L262Q + N76D | S256V + S259D + N76D |
| S256V + T260A + N76D | S256V + T260E + N76D | S256V + T260P + N76D | S256V + N261D + N76D |

TABLE 2-continued

Subtilase Variants

| | | | |
|---|---|---|---|
| S256V + N261C + N76D | S256V + N261E + N76D | S256V + N261L + N76D | S256V + N261M + N76D |
| S256V + N261R + N76D | S256V + N261V + N76D | S256V + N261W + N76D | S256V + N261Y + N76D |
| S256V + N261F + N76D | S256V + L262Y + N76D | S256V + L262C + N76D | S256V + L262E + N76D |
| S256V + L262Q + N76D | S256V + S259D + N76D | S256V + T260A + N76D | S256V + T260E + N76D |
| S256V + T260P + N76D | S256Y + N261D + N76D | S256Y + N261C + N76D | S256Y + N261E + N76D |
| S256Y + N261L + N76D | S256Y + N261M + N76D | S256Y + N261R + N76D | S256Y + N261V + N76D |
| S256Y + N261W + N76D | S256Y + N261Y + N76D | S256Y + N261F + N76D | S256Y + L262Y + N76D |
| S256Y + L262C + N76D | S256Y + L262E + N76D | S256Y + L262Q + N76D | S259D + T260A + N76D |
| S259D + T260E + N76D | S259D + T260P + N76D | S259D + N261D + N76D | S259D + N261C + N76D |
| S259D + N261E + N76D | S259D + N261L + N76D | S259D + N261M + N76D | S259D + N261R + N76D |
| S259D + N261V + N76D | S259D + N261W + N76D | S259D + N261Y + N76D | S259D + N261F + N76D |
| S259D + L262Y + N76D | S259D + L262C + N76D | S259D + L262E + N76D | S259D + L262Q + N76D |
| T260A + N261D + N76D | T260A + N261C + N76D | T260A + N261E + N76D | T260A + N261L + N76D |
| T260A + N261M + N76D | T260A + N261R + N76D | T260A + N261V + N76D | T260A + N261W + N76D |
| T260A + N261Y + N76D | T260A + N261F + N76D | T260A + L262Y + N76D | T260A + L262C + N76D |
| T260A + L262E + N76D | T260A + L262Q + N76D | T260E + N261D + N76D | T260E + N261C + N76D |
| T260E + N261E + N76D | T260E + N261L + N76D | T260E + N261M + N76D | T260E + N261R + N76D |
| T260E + N261V + N76D | T260E + N261W + N76D | T260E + N261Y + N76D | T260E + N261F + N76D |
| T260E + L262Y + N76D | T260E + L262C + N76D | T260E + L262E + N76D | T260E + L262Q + N76D |
| T260P + N261D + N76D | T260P + N261C + N76D | T260P + N261E + N76D | T260P + N261L + N76D |
| T260P + N261M + N76D | T260P + N261R + N76D | T260P + N261V + N76D | T260P + N261W + N76D |
| T260P + N261Y + N76D | T260P + N261F + N76D | T260P + L262Y + N76D | T260P + L262C + N76D |
| T260P + L262E + N76D | T260P + L262Q + N76D | N261D + L262Y + N76D | N261D + L262C + N76D |
| N261D + L262E + N76D | N261D + L262Q + N76D | N261C + L262Y + N76D | N261C + L262C + N76D |
| N261C + L262E + N76D | N261C + L262Q + N76D | N261E + L262Y + N76D | N261E + L262C + N76D |
| N261E + L262E + N76D | N261E + L262Q + N76D | N261L + L262Y + N76D | N261L + L262C + N76D |
| N261L + L262E + N76D | N261L + L262Q + N76D | N261M + L262Y + N76D | N261M + L262C + N76D |
| N261M + L262E + N76D | N261M + L262Q + N76D | N261R + L262Y + N76D | N261R + L262C + N76D |
| N261R + L262E + N76D | N261R + L262Q + N76D | N261V + L262Y + N76D | N261V + L262C + N76D |
| N261V + L262E + N76D | N261V + L262Q + N76D | N261W + L262Y + N76D | N261W + L262C + N76D |
| N261W + L262E + N76D | N261W + L262Q + N76D | N261Y + L262Y + N76D | N261Y + L262C + N76D |
| N261Y + L262E + N76D | N261Y + L262Q + N76D | | |

In another aspect of the invention, the subtilase variant of the invention comprises the substitution N76D and three of the substitutions selected from the list consisting of Q2R, W6I, I8{C,H}, S9{C,D,E,Q}, N18S, N43{A,C,L,R,W}, S49T, G53{A,L}, G6I D, I72{A,V}, S78{D,N}, V104{F,P,T,Y}, A114V, G115{T,W}, H120{I,T,V}, P129D, V147W, V149{C,N,Q}, A158E, G160{D,P}, S161{C,Y,E}, I162L, S163{A, D}, Q182{C,E}, N184D, N185{C,E}, S188{C,D,E}, Q191N, A194{D,E}, N204{D,V}, V205{I,L}, Q206{C,E,I,K,T,V,W,L}, Y209{L,W}, S212{A,D,G,N}, S216{I,T,V}, L217{C,M}, N218T, M222{C,N,R}, P225{A,S}, T255{C,E,Q}, S256{A,C,D,V, Y}, S259D, T260{A,E,P}, N261{D,C,E,L,M,R,V,W,Y,F} and L262{Y,C,E,Q}, wherein each position corresponds to the corresponding position of the polypeptide of SEQ ID NO: 2. In one embodiment, the subtilase variant has improved stability, in particular improved storage stability, compared to the polypeptide of SEQ ID NO: 1 or to the polypeptide of SEQ ID NO: 2. In a preferred embodiment, the subtilase variant has improved stability, in particular improved in storage stability, and on par or improved wash performance compared to the polypeptide of SEQ ID NO: 1 or to the polypeptide of SEQ ID NO: 2.

In another aspect of the invention, the subtilase variant of the invention comprises the substitution N76D and four or five or six or seven or eight of the substitutions selected from the list consisting of Q2R, W6I, I8{C,H}, S9{C,D,E,Q}, N18S,N43{A,C,L,R,W}, S49T, G53{A,L}, G61D, I72{A,V}, S78{D,N}, V104{F,P,T,Y}, A114V, G115{T,W}, H120{I,T,V}, P129D, V147W, V149{C,N,Q}, A158E, G160{D,P}, S161{C,Y,E}, I162L, S163{A, D}, Q182{C,E}, N184D, N185{C,E}, S188{C, D,E}, Q191N, A194{D,E}, N204{D,V}, V205{I,L}, Q206{C,E,I,K,T,V,W,L}, Y209{L,W}, S212{A,D,G,N}, S216{I,T,V}, L217{C,M}, N218T, M222{C,N,R}, P225{A,S}, T255{C,E,Q}, S256{A,C,D,V, Y}, S259D, T260{A,E,P}, N261{D,C,E,L,M,R,V,W,Y,F} and L262{Y,C,E,Q}, wherein each position corresponds to the position of the polypeptide of SEQ ID NO: 2, wherein said variant comprises any of the further mutations selected from the list consisting of Q2R, W6I, I8{C,H}, S9R A15T, N18S, S24H, *35aD, A48H, S49T, G53{A,L}, T58Y, G61{E,D}, S99D, *99aE, V104{P,T,Y}, N117H, H120{N,D}, P131*, Q137H, S141H, R145H V149Q, S161Y, I162L, N184D, A194{P,D,E}, V205L, M222N, P225S, K235L, N238H, T255Q, T260A, N261{D,R,W}, *275aR, *275aF, *275aH, *275bH and *275cH.

In yet another aspect of the invention, the subtilase variant is a variant of the parent subtilase with SEQ ID NO 3 which comprises or consists of one or more of the alterations selected from the group consisting of Q2R, W6I, I8{C,H}, S9{C,D,E,Q}, N18S, N43{A,C,L,R,W}, S49T, G53{A,L}, G61D, I72{A,V}, S78{D,N}, V104{F,P,T,Y}, A114V, G115{T,W}, H120{I,T,V}, P129D, V147W, V149{C,N,Q}, A158E, G160{D,P}, S161{C,Y,E}, I162L, S163{A, D}, Q182{C,E}, N184D, N185{C,E}, S188{C,D,E}, Q191N, A194{D,E}, N204{D,V}, V205{I,L}, Q206{C,E,I,K,T,V,W,L}, Y209{L,W}, S212{A,D,G,N}, S216{I,T,V}, L217{C,M}, N218T, M222{C,N,R}, P225{A,S}, T255{C,E,Q}, S256{A,C,D,V,Y}, S259D, T260{A,E,P}, N261{D,C,E,L,M,R,V,W,Y,F} and L262{Y,C,E,Q}, wherein each position corresponds to the corresponding position of the polypeptide of SEQ ID NO: 2. In one embodiment, the subtilase variant has improved stability, in particular improved storage stability, compared to the polypeptide of SEQ ID NO: 1. In a preferred embodiment, the subtilase variant has improved stability, in particular improved in storage stability, and on par or improved wash performance compared to the polypeptide of SEQ ID NO:1.

In another aspect of the invention, the subtilase variant is a variant of the parent subtilase with SEQ ID NO: 4 which comprises or consists of one or more of the alterations selected from the group consisting of Q2R, Y6I, V8{C,H}, S9{C,D,E,Q}, K43{A,C,L,R,W}, S49T, S53{A,L}, N61D, V72A, S78{D,N}, Y104{F,P,T}, A114V, I115{T,W}, D120{I,T,V}, P129D, V147W, V149{C,N,Q}, T158E, G160{D,P}, S161{C,Y,E}, S162L, S163{A, D}, S182{C, E}, N184D, Q185{C,E}, S188{C, D,E}, S191N, P194{D, E}, S204{D,V}, I205L, Q206{C,E,I,K,T,V,W,L}, L209W, N212{A,D,G}, A216{I,T,V}, Y217{C,M}, N218T, M222{C,N,R}, P225{A,S}, T255{C,E,Q}, K256{A,C,D,V, Y}, S260{A,E,P}, F261{D,C,E,L,M,R,V,W,Y,F} and Y262{C,E,Q}, wherein each position corresponds to the corresponding position of the polypeptide of SEQ ID NO: 2. In one embodiment, the subtilase variant has improved stability, in particular improved storage stability, compared to the polypeptide of SEQ ID NO: 2. In a preferred embodiment, the subtilase variant has improved stability, in particular improved storage stability, and on par or improved wash performance compared to the polypeptide of SEQ ID NO: 2.

The subtilase variants may further comprise one or more substitutions selected from the group consisting of S3T, V4I, A15T, S24{G,R}, V68A, S99{D,E}, S101{R,K,N,M,E,D, L,I}, S103A, V104I, S128{A,L,S}, P129{N,Q} S130A, V199M, L217{Y,D,E,Q}, N218{D,E} and Q245{K,R} (numbering according to SEQ ID NO: 2).

Thus in further embodiments of the invention, the subtilase variant described in table 1 and 2 further comprises or consists of one or more of the substitutions S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2) in the polypeptide of SEQ ID NO: 1 or SEQ ID NO: 2, wherein each position corresponds to the corresponding position of the polypeptide of SEQ ID NO: 2. In one embodiment, the subtilase variant has improved stability, in particular improved in storage stability, compared to the polypeptide of SEQ ID NO: 2 or SEQ ID NO: 2 or relative to a subtilase having the identical amino acid sequence of said variant but excluding the alterations in said variant.

In one embodiment of the invention, the subtilase variant comprises or consists of one of the substitutions N76D+Q2R and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+G115W and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E, Q}, N218{D,E} and Q245{K,R} (numbering according to SEQ ID NO: 2).

In one embodiment of the invention, the subtilase variant comprises or consists of one of the substitutions N76D+A194E and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E, Q}, N218{D,E} and Q245{K,R} (numbering according to SEQ ID NO: 2).

In one embodiment of the invention, the subtilase variant comprises or consists of one of the substitutions N76D+T255C and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E, Q}, N218{D,E} and Q245{K,R} (numbering according to SEQ ID NO: 2).

In one embodiment of the invention, the subtilase variant comprises or consists of one of the substitutions N76D+W6I and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+H120I and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E, Q}, N218{D,E} and Q245{K,R} (numbering according to SEQ ID NO: 2).

In one embodiment of the invention, the subtilase variant comprises or consists of one of the substitutions N76D+N204D and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E, Q}, N218{D,E} and Q245{K,R} (numbering according to SEQ ID NO: 2).

In one embodiment of the invention, the subtilase variant comprises or consists of one of the substitutions N76D+T255E and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E, Q}, N218{D,E} and Q245{K,R} (numbering according to SEQ ID NO: 2).

In one embodiment of the invention, the subtilase variant comprises or consists of one of the substitutions N76D+I8C and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+H120T and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E, Q}, N218{D,E} and Q245{K,R} (numbering according to SEQ ID NO: 2).

In one embodiment of the invention, the subtilase variant comprises or consists of one of the substitutions N76D+N204V and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E, Q}, N218{D,E} and Q245{K,R} (numbering according to SEQ ID NO: 2).

In one embodiment of the invention, the subtilase variant comprises or consists of one of the substitutions N76D+T255Q and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E, Q}, N218{D,E} and Q245{K,R} (numbering according to SEQ ID NO: 2).

In one embodiment of the invention, the subtilase variant comprises or consists of one of the substitutions N76D+18H and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+H120V and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+V205I and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+S256A and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+S9C and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+P129D and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+V205L and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+S256C and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+S9D and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+V147W and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+Q206C and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+S256D and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+S9E and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+V149C and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+Q206E and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+S256V and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+S9Q and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+V149N and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+Q206I and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+S256Y and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+N185 and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+V149Q and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+Q206K and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+S259D and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+N43A and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+A158E and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+Q206T and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+T260A and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+N43C and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+G160D and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+Q206V and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+T260E and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+N43L and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+G160P and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+Q206W and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+Q206L and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+T260P and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+N43R and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+S161C and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+Y209L and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+N261 D and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+N43W and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+S161Y and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+Y209W and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+N261C and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+S49T and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+5161E and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+S212A and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+N261E and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+G53A and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+I162L and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E, Q}, N218{D,E} and Q245{K,R} (numbering according to SEQ ID NO: 2).

In one embodiment of the invention, the subtilase variant comprises or consists of one of the substitutions N76D+ S212D and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E, Q}, N218{D,E} and Q245{K,R} (numbering according to SEQ ID NO: 2).

In one embodiment of the invention, the subtilase variant comprises or consists of one of the substitutions N76D+ N261L and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E, Q}, N218{D,E} and Q245{K,R} (numbering according to SEQ ID NO: 2).

In one embodiment of the invention, the subtilase variant comprises or consists of one of the substitutions N76D+ G53L and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E, Q}, N218{D,E} and Q245{K,R} (numbering according to SEQ ID NO: 2).

In one embodiment of the invention, the subtilase variant comprises or consists of one of the substitutions N76D+ S163A and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E, Q}, N218{D,E} and Q245{K,R} (numbering according to SEQ ID NO: 2).

In one embodiment of the invention, the subtilase variant comprises or consists of one of the substitutions N76D+ S212G and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E, Q}, N218{D,E} and Q245{K,R} (numbering according to SEQ ID NO: 2).

In one embodiment of the invention, the subtilase variant comprises or consists of one of the substitutions N76D+ N261M and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E, Q}, N218{D,E} and Q245{K,R} (numbering according to SEQ ID NO: 2).

In one embodiment of the invention, the subtilase variant comprises or consists of one of the substitutions N76D+G61D and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E, Q}, N218{D,E} and Q245{K,R} (numbering according to SEQ ID NO: 2).

In one embodiment of the invention, the subtilase variant comprises or consists of one of the substitutions N76D+ S163D and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E, Q}, N218{D,E} and Q245{K,R} (numbering according to SEQ ID NO: 2).

In one embodiment of the invention, the subtilase variant comprises or consists of one of the substitutions N76D+ S212N and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E, Q}, N218{D,E} and Q245{K,R} (numbering according to SEQ ID NO: 2).

In one embodiment of the invention, the subtilase variant comprises or consists of one of the substitutions N76D+ N261R and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E, Q}, N218{D,E} and Q245{K,R} (numbering according to SEQ ID NO: 2).

In one embodiment of the invention, the subtilase variant comprises or consists of one of the substitutions N76D+ I72A and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E, Q}, N218{D,E} and Q245{K,R} (numbering according to SEQ ID NO: 2).

In one embodiment of the invention, the subtilase variant comprises or consists of one of the substitutions N76D+ Q182C and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E, Q}, N218{D,E} and Q245{K,R} (numbering according to SEQ ID NO: 2).

In one embodiment of the invention, the subtilase variant comprises or consists of one of the substitutions N76D+ S216I and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E, Q}, N218{D,E} and Q245{K,R} (numbering according to SEQ ID NO: 2).

In one embodiment of the invention, the subtilase variant comprises or consists of one of the substitutions N76D+ N261V and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E, Q}, N218{D,E} and Q245{K,R} (numbering according to SEQ ID NO: 2).

In one embodiment of the invention, the subtilase variant comprises or consists of one of the substitutions N76D+ I72V and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E, Q}, N218{D,E} and Q245{K,R} (numbering according to SEQ ID NO: 2).

In one embodiment of the invention, the subtilase variant comprises or consists of one of the substitutions N76D+ Q182E and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E, Q}, N218{D,E} and Q245{K,R} (numbering according to SEQ ID NO: 2).

In one embodiment of the invention, the subtilase variant comprises or consists of one of the substitutions N76D+ S216T and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+S216V and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+N261W and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+S78D and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+N184D and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+L217C and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+N261Y and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+S78N and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+N185C and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+L217M and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+N261 F and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+V104F and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+N185E and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+N218T and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+L262Y and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+V104P and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+S188C and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+M222C and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+L262O and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+V104T and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+S188D and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+M222N and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+L262E and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+V104Y and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+S188E and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+M222R and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+L262Q and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+A114V and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+Q191N and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+P225A and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+G115T and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+A194D and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In one embodiment of the invention, the subtilase variant comprises or consists of one of the substitutions N76D+P225S and one or more of the substitutions selected from the group consisting of S3T, V4I, A15T, S24{G,R}, V68A, S99{D,E}, S101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, AlaNal, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for protease activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. For BPN' (SEQ ID NO: 2) the catalytic triad comprising the amino acids S221, H64, and D32 is essential for protease activity of the enzyme.

The subtilase variants may consist of 150 to 350, e.g., 175 to 330, 200 to 310, 220 to 300, 240 to 290, 260 to 280 or 269, 270, 271, 272, 273, 274 or 275 amino acids.

In one embodiment, the subtilase variant has improved stability, in particular improved storage stability, compared to the polypeptide of the parent subtilase, to the polypeptide of SEQ ID NO: 1 or relative to a subtilase having the identical amino acid sequence of said variant but excluding the alterations in said variant. In a preferred embodiment, the subtilase variant has improved stability, in particular improved in storage stability, and on par or improved wash performance compared to the mature polypeptide of the parent subtilase, to the polypeptide of SEQ ID NO: 1 or relative to a subtilase having the identical amino acid sequence of said variant but excluding the alterations in said variant.

In an embodiment, the subtilase variant has improved stability, in particular improved in storage stability, compared to the parent enzyme wherein in storage stability is measured using the 'accelerated storage stability assay' as described in the Materials and Methods Example 3 herein. In an embodiment, the subtilase variant has improved stability, in particular improved in storage stability, compared to the polypeptide of SEQ ID NO: 1 wherein in stability is measured using the 'accelerated storage stability assay' as described in the Materials and Methods section herein.

In an embodiment, the subtilase variant has improved stability, in particular improved storage stability, and on par or improved wash performance compared to the parent enzyme wherein storage stability is measured using the 'storage stability assay' and wash performance is measured using the Automatic Mechanical Stress Assay (AMSA) for laundry as described in the Materials and Methods section herein. In an embodiment, the subtilase variant has improved stability, in particular improved storage stability, and on par or improved wash performance compared to the polypeptide of SEQ ID NO: 1wherein storage stability is measured using the 'accelerated storage stability assay' and wash performance is measured using the Automatic Mechanical Stress Assay (AMSA) for laundry as described in "Materials and Methods" section herein.

Parent Protease

The parent or the precursor protease may be any subtilase or even more preferred any subtilisin as defined below. The amino acid sequences of the subtilases can be aligned to identify corresponding amino acids in a given sequence. As mentioned above SEQ ID NO: 2 (BPN') is used for numbering. However, the parent or precursor protease maybe any subtilase thus the amino acid at a given position maybe different among various subtilases it will be clear to the person skilled in the art that for example the following mutation V205{I,L} in the context of the present invention do not require that it's the amino acid valine which is replaced by isoleucine or leucine. Thus the mutations according to the invention maybe written as follows:

X2R, X6I, X8{C,H}, X9{C,D,E,Q}, X18S, X43{A,C,L,R,W}, X49T, X53{A,L}, X61D, X72{A,V}, X78{D,N}, X104{F,P,T,Y}, X114V, X115{T,W}, X120{I,T,V}, X129D, X147W, X149{C,N,Q}, X158E, X160D,P, X161{C,Y,E}, X162L, X163{A, D}, X182{C,E}, X184D, X185{C,E}, X188{C, D,E}, X191N, X194{D,E}, X204{D, V}, X205{I,L}, X206{C,E,I,K,T,V,W,L}, X209{L,W}, X212{A,D,G,N}, X216{I,T,V}, X217{C,M}, X218T, X222{C,N,R}, X225{A,S}, X255{C,E,Q}, X256{A,C,D,V,Y}, X259D, X260{A,E,P}, X261{D,C,E,L,M,R,V,W,Y,F} and X262{Y,C,E,Q}.

It will be clear that if the parent, precursor or starting protease already comprises e.g. I at position corresponding to positions 205 of SEQ ID NO: 2 this will not be substituted.

Enzymes cleaving the amide linkages in protein substrates are classified as proteases, or (interchangeably) peptidases (see Walsh, 1979, Enzymatic Reaction Mechanisms. W.H. Freeman and Company, San Francisco, Chapter 3).

Serine Proteases

A serine protease is an enzyme which catalyzes the hydrolysis of peptide bonds, and in which there is an essential serine residue at the active site (White, Handler and Smith, 1973 "Principles of Biochemistry," Fifth Edition, McGraw-Hill Book Company, NY, pp. 271-272).

The bacterial serine proteases have molecular weights in the 20,000 to 45,000 Dalton range. They are inhibited by diisopropylfluorophosphate. They hydrolyze simple terminal esters and are similar in activity to eukaryotic chymotrypsin, also a serine protease. A more narrow term, alkaline protease, covering a sub-group, reflects the high pH optimum of some of the serine proteases, from pH 9.0 to 11.0 (for review, see Priest (1977) Bacteriological Rev. 41:711-753).

Subtilases

A sub-group of the serine proteases tentatively designated subtilases has been proposed by Siezen et al. (1991), *Protein Eng.* 4:719-737 and Siezen et al. (1997), *Protein Science* 6:501-523. They are defined by homology analysis of more than 170 amino acid sequences of serine proteases previously referred to as subtilisin-like proteases. A subtilisin was previously often defined as a serine protease produced by Gram-positive bacteria or fungi, and according to Siezen et al. now is a subgroup of the subtilases. A wide variety of subtilases have been identified, and the amino acid sequence of a number of subtilases has been determined. For a more detailed description of such subtilases and their amino acid sequences reference is made to Siezen et al. (1997).

Subtilisins

A subgroup of the subtilases is the subtilisins which are serine proteases from the family S8, in particular from the subfamily S8A, as defined by the MEROPS database (http://merops.sanger.ac.uk/cgi-bin/famsum?family=S8).

BPN' and Savinase have the MEROPS numbers S08.034 and S08.003, respectively.

Parent Subtilase

The term "parent subtilase" describes a subtilase defined according to Siezen et al. (1997), *Protein Science* 6:501-523. For further details see description of "Subtilases" above. A parent subtilase may also be a subtilase isolated from a natural source, wherein subsequent modifications (such as replacement(s) of the amino acid side chain(s), substitution(s), deletion(s) and/or insertion(s)) have been made while retaining the characteristic of a subtilase. Furthermore, a parent subtilase may be a subtilase which has been prepared by the DNA shuffling technique, such as described by J. E. Ness et al. (1999) *Nature Biotechnology*, 17:893-896.

Alternatively, the term "parent subtilase" may be termed "precursor subtilase" and is used to describe the starting protease into which mutations are made to obtain the variant of the invention. The parent subtilase is preferably of the subtilisin subgroups.

One subgroup of the subtilases, I-S1 or "true" subtilisins, comprises the "classical" subtilisins, such as subtilisin 168 (BSS168), subtilisin BPN', subtilisin Carlsberg (ALCALASE®, NOVOZYMES NS), and subtilisin DY (BSSDY). BPN' is subtilisin BPN' from *B. amyloliquefaciens*, BPN' has the amino acid sequence SEQ ID NO: 2. A further subgroup of the subtilases, I-S2 or high alkaline subtilisins, is recognized by Siezen et al. (supra). Sub-group I-S2 proteases are described as highly alkaline subtilisins and comprises enzymes such as subtilisin PB92 (BAALKP) (MAXACAL®, Genencor International Inc.), subtilisin 147 (BLS147) (ESPERASE®, Novozymes NS), alkaline elastase YaB (BSEYAB) and subtilisin 309 (SAVINASE®, Novozymes NS) having the amino acid sequence SEQ ID NO 1.

For reference, table 4 below gives a list of some acronyms for various subtilases mentioned herein. For further acronyms, see Siezen et al. (1991 and 1997).

TABLE 4

Acronyms of various subtilases

| Organism | Enzyme | Acronym |
|---|---|---|
| *Bacillus subtilis* 168 | subtilisin I168, apr | BSS168 |
| *Bacillus amyloliquefaciens* | subtilisin BPN' (NOVO) | BASBPN |
| *Bacillus subtilis* DY | subtilisin DY | BSSDY |
| *Bacillus licheniformis* | subtilisin Carlsberg | BLSCAR |
| *Bacillus lentus* | subtilisin 309 | BLSAVI |

TABLE 4-continued

Acronyms of various subtilases

| Organism | Enzyme | Acronym |
|---|---|---|
| *Bacillus lentus* | subtilisin 147 | BLS147 |
| *Bacillus alcalophilus* PB92 | subtilisin PB92 | BAPB92 |
| *Bacillus* YaB | alkaline elastase YaB | BYSYAB |
| *Bacillus* sp. NKS-21 | subtilisin ALP I | BSAPRQ |
| *Bacillus* sp. G-825-6 | subtilisin Sendai | BSAPRS |
| *Thermoactinomyces vulgaris* | Thermitase | TVTHER |

Homologous Subtilase Sequences

The homology between two amino acid sequences is in this context described by the parameter "identity" for purposes of the present invention, the degree of identity between two amino acid sequences is determined using the Needleman-Wunsch algorithm as described above. The output from the routine is besides the amino acid alignment the calculation of the "Percent Identity" between the two sequences.

Based on this description it is routine for a person skilled in the art to identify suitable homologous subtilases, which can be modified according to the invention.

The parent protease may be a polypeptide having at least 60% sequence identity to the polypeptide of SEQ ID NO: 1.

In an aspect, the parent has a sequence identity to the polypeptide of SEQ ID NO: 1 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have protease activity. In one aspect, the amino acid sequence of the parent differs by up to 10 amino acids, e.g., 1, 2, 3, 4, 5, 6, 7, 8, 9, or 10, from the polypeptide of SEQ ID NO: 1.

In another aspect, the parent comprises or consists of the amino acid sequence of SEQ ID NO: 1. In another aspect, the parent comprises or consists of amino acids 1 to 269 of SEQ ID NO: 1.

In one aspect, the parent has a sequence identity to the polypeptide of SEQ ID NO: 2 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have protease activity. In one aspect, the amino acid sequence of the parent differs by up to 10 amino acids, e.g., 1, 2, 3, 4, 5, 6, 7, 8, 9, or 10, from the polypeptide of SEQ ID NO: 2.

In another aspect, the parent comprises or consists of the amino acid sequence of SEQ ID NO: 2. In another aspect, the parent comprises or consists of amino acids 1 to 275 of SEQ ID NO: 2.

The polypeptide may be a hybrid polypeptide in which a region of one polypeptide is fused at the N-terminus or the C-terminus of a region of another polypeptide.

The parent subtilase may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly.

The parent may be a bacterial protease. For example, the parent may be a Gram-positive bacterial polypeptide such as a *Bacillus, Clostridium, Enterococcus, Geobacillus, Lactobacillus, Lactococcus, Oceanobacillus, Staphylococcus, Streptococcus,* or *Streptomyces* protease, or a Gram-negative bacterial polypeptide such as a *Campylobacter*, *E. coli*, *Flavobacterium*, *Fusobacterium*, *Helicobacter*, *Ilyobacter*, *Neisseria*, *Pseudomonas*, *Salmonella*, or *Ureaplasma* protease.

In one aspect, the parent is a *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, or *Bacillus thuringiensis* protease In one aspect, the parent is a *Bacillus amyloliquefaciens* protease, e.g., the protease of SEQ ID NO: 2.

In another aspect, the parent is a *Bacillus lentus* or a *Bacillus clausii* protease, e.g., the protease of SEQ ID NO: 1.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The present invention also relates to methods for obtaining a subtilase variant having protease activity, comprising:

(a) introducing into a parent subtilase the substitution N76D and one or more substitutions selected from the group consisting of Q2R, W6I, I8{C,H}, S9{C,D,E,Q}, N18S, N43{A,C,L,R,W}, S49T, G53{A,L}, G61D, I72{A,V}, S78{D,N}, V104{F,P,T,Y}, A114V, G115{T,W}, H120{I,T,V}, P129D, V147W, V149{C,N,Q}, A158E, G160{D,P}, S161{C,Y,E}, I162L, S163{A, D}, Q182{C,E}, N184D, N185{C,E}, S188{C, D,E}, Q191N, A194{D,E}, N204{D,V}, V205{I, L}, Q206{C,E,I,K,T,V,W,L}, Y209{L,W}, S212{A,D,G, N}, S216{I,T,V}, L217{C,M}, N218T, M222{C,N,R}, P225{A,S}, T255{C,E,Q}, S256{A,C,D,V,Y}, S259D, T260{A,E,P}, N261{D,C,E,L,M,R,V,W,Y,F} and L262{Y, C,E,Q}, wherein each position corresponds to the position of SEQ ID NO: 2, and (b) recovering the variant.

Another aspect of the invention to methods for obtaining a subtilase variant having protease activity, comprising:

(a) introducing into a subtilase having the amino acid sequence with SEQ ID NO 1 the substitution N76D and one or more substitutions selected from the group consisting Q2R, W6I, I8{C,H}, S9{C,D,E,Q}, N18S, N43{A,C,L,R, W}, S49T, G53{A,L}, G6I D, I72{A,V}, S78{D,N}, V104{F,P,T,Y}, A114V, G115{T,W}, H120{1,T,V}, P129D, V147W, V149{C,N,Q}, A158E, G160{D,P}, S161{C,Y,E}, I162L, S163{A, D}, Q182{C,E}, N184D, N185{C,E}, S188{C, D,E}, Q191N, A194{D,E}, N204{D,V}, V205{I, L}, Q206{C,E,I,K,T,V,W,L}, Y209{L,W}, S212{A,D,G, N}, S216{I,T,V}, L217{C,M}, N218T, M222{C,N,R}, P225{A,S}, T255{C,E,Q}, S256{A,C,D,V, Y}, S259D, T260{A,E,P}, N261{D,C,E,L,M,R,V,W,Y,F} and L262{Y, C,E,Q}, wherein each position corresponds to the position of SEQ ID NO: 2, and (b) recovering the variant.

In an embodiment, the invention relates to a method for obtaining a subtilase variant having protease activity, comprising:

a) introducing into a parent subtilase the substitution N76D and one or more substitutions selected from the group consisting of Q2R, W6I, I8{C,H}, S9{C,D,E,Q}, N18S, N43{A,C,L,R,W}, S49T, G53{A,L}, G61D, I72{A,V}, S78{D,N}, V104{F,P,T,Y}, A114V, G115{T,W}, H120{I,T, V}, P129D, V147W, V149{C,N,Q}, A158E, G160{D,P}, S161{C,Y,E}, I162L, S163{A, D}, Q182{C,E}, N184D, N185{C,E}, S188{C, D,E}, Q191N, A194{D,E}, N204{D, V}, V205{I,L}, Q206{C,E,I,K,T,V,W,L}, Y209{L,W}, S212{A,D,G,N}, S216{I,T,V}, L217{C,M}, N218T, M222{C,N,R}, P225{A,S}, T255{C,E,Q}, S256{A,C,D,V, Y}, S259D, T260{A,E,P}, N261{D,C,E,L,M,R,V,W,Y,F} and L262{Y,C,E,Q}, wherein each position corresponds to the position of the mature polypeptide of SEQ ID NO: 2 and wherein the subtilase variant is a polypeptide that has at least 60%, e.g., at least 65%, at least 70%, at least 75%, at least 80%, at least 85%, at least 90%, at least 95%, at least 96%, at least 97%, at least 98% but less than 100% sequence identity to the mature polypeptide of the parent subtilase;

b) recovering the variant.

In an embodiment, the invention relates to a method for obtaining a subtilase variant having protease activity, comprising:

a) introducing into a subtilase having the amino acid sequence with SEQ ID NO 1 the substitution N76D and one or more substitutions selected from the group consisting of Q2R, W6I, I8{C,H}, S9{C,D,E,Q}, N18S,N43{A,C,L,R, W}, S49T, G53{A,L}, G61D,I72{A,V}, S78{D,N}, V104{F,P,T,Y}, A114V, G115{T,W}, H120{I,T,V}, P129D, V147W, V149{C,N,Q}, A158E, G160{D,P}, S161{C,Y,E}, I162L, S163{A, D}, Q182{C,E}, N184D, N185{C,E}, S188{C, D,E}, Q191N, A194{D,E}, N204{D,V}, V205{I, L}, Q206{C,E,I,K,T,V,W,L}, Y209{L,W}, S212{A,D,G, N}, S216{1,T,V}, L217{C,M}, N218T, M222{C,N,R}, P225{A,S}, T255{C,E,Q}, S256{A,C,D,V, Y}, S259D, T260{A,E,P}, N261{D,C,E,L,M,R,V,W,Y,F} and L262{Y, C,E,Q}, wherein each position corresponds to the position of the mature polypeptide of SEQ ID NO: 2 and wherein the subtilase variant is a polypeptide that has at least 60%, e.g., at least 65%, at least 70%, at least 75%, at least 80%, at least 85%, at least 90%, at least 95%, at least 96%, at least 97%, at least 98% but less than 100% sequence identity to the polypeptide of SEQ ID NO 1;

b) recovering the variant.

In an embodiment, the invention relates to a method for obtaining a subtilase variant having protease activity, comprising:

a) introducing into a parent subtilase having the amino acid sequence with SEQ ID NO 2 one or more substitutions selected from the group consisting of Q2R, Y6I, V8{C,H}, S9{C,D,E,Q}, K43{A,C,L,R,W}, S49T, S53{A,L}, N61D, V72A, S78{D,N}, Y104{F,P,T}, A114V, I115{T,W}, D120{,I,T,V}, P129D, V147W, V149{C,N,Q}, T158E, G160{D,P}, S161{C,Y,E}, S162L, S163{A, D}, S182{C, E}, N184D, Q185{C,E}, S188{C, D,E}, S191N, P194{D, E}, S204{D,V}, I205L, Q206{C,E,I,K,T,V,W,L}, L209W, N212{A,D,G}, A216{1,T,V}, Y217{C,M}, N218T, M222{C,N,R}, P225{A,S}, T255{C,E,Q}, K256{A,C,D,V, Y}, S260{A,E,P}, F261{D,C,E,L,M,R,V,W,Y,F} and Y262{C,E,Q}, wherein each position corresponds to the position of the polypeptide of SEQ ID NO: 2 and wherein the subtilase variant is a polypeptide that has at least 60%, e.g., at least 65%, at least 70%, at least 75%, at least 80%, at least 85%, at least 90%, at least 95%, at least 96%, at least 97%, at least 98% but less than 100% sequence identity to the polypeptide with SEQ ID NO 2;

b) recovering the variant.

The subtilase variants may further comprise a substitution selected from the group consisting of S3T, V4I, A15T, 524{G,R}, V68A, 599{D,E}, 5101{R,K,N,M,E,D,L,I}, S103A, V104I, S128{A,L,S}, P129{N,Q} S130A, V199M, L217{Y,D,E,Q}, N218{D,E} and Q245{K,R} (numbering according to SEQ ID NO: 2).

In another embodiment, the invention relates to a method for obtaining a subtilase variant having protease activity and having at least 25% improved stability compared to a subtilase with SEQ ID NO 1 when measured as described in the accelerated storage stability assay in Example 3 herein, comprising:

a) introducing into polypeptide of SEQ ID NO: 1 the substitution N76D and one or more substitutions selected from the group consisting of Q2R, W6I, I8{C,H}, S9{C,D,E,Q}, N18S,N43{A,C,L,R,W}, S49T, G53{A,L}, G61D, I72{A,V}, S78{D,N}, V104{F,P,T,Y}, A114V, G115{T,W}, H120{I,T,V}, P129D, V147W, V149{C,N,Q}, A158E, G160{D,P}, S161{C,Y,E}, I162L, S163{A, D}, Q182{C, E}, N184D, N185{C,E}, S188{C, D,E}, Q191N, A194{D, E}, N204{D,V}, V205{I,L}, Q206{C,E,I,K,T,V,W,L}, Y209{L,W}, S212{A,D,G,N}, S216{1,T,V}, L217{C,M}, N218T, M222{C,N,R}, P225{A,S}, T255{C,E,Q}, S256{A,C,D,V, Y}, S259D, T260{A,E,P}, N261{D,C,E,L, M,R,V,W,Y,F} and L262{Y,C,E,Q}, wherein each position corresponds to the position of the polypeptide of SEQ ID NO: 2 and wherein the subtilase variant is a polypeptide that has at least 60%, e.g., at least 65%, at least 70%, at least 75%, at least 80%, at least 85%, at least 90%, at least 95%, at least 96%, at least 97%, at least 98% but less than 100% sequence identity to the polypeptide of SEQ ID NO: 1; and b) recovering the variant.

In yet another embodiment, the invention relates to a method for obtaining a subtilase variant having protease activity and having at least 25% improved stability compared to a subtilase with SEQ ID NO 1 when measured as described in the accelerated storage stability assay in Example 3 herein, comprising:

a) introducing into polypeptide of SEQ ID NO: 2 the substitution N76D and one or more substitutions selected from the group consisting of Q2R, Y6I, V8{C,H}, S9{C,D,E,Q}, K43{A,C,L,R,W}, S49T, S53{A,L}, N61D, V72A, S78{D,N}, Y104{F,P,T}, A114V, I115{T,W}, D120{I,T,V}, P129D, V147W, V149{C,N,Q}, T158E, G160{D,P}, S161{C,Y,E}, S162L, S163{A, D}, S182{C,E}, N184D, Q185{C,E}, S188{C, D,E}, S191N, P194{D,E}, S204{D, V}, I205L, Q206{C,E,I,K,T,V,W,L}, L209W, N212{A,D, G}, A216{I,T,V}, Y217{C,M}, N218T, M222{C,N,R}, P225{A,S}, T255{C,E,Q}, K256{A,C,D,V,Y}, S260{A,E, P}, F261{D,C,E,L,M,R,V,W,Y,F} and Y262{C,E,Q}, wherein each position corresponds to the position of the polypeptide of SEQ ID NO: 2 and wherein the subtilase variant is a polypeptide that has at least 60%, e.g., at least 65%, at least 70%, at least 75%, at least 80%, at least 85%, at least 90%, at least 95%, at least 96%, at least 97%, at least 98% but less than 100% sequence identity to the mature polypeptide of SEQ ID NO: 2; and b) recovering the variant.

The subtilase variants may further comprise a substitution at one or more positions (e.g. several) that is selected from the group consisting of S3T, V4I, A15T, 524{G,R}, V68A, D99{S,E}, S101{R,K,N,M,E,D,L,I}, Q103A, Y104I, G128{A,L,S}, P129{N,Q} S130A, Y217{Y,D,E,Q}, N218{D,E} and Q245{K,R} (numbering according to SEQ ID NO: 2).

In an embodiment, the subtilase variant has improved stability, in particular improved in storage and/or detergent stability, compared to the parent enzyme wherein storage stability is measured using the 'storage stability assay' as described in the Materials and Methods section herein. In an embodiment, the subtilase variant has improved stability, in particular improved in storage stability, compared to the polypeptide of SEQ ID NO: 1 wherein in stability is measured using the 'in stability assay' as described in the Materials and Methods section herein.

In an embodiment, the subtilase variant has improved stability, in particular improved in storage stability, and on par or improved wash performance compared to the parent enzyme wherein in stability is measured using the 'accelerated storage stability assay' and wash performance is measured using the Automatic Mechanical Stress Assay (AMSA) for laundry as described in the Materials and Methods section herein. In an embodiment, the subtilase variant has improved stability, in particular improved in storage stability, and on par or improved wash performance compared to the polypeptide of SEQ ID NO: 1 wherein in stability is measured using the 'accelerated storage stability assay' and wash performance is measured using the Automatic Mechanical Stress Assay (AMSA) for laundry as described in the Materials and Methods section herein.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432:

1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to polynucleotides encoding a variant of the present invention.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xyIA and xyIB genes, *Bacillus thuringiensis* ctyIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

The control sequence may also be a transcription terminator, which is recognized by a host cell to terminate transcription. The terminator sequence is operably linked to the 3'-terminus of the polynucleotide encoding the variant. Any terminator that is functional in the host cell may be used.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* ctyIIIA gene (WO 94/25612) and a *Bacillus subtilis* SP82 gene (Hue et al., 1995, *Journal of Bacteriology* 177: 3465-3471).

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin or tetracycline resistance.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus,*

*Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

Methods of Production

The present invention also relates to methods of producing a variant, comprising: (a) cultivating a host cell of the present invention under conditions suitable for expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants with protease activity. These detection methods include, but are not limited to, use of specific antibodies, formation of an enzyme product, or disappearance of an enzyme substrate. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the variant is not recovered, but rather a host cell of the present invention expressing the variant is used as a source of the variant.

Compositions

In one certain aspect, the variants according to the invention have improved wash performance compared to the parent enzyme or compared to a protease having the identical amino acid sequence of said variant but excluding the said substitutions at one or more of said specified positions or compared to a protease with SEQ ID NO: 1, wherein wash performance is measured using the Automatic Mechanical Stress Assay (AMSA) for laundry as described in the Materials and Methods section herein.

In another certain aspect, the variants according to the invention have improved stability, preferably improved storage stability, compared to the parent enzyme or compared to a protease having the identical amino acid sequence of said variant but excluding the said substitutions at one or more of said specified positions or compared to a protease with SEQ ID NO: 1, wherein storage stability is measured using the 'accelerated storage stability assay' as described in example 3 in the Materials and Methods section herein.

Thus, in a preferred embodiment the composition is a detergent composition, and one aspect of the invention relates to the use of a detergent composition comprising a variant according to the invention in a cleaning process such as laundry or hard surface cleaning.

The choice of additional components is within the skill of the artisan and includes conventional ingredients, including the exemplary non-limiting components set forth below. The choice of components may include, for fabric care, the consideration of the type of fabric to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

Enzyme of the Present Invention

In one embodiment of the present invention, the subtilase variant of the present invention may be added to a detergent composition in an amount corresponding to 0.01-200 mg of enzyme protein per liter of wash liqour, preferably 0.05-50 mg of enzyme protein per liter of wash liqour, in particular 0.1-10 mg of enzyme protein per liter of wash liqour.

A composition for use in automatic dishwash (ADW), for example, may include 0.0001%-50%, such as 0.001%-30%, such as 0.01%-20%, such as 0.5-15% of enzyme protein by weight of the composition.

A composition for use in laundry granulation, for example, may include 0.0001%-50%, such as 0.001%-20%, such as 0.01%-10%, such as 0.05%-5% of enzyme protein by weight of the composition.

A composition for use in laundry liquid, for example, may include 0.0001%-10%, such as 0.001-7%, such as 0.1%-5% of enzyme protein by weight of the composition.

The enzymes such as the subtilase variant of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO 92/19709 and WO 92/19708 or the variants according to the invention may be stabilized using peptide aldehydes or ketones such as described in WO 2005/105826 and WO 2009/118375.

A variant of the present invention may also be incorporated in the detergent formulations disclosed in WO 97/07202, which is hereby incorporated by reference.

Surfactants

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and includes any conventional surfactant(s) known in the art. Any surfactant known in the art for use in detergents may be utilized.

When included therein, the detergent will usually contain from about 1% to about 40% by weight, such as from about 5% to about 30%, including from about 5% to about 15%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or soap, and combinations thereof.

When included therein, the detergent will usually contain from about 0% to about 10% by weight of a cationic surfactant. Non-limiting examples of cationic surfactants include alkyldimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, and combinations thereof.

When included therein, the detergent will usually contain from about 0.2% to about 40% by weight of a non-ionic surfactant, for example from about 0.5% to about 30%, in particular from about 1% to about 20%, from about 3% to about 10%, such as from about 3% to about 5%, or from about 8% to about 12%. Non-limiting examples of non-ionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxy alkyl fatty acid amides, or N-acyl N-alkyl derivatives of glucosamine (glucamides, GA, or fatty acid glucamide, FAGA), as well as products available under the trade names SPAN and TWEEN, and combinations thereof.

When included therein, the detergent will usually contain from about 0% to about 10% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, fatty acid alkanolamides and ethoxylated fatty acid alkanolamides, and combinations thereof.

When included therein, the detergent will usually contain from about 0% to about 10% by weight of a zwitterionic surfactant. Non-limiting examples of zwitterionic surfactants include betaine, alkyldimethylbetaine, sulfobetaine, and combinations thereof.

Hydrotropes

A hydrotrope is a compound that solubilises hydrophobic compounds in aqueous solutions (or oppositely, polar substances in a non-polar environment). Typically, hydrotropes have both hydrophilic and a hydrophobic character (so-called amphiphilic properties as known from surfactants); however the molecular structure of hydrotropes generally do not favor spontaneous self-aggregation, see e.g. review by Hodgdon and Kaler (2007), Current Opinion in Colloid & Interface Science 12: 121-128. Hydrotropes do not display a critical concentration above which self-aggregation occurs as found for surfactants and lipids forming miceller, lamellar or other well defined meso-phases. Instead, many hydrotropes show a continuous-type aggregation process where the sizes of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

The detergent may contain 0-5% by weight, such as about 0.5 to about 5%, or about 3% to about 5%, of a hydrotrope. Any hydrotrope known in the art for use in detergents may be utilized. Non-limiting examples of hydrotropes include sodium benzene sulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Builders and Co-Builders

The detergent composition may contain about 0-65% by weight, such as about 5% to about 45% of a detergent builder or co-builder, or a mixture thereof. In a dish wash deteregent, the level of builder is typically 40-65%, particularly 50-65%. The builder and/or co-builder may particularly be a chelating agent that forms water-soluble complexes with Ca and Mg. Any builder and/or co-builder known in the art for use in laundry detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as iminodiethanol), triethanolamine (TEA, also known as 2,2',2''-nitrilotriethanol), and carboxymethyl inulin (CMI), and combinations thereof.

The detergent composition may also contain 0-20% by weight, such as about 5% to about 10%, of a detergent co-builder, or a mixture thereof. The detergent composition may include include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2''-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra-(methylenephosphonic acid) (EDTMPA), diethylenetriaminepentakis(methylenephosphonic acid) (DTPMPA or DTMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), α-alanine-N, N-diacetic acid (α-ALDA), serine-N, N-diacetic acid (SEDA), isoserine-N, N-diacetic acid (ISDA), phenylalanine-N, N-diacetic acid (PHDA), anthranilic acid-N, N-diacetic acid (ANDA), sulfanilic acid-N, N-diacetic acid (SLDA), taurine-N, N-diacetic acid (TUDA) and sulfomethyl-N, N-diacetic acid (SMDA), N-(2-hydroxyethyl-ethylidenediamine-N, N, N'-triacetate (HEDTA), diethanolglycine (DEG), diethylenetriamine penta(methylenephosphonic acid) (DTPMP), aminotris(methylenephosphonic acid) (ATMP), and combinations and salts thereof. Further exemplary builders and/or co-builders are described in, e.g., WO 09/102854, U.S. Pat. No. 5,977,053

Bleaching Systems

The detergent may contain 0-50% by weight, such as about 0.1% to about 25%, of a bleaching system. Any bleaching system known in the art for use in laundry detergents may be utilized. Suitable bleaching system components include bleaching catalysts, photobleaches, bleach activators, sources of hydrogen peroxide such as sodium percarbonate and sodium perborates, preformed peracids and mixtures thereof. Suitable preformed peracids include, but are not limited to, peroxycarboxylic acids and salts, percarbonic acids and salts, perimidic acids and salts, peroxymonosulfuric acids and salts, for example, Oxone (R), and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a peracid-forming bleach activator. The term bleach activator is meant herein as a compound which reacts with peroxygen bleach like hydrogen peroxide to form a peracid. The peracid thus formed constitutes the activated bleach. Suitable bleach activators to be used herein include those belonging to the class of esters amides, imides or anhydrides. Suitable examples are tetracetylethylene diamine (TAED), sodium 4-[(3,5,5-trimethylhexanoyl)oxy]benzene sulfonate (ISONOBS), diperoxy dodecanoic acid, 4-(dodecanoyloxy)benzenesulfonate (LOBS), 4-(decanoyloxy)benzenesulfonate, 4-(decanoyloxy)benzoate (DOBS), 4-(nonanoyloxy)-benzenesulfonate (NOBS), and/or those disclosed in WO98/17767. A particular family of bleach activators of interest was disclosed in EP624154 and particulary preferred in that family is acetyl triethyl citrate (ATC). ATC or a short chain triglyceride like triacetin has the advantage that it is environmental friendly as it eventually degrades into citric acid and alcohol. Furthermore acetyl triethyl citrate and triacetin has a good hydrolytical stability in the product upon storage and it is an efficient bleach activator. Finally ATC provides a good building capacity to the laundry additive. Alternatively, the bleaching system may comprise peroxyacids of, for example, the amide, imide, or sulfone type. The bleaching system may also comprise peracids such as 6-(phthalimido)peroxyhexanoic acid (PAP). The bleaching system may also include a bleach catalyst. In some embodiments the bleach component may be an organic catalyst selected from the group consisting of organic catalysts having the following formulae:

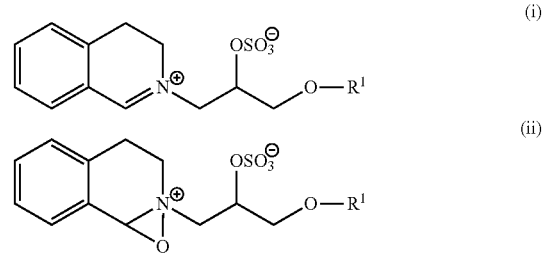

(iii) and mixtures thereof; wherein each $R^1$ is independently a branched alkyl group containing from 9 to 24 carbons or linear alkyl group containing from 11 to 24 carbons, preferably each $R^1$ is independently a branched alkyl group containing from 9 to 18 carbons or linear alkyl group containing from 11 to 18 carbons, more preferably each $R^1$ is independently selected from the group consisting of 2-propylheptyl, 2-butyloctyl, 2-pentylnonyl, 2-hexyldecyl, n-dodecyl, n-tetradecyl, n-hexadecyl, n-octadecyl, iso-nonyl, iso-decyl, iso-tridecyl and iso-pentadecyl. Other exemplary bleaching systems are described, e.g. in WO2007/087258, WO2007/087244, WO2007/087259 and WO2007/087242. Suitable photobleaches may for example be sulfonated zinc phthalocyanine Polymers The detergent may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or antifoaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly (ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly (oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

Fabric Hueing Agents

The detergent compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO2007/087243.

Additional Enzymes

The detergent additive as well as the detergent composition may comprise one or more (additional) enzymes such as a protease, lipase, cutinase, an amylase, carbohydrase, cellulase, pectinase, mannanase, arabinase, galactanase, xylanase, oxidase, e.g., a laccase, and/or peroxidase.

In general, the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and PCT/DK98/00299.

Example of cellulases exhibiting endo-beta-1,4-glucanase activity (EC 3.2.1.4) are those having described in WO02/099091.

Other examples of cellulases include the family 45 cellulases described in WO96/29397, and especially variants thereof having substitution, insertion and/or deletion at one or more of the positions corresponding to the following positions in SEQ ID NO: 8 of WO 02/099091:2, 4, 7, 8, 10, 13, 15, 19, 20, 21, 25, 26, 29, 32, 33, 34, 35, 37, 40, 42, 42a, 43, 44, 48, 53, 54, 55, 58, 59, 63, 64, 65, 66, 67, 70, 72, 76, 79, 80, 82, 84, 86, 88, 90, 91, 93, 95, 95d, 95h, 95j, 97, 100, 101, 102, 103, 113, 114, 117, 119, 121, 133, 136, 137, 138, 139, 140a, 141, 143a, 145, 146, 147, 150e, 150j, 151, 152, 153, 154, 155, 156, 157, 158, 159, 160c, 160e, 160k, 161, 162, 164, 165, 168, 170, 171, 172, 173, 175, 176, 178, 181, 183, 184, 185, 186, 188, 191, 192, 195, 196, 200, and/or 20, preferably selected among P19A, G20K, Q44K, N48E, Q119H or Q146R.

Commercially available cellulases include Celluzyme™, and Carezyme™ (Novozymes NS), Clazinase™, and Puradax HA™ (Genencor International Inc.), and KAC-500 (B)™ (Kao Corporation).

Proteases

The composition may comprise additional proteases. Suitable proteases include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloprotease such as those from M5, M7 or M8 families.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those derived from *Bacillus* such as *Bacillus lentus, B. alkalophilus, B. subtilis, B. amyloliquefaciens, Bacillus pumilus* and *Bacillus gibsonii* described in; U.S. Pat. No. 7,262,042 and WO09/021867, and subtilisin lentus, subtilisin Novo, subtilisin Carlsberg, *Bacillus licheniformis*, subtilisin BPN', subtilisin 309, subtilisin 147 and subtilisin 168 described in WO89/06279 and protease PD138 described in (WO93/18140). Other useful proteases may be those described in WO92/175177, WO01/016285, WO02/026024 and WO02/016547. Examples of trypsin-like proteases are trypsin (e.g. of porcine or bovine origin) and the *Fusarium* protease described in WO89/06270, WO94/25583 and WO05/040372, and the chymotrypsin proteases derived from Cellumonas described in WO05/052161 and WO05/052146.

A further preferred protease is the alkaline protease from *Bacillus lentus* DSM 5483, as described for example in WO95/23221, and variants thereof which are described in WO92/21760, WO95/23221, EP1921147 and EP1921148.

Examples of metalloproteases are the neutral metalloprotease as described in WO07/044993 (Genencor Int.) such as those derived from *Bacillus amyloliquefaciens*. Examples of useful proteases are the variants described in: WO92/19729, WO96/034946, WO98/20115, WO98/20116, WO99/011768, WO01/44452, WO03/006602, WO04/03186, WO04/041979, WO07/006305, WO11/036263, WO11/036264, especially the variants with substitutions in one or more of the following positions: 3, 4, 9, 15, 27, 36, 57, 68, 76, 87, 95, 96, 97, 98, 99, 100, 101, 102, 103, 104, 106, 118, 120, 123, 128, 129, 130, 160, 167, 170, 194, 195, 199, 205, 206, 217, 218, 222, 224, 232, 235, 236, 245, 248, 252 and 274 using the BPN' numbering. More preferred the subtilase variants may comprise the mutations: S3T, V4I, S9R, A15T, K27R, *36D, V68A, N76D, N87S,R, *97E, A98S, S99G, D,A, S99AD, S101G,M,R S103A, V104I,Y,N, S106A, G118V,R, H120D,N, N123S, S128L, P129Q, S130A, G160D, Y167A, R170S, A194P, G195E, V199M, V205I, L217D, N218D, M222S, A232V, K235L, Q236H, Q245R, N252K, T274A (using BPN' numbering).

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Neutrase®, Everlase® and Esperase® (Novozymes NS), those sold under the tradename Maxatase®, Maxacal®, Maxapem®, Purafect®, Purafect Prime®, Purafect MA®, Purafect Ox®, Purafect OxP®, Puramax®, Properase®, FN2®, FN3®, FN4®, Excellase®, Eraser® Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

Lipases and Cutinases

Suitable lipases and cutinases include those of bacterial or fungal origin. Chemically modified or protein engineered mutant enzymes are included. Examples include lipase from *Thermomyces*, e.g. from *T. lanuginosus* (previously named *Humicola lanuginosa*) as described in EP258068 and EP305216, cutinase from *Humicola*, e.g. *H. insolens* (WO96/13580), lipase from strains of *Pseudomonas* (some of these now renamed to *Burkholderia*), e.g. *P. alcaligenes* or *P. pseudoalcaligenes* (EP218272), *P. cepacia* (EP331376), *P.* sp. strain SD705 (WO95/06720 & WO96/27002), *P. wisconsinensis* (WO96/12012), GDSL-type *Streptomyces* lipases (WO10/065455), cutinase from *Magnaporthe grisea* (WO10/107560), cutinase from *Pseudomonas mendocina* (U.S. Pat. No. 5,389,536), lipase from *Thermobifida fusca* (WO11/084412), *Geobacillus stearothermophilus* lipase (WO11/084417), lipase from *Bacillus subtilis* (WO11/084599), and lipase from *Streptomyces griseus* (WO11/150157) and *S. pristinaespiralis* (WO12/137147).

Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include include Lipolase™, Lipex™; Lipolex™ and Lipoclean™ (Novozymes NS), Lumafast (originally from Genencor) and Lipomax (originally from Gist-Brocades).

Still other examples are lipases sometimes referred to as acyltransferases or perhydrolases, e.g. acyltransferases with homology to *Candida antarctica* lipase A (WO10/111143), acyltransferase from *Mycobacterium smegmatis* (WO05/56782), perhydrolases from the CE 7 family (WO09/67279), and variants of the *M. smegmatis* perhydrolase in particular the S54V variant used in the commercial product Gentle Power Bleach from Huntsman Textile Effects Pte Ltd (WO10/100028).

Amylases

Suitable amylases which can be used together with the subtilase variants of the invention may be an alpha-amylase or a glucoamylase and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase derived from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase derived from *B. amyloliquefaciens* shown in SEQ ID NO: 6 of WO 2006/066594 and residues 36-483 of SEQ ID NO: 4 are those having the substitutions:

M197T;

H156Y+A181T+N190F+A209V+Q264S; or

G48A+T49I+G107A+H156Y+A181T+N190F+I201F+A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO 96/023873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E,R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T182G+Y305R+G475K;

N128C+K178L+T182G+F202Y+Y305R+D319T+G475K;

S125A+N128C+K178L+T182G+Y305R+G475K; or

S125A+N128C+T131I+T165I+K178L+T182G+Y305R+G475K, wherein the variants are C-terminally truncated and optionally further comprises a substitution at position 243 and/or a deletion at position I8C and/or position I81.

Further suitable amylases are amylases having SEQ ID NO: 1 of WO13184577 or variants having 90% sequence identity to SEQ ID NO: 1 thereof. Preferred variants of SEQ ID NO: 1 are those having a substitution, a deletion or an insertion in one or more of the following positions: K176, R178, G179, T180, G181, E187, N192, M199, I203, S241, R458, T459, D460, G476 and G477. More preferred variants of SEQ ID NO: 1 are those having the substitution in one of more of the following positions: K176L, E187P, N192FYH, M199L, I203YF, S241QADN, R458N, T459S, D460T, G476K and G477K and/or deletion in position R178 and/or S179 or of T180 and/or G181. Most preferred amylase variants of SEQ ID NO: 1 are those having the substitutions:

E187P+I203Y+G476K

E187P+I203Y+R458N+T459S+D460T+G476K, wherein the variants optionally further comprises a substitution at position 241 and/or a deletion at position 178 and/or position 179.

Further suitable amylases are amylases having SEQ ID NO: 1 of WO10104675 or variants having 90% sequence identity to SEQ ID NO: 1 thereof. Preferred variants of SEQ ID NO: 1 are those having a substitution, a deletion or an insertion in one of more of the following positions: N21, D97, V128I K177, R179, S180, I181, G182, M200, L204, E242, G477 and G478. More preferred variants of SEQ ID NO: 1 are those having the substitution in one of more of the following positions: N21D, D97N, V128I K177L, M200L, L204YF, E242QA, G477K and G478K and/or deletion in position R179 and/or S180 or of I181 and/or G182. Most preferred amylase variants of SEQ ID NO: 1 are those having the substitutions:

N21D+D97N+V128I, wherein the variants optionally further comprises a substitution at position 200 and/or a deletion at position 180 and/or position 181.

Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO2011/098531, WO2013/001078 and WO2013/001087. Commercially available amylases are Duramyl™, Termamyr™, Fungamyl™, Stainzyme™, Stainzyme Plus™, Natalase™, Liquozyme X and BAN™ (from Novozymes NS), and Rapidase™, Purastar™/Effectenz™, Powerase, Preferenz S1000, Preferenz S100 and Preferenz S110 (from Genencor International Inc./DuPont).

Peroxidases/Oxidases

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include Guardzyme™ (Novozymes NS).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

Adjunct Materials

Any detergent components known in the art for use in laundry detergents may also be utilized. Other optional detergent components include anti-corrosion agents, anti-shrink agents, anti-soil redeposition agents, anti-wrinkling agents, bactericides, binders, corrosion inhibitors, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. Any ingredient known in the art for use in laundry detergents may be utilized. The choice of such ingredients is well within the skill of the artisan.

Dispersants: The detergent compositions of the present invention can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents: The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent whitening agent: The detergent compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulphonic acid derivatives, diarylpyrazoline derivatives and bisphenyl-distyryl derivatives. Examples of the diaminostilbene-sulphonic acid derivative type of fluorescent whitening agents include the sodium salts of: 4,4'-bis-(2-diethanolamino-4-anilino-s-triazin-6-ylamino) stilbene-2,2'-disulphonate; 4,4'-bis-(2,4-dianilino-s-triazin-6-ylamino) stilbene-2.2'-disuophonate; 4,4'-bis-(2-anilino-4(N-methyl-N-2-hydroxy-ethylamino)-s-triazin-6-ylamino) stilbene-2,2'-disulphonate, 4,4'-bis-(4-phenyl-2,1,3-triazol-2-yl)stilbene-2,2'-disulphonate; 4,4'-bis(2-anilino-4(1-methyl-2-hydroxy-ethylamino)-s-triazin-6-ylamino) stilbene-2,2'-disulphonate and 2-(stilbyl-4''-naptho-1,2':4,5)-1,2,3-trizole-2''-sulphonate. Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4 anilino-s-triazin-6-ylamino) stilbene disulphonate. Tinopal CBS is the disodium salt of 2,2'-bis-(phenyl-styryl) disulphonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins. Suitable fluorescent brightener levels include lower levels of from about 0.01, from 0.05, from about 0.1 or even from about 0.2 wt % to upper levels of 0.5 or even 0.75 wt %.

Soil release polymers: The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore random graft co-polymers are suitable soil release polymers Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-redeposition agents: The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Formulation of Detergent Products

The detergent composition of the invention may be in any convenient form, e.g., a bar, a homogenous tablet, a tablet having two or more layers, a pouch having one or more compartments, a regular or compact powder, a granule, a paste, a gel, or a regular, compact or concentrated liquid. There are a number of detergent formulation forms such as layers (same or different phases), pouches, as well as forms for machine dosing unit.

Pouches can be configured as single or multicompartments. It can be of any form, shape and material which is suitable for hold the composition, e.g. without allowing the release of the composition from the pouch prior to water contact. The pouch is made from water soluble film which encloses an inner volume. Said inner volume can be devided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxyprpyl methyl cellulose (HPMC). Preferably the level of polymer in the film for example PVA is at least about 60%. Preferred average molecular weight will typically be about 20,000 to about 150,000. Films can also be of blend compositions comprising hydrolytically degradable and water soluble polymer blends such as polyactide and polyvinyl alcohol (known under the Trade reference M8630 as sold by Chris Craft In. Prod. Of Gary, Ind., US) plus plasticisers like glycerol, ethylene glycerol, Propylene glycol, sorbitol and mixtures thereof. The pouches can comprise a solid laundry detergent composition or part components and/or a liquid cleaning composition or part components separated by the water soluble film. The compartment for liquid components can be different in composition than compartments containing solids. Ref: (US2009/0011970 A1).

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent. A liquid or gel detergent may be non-aqueous.

Laundry Soap Bars

The enzymes of the invention may be added to laundry soap bars and used for hand washing laundry, fabrics and/or textiles. The term laundry soap bar includes laundry bars, soap bars, combo bars, syndet bars and detergent bars. The types of bar usually differ in the type of surfactant they contain, and the term laundry soap bar includes those containing soaps from fatty acids and/or synthetic soaps. The laundry soap bar has a physical form which is solid and not a liquid, gel or a powder at room temperature. The term solid is defined as a physical form which does not significantly change over time, i.e. if a solid object (e.g. laundry soap bar) is placed inside a container, the solid object does not change to fill the container it is placed in. The bar is a solid typically in bar form but can be in other solid shapes such as round or oval.

The laundry soap bar may contain one or more additional enzymes, protease inhibitors such as peptide aldehydes (or hydrosulfite adduct or hemiacetal adduct), boric acid, borate, borax and/or phenylboronic acid derivatives such as 4-formylphenylboronic acid, one or more soaps or synthetic surfactants, polyols such as glycerine, pH controlling compounds such as fatty acids, citric acid, acetic acid and/or formic acid, and/or a salt of a monovalent cation and an organic anion wherein the monovalent cation may be for example $Na^+$, $K^+$ or $NH_4^+$ and the organic anion may be for example formate, acetate, citrate or lactate such that the salt of a monovalent cation and an organic anion may be, for example, sodium formate.

The laundry soap bar may also contain complexing agents like EDTA and HEDP, perfumes and/or different type of fillers, surfactants e.g. anionic synthetic surfactants, builders, polymeric soil release agents, detergent chelators, stabilizing agents, fillers, dyes, colorants, dye transfer inhibitors, alkoxylated polycarbonates, suds suppressers, structurants, binders, leaching agents, bleaching activators, clay soil removal agents, anti-redeposition agents, polymeric dispersing agents, brighteners, fabric softeners, perfumes and/or other compounds known in the art.

The laundry soap bar may be processed in conventional laundry soap bar making equipment such as but not limited to: mixers, plodders, e.g. a two stage vacuum plodder, extruders, cutters, logo-stampers, cooling tunnels and wrappers. The invention is not limited to preparing the laundry soap bars by any single method. The premix of the invention may be added to the soap at different stages of the process. For example, the premix containing a soap, an enzyme, optionally one or more additional enzymes, a protease inhibitor, and a salt of a monovalent cation and an organic anion may be prepared and the mixture is then plodded. The enzyme and optional additional enzymes may be added at the same time as the protease inhibitor for example in liquid form. Besides the mixing step and the plodding step, the process may further comprise the steps of milling, extruding, cutting, stamping, cooling and/or wrapping.

Granular Detergent Formulations

A granular detergent may be formulated as described in WO09/092699, EP1705241, EP1382668, WO07/001262, U.S. Pat. No. 6,472,364, WO04/074419 or WO09/102854. Other useful detergent formulations are described in WO09/124162, WO09/124163, WO09/117340, WO09/117341, WO09/117342, WO09/072069, WO09/063355, WO09/132870, WO09/121757, WO09/112296, WO09/112298, WO09/103822, WO09/087033, WO09/050026, WO09/047125, WO09/047126, WO09/047127, WO09/047128, WO09/021784, WO09/010375, WO09/000605, WO09/122125, WO09/095645, WO09/040544, WO09/040545, WO09/024780, WO09/004295, WO09/004294, WO09/121725, WO09/115391, WO09/115392, WO09/074398, WO09/074403, WO09/068501, WO09/065770, WO09/021813, WO09/030632, and WO09/015951.

WO2011025615, WO2011016958, WO2011005803, WO2011005623, WO2011005730, WO2011005844, WO2011005904, WO2011005630, WO2011005830, WO2011005912, WO2011005905, WO2011005910, WO2011005813, WO2010135238, WO2010120863, WO2010108002, WO2010111365, WO2010108000, WO2010107635, WO2010090915, WO2010033976, WO2010033746, WO2010033747, WO2010033897, WO2010033979, WO2010030540, WO2010030541, WO2010030539, WO2010024467, WO2010024469, WO2010024470, WO2010025161, WO2010014395, WO2010044905,

WO2010145887, WO2010142503, WO2010122051, WO2010102861, WO2010099997, WO2010084039, WO2010076292, WO2010069742, WO2010069718, WO2010069957, WO2010057784, WO2010054986, WO2010018043, WO2010003783, WO2010003792,

WO2011023716, WO2010142539, WO2010118959, WO2010115813, WO2010105942, WO2010105961, WO2010105962, WO2010094356, WO2010084203, WO2010078979, WO2010072456, WO2010069905, WO2010076165, WO2010072603, WO2010066486, WO2010066631, WO2010066632, WO2010063689, WO2010060821, WO2010049187, WO2010031607, WO2010000636.

Uses

The present invention is also directed to methods for using the subtilase variants according to the invention or compositions thereof in laundering of textile and fabrics, such as house hold laundry washing and industrial laundry washing.

The invention is also directed to methods for using the variants according to the invention or compositions thereof in cleaning hard surfaces such as floors, tables, walls, roofs etc. as well as surfaces of hard objects such as cars (car wash) and dishes (dish wash).

The subtilase variants of the present invention may be added to and thus become a component of a detergent composition. Thus one aspect of the invention relates to the use of a subtilase variant comprising the substitution N76D and one or more substitutions selected from the group consisting of Q2R, W6I, I8{C,H}, S9{C,D,E,Q}, N18S, N43{A,C,L,R,W}, S49T, G53{A,L}, G61D, I72{A,V}, S78{D,N}, V104{F,P,T,Y}, A114V, G115{T,W}, H120{1,T,V}, P129D, V147W, V149{C,N,Q}, A158E, G160{D,P}, S161{C,Y,E}, I162L, S163{A, D}, Q182{C,E}, N184D, N185{C,E}, S188{C, D,E}, Q191N, A194{D,E}, N204{D,V}, V205{I,L}, Q206{C,E,I,K,T,V,W,L}, Y209{L,W}, S212{A,D,G,N}, S216{I,T,V}, L217{C,M}, N218T, M222{C,N,R}, P225{A,S}, T255{C,E,Q}, S256{A,C,D,V, Y}, S259D, T260{A,E,P}, N261{D,C,E,L,M,R,V,W,Y,F} and L262{Y,C,E,Q}, wherein each position corresponds to the position of the polypeptide of SEQ ID NO: 2 in a cleaning process such as laundering and/or hard surface cleaning.

In another aspect, the invention relates to the use of a subtilase variant comprising the substitution N76D and one or more substitutions selected from the group consisting of Q2R, W6I, I8{C,H}, S9{C,D,E,Q}, N18S, N43{A,C,L,R,W}, S49T, G53{A,L}, G61D, I72{A,V}, S78{D,N}, V104{F,P,T,Y}, A114V, G115{T,W}, H120{1,T,V}, P129D, V147W, V149{C,N,Q}, A158E, G160{D,P}, S161{C,Y,E}, I162L, S163{A, D}, Q182{C,E}, N184D, N185{C,E}, S188{C, D,E}, Q191N, A194{D,E}, N204{D,V}, V205{I,L}, Q206{C,E,I,K,T,V,W,L}, Y209{L,W}, S212{A,D,G,N}, S216{1,T,V}, L217{C,M}, N218T, M222{C,N,R}, P225{A,S}, T255{C,E,Q}, S256{A,C,D,V, Y}, S259D, T260{A,E,P}, N261{D,C,E,L,M,R,V,W,Y,F} and L262{Y,C,E,Q}, wherein each position corresponds to the position of the polypeptide of SEQ ID NO: 2 wherein the variant has a sequence identity of at least 60%, such as at least 65%, such as at least 70%, e.g., at least 75%, at least 76% at least 77% at least 78% at least 79% at least 80%, at least 81% at least 82% at least 83% at least 84% at least 85%, at least 86% at least 87% at least 88% at least 89%, at least 90%, at least 91%, at least 92%, at least 93%, at least 94%, at least 95% identity, at least 96%, at least 97%, or at least 98%, but less than 100%, sequence identity to the polypeptide of SEQ ID NO: 1 in a cleaning process such as laundering and/or hard surface cleaning.

In a further aspect, the invention relates to the use of a subtilase variant comprising the substitution N76D and one or more substitutions selected from the group consisting of Q2R, Y6I, V8{C,H}, S9{C,D,E,Q}, K43{A,C,L,R,W}, S49T, S53{A,L}, N61D, V72A, S78{D,N}, Y104{F,P,T}, A114V, I115{T,W}, D120{I,T,V}, P129D, V147W, V149{C,N,Q}, T158E, G160{D,P}, S161{C,Y,E}, S162L, S163{A, D}, S182{C,E}, N184D, Q185{C,E}, S188{C, D,E}, Q191N, P194{D,E}, S204{D,V}, I205L, Q206{C,E,I,K,T,V,W,L}, L209W, N212{A,D,G}, A216{I,T,V}, Y217{C,M}, N218T, M222{C,N,R}, P225{A,S}, T255{C, E,Q}, K256{A,C,D,V, Y}, S260{A,E,P}, F261{D,C,E,L,M,R,V,W,Y,F} and Y262{C,E,Q}, wherein each position corresponds to the position of the polypeptide of SEQ ID NO: 2 wherein the variant has a sequence identity of at least 60%, such as at least 65%, such as at least 70%, e.g., at least 75%, at least 76% at least 77% at least 78% at least 79% at least 80%, at least 81% at least 82% at least 83% at least 84% at least 85%, at least 86% at least 87% at least 88% at least 89%, at least 90%, at least 91%, at least 92%, at least 93%, at least 94%, at least 95% identity, at least 96%, at least 97%, or at least 98%, but less than 100%, sequence identity to the polypeptide of SEQ ID NO: 2 in a cleaning process such as laundering and/or hard surface cleaning.

In one aspect of the invention relates to the use of a subtilase variant comprising the substitution N76D and one or more substitutions selected from the group consisting of Q2R, W6I, I8{C,H}, S9{C,D,E,Q}, N18S, N43{A,C,L,R,W}, S49T, G53{A,L}, G61D,I72{A,V}, S78{D,N}, V104{F,P,T,Y}, A114V, G115{T,W}, H120{I,T,V}, P129D, V147W, V149{C,N,Q}, A158E, G160{D,P}, S161{C,Y,E}, I162L, S163{A, D}, Q182{C,E}, N184D, N185{C,E}, S188{C, D,E}, Q191N, A194{D,E}, N204{D,V}, V205{I, L}, Q206{C,E,I,K,T,V,W,L}, Y209{L,W}, S212{A,D,G, N}, S216{1,T,V}, L217{C,M}, N218T, M222{C,N,R}, P225{A,S}, T255{C,E,Q}, S256{A,C,D,V, Y}, S259D, T260{A,E,P}, N261{D,C,E,L,M,R,V,W,Y,F} and L262{Y, C,E,Q} and L262{C,E,Q} wherein each position corresponds to the position of the polypeptide of SEQ ID NO: 2 in a cleaning process such as laundering and/or hard surface cleaning and wherein the subtilase variant has improved stability, in particular improved storage stability, relative to the parent or relative to a protease parent having the identical amino acid sequence of said variant but excluding the substitutions at one or more of said positions when measured using the 'accelerated storage stability assay' as described in example 3 in the Materials and Methods section herein.

In another aspect, the invention relates to the use of a subtilase variant comprising the substitution N76D and one or more substitutions selected from the group consisting of Q2R, W6I, I8{C,H}, S9{C,D,E,Q}, N18S, N43{A,C,L,R,W}, S49T, G53{A,L}, G61D,I72{A,V}, S78{D,N}, V104{F,P,T,Y}, A114V, G115{T,W}, H120{I,T,V}, P129D, V147W, V149{C,N,Q}, A158E, G160{D,P}, S161{C,Y,E}, I162L, S163{A, D}, Q182{C,E}, N184D, N185{C,E}, S188{C, D,E}, Q191N, A194{D,E}, N204{D,V}, V205{I,L}, Q206{C,E,I,K,T,V,W,L}, Y209{L,W}, S212{A,D,G,N}, S216{1,T,V}, L217{C,M}, N218T, M222{C,N,R}, P225{A,S}, T255{C,E,Q}, S256{A,C,D,V, Y}, S259D, T260{A,E,P}, N261{D,C,E,L,M,R,V,W,Y,F} and L262{Y,C,E,Q}, wherein each position corresponds to the position of the polypeptide of SEQ ID NO: 2 wherein the variant has a sequence identity of at least 60%, such as at least 65%, such as at least 70%, e.g., at least 75%, at least 76% at least 77% at least 78% at least 79% at least 80%, at least 81% at least 82% at least 83% at least 84% at least 85%, at least 86% at least 87% at least 88% at least 89%, at least 90%, at least 91%, at least 92%, at least 93%, at least 94%, at least 95% identity, at least 96%, at least 97%, or at least 98%, but less than 100%, sequence identity to the polypeptide of SEQ ID NO: 1 in a cleaning process such as laundering and/or hard surface cleaning and wherein the subtilase variant has improved stability, in particular improved in storage stability, relative to the polypeptide of SEQ ID NO: 1 when measured using the 'accelerated storage stability assay' as described in example 3 in the Materials and Methods section herein.

In a further aspect, the invention relates to the use of a subtilase variant comprising the substitution N76D and one or more substitutions selected from the group consisting Q2R, Y6I, V8{C,H}, S9{C,D,E,Q}, K43{A,C,L,R,W}, S49T, S53{A,L}, N61D, V72A, S78{D,N}, Y104{F,P,T}, A114V, I115{T,W}, D120{I,T,V}, P129D, V147W, V149{C,N,Q}, T158E, G160{D,P}, S161{C,Y,E}, S162L, S163{A, D}, S182{C,E}, N184D, Q185{C,E}, S188{C, D,E}, S191N, P194{D,E}, S204{D,V}, I205L, Q206{C,E, I,K,T,V,W,L}, L209W, N212{A,D,G}, A216{I,T,V}, Y217{C,M}, N218T, M222{C,N,R}, P225{A,S}, T255{C, E,Q}, K256{A,C,D,V, Y}, S260{A,E,P}, F261{D,C,E,L,M, R,V,W,Y,F} and Y262{C,E,Q}, wherein each position corresponds to the position of the polypeptide of SEQ ID NO: 2 wherein the variant has a sequence identity of at least 60%, such as at least 65%, such as at least 70%, e.g., at least 75%, at least 76% at least 77% at least 78% at least 79% at least 80%, at least 81% at least 82% at least 83% at least 84% at least 85%, at least 86% at least 87% at least 88% at least 89%, at least 90%, at least 91%, at least 92%, at least 93%, at least 94%, at least 95% identity, at least 96%, at least 97%, or at least 98%, but less than 100%, sequence identity to the polypeptide of SEQ ID NO: 2 in a cleaning process such as laundering and/or hard surface cleaning and wherein the subtilase variant has improved stability, in particular improved in storage stability, relative to the polypeptide of SEQ ID NO: 2 when measured using the 'accelerated storage stability assay' as described in the Materials and Methods section herein.

The subtilase variants of the present invention may be added to and thus become a component of a detergent composition. Thus one aspect of the invention relates to the use of a subtilase variant comprising the substitution N76D and one or more substitutions selected from the group consisting of Q2R, W6I, I8{C,H}, S9{C,D,E,Q}, N18S, N43{A,C,L,R,W}, S49T, G53{A,L}, G61D, I72{A,V}, S78{D,N}, V104{F,P,T,Y}, A114V, G115{T,W}, H120{I,T, V}, P129D, V147W, V149{C,N,Q}, A158E, G160{D,P}, S161{C,Y,E}, I162L, S163{A, D}, Q182{C,E}, N184D, N185{C,E}, S188{C, D,E}, Q191N, A194{D,E}, N204{D, V}, V205{I,L}, Q206{C,E,I,K,T,V,W,L}, Y209{L,W}, S212{A,D,G,N}, S216{1,T,V}, L217{C,M}, N218T, M222{C,N,R}, P225{A,S}, T255{C,E,Q}, S256{A,C,D,V, Y}, S259D, T260{A,E,P}, N261{D,C,E,L,M,R,V,W,Y,F} and L262{Y,C,E,Q}, wherein each position corresponds to the position of the polypeptide of SEQ ID NO: 2 in a cleaning process such as laundering and/or hard surface cleaning and wherein the subtilase variant has improved stability, in particular improved in storage stability, and on par or improved wash performance relative to the parent or relative to a protease parent having the identical amino acid sequence of said variant but excluding the substitutions at one or more of said positions when measured using the 'accelerated storage stability assay' and the Automatic Mechanical Stress Assay (AMSA) for laundry respectively as described in the Materials and Methods section herein.

In another aspect, the invention relates to the use of a subtilase variant comprising the substitution N76D and one or more substitutions selected from the group consisting of Q2R, W6I, I8{C,H}, S9{C,D,E,Q}, N18S, N43{A,C,L,R,W}, S49T, G53{A,L}, G61D,I72{A,V}, S78{D,N}, V104{F,P,T,Y}, A114V, G115{T,W}, H120{1,T,V}, P129D, V147W, V149{C,N,Q}, A158E, G160{D,P}, S161{C,Y,E}, I162L, S163{A, D}, Q182{C,E}, N184D, N185{C,E}, S188{C, D,E}, Q191N, A194{D,E}, N204{D,V}, V205{I, L}, Q206{C,E,I,K,T,V,W,L}, Y209{L,W}, S212{A,D,G, N}, S216{1,T,V}, L217{C,M}, N218T, M222{C,N,R}, P225{A,S}, T255{C,E,Q}, S256{A,C,D,V, Y}, S259D, T260{A,E,P}, N261{D,C,E,L,M,R,V,W,Y,F} and L262{Y, C,E,Q}, wherein each position corresponds to the position of the polypeptide of SEQ ID NO: 2 wherein the variant has a sequence identity of at least 60%, such as at least 65%, such as at least 70%, e.g., at least 75%, at least 76% at least 77% at least 78% at least 79% at least 80%, at least 81% at least 82% at least 83% at least 84% at least 85%, at least 86% at least 87% at least 88% at least 89%, at least 90%, at least 91%, at least 92%, at least 93%, at least 94%, at least 95% identity, at least 96%, at least 97%, or at least 98%, but less than 100%, sequence identity to the polypeptide of SEQ ID NO: 1 in a cleaning process such as laundering and/or hard surface cleaning and wherein the subtilase variant has improved stability, in particular improved in storage stability, and on par or improved wash performance relative to the mature polypeptide of SEQ ID NO: 1 measured using the 'accelerated storage stability assay and the Automatic Mechanical Stress Assay (AMSA) for laundry respectively as described in the Materials and Methods section herein.

In a further aspect, the invention relates to the use of a subtilisin variant comprising the substitution N76D and one or more substitutions selected from the group consisting of Q2R, Y6I, V8{C,H}, S9{C,D,E,Q}, K43{A,C,L,R,W}, S49T, S53{A,L}, N61D, V72A, S78{D,N}, Y104{F,P,T}, A114V, I115{T,W}, D120{1,T,V}, P129D, V147W, V149{C,N,Q}, T158E, G160{D,P}, S161{C,Y,E}, S162L, S163{A, D}, S182{C,E}, N184D, Q185{C,E}, S188{C, D,E}, S191N, P194{D,E}, S204{D,V}, I205L, Q206{C,E, I,K,T,V,W,L}, L209W, N212{A,D,G}, A216{I,T,V}, Y217{C,M}, N218T, M222{C,N,R}, P225{A,S}, T255{C, E,Q}, K256{A,C,D,V, Y}, S260{A,E,P}, F261{D,C,E,L,M, R,V,W,Y,F} and Y262{C,E,Q}, wherein each position corresponds to the position of the polypeptide of SEQ ID NO: 2 wherein the variant has a sequence identity of at least 60%, such as at least 65%, such as at least 70%, e.g., at least 75%, at least 76% at least 77% at least 78% at least 79% at least 80%, at least 81% at least 82% at least 83% at least 84% at least 85%, at least 86% at least 87% at least 88% at least 89%, at least 90%, at least 91%, at least 92%, at least 93%, at least 94%, at least 95% identity, at least 96%, at least 97%, or at least 98%, but less than 100%, sequence identity to the polypeptide of SEQ ID NO: 2 in a cleaning process such as laundering and/or hard surface cleaning and wherein the subtilase variant has improved stability, in particular improved in storage stability, and on par or improved wash performance relative to the polypeptide of SEQ ID NO: 2 when measured using the 'Accelerated storage stability assay' and the Automatic Mechanical Stress Assay (AMSA) for laundry respectively as described in the Materials and Methods section herein.

A detergent composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the present invention provides a detergent additive comprising a polypeptide of the present invention as described herein.

The cleaning process or the textile care process may for example be a laundry process, a dishwashing process or cleaning of hard surfaces such as bathroom tiles, floors, table tops, drains, sinks and washbasins. Laundry processes can for example be household laundering, but it may also be industrial laundering. Furthermore, the invention relates to a process for laundering of fabrics and/or garments where the process comprises treating fabrics with a washing solution containing a detergent composition, and at least one protease variant of the invention. The cleaning process or a textile care process can for example be carried out in a machine washing process or in a manual washing process. The washing solution can for example be an aqueous washing solution containing a detergent composition.

The last few years there has been an increasing interest in replacing components in detergents, which is derived from petrochemicals with renewable biological components such as enzymes and polypeptides without compromising the wash performance. When the components of detergent compositions change new enzyme activities or new enzymes having alternative and/or improved properties compared to the common used detergent enzymes such as proteases, lipases and amylases is needed to achieve a similar or improved wash performance when compared to the traditional detergent compositions.

The invention further concerns the use of subtilase variants of the invention in a proteinaceous stain removing processes. The proteinaceous stains may be stains such as food stains, e.g., baby food, sebum, cocoa, egg, blood, milk, ink, grass, or a combination hereof.

Typical detergent compositions include various components in addition to the enzymes, these components have different effects, some components like the surfactants lower the surface tension in the detergent, which allows the stain being cleaned to be lifted and dispersed and then washed away, other components like bleach systems remove discolor often by oxidation and many bleaches also have strong bactericidal properties, and are used for disinfecting and sterilizing. Yet other components like builder and chelator softens, e.g., the wash water by removing the metal ions form the liquid.

In a particular embodiment, the invention concerns the use of a composition comprising a subtilase variant of the invention and one or more detergent components, such as surfactants, hydrotropes, builders, co-builders, chelators or chelating agents, bleaching system or bleach components, polymers, fabric hueing agents, fabric conditioners, foam boosters, suds suppressors, dispersants, dye transfer inhibitors, fluorescent whitening agents, perfume, optical brighteners, bactericides, fungicides, soil suspending agents, soil release polymers, anti-redeposition agents, enzyme inhibitors or stabilizers, enzyme activators, antioxidants, and solubilizers.

In a particular embodiment, the invention concerns the use of a composition comprising a subtilase variant of the invention and one or more additional enzymes selected from the group comprising of proteases, amylases, lipases, cutinases, cellulases, endoglucanases, xyloglucanases, pectinases, pectin lyases, xanthanases, peroxidaes, haloperoxygenases, catalases and mannanases, or any mixture thereof.

In a particular embodiment, the invention concerns the use of a composition comprising a subtilase variant of the invention, one or more additional enzymes selected from the group comprising of proteases, amylases, lipases, cutinases, cellulases, endoglucanases, xyloglucanases, pectinases, pectin lyases, xanthanases, peroxidaes, haloperoxygenases, catalases and mannanases, or any mixture thereof and one or more detergent components, such as surfactants, hydrotropes, builders, co-builders, chelators or chelating agents, bleaching system or bleach components, polymers, fabric hueing agents, fabric conditioners, foam boosters, suds suppressors, dispersants, dye transfer inhibitors, fluorescent whitening agents, perfume, optical brighteners, bactericides, fungicides, soil suspending agents, soil release polymers, anti-redeposition agents, enzyme inhibitors or stabilizers, enzyme activators, antioxidants, and solubilizers.

Washing Method

The present invention relates to a method of cleaning a fabric, a dishware or hard surface with a detergent composition comprising a protease variant of the invention.

A preferred embodiment concerns a method of cleaning, said method comprising the steps of: contacting an object with a detergent composition comprising a protease variant of the invention under conditions suitable for cleaning said object. In a preferred embodiment the detergent composition is used in a laundry or a dish wash process.

Still another embodiment relates to a method for removing stains from fabric or dishware which comprises contacting said fabric or dishware with a composition comprising a protease of the invention under conditions suitable for cleaning said object.

Also contemplated are compositions and methods of treating fabrics (e.g., to desize a textile) using one or more of the protease of the invention. The protease can be used in any fabric-treating method which is well known in the art (see, e.g., U.S. Pat. No. 6,077,316). For example, in one aspect, the feel and appearance of a fabric is improved by a method comprising contacting the fabric with a protease in a solution. In one aspect, the fabric is treated with the solution under pressure.

The detergent compositions of the present invention are suited for use in laundry and hard surface applications, including dish wash. Accordingly, the present invention includes a method for laundering a fabric or washing dishware. The method comprises the steps of contacting the fabric/dishware to be cleaned with a solution comprising the detergent composition according to the invention. The fabric may comprise any fabric capable of being laundered in normal consumer use conditions. The dishware may comprise any dishware such as crockery, cutlery, ceramics, plastics such as melamine, metals, china, glass and acrylics. The solution preferably has a pH from about 5.5 to about 11.5. The compositions may be employed at concentrations from about 100 ppm, preferably 500 ppm to about 15,000 ppm in solution. The water temperatures typically range from about 5° C. to about 95° C., including about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C. and about 90° C. The water to fabric ratio is typically from about 1:1 to about 30:1.

The enzyme(s) of the detergent composition of the invention may be stabilized using conventional stabilizing agents and protease inhibitors, e.g. a polyol such as propylene glycol or glycerol, a sugar or sugar alcohol, different salts such as NaCl; KCl; lactic acid, formic acid, boric acid, or a boric acid derivative, e.g., an aromatic borate ester, or a phenyl boronic acid derivative such as 4-formylphenyl boronic acid, or a peptide aldehyde such as di-, tri- or tetrapeptide aldehydes or aldehyde analogues (either of the form B1-B0-R wherein, R is H, CH3, CX3, CHX2, or CH2X (X=halogen), B0 is a single amino acid residue (preferably with an optionally substituted aliphatic or aromatic side chain); and B1 consists of one or more amino acid residues (preferably one, two or three), optionally comprising an N-terminal protection group, or as described in WO09118375, WO98/13459) or a protease inhibitor of the protein type such as RASI, BASI, WASI (bifunctional alpha-amylase/subtilisin inhibitors of rice, barley and wheat) or C12 or SSI. The composition may be formulated as described in e.g. WO 92/19709, WO 92/19708 and U.S. Pat. No. 6,472,364. In some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), Tin (II), cobalt (II), copper (II), Nickel (II), and oxovanadium (IV)).

In some preferred embodiments, the detergent compositions provided herein are typically formulated such that, during use in aqueous cleaning operations, the wash water has a pH of from about 5.0 to about 11.5, or in alternative embodiments, even from about 6.0 to about 10.5. In some preferred embodiments, granular or liquid laundry products are formulated to have a pH from about 6 to about 8. Techniques for controlling pH at recommended usage levels include the use of buffers, alkalis, acids, etc., and are well known to those skilled in the art.

The present invention is further described by the following examples that should not be construed as limiting the scope of the invention.

EXAMPLES

Materials and Methods
Automatic Mechanical Stress Assay (AMSA) for laundry
In order to assess the wash performance in laundry, washing experiments are performed, using the Automatic Mechanical Stress Assay (AMSA). With the AMSA, the wash performance of a large quantity of small volume enzyme-detergent solutions can be examined. The AMSA plate has a number of slots for test solutions and a lid firmly squeezing the laundry sample, the textile to be washed against all the slot openings. During the washing time, the plate, test solutions, textile and lid are vigorously shaken to bring the test solution in contact with the textile and apply mechanical stress in a regular, periodic oscillating manner. For further description see WO 02/42740 especially the paragraph "Special method embodiments" at page 23-24.

TABLE 3

| | |
|---|---|
| Detergent dosage | 5 g/L (liquid detergent) |
| | 2.5 g/L (powder detergent) |
| Test solution volume | 160 micro L |
| pH | Adjusted to pH 7 or pH 6 (liquid detergent) |
| | As is (powder detergent) |
| Wash time | 20 minutes |
| Temperature | 60° C., 40° C. and 20° C. or 15° C. |
| Water hardness | 15° dH |

TABLE 4

Composition of model detergents and test materials
Model detergent and test materials were as follows:

| | |
|---|---|
| Laundry liquid model detergent | Sodium alkylethoxy sulfate (C-9-15, 2EO) 6.0% |
| | Sodium dodecyl benzene sulfonate 3.0% |
| | Sodium toluene sulfonate 3.0% |
| | Oleic acid 2.0% |
| | Primary alcohol ethoxylate (C12-15, 7EO) 3.0% |
| | Primary alcohol ethoxylate (C12-15, 3EO) 2.5% |
| | Ethanol 0.5% |
| | Monopropylene glycol 2.0% |
| | Tri-sodium citrate dihydrate 4.0% |
| | Triethanolamine 0.4% |
| | De-ionized water ad 100% |
| | pH adjusted to 8.5 with NaOH |
| Laundry powder model detergent | Sodium citrate dihydrate 32.3% |
| | Sodium-LAS 24.2% |
| | Sodium lauryl sulfate 32.2% |
| | Neodol 25-7 (alcohol ethoxylate) 6.4% |
| | Sodium sulfate 4.9% |
| Model O | LAS, (C10-C13)alkylbenzene-sulfonic acid 3.8% |
| | AES, AEOS, sodium lauryl ether sulfate 8% |
| | AEO, Alcohol ethoxylate 4% |
| | Soap, lauric acid 1% |
| | Trisodium citrate dihydrate 2% |
| | Sodium hydroxide 3% |
| | CaCl2, 2H2O 0.02% |
| | Kathon, preservative 0.1% |
| | Triethanolamine 0.4% |
| CNS EDTA pH9 | Alkylbenzenesulfonic acid 8% |
| | Alcohol ethoxylate 4% |
| | Sodium lauryl ether sulfate 4% |
| | Triethanolamine;2,2',2"-nitrilotri(ethan-1-ol) 0.5% |
| | Trisodium citrate dihydrate 0.5% |
| | Sodium hydroxide 1% |
| | EDTA 0.001% |
| | pH adjusted to 9 |
| Test material | EMPA112 (Cocoa on cotton) |
| | PC-05 (Blood/milk/ink on cotton/polyester) |
| | WFK10PPM (Vegetable oil/milk/pigment on cotton) |
| | C-10 (Oil/milk/pigment on cotton) |

Test materials are obtained from EMPA Testmaterials AG, Movenstrasse 12, CH-9015 St. Gallen, Switzerland, from Center For Testmaterials BV, P.O. Box 120, 3133 KT Vlaardingen, the Netherlands, and WFK Testgewebe GmbH, Christenfeld 10, D-41379 Bruggen, Germany.

Water hardness was adjusted to 15° dH by addition of CaCl$_2$, MgCl$_2$, and NaHCO$_3$ ($Ca^{2+}$:$Mg^{2+}$=4:1:7.5) to the test system. After washing the textiles were flushed in tap water and dried.

The wash performance is measured as the brightness of the colour of the textile washed. Brightness can also be expressed as the intensity of the light reflected from the sample when illuminated with white light. When the sample is stained the intensity of the reflected light is lower, than that of a clean sample. Therefore the intensity of the reflected light can be used to measure wash performance.

Colour measurements are made with a professional flatbed scanner (Kodak iQsmart, Kodak, Midtager 29, DK-2605 Brondby, Denmark), which is used to capture an image of the washed textile.

To extract a value for the light intensity from the scanned images, 24-bit pixel values from the image are converted into values for red, green and blue (RGB). The intensity value (Int) is calculated by adding the RGB values together as vectors and then taking the length of the resulting vector:

$$Int=\sqrt{r^2+g^2+b^2}$$

Protease Activity Assays:
1) Suc-AAPF-pNA Activity Assay:

The proteolytic activity can be determined by a method employing the Suc-AAPF-PNA substrate. Suc-AAPF-PNA is an abbreviation for N-Succinyl-Alanine-Alanine-Proline-Phenylalanine-p-Nitroanilide, and it is a blocked peptide which can be cleaved by endo-proteases. Following cleavage a free PNA molecule is liberated and it has a yellow colour and thus can be measured by visible spectrophotometry at wavelength 405 nm. The Suc-AAPF-PNA substrate is manufactured by Bachem (cat. no. L1400, dissolved in DMSO).

The protease sample to be analyzed was diluted in residual activity buffer (100 nM Tris pH 8.6). The assay was performed by transferring 30 μl of diluted enzyme samples to 96 well microtiter plate and adding 70 μl substrate working solution (0.72 mg/ml in 100 nM Tris pH8.6). The solution was mixed at room temperature and absorption is measured every 20 sec. over 5 minutes at OD 405 nm.

The slope (absorbance per minute) of the time dependent absorption-curve is directly proportional to the activity of the protease in question under the given set of conditions. The protease sample should be diluted to a level where the slope is linear.

General Molecular Biology Methods:

Unless otherwise mentioned the DNA manipulations and transformations were performed using standard methods of molecular biology (Sambrook et al. (1989); Ausubel et al. (1995); Harwood and Cutting (1990).

Example 1

Preparation and Expression of Variants

The following summarizes the mutation and introduction of an expression cassette into *Bacillus subtilis*. All DNA manipulations were done by PCR (e.g. Sambrook et al.; Molecular Cloning; Cold Spring Harbor Laboratory Press) and can be repeated by everybody skilled in the art.

Recombinant *B. subtilis* constructs encoding subtilase variants were used to inoculate shakeflasks containing a rich media (e.g. 100 g/L Sucrose (Danisco cat.no. 109-0429), 40 g/L crust soy (soy bean flour), 10 g/L Na2HPO4.12H2O (Merck cat.no. 6579), 0.1 ml/L replace-Dowfax63N10 (Dow). Cultivation typically takes 4 days at 30° C. shaking with 220 rpm.

Example 2

Purification of Variants

The culture broth was centrifuged (26000× g, 20 min) and the supernatant was carefully decanted from the precipitate. The supernatant was filtered through a Nalgene 0.2 μm filtration unit in order to remove the rest of the *Bacillus* host cells. pH in the 0.2 μm filtrate was adjusted to pH 8 with 3M Tris base and the pH adjusted filtrate was applied to a MEP Hypercel column (from Pall corporation) equilibrated in 20 nM Tris/HCl, 1 nM CaCl$_2$, pH 8.0. After washing the column with the equilibration buffer, the column was stepeluted with 20 nM CH$_3$COOH/NaOH, 1 nM CaCl$_2$, pH 4.5. Fractions from the column were analysed for protease activity (using the Suc-AAPF-pNA assay at pH 9) and peak-fractions were pooled. The pH of the pool from the MEP Hypercel column was adjusted to pH 6 with 20% (v/v) CH$_3$COOH or 3M Tris base and the pH adjusted pool was diluted with deionized water to the same conductivity as 20 nM MES/NaOH, 2 nM CaCl$_2$, pH 6.0. The diluted pool was applied to a SP-sepharose FF column (from GE Healthcare) equilibrated in 20 nM MES/NaOH, 2 nM CaCl$_2$, pH 6.0. After washing the column with the equilibration buffer, the protease was eluted with a linear NaCl gradient (0→0.5M) in the same buffer over five column volumes. Fractions from the column were analysed for protease activity (using the Suc-AAPF-pNA assay at pH 9) and active fractions were analysed by SDS-PAGE. The fractions, where only one band was seen on the coomassie stained SDS-PAGE gel, were pooled as the purified preparation and was used for further experiments.

Example 3

Accelerated Storage Stability Assay

Storage stability of protease variants in liquid detergent was evaluated using an accelerated assay with incubation at elevated temperatures for up to 24 hours.

All purified protease samples were diluted to concentrations of 0.2 and 0.1 mg/ml based on absorbance at 280 nm and theoretical extinction coefficient using 0.01% Triton X-100. For each variant 2 wells with high protease concentration and 2 wells with low concentration were included. As reference SEQ ID NO: 3 was included on each microtiter plate. 30 μl protease sample was mixed with 270 μl detergent (Model 0 or CNS EDTA pH9) in the well of a microtiter plate (Nunc U96 PP 0.5 ml) using a magnetic bar (on Zephyr pipetting station (Caliper LifeSciences) for 30 min). 20 μl of this mixture was then transferred to another microtiter plate (Nunc U96 PP 0.5 ml with added magnetic bars) and mixed with 150 μl 100 nM Tris pH 8.6 (at least 5 min on Zephyr). 30 μl of this dilution was transferred to a Nunc F 96-MTP, and after addition of 70 μl substrate solution initial activity of unstressed sample was determined by measuring absorbance at 405 nm every 20 sec for 5 min (on a SpectraMax Plus). After sealing, the detergent plate was incubated at appropriate temperature (50-62° C. for Model O, 35° C. for CNS EDTA pH9) in an Eppendorf Thermomixer (no shaking). After 1-4 and 20-25 hours incubation, 20 μl samples were withdrawn and residual activity of stressed sample was measured as with the initial, unstressed activity.

Decrease in activity during incubation with detergent was assumed to be exponential. Half lifes (T½) were found from linear regression of Log(Activity) versus incubation time (0, 1-4 and 20-25 hours), and half life improvement factors (T½ IF) were calculated as half life of protease variant relative to half life of SEQ ID NO 3 reference.

TABLE 5

| Detergent | Model O or CNS EDTA |
|---|---|
| pH | 9 |
| Temperature | 52 to 58° C. |

TABLE 6

Accelerated storage stability of variants T½ IF: Half life improvement factor was measured relative to SEQ ID NO 3

| Mutations | Improvement factor |
|---|---|
| I8H + N76D | 1.24 |
| S9C + N76D | 3.97 |
| S9D + N76D | 2.26 |
| S9E + N76D | 4.6 |
| S9Q + N76D | 2.18 |
| N18S + N76D | 1.10 |
| N43A + N76D | 1.88 |
| N43C + N76D | 2.43 |
| N43L + N76D | 1.71 |
| N43R + N76D | 2.42 |
| N43W + N76D | 1.92 |
| G53A + N76D | 1.14 |
| S49T + N76D | 1.24 |
| I72A + N76D | 2.48 |
| I72V + N76D | 1.91 |
| N76D + S78D | 1.27 |
| N76D + V104F | 1.32 |
| N76D + V104Y | 1.20 |
| N76D + Q109H | 1.18 |
| N76D + A114V | 1.41 |
| N76D + G115T | 1.81 |
| N76D + G115W | 2.66 |
| N76D + N117H | 1.20 |
| N76D + H120I | 1.63 |
| N76D + H120T | 1.44 |
| N76D + H120V | 2.18 |
| N76D + P129D | 2.05 |
| N76D + V147W | 1.56 |
| N76D + V149C | 1.55 |
| N76D + V149N | 1.42 |
| N76D + V149Q | 1.18 |
| N76D + A158E | 2.06 |
| N76D + A158E | 2.06 |
| N76D + G160D | 2.69 |
| N76D + G160P | 2.67 |
| N76D + S161C | 1.38 |
| N76D + S161E | 1.69 |
| N76D + S161Y | 1.17 |
| N76D + I162L | 1.19 |
| N76D + S163A | 1.37 |
| N76D + S163D | 1.55 |
| N76D + Q182C | 1.36 |
| N76D + Q182E | 2.71 |
| N76D + N183H | 1.18 |
| N76D + N184D | 1.14 |
| N76D + N185C | 1.47 |
| N76D + N185E | 1.75 |
| N76D + S188C | 1.25 |
| N76D + S188D | 1.31 |
| N76D + S188E | 1.89 |
| N76D + Q191N | 2.16 |
| N76D + N204D | 2.47 |
| N76D + N204V | 4.11 |
| N76D + V205I | 2.43 |
| N76D + Q206E | 1.68 |
| N76D + Q206I | 2.73 |
| N76D + Q206K | 1.6 |
| N76D + Q206L | 5.36 |
| N76D + Q206T | 1.51 |
| N76D + Q206V | 3.56 |
| N76D + Q206W | 3.83 |
| N76D + Q206C | 14.17 |
| N76D + Y209W | 5.1 |
| N76D + S212A | 1.5 |
| N76D + S212D | 2.29 |
| N76D + S212G | 2.79 |
| N76D + S212N | 2.06 |
| N76D + S216I | 1.82 |
| N76D + S216T | 1.89 |
| N76D + S216V | 1.94 |
| N76D + L217C | 5.3 |
| N76D + L217M | 2.74 |
| N76D + N218T | 2.3 |
| N76D + M222C | 1.77 |
| N76D + M222R | 1.26 |
| N76D + M222A | 1.22 |
| N76D + P225A | 10.04 |
| N76D + V244H | 1.15 |
| N76D + N248H | 1.14 |
| N76D + T255C | 1.79 |
| N76D + T255E | 1.55 |
| N76D + T255Q | 1.13 |
| N76D + S256A | 1.47 |
| N76D + S256C | 2.28 |
| N76D + S256D | 2.24 |
| N76D + S256V | 1.36 |
| N76D + S256Y | 1.46 |
| N76D + S259D | 3.09 |
| N76D + T260E | 2.6 |
| N76D + T260P | 1.31 |
| N76D + T260A | 1.24 |
| N76D + N261C | 2.88 |
| N76D + N261E | 3.49 |
| N76D + N261L | 2.47 |
| N76D + N261M | 1.64 |
| N76D + N261V | 2.18 |
| N76D + N261W | 4.07 |
| N76D + N261Y | 3.38 |
| N76D + L262C | 5.12 |
| N76D + L262E | 9.46 |
| N76D + L262Q | 2.72 |

Table 6 shows that all the variants above have improved the stability compared to SEQ ID NO 3.

TABLE 7

Accelerated storage stability of variants T½ IF: Half life improvement factor was measured relative to SEQ ID NO 3

| Mutations | Improvement factor |
|---|---|
| N76D + S9E + L262E | 27.1 |
| N76D + P225A + S259D | 22.3 |
| N76D + S212D + P225A | 16.1 |
| N76D + N43R + L262E | 14.0 |
| N76D + S212D + S259D | 12.3 |
| N76D + Q206C + Y209W | 8.9 |
| N76D + V205I + Q206L | 8.3 |
| N76D + P131* + S212D | 7.4 |
| N76D + P131* + S259D | 7.0 |
| N76D + V205I + Q206I | 6.9 |
| N76D + G160P + S161E | 6.5 |
| N76D + N204D + Q206L | 6.1 |
| N76D + V205I + Q206V | 6.0 |
| N76D + A194P + Q206E | 5.9 |
| N76D + P131* + P225A | 5.4 |
| N76D + N204D + Q206I | 5.4 |
| N76D + N204D + V205I | 5.3 |
| N76D + N204D + Q206V | 4.9 |
| N76D + N204D + Q206W | 4.9 |
| N76D + N261W + L262E | 4.9 |
| N76D + N261L + L262E | 4.8 |
| N76D + G160P + S161Y | 4.7 |
| N76D + N261E + L262E | 4.6 |
| N76D + N261V + L262E | 4.6 |
| N76D + Q206L + Y209W | 4.5 |
| N76D + N261Y + L262E | 4.5 |
| N76D + V205I + Q206W | 4.1 |
| N76D + G160D + S161E | 4.0 |
| N76D + V205I + Q206E | 4.0 |
| N76D + Q206L + S256D | 4.0 |
| N76D + G115T + H120T | 3.7 |

TABLE 7-continued

Accelerated storage stability of variants T½ IF: Half life improvement factor was measured relative to SEQ ID NO 3

| Mutations | Improvement factor |
|---|---|
| N76D + G160D + S161Y | 3.5 |
| N76D + N18S + V205I | 3.2 |
| N76D + A194P + M222S | 3.2 |
| N76D + Y209W + S256D | 3.2 |
| N76D + N18S + Q206E | 2.7 |
| N76D + Y209W + S256C | 2.5 |
| N76D + G115T + H120V | 2.4 |
| N76D + T255E + S256D | 2.3 |
| N76D + G115T + H120I | 2.0 |
| N76D + T255Q + S256D | 1.8 |

The invention claimed is:

1. A protein comprising a subtiliase variant comprising the substitutions N76D, X9{C,D,E,Q}, and X43{A,C,L,R,W}
   wherein each position corresponds to the position of the polypeptide of SEQ ID NO: 2, and
   wherein the variant has protease activity and is a polypeptide that has at least 85% but less than 100% sequence identity to the polypeptide of SEQ ID NO: 1.

2. The variant of claim 1, wherein the total number of alterations compared to a parent subtilase is between 3 and 30 alterations.

3. The variant of claim 2, wherein the parent subtilase is amino acids 1 to 269 of SEQ ID NO: 1 or amino acids 1 to 275 of SEQ ID NO: 2.

4. The variant of claim 1, wherein the variant comprises one or more of the substitutions selected from the group consisting of:

N76D+X2R
N76D+X115W
N76D+X194E
N76D+X255C
N76D+X6I
N76D+X120I
N76D+X204D
N76D+X255E
N76D+X8C
N76D+X120T
N76D+X204V
N76D+X255Q
N76D+X8H
N76D+X120V
N76D+X205I
N76D+X256A
N76D+X9C
N76D+X129D
N76D+X205L
N76D+X256C
N76D+X9D
N76D+X147W
N76D+X206C
N76D+X256D
N76D+X9E
N76D+X149C
N76D+X206E
N76D+X256V
N76D+X9Q
N76D+X149N
N76D+X206I
N76D+X256Y
N76D+X18S
N76D+X149Q
N76D+X206K
N76D+X259D
N76D+X43A
N76D+X158E
N76D+X206T
N76D+X260A
N76D+X43C
N76D+X160D
N76D+X206V
N76D+X260E
N76D+X43L
N76D+X160P
N76D+X206W
N76D+X260P
N76D+X43R
N76D+X161C
N76D+X209L
N76D+X261D
N76D+X43W
N76D+X161Y
N76D+X209W
N76D+X261C
N76D+X49T
N76D+X161E
N76D+X212A
N76D+X261E
N76D+X53A
N76D+X162L
N76D+X212D
N76D+X261L
N76D+X53L
N76D+X163A
N76D+X212G
N76D+X261M
N76D+X61D
N76D+X163D
N76D+X212N
N76D+X261R

N76D+X72A
N76D+X182C
N76D+X216I
N76D+X261V
N76D+X72V
N76D+X182E
N76D+X216T
N76D+X261W
N76D+X78D
N76D+X184D
N76D+X217C
N76D+X261Y
N76D+X78N
N76D+X185C
N76D+X217M
N76D+X261F
N76D+X104F
N76D+X185E
N76D+X218T
N76D+X262Y
N76D+X104P
N76D+X188C
N76D+X222C
N76D+X262C
N76D+X104T
N76D+X188D
N76D+X222N
N76D+X262E
N76D+X104Y
N76D+X188E
N76D+X222R
N76D+X262Q
N76D+X114V
N76D+X191N
N76D+X225A
N76D+X115T
N76D+X194D
N76D+X225S
N76D+X216V and
N76D+X206L.

5. The variant of claim 1, further comprising one or more substitutions selected from the group consisting of X3T, X4I, X15T, X24{G,R}, X68A, X99{D,E}, X101{R,K,N,M,E,D,L,I}, X103A, X104I, X128{A,L,S}, X129{N,Q} X130A, X199M, L217{Y,D,E,Q}, X218{D,E} and X245{K,R} (numbering according to SEQ ID NO: 2).

6. The variant of claim 1, which has an improved stability compared to SEQ ID NO: 3.

7. The variant of claim 6, which has an improved wash performance compared to SEQ ID NO: 3.

8. A detergent composition comprising the variant according to claim 1 and one or more detergent components.

9. The detergent composition according to claim 8, further comprising one or more additional enzymes selected from the group consisting of proteases, amylases, lipases, cutinases, cellulases, endoglucanases, xyloglucanases, pectinases, pectin lyases, xanthanases, peroxidases, haloperoxygenases, catalases and mannanases, or any mixture thereof.

10. The detergent composition according to claim 8 in the form of a bar, a homogenous tablet, a tablet having two or more layers, a pouch having one or more compartments, a regular or compact powder, a granule, a paste, a gel, or a regular, compact or concentrated liquid.

11. The variant of claim 5, comprising N76D and at least one substitution selected from X205I, X206L, X209W, X212G and X216V.

12. The variant of claim 1, which is (i) a polypeptide that has at least 90% but less than 100% sequence identity to the polypeptide of SEQ ID NO: 1.

13. The protein of claim 1 wherein the variant further comprises one or more substitutions selected from the group consisting of: X2R, X6I, X8{C,H}, X18S, X49T, X53{A,L}, X61 D, X72{A,V}, X78{D,N}, X104{F,P,T,Y}, X114V, X115{T,W}, X120{I,T,V}, X129D, X147W, X149{C,N,Q}, X158E, X160{D,P}, X161{C,Y,E}, X162L, X163{A,D}, X182{C,E}, X184D, X185{C,E}, X188{C, D,E}, X191N, X194{D,E}, X204{D,V}, X205{I,L}, X206{C,E,I,K,T,V,W,L}, X209{L,W}, X212{A,D,G,N}, X216{I,T,V}, X217{C,M}, X218T, X222{C,N,R}, X225{A,S}, X255{C,E,Q}, X256{A,C,D,V,Y}, X259D, X260{A,E,P}, X261{D,C,E,L,M,R,V,W,Y,F} and X262{Y,C,E,Q}.

* * * * *